(12) United States Patent
Gray et al.

(10) Patent No.: US 11,773,063 B1
(45) Date of Patent: Oct. 3, 2023

(54) PHARMACEUTICALLY ACCEPTABLE SALTS AND COMPOSITIONS THEREOF

(71) Applicant: BECKLEY PSYTECH LIMITED, Oxford (GB)

(72) Inventors: Jason Gray, Oxford (GB); Susana Del Rio Gancedo, Oxford (GB); Dita Davis, Oxford (GB); David James Pearson, Oxford (GB); Daniel Rixson, Oxford (GB)

(73) Assignee: Beckley Psytech Limited, Oxford (GB)

( * ) Notice: Subject to any disclaimer, the term of this patent is extended or adjusted under 35 U.S.C. 154(b) by 0 days.

(21) Appl. No.: 17/941,410

(22) Filed: Sep. 9, 2022

(30) Foreign Application Priority Data

Aug. 19, 2022 (GB) ...................... 2212116

(51) Int. Cl.
C07D 209/16 (2006.01)
(52) U.S. Cl.
CPC ........ C07D 209/16 (2013.01); *C07B 2200/13* (2013.01)
(58) Field of Classification Search
CPC .................................................. C07D 209/16
See application file for complete search history.

(56) References Cited

U.S. PATENT DOCUMENTS

| | | |
|---|---|---|
| 2,774,763 A | 12/1956 | Garbrecht |
| 2,997,470 A | 8/1961 | Pioch |
| 3,078,214 A | 2/1963 | Hofmann et al. |
| 3,224,945 A | 12/1965 | Tyler, Jr. |
| 5,811,436 A | 9/1998 | Leonard et al. |
| 11,518,742 B2 | 12/2022 | Feilding-Mellen et al. |
| 11,518,743 B2 | 12/2022 | Feilding-Mellen et al. |
| 2005/0019411 A1 | 1/2005 | Colombo et al. |
| 2012/0108510 A1 | 5/2012 | Young et al. |
| 2017/0348303 A1 | 12/2017 | Bosse et al. |
| 2018/0021326 A1 | 1/2018 | Stamets |
| 2018/0147142 A1 | 5/2018 | Knight |
| 2020/0179349 A1 | 6/2020 | Yun et al. |
| 2020/0187777 A1 | 6/2020 | Luderer et al. |
| 2021/0058956 A1 | 2/2021 | Chatterjee et al. |
| 2021/0069170 A1 | 3/2021 | Stamets |
| 2021/0085671 A1 | 3/2021 | Chadeayne |
| 2021/0322743 A1 | 10/2021 | Rinti et al. |
| 2022/0062238 A1 * | 3/2022 | Layzell .............. A61K 31/4045 |
| 2022/0396552 A1 | 12/2022 | Feilding-Mellen et al. |
| 2023/0031944 A1 | 2/2023 | Feilding-Mellen et al. |

FOREIGN PATENT DOCUMENTS

| | | |
|---|---|---|
| CH | 578565 A5 | 8/1976 |
| CN | 103816150 A | 5/2014 |
| CN | 113288883 A | 8/2021 |
| DE | 2617738 A1 | 11/1976 |
| EP | 0026899 A1 | 4/1981 |
| EP | 3868364 A1 | 8/2021 |
| GB | 981192 A | 1/1965 |
| GB | 1410349 A | 10/1975 |
| GB | 1584464 A | 2/1981 |
| GB | 2596884 A | 1/2022 |
| WO | 0115677 A2 | 3/2001 |
| WO | 0115677 A3 | 3/2001 |
| WO | 0238142 A2 | 5/2002 |
| WO | 2004000849 A2 | 12/2003 |
| WO | 2008003028 A2 | 1/2008 |
| WO | 2010054202 A2 | 5/2010 |
| WO | 2012/173701 A1 | 12/2012 |
| WO | 2013063492 A1 | 5/2013 |
| WO | 2018195455 A1 | 10/2018 |
| WO | 2019073379 A1 | 4/2019 |
| WO | 2019081764 A1 | 5/2019 |
| WO | 2019173797 A1 | 9/2019 |
| WO | 2019246532 A1 | 12/2019 |
| WO | 2020169850 A1 | 8/2020 |
| WO | 2020169851 A1 | 8/2020 |
| WO | 2020176597 A1 | 9/2020 |
| WO | 2020181194 A1 | 9/2020 |
| WO | 2020212951 A1 | 10/2020 |
| WO | 2021003467 A1 | 1/2021 |
| WO | 2021041407 A1 | 3/2021 |
| WO | 2021089872 A1 | 5/2021 |
| WO | 2021209815 A1 | 10/2021 |
| WO | 2021222885 A1 | 11/2021 |
| WO | 2021225796 A1 | 11/2021 |
| WO | 2021250435 A1 | 12/2021 |
| WO | WO 2022/246572 * | 12/2022 |
| WO | 2023002005 A1 | 1/2023 |

OTHER PUBLICATIONS

Berge et al., "Pharmaceutical Salts" Journal of Pharmaceutical Sciences; 1977; vol. 66, No. 1; pp. 1-19.*
Registry No. 2761182-82-3, File Registry on STN, entered STN: Mar. 3, 2022.*
International Search Report in International Application No. PCT/GB2021/051475, dated Sep. 16, 2021 (3 pages).
International Search Report in International Application No. PCT/GB2021/051476, dated Sep. 15, 2021 (5 pages).
Uthaug, M.V et al., "Prospective examination of synthetic 5-methoxy-N,N-dimethyltryptamine inhalation: effects on IL-6, cortisol levels, affect, and non-judgment," Psychopharmacology, vol. 237, pp. 773-785 (2020).
Database Registry. Chemical Abstracts Service: Columbus, OH. Chemical Name: 1H-Indole-3-ethanamine, 5-methoxy-N,N dimethyl-, benzoate (1:1); RN 282103-25-7; ED Aug. 1, 2000 (1 page).
Benington, F. et al., "Synthesis of O- and N-Methylated Derivatives of 5-Hydroxytryptamine," The Journal of Organic Chemistry, vol. 23, pp. 1977-1979 (1958).
Falkenberg, G. et al., "The Crystal and Molecular Structure of 5-Methoxy-(N,N)-dimethyltryptamine Hydrochloride," Acta Crystallographica Section B, vol. 27, pp. 411-418 (1971).

(Continued)

Primary Examiner — Rebecca L Anderson
(74) Attorney, Agent, or Firm — Bookoff McAndrews, PLLC

(57) ABSTRACT

Pharmaceutically acceptable salts of 5-methoxy-N,N-dimethyltryptamine are described, as well as compositions/formulations and uses thereof as a medicament.

10 Claims, 112 Drawing Sheets

(56) References Cited

OTHER PUBLICATIONS

Roseman, L. et al., "Increased amygdala responses to emotional faces after psilocybin treatment-resistant depression," Neuropharmacology, vol. 142, pp. 263-269 (2018).
Griffiths, R.R. et al., "Psilocybin produces substantial and sustained decreases in depression and anxiety in patients with life-threatening cancer: a randomized double-blind trial," Journal of Psychopharmacology, vol. 30, pp. 1181-1197 (2016).
Carhart-Harris, R.L. et al., "Psilocybin with psychological support for treatment-resistant depression: six-month follow-up," Psychopharmacology, vol. 235, pp. 399-408 (2018).
Monte, A.P. et al., "Stereoselective LSD-like Activity in a Series of d-Lysergic Acid Amides of (R) and (S)-2-Aminoalkanes," Journal of Medicinal Chemistry, vol. 38, pp. 958-966 (1995).
Ishii, H. et al., "Studies on Lysergic Acid Diethylamide and Related Compounds. Part 8. Structural Identification of New Metabolites of Lysergic Acid Diethylamide obtained by Microbial Transformation using Streptomyces roseochromogenes," Journal of the Chemical Society, Perkin Transactions 1: Organic & Bio-organic Chemistry, vol. 4, pp. 902-905 (1980).
Nakahara, Y. et al., "Studies on Lysergic Acid Diethylamide and Related Compounds. III. Improvement of Amidation of Lysergic Acid," Yakugaku Zasshi, vol. 94, pp. 407-412 (1974).
Huang, X. et al., "Drug Discrimination and Receptor Binding Studies of N-Isopropyl Lysergamide Derivatives," Pharmacology Biochemistry and Behavior, vol. 47, pp. 667-673 (1994).
Ishii, H. et al., "Studies on Lysergic Acid Diethylamide and Related Compounds. IX. Microbial Transformation of Amides Related to Lysergic Acid Diethylamide by Streptomyces roseochromogenes," Chemical & Pharmaceutical Bulletin, vol. 27, pp. 3029-3038 (1979).
Johnson, F.N. et al., "Emetic Activity of Reduced Lysergamides," Journal of Medicinal Chemistry, vol. 16, pp. 532-537 (1973).
Vangveravong, S. et al., "Synthesis and Serotonin Receptor Affinities of a Series of trans-2-(Indol-3-yl) cyclopropylamine Derivatives," Journal of Medicinal Chemistry, vol. 41, pp. 4995-5001 (1998).
Schneller, S.W. et al., "Synthesis of 4-Amino-1H-pyrrolo[2,3-b]pyridine (1,7-Dideazaadenine) and 1H-Pyrrolo[2,3-b]pyridin-4-ol (1,7-Dideazahypoxanthine)," The Journal of Organic Chemistry A, vol. 45, pp. 4045-4048 (1980).
Singh, S.K. et al., "An ab Initio Study of the Effect of Substituents on the n →π* Interactions between 7-Azaindole and 2,6 Difluorosubstituted Pyridines," The Journal of Physical Chemistry A, vol. 120, pp. 6258-6269 (2016).
Monson, C.M. et al., "MDMA-facilitated cognitive-behavioural conjoint therapy for posttraumatic stress disorder: an uncontrolled trial," European Journal of Psychotraumatology, vol. 11, pp. 1-7 (2020).
Wolfson, P.E. et al., "MDMA-assisted psychotherapy for treatment of anxiety and other psychological distress related to life-threatening illnesses: a randomized pilot study," Scientific Reports, vol. 10, pp. 1-15 (2020).
Yazar-Klosinski, B.B. et al., "Potential Psychiatric Uses for MDMA," Developments, vol. 101, pp. 194-196 (2017).
PharmaTher Holdings Ltd. Dec. 14, 2021. PharmaTher Announces Positive Research Results for LSD Microneedle Patch. Press Release. <URL: https://psychedelicinvest.com/pharmather-announces-positive-research-results-for-lsd-microneedle-patch/>.
Szabo, A. et al., "Psychedelic N,N-Dimethyltryptamine and 5-Methoxy-N,N-Dimethyltryptamine Modulate Innate and Adaptive Inflammatory Responses through the Sigma-1 Receptor of Human Monocyte-Derived Dendritic Cells," PLoS One, vol. 9, pp. 1-12 (2014).
Sherwood, A.M. et al., "Synthesis and Characterization of 5-MeO-DMT Succinate for Clinical Use," ACS Omega, vol. 5, pp. 32067-32075 (2020).
Galeffi, C. et al., "N,N-Dimethyl-5-Methoxytryptamine, a Component of a Dart Poison of the Yanoáma Indians," Journal of Natural Products, vol. 46, pp. 586-587 (1983).

CAplus. Chemical Abstracts Service: Columbus. CAplus Accession No. 2017:1595854. Title: Preparation of tetrahydropyridoindolylcycloalkylacrylic acid derivatives and analogs for us as estrogen receptor modulators. Inventor: Huang, P.Q. et al. (4 pages).
Sohlberg, E. et al., "The impact of the site of blood sampling on pharmacokinetic parameters following sublingual dosing to dogs," Journal of Pharmacological and Toxicological Methods, vol. 67, pp. 1-4 (2013).
Illum, L. et al., "The Effect of Blood Sampling Site and Physicochemical Characteristics of Drugs on Bioavailability after Nasal Administration in the Sheep Model," Pharmaceutical Research, vol. 20, pp. 1474-1484 (2003).
Gupta, S.P., "QSAR Studies on Drugs Acting at the Central Nervous System," Chemical Reviews, vol. 89, pp. 1765-1800 (1989).
Stoll, A. et al., "49. Amide der stereoisomeren Lysergsäuren und Dihydro-lysergsäuren," Helvetica Chimica Acta, vol. 38, pp. 421-433 (1955).
Halberstadt, A.L. et al., "Pharmacological characterization of the LSD analog N-ethyl-N-cyclopropyl lysergamide (ECPLA)," Psychopharmacology, vol. 236, pp. 799-808 (2019).
McKenna, D.J. et al., "Differential interactions of indolealkylamines with 5-hydroxytryptamine receptor subtypes," Neuropharmacology, vol. 29, pp. 193-198 (1990).
Glennon, R.A. et al., "Serotonin Receptor Binding Affinities of Tryptamine Analogues," Journal of Medicinal Chemistry, vol. 22, pp. 428-432 (1979).
Klein, A.K. et al., "Investigation of the Structure—Activity Relationships of Psilocybin Analogues," ACS Pharmacology & Translational Science, vol. 4, pp. 533-542 (2021).
Sard, H. et al., "SAR of psilocybin analogs: Discovery of a selective 5-HT2C agonist," Bioorganic & Medicinal Chemistry Letters, vol. 15, pp. 4555-4559 (2005).
Medline Plus, "Cancer," National Institute of Health (2007) <URL: www.nlm,nih,gov/medlineplus.cancer.html>.
Lala, P.K. et al., "Role of nitric oxide in tumor progression: Lessons from experimental tumors," Cancer and Metastasis Reviews, vol. 17, pp. 91-106 (1998).
Golub, T.R. et al., Molecular Classification of Cancer: Class Discovery and Class Prediction by Gene Expression Monitoring, vol. 286, pp. 531-537 (1999).
Glässer, A., "Some Pharmacological Actions of D-Lysergic Acid Methyl Carbinolamide," Nature, vol. 189, pp. 313-314 (1961).
Lyon, R.A. et al., "Indolealkylamine analogs share 5-HT2 binding characteristics with phenylalkylamine hallucinogens," European Journal of Pharmacology, vol. 145, pp. 291-297 (1988).
U.S. Appl. No. 18/065,030, filed Dec. 13, 2022 (55 pages).
U.S. Appl. No. 18/162,976, filed Feb. 1, 2023 (176 pages).
Shen et al., Psychedelic 5-Methoxy-N, N-dimethyltryptamine: Metabolism, Pharmacokinectis, Drug Interactions, and Pharmacological Actions, Curr Drug Metab., Oct. 2010, 11(8), pp. 659-666.
DMT-Nexus Wiki. Feb. 10, 2023. Psychedelic Compounds Chemical and Physical Properties. <URL: http://wiki.dmt-nexus.me/Psychedelic_Compounds_Chemical_and_Physical_Properties#DMT_Benzoate>.
Shulgin, A. et al. TiHKAL: The Continuation. #38. 5-MEO-DMT. Tryptamine, 5-Methoxy-N,N-Dimethyl; Indole, 5-Methoxy-3-[2-(Dimethylamino]; 5-Methoxy-N,N-Dimethyltryptamine; 5- Methoxy-3-[2-(Dimethylamino)Ethyl]indole; N,N,O-Trimethylserotonin; N,N,O-Tms; Bufotenine Methyl Ether; O-Methylbufotenine; OMB., Feb. 21, 2015. < URL: https://erowid.org/library/books_online/tihkal/tihkal38.shtml.>.
CHEMCATS. Chemical Abstracts Service: Columbus, OH. Chemical Name: 4H-Pyrrolo[2,3-b]pyridine-4-one, 1,7- dihydro -. CHEMCATS Accession No. 1756550559. Catalog Name: Sagechem Limited Product List. Order No. Catalog: S243355. CAS Registry No. 1076197-59-5, May 28, 2020 (1 page).
CHEMCATS. Chemical Abstracts Service: Columbus, OH. Chemical Name: 1-methyl-1H-pyrrolo[2,3-b]pyridin-4-ol. CHEMCATS Accession No. 1545199867. Catalog Name: Azepine Product List. Order No. Catalog: AZ04819515. CAS Registry No. 1781876-60-5, Mar. 1, 2019 (1 page).
CHEMCATS. Chemical Abstracts Service: Columbus, OH. Chemical Name: 1-methylpyrrolo[2,3-b]pyridin-4-ol. CHEMCATS Acces-

(56) References Cited

OTHER PUBLICATIONS sion No. 1442516433. Catalog Name: Aurora Building Blocks 2. Order No. Catalog: 115.267.167. CAS Registry No. 1781876-60-5, Apr. 19, 2021 (1 page).

CHEMCATS. Chemical Abstracts Service: Columbus, OH. Chemical Name: 1-methyl-1H-pyrrolo[2,3-b]pyridin-4-ol. CHEMCATS Accession No. 0002254898. Catalog Name: FCH Group Reagents for Synthesis. Order No. Catalog: FCH1635008. CAS Registry No. 1781876-60-5, May 5, 2021 (1 page).

CHEMCATS. Chemical Abstracts Service: Columbus, OH. Chemical Name: 1H-Pyrrolo[2,3-B]Pyridin-4(7H)-One. CHEMCATS Accession No. 2022337458. Catalog Name: Chemieliva Pharmaceutical Product List. Order No. Catalog: CE0957308. CAS Registry No. 1076197-59-5, Jan. 28, 2021 (1 page).

CHEMCATS. Chemical Abstracts Service: Columbus, OH. Chemical Name: 1H-Pyrrolo[2,3-b]pyridin-4(7H)-one. CHEMCATS Accession No. 1621739382. Catalog Name: Ambeed, Inc. Product List. Order No. Catalog: A763560. CAS Registry No. 1076197-59-5, May 7, 2021 (1 page).

CHEMCATS. Chemical Abstracts Service: Columbus, OH. Chemical Name: 1H-Pyrrolo[2,3-b]pyridin-4-ol hydrate. CHEMCATS Accession No. 1773869211. Catalog Name: Aurora Building Blocks 3. Order No. Catalog: 129.194.895. CAS Registry No. 2031269-35- Apr. 7, 19, 2021 (1 page).

CHEMCATS. Chemical Abstracts Service: Columbus, OH. Chemical Name: 1H-pyrrolo[2,3-b]pyridin-4-ol hydrate. CHEMCATS Accession No. 0968477988. Catalog Name: ASW MedChem Product List. Order No. Catalog: TH-45275. CAS Registry No. 2031269-35-7, Jun. 5, 2020 (1 page).

\* cited by examiner

PHARMACEUTICALLY ACCEPTABLE SALTS AND COMPOSITIONS THEREOF

CROSS-REFERENCE TO RELATED APPLICATIONS

This application claims priority to GB Application No. 2212116.4, filed on Aug. 19, 2022, which is incorporated by reference herein in its entirety.

FIELD OF THE INVENTION

This invention relates to pharmaceutically acceptable salts of 5-methoxy-N,N-dimethyltryptamine. In particular, though not exclusively, the invention relates to compositions/formulations and uses of the same as a medicament.

BACKGROUND OF THE INVENTION 5-methoxy-N,N-dimethyltryptamine (5-MeO-DMT) is a pharmacologically active compound of the tryptamine class and has the chemical formula:

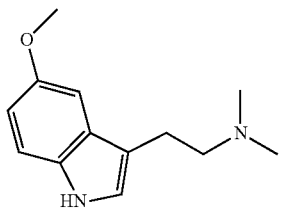 [SMILES: COc1ccc2[nH]cc(CCN(C)C)c2c1]

5-MeO-DMT is a psychoactive/psychedelic substance found in nature and is believed to act mainly through serotonin receptors. It is also believed to have a high affinity for the 5-HT2 and 5-HT1A subtypes, and/or inhibits monoamine reuptake.

However, 5-MeO-DMT is not well understood and uses of this compound have not been well explored. Further, 5-MeO-DMT is not easy to handle, and there are challenges in formulating it for effective delivery in pharmaceutically useful compositions/formulations.

There remains a need in the art for improved compositions/formulations and uses of 5-MeO-DMT.

SUMMARY OF THE INVENTION

Herein disclosed is a non-hygroscopic salt of 5-MeO-DMT.

In an embodiment, the non-hygroscopic salt is 5-MeO-DMT hydrobromide.

In an embodiment, there is provided a crystalline form of 5-MeO-DMT hydrobromide.

In an embodiment, there is provided a crystalline form of 5-MeO-DMT hydrobromide, characterised by peaks in an XRPD diffractogram at 14.6, 16.8, 20.8, 24.3, 24.9 and 27.5° 2θ±0.1° 2θ as measured by x-ray powder diffraction using an x-ray wavelength of 1.5406 Å.

In an embodiment, there is provided a crystalline form of 5-MeO-DMT hydrobromide, characterised by peaks in an XRPD diffractogram as shown in, or substantially as shown in, FIG. 109 or FIG. 171.

In an embodiment, there is provided a crystalline form of 5-MeO-DMT hydrobromide, characterised by peaks in an XRPD diffractogram at 14.6, 21.6 and 24.3° 2θ±0.1° 2θ as measured by x-ray powder diffraction using an x-ray wavelength of 1.5406 Å.

In an embodiment, there is provided a crystalline form of 5-MeO-DMT hydrobromide, characterised by peaks in an XRPD diffractogram at 18.6, 19.7 and 24.8° 2θ±0.1° 2θ as measured by x-ray powder diffraction using an x-ray wavelength of 1.5406 Å.

In an embodiment, there is provided a crystalline form of 5-MeO-DMT hydrobromide, characterised by peaks in an XRPD diffractogram at 14.6, 20.8, 21.6, 24.3 and 25.4° 2θ±0.1° 2θ as measured by x-ray powder diffraction using an x-ray wavelength of 1.5406 Å.

In an embodiment, there is provided a pharmaceutical composition comprising 5-MeO-DMT hydrobromide. In an embodiment, the pharmaceutical composition is for use as a medicament.

In an embodiment, there is provided a pharmaceutical composition comprising crystalline 5-MeO-DMT hydrobromide. In an embodiment, the pharmaceutical composition is for use as a medicament.

In an embodiment, there is provided 5-MeO-DMT phosphate.

In an embodiment, there is provided a crystalline form of 5-MeO-DMT phosphate, characterised by peaks in an XRPD diffractogram at 12.9, 20.4 and 23.1° 2θ±0.1° 2θ as measured by x-ray powder diffraction using an x-ray wavelength of 1.5406 Å.

In an embodiment, there is provided a crystalline form of 5-MeO-DMT phosphate, characterised by peaks in an XRPD diffractogram as shown in, or substantially as shown in, FIG. 6.

In an embodiment, there is provided a pharmaceutical composition comprising 5-MeO-DMT phosphate.

In an embodiment, the pharmaceutical composition is for use as a medicament.

In an embodiment, there is provided a pharmaceutical composition comprising a crystalline form of 5-MeO-DMT phosphate In an embodiment, the pharmaceutical composition is for use as a medicament.

In an embodiment, there is provided 5-MeO-DMT fumarate.

In an embodiment, there is provided a crystalline form of 5-MeO-DMT fumarate, characterised by peaks in an XRPD diffractogram at 13.0, 16.3 and 22.1° 2θ±0.1° 2θ as measured by x-ray powder diffraction using an x-ray wavelength of 1.5406 Å.

In an embodiment, there is provided a crystalline form of 5-MeO-DMT fumarate, characterised by peaks in an XRPD diffractogram as shown in, or substantially as shown in, FIG. 14.

In an embodiment, there is provided a pharmaceutical composition comprising 5-MeO-DMT fumarate.

In an embodiment, the pharmaceutical composition is for use as a medicament.

In an embodiment, there is provided a pharmaceutical composition comprising a crystalline form of 5-MeO-DMT fumarate. In an embodiment, the pharmaceutical composition is for use as a medicament.

In an embodiment, there is provided 5-MeO-DMT oxalate.

In an embodiment, there is provided a crystalline form of 5-MeO-DMT oxalate, characterised by peaks in an XRPD diffractogram at 13.0, 19.9 and 26.0° 2θ±0.1° 2θ as measured by x-ray powder diffraction using an x-ray wavelength of 1.5406 Å.

In an embodiment, there is provided a crystalline form of 5-MeO-DMT oxalate, characterised by peaks in an XRPD diffractogram as shown in, or substantially as shown in, FIG. 19 or FIG. 28.

In an embodiment, there is provided a pharmaceutical composition comprising 5-MeO-DMT oxalate. In an embodiment, the pharmaceutical composition is for use as a medicament.

In an embodiment, there is provided a pharmaceutical composition comprising a crystalline form of 5-MeO-DMT oxalate. In an embodiment, the pharmaceutical composition is for use as a medicament.

In an embodiment, there is provided 5-MeO-DMT tartrate.

In an embodiment, there is provided a crystalline form of 5-MeO-DMT tartrate, characterised by peaks in an XRPD diffractogram at 18.3, 18.6, and 20.7° 2θ±0.1° 2θ as measured by x-ray powder diffraction using an x-ray wavelength of 1.5406 Å.

In an embodiment, there is provided a crystalline form of 5-MeO-DMT tartrate, characterised by peaks in an XRPD diffractogram as shown in, or substantially as shown in, FIG. 34 or FIG. 41.

In an embodiment, there is provided a pharmaceutical composition comprising 5-MeO-DMT tartrate. In an embodiment, the pharmaceutical composition is for use as a medicament.

In an embodiment, there is provided a pharmaceutical composition comprising a crystalline form of 5-MeO-DMT tartrate. In an embodiment, the pharmaceutical composition is for use as a medicament.

In an embodiment, there is provided 5-MeO-DMT benzenesulfonate.

In an embodiment, there is provided a crystalline form of 5-MeO-DMT benzenesulfonate, characterised by peaks in an XRPD diffractogram at 9.5, 21.2, and 23.6° 2θ±0.1° 2θ as measured by x-ray powder diffraction using an x-ray wavelength of 1.5406 Å.

In an embodiment, there is provided a crystalline form of 5-MeO-DMT benzenesulfonate, characterised by peaks in an XRPD diffractogram as shown in, or substantially as shown in, FIG. 42.

In an embodiment, there is provided a pharmaceutical composition comprising 5-MeO-DMT benzenesulfonate. In an embodiment, the pharmaceutical composition is for use as a medicament.

In an embodiment, there is provided a pharmaceutical composition comprising a crystalline form of 5-MeO-DMT benzenesulfonate. In an embodiment, the pharmaceutical composition is for use as a medicament.

In an embodiment, there is provided 5-MeO-DMT tosylate.

In an embodiment, there is provided a crystalline form of 5-MeO-DMT tosylate, characterised by peaks in an XRPD diffractogram at 19.3, 23.6 and 24.1° 2θ±0.1° 2θ as measured by x-ray powder diffraction using an x-ray wavelength of 1.5406 Å.

In an embodiment, there is provided a crystalline form of 5-MeO-DMT tosylate, characterised by peaks in an XRPD diffractogram as shown in, or substantially as shown in, FIG. 49 or 56.

In an embodiment, there is provided a pharmaceutical composition comprising 5-MeO-DMT tosylate. In an embodiment, the pharmaceutical composition is for use as a medicament.

In an embodiment, there is provided a pharmaceutical composition comprising a crystalline form of 5-MeO-DMT tosylate. In an embodiment, the pharmaceutical composition is for use as a medicament.

In an embodiment, there is provided 5-MeO-DMT glycolate.

In an embodiment, there is provided a crystalline form of 5-MeO-DMT glycolate, characterised by peaks in an XRPD diffractogram at 20.2, 21.1 and 23.4° 2θ±0.1° 2θ as measured by x-ray powder diffraction using an x-ray wavelength of 1.5406 Å.

In an embodiment, there is provided a crystalline form of 5-MeO-DMT glycolate, characterised by peaks in an XRPD diffractogram as shown in, or substantially as shown in, FIG. 62.

In an embodiment, there is provided a pharmaceutical composition comprising 5-MeO-DMT glycolate.

In an embodiment, the pharmaceutical composition is for use as a medicament.

In an embodiment, there is provided a pharmaceutical composition comprising a crystalline form of 5-MeO-DMT glycolate. In an embodiment, the pharmaceutical composition is for use as a medicament.

In an embodiment, there is provided 5-MeO-DMT ketoglutarate.

In an embodiment, there is provided a crystalline form of 5-MeO-DMT ketoglutarate, characterised by peaks in an XRPD diffractogram at 14.4, 18.2 and 20.9° 2θ±0.1° 2θ as measured by x-ray powder diffraction using an x-ray wavelength of 1.5406 Å.

In an embodiment, there is provided a crystalline form of 5-MeO-DMT ketoglutarate, characterised by peaks in an XRPD diffractogram as shown in, or substantially as shown in, FIG. 69.

In an embodiment, there is provided a pharmaceutical composition comprising 5-MeO-DMT ketoglutarate. In an embodiment, the pharmaceutical composition is for use as a medicament.

In an embodiment, there is provided a pharmaceutical composition comprising a crystalline form of 5-MeO-DMT ketoglutarate. In an embodiment, the pharmaceutical composition is for use as a medicament.

In an embodiment, there is provided 5-MeO-DMT malate.

In an embodiment, there is provided a crystalline form of 5-MeO-DMT malate, characterised by peaks in an XRPD diffractogram at 18.3, 18.7 and 18.9° 2θ±0.1° 2θ as measured by x-ray powder diffraction using an x-ray wavelength of 1.5406 Å.

In an embodiment, there is provided a crystalline form of 5-MeO-DMT malate, characterised by peaks in an XRPD diffractogram as shown in, or substantially as shown in, FIG. 76.

In an embodiment, there is provided a pharmaceutical composition comprising 5-MeO-DMT malate. In an embodiment, the pharmaceutical composition is for use as a medicament.

In an embodiment, there is provided a pharmaceutical composition comprising a crystalline form of 5-MeO-DMT malate. In an embodiment, the pharmaceutical composition is for use as a medicament.

In an embodiment, there is provided 5-MeO-DMT saccharinate.

In an embodiment, there is provided a crystalline form of 5-MeO-DMT saccharinate, characterised by peaks in an XRPD diffractogram at 8.7, 15.2 and 20.9° 2θ±0.1° 2θ as measured by x-ray powder diffraction using an x-ray wavelength of 1.5406 Å.

In an embodiment, there is provided a crystalline form of 5-MeO-DMT saccharinate, characterised by peaks in an XRPD diffractogram as shown in, or substantially as shown in, FIG. 81.

In an embodiment, there is provided a pharmaceutical composition comprising 5-MeO-DMT saccharinate. In an embodiment, the pharmaceutical composition is for use as a medicament.

In an embodiment, there is provided a pharmaceutical composition comprising a crystalline form of 5-MeO-DMT saccharinate. In an embodiment, the pharmaceutical composition is for use as a medicament.

Herein disclosed, there is provided a composition comprising a pharmaceutically effective amount of a pharmaceutically acceptable salt of 5-methoxy-N,N-dimethyltryptamine (5-MeO-DMT).

In a first aspect of the invention, there is provided a composition comprising a pharmaceutically effective amount of a pharmaceutically acceptable hydrobromide salt of 5-methoxy-N,N-dimethyltryptamine (5-MeO-DMT).

The invention provides for improved formulations and uses of 5-MeO-DMT salts.

In an embodiment the composition comprises a dosage amount of 5-MeO-DMT in the range of 0.05 mg to 100 mg.

In an embodiment the composition comprises a dosage amount of 5-MeO-DMT in the range of 0.1 mg to 50 mg.

In an embodiment the composition comprises a dosage amount of 5-MeO-DMT in the range of 0.5 mg to 25 mg.

In an embodiment the composition comprises a dosage amount of 5-MeO-DMT in the range of 0.5 mg to 10 mg.

In an embodiment the composition comprises a dosage amount of 5-MeO-DMT in the range of 1 mg to 10 mg.

In an embodiment the composition comprises a dosage amount of 5-MeO-DMT in the range of 1 mg to 8 mg.

In an embodiment the composition comprises a dosage amount of 5-MeO-DMT in the range of 3 mg to 15 mg.

In an embodiment the composition comprises a dosage amount of 5-MeO-DMT in the range of 0.005 mg to 100 mg.

In an embodiment the composition comprises a dosage amount of 5-MeO-DMT in the range of 0.001 mg to 100 mg.

In an embodiment the composition comprises a dosage amount of 5-MeO-DMT in the range of 0.0005 mg to 100 mg.

The level of the active agent can be adjusted as required by need for example to suit a certain patient group (e.g. the elderly) or the conditions being treated.

In an embodiment the composition is formulated in a dosage form selected from: oral, transdermal, inhalable, intravenous, subcutaneous or rectal dosage form.

It is advantageous to be able to deliver the active agent in different forms, for example to suit a certain patient group (e.g. the elderly) or the conditions being treated.

In an embodiment the composition is formulated in a dosage form selected from: tablet, capsule, granules, powder, free-flowing powder, inhalable powder, aerosol, nebulised, vaping, buccal, sublingual, sublabial, injectable, or suppository dosage form.

In an embodiment the powder is suitable for administration by inhalation via a medicament dispenser selected from a reservoir dry powder inhaler, a unit-dose dry powder inhaler, a pre-metered multi-dose dry powder inhaler, a nasal inhaler or a pressurized metered dose inhaler.

In an embodiment the powder comprises particles, the particles having a median diameter of less than 2000 μm, 1000 μm, 500 μm, 250 μm, 100 μm, 50 μm, or 1 μm.

In an embodiment the powder comprises particles, the particles having a median diameter of greater than 500 μm, 250 μm, 100 μm, 50 μm, 1 μm or 0.5 μm.

In an embodiment the powder comprises particles, and wherein the powder has a particle size distribution of d10=20-60 μm, and/or d50=80-120 μm, and/or d90=130-300 μm.

The nature of the powder can be adjusted to suit need. For example, if being made for nasal inhalation, then the particles may be adjusted to be much finer than if the powder is going to be formulated into a gelatine capsule, or differently again if it is going to be compacted into a tablet.

In an embodiment the 5-MeO-DMT salt is amorphous or crystalline. In an embodiment, the 5-MeO-DMT salt is in a polymorphic crystalline form.

For the salt, the dosage amount is the equivalent amount of the free base delivered when the salt is taken. So 100 mg dosage amount of 5MeODMT corresponds to 117 mg of the hydrochloride salt (i.e. both providing the same molar amount of the active substance). The greater mass of the salt needed is due to the larger formula weight of the hydrogen chloride salt (i.e. 218.3 g/mol for the free base as compared to 254.8 g/mol for the salt). Similarly, for the deuterated or triturated version of 5MeODMT (also considered within the scope of the invention), a slight increase in mass can be expected due to the increased formula weight of these isotopic compounds.

Amorphous and crystalline substances often show different chemical/physical properties, e.g. improved rate of dissolution in a solvent, or improved thermal stability. Similarly, different polymorphs may also show different and useful chemical/physical properties.

In an embodiment the composition comprises one or more pharmaceutically acceptable carriers or excipients.

In an embodiment the composition comprises one or more of: mucoadhesive enhancer, penetrating enhancer, cationic polymers, cyclodextrins, Tight Junction Modulators, enzyme inhibitors, surfactants, chelators, and polysaccharides.

In an embodiment the composition comprises one or more of: chitosan, chitosan derivatives (such as N,N,N-trimethyl chitosan (TMC), n-propyl-(QuatPropyl), n-butyl-(QuatButyl) and n-hexyl (QuatHexyl)-N,N-dimethyl chitosan, chitosan chloride), β-cyclodextrin, *Clostridium perfringens* enterotoxin, zonula occludens toxin (ZOT), human neutrophil elastase inhibitor (ER143), sodium taurocholate, sodium deoxycholate sodium, sodium lauryl sulphate, glycodeoxycholat, palmitic acid, palmitoleic acid, stearic acid, oleyl acid, oleyl alchohol, capric acid sodium salt, DHA, EPA, dipalmitoyl phophatidyl choline, soybean lecithin, lysophosphatidylcholine, dodecyl maltoside, tetradecyl maltoside, EDTA, lactose, cellulose, and citric acid.

In an embodiment the composition disclosed herein is for use as a medicament. In an embodiment the composition disclosed herein is for use in a method of treatment of a human or animal subject by therapy.

In an embodiment the method of treatment is a method of treatment of:
  conditions caused by dysfunctions of the central nervous system,
  conditions caused by dysfunctions of the peripheral nervous system,
  conditions benefiting from sleep regulation (such as insomnia),
  conditions benefiting from analgesics (such as chronic pain),
  migraines, trigeminal autonomic cephalgias (such as short-lasting unilateral neuralgiform headache with conjunctival injection and tearing (SUNCT), and short-lasting neuralgiform headaches with cranial autonomic symptoms (SUNA)), conditions benefiting from neurogenesis (such as stroke, traumatic brain injury, Parkinson's dementia), conditions benefiting from anti-inflammatory treatment, depression, treatment resistant depression anxiety, substance use disorder, addictive disorder, gambling disorder, eating disorders, obsessive-compulsive disorders, or body dysmorphic disorders, optionally the condition is SUNCT and/or SUNA.

Treatment of the above conditions may be beneficially improved by taking the invention.

In an embodiment, the method of treatment is a method of treatment of alcohol-related diseases and disorders, eating disorders, impulse control disorders, nicotine-related disorders, tobacco-related disorders, methamphetamine-related disorders, amphetamine-related disorders, cannabis-related disorders, cocaine-related disorders, hallucinogen use disorders, inhalant-related disorders, benzodiazepine abuse or dependence related disorders, and/or opioid-related disorders.

In an embodiment, the method of treatment is a method of treatment of tobacco addiction. In an embodiment, the method is a method of reducing tobacco use. In an embodiment, the method of treatment is a method of treatment of nicotine addiction. In an embodiment, the method is a method of reducing nicotine use.

In an embodiment, the method of treatment is a method of treating alcohol abuse and/or addiction. In an embodiment, the method of treatment is a method of reducing alcohol use.

In an embodiment, the method of treatment is a method of treating or preventing heavy drug use.

In an embodiment, the method of treatment is a method of treating or preventing heavy drug use, including, but not limited to, alcohol, tobacco, nicotine, cocaine, methamphetamine, other stimulants, phencyclidine, other hallucinogens, marijuana, sedatives, tranquilizers, hypnotics, and opiates. It will be appreciated by one of ordinary skill in the art that heavy use or abuse of a substance does not necessarily mean the subject is dependent on the substance.

In an embodiment the method of treatment is a method of treatment of more than one of the above conditions, for example, the method of treatment may be a method of treatment of depression and anxiety.

In an embodiment the composition is administered one or more times a year.

In an embodiment the composition is administered one or more times a month.

In an embodiment the composition is administered one or more times a week.

In an embodiment the composition is administered one or more times a day.

In an embodiment the composition is administered at such a frequency as to avoid tachyphylaxis.

In an embodiment the composition is administered together with a complementary treatment and/or with a further active agent.

In an embodiment the further active agent is a psychedelic compound, optionally a tryptamine.

In an embodiment the further active agent is lysergic acid diethylamide (LSD), psilocybin, psilocin or a prodrug thereof.

In an embodiment the further active agent is an antidepressant compound.

In an embodiment the further active agent is selected from an SSRI, SNRI, TCA or other antidepressant compounds.

In an embodiment the further active agent is selected from Citalopram (Celexa, Cipramil), Escitalopram (Lexapro, Cipralex), Fluoxetine (Prozac, Sarafem), Fluvoxamine (Luvox, Faverin), Paroxetine (Paxil, Seroxat), Sertraline (Zoloft, Lustral), Desvenlafaxine (Pristiq), Duloxetine (Cymbalta), Levomilnacipran (Fetzima), Milnacipran (Ixel, Savella), Venlafaxine (Effexor), Vilazodone (Viibryd), Vortioxetine (Trintellix), Nefazodone (Dutonin, Nefadar, Serzone), Trazodone (Desyrel), Reboxetine (Edronax), Teniloxazine (Lucelan, Metatone), Viloxazine (Vivalan), Bupropion (Wellbutrin), Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Opipramol (Insidon), Pipofezine (Azafen/Azaphen), Protriptyline (Vivactil), Trimipramine (Surmontil), Amoxapine (Asendin), Maprotiline (Ludiomil), Mianserin (Tolvon), Mirtazapine (Remeron), Setiptiline (Tecipul), Isocarboxazid (Marplan), Phenelzine (Nardil), Tranylcypromine (Parnate), Selegiline (Eldepryl, Zelapar, Emsam), Caroxazone (Surodil, Timostenil), Metralindole (Inkazan), Moclobemide (Aurorix, Manerix), Pirlindole (Pirazidol), Toloxatone (Humoryl), Agomelatine (Valdoxan), Esketamine (Spravato), Ketamine (Ketalar), Tandospirone (Sediel), Tianeptine (Stablon, Coaxil), Amisulpride (Solian), Aripiprazole (Abilify), Brexpiprazole (Rexulti), Lurasidone (Latuda), Olanzapine (Zyprexa), Quetiapine (Seroquel), Risperidone (Risperdal), Trifluoperazine (Stelazine), Buspirone (Buspar), Lithium (Eskalith, Lithobid), Modafinil (Provigil), Thyroxine (T4), Triiodothyronine (T3).

In an embodiment the further active agent is selected from Celexa (citalopram), Cymbalta (duloxetine), Effexor (venlafaxine), Lexapro (escitalopram), Luvox (fluvoxamine), Paxil (paroxetine), Prozac (fluoxetine), Remeron (mirtazapine), Savella (milnacipran), Trintellix (vortioxetine), Vestra (reboxetine), Viibryd (vilazodone), Wellbutrin (bupropion), Zoloft (sertraline).

In an embodiment the complementary treatment is psychotherapy.

In an embodiment, there is provided a composition comprising a pharmaceutically effective amount of a pharmaceutically acceptable salt of 5MeODMT for use in a method of treatment of treatment resistant depression.

In an embodiment, there is provided a composition comprising a pharmaceutically effective amount of a pharmaceutically acceptable salt of 5MeODMT for use in a method of treatment of depression.

In an embodiment, there is provided a composition comprising a pharmaceutically effective amount of a pharmaceutically acceptable salt of 5MeODMT for use in a method of treatment of PTSD.

In an embodiment, there is provided a composition comprising a pharmaceutically effective amount of a pharmaceutically acceptable salt of 5MeODMT for use in a method of treatment of addiction/substance misuse disorders.

In an embodiment, there is provided a nasal inhalation composition comprising a pharmaceutically effective amount of a pharmaceutically acceptable salt of 5MeODMT for use in a method of treatment of treatment resistant depression.

Treatment of the above conditions may be beneficially improved by taking the invention together with some complementary treatments; also these treatments may occur much less regularly than some other treatments that require daily treatments or even multiple treatments a day.

For the avoidance of doubt, the person skilled in the art will appreciate that numerical values relating to measurements are subject to instrument setup and measurement errors which can result in small discrepancies in the measurement values obtained. As such, it will be readily understood that where herein, for example, an XRPD peak is given a value of XX.Y°2θ, included with the scope of the disclosure of this application are values XX.Y° 2θ±0.1° 2θ, XX.Y° 2θ±0.2*2θ, XX.Y*2θ±0.3° 2θ, XX.Y° 2θ±0.4° 2θ and XX.Y° 2θ±0.5° 2θ. The skilled person will doubtless understand that the same applies for numerical values given for temperatures and enthalpies (joules). Again, solely as an example, a temperature value of XX.Y° C. (or XX° C.) will be understood to encompass values of XX.Y° C.±0.1° C., XX.Y° C.±0.2° C., XX.Y° C.±0.3° C., XX.Y° C.±0.4° C. and XX.Y° C.±0.5° C.

Similarly, it should be understood that values measured herein may be rounded down and that these rounded values are within the scope of the original disclosure. For example, values measured at 2 decimal places herein may be expressed at 1 decimal place (with the appropriate rounding) and so are still within the original disclosure.

Terms such as "a", "an," and "the" are not intended to refer to only a singular entity but include the general class of which a specific example may be used for illustration.

As used herein, the terms "about" and/or "around" refer to a value that is within 10% above or below the value being described.

The different polymorphic forms of the various salts described herein have been labelled sequentially as Pattern 1, Pattern 2 etc., principally numbering these patterns in the order in which they appear in the application. For the sake of completeness, we add that no inference should be taken from the ordering of the polymorphs using this numbering system.

Figure 120:
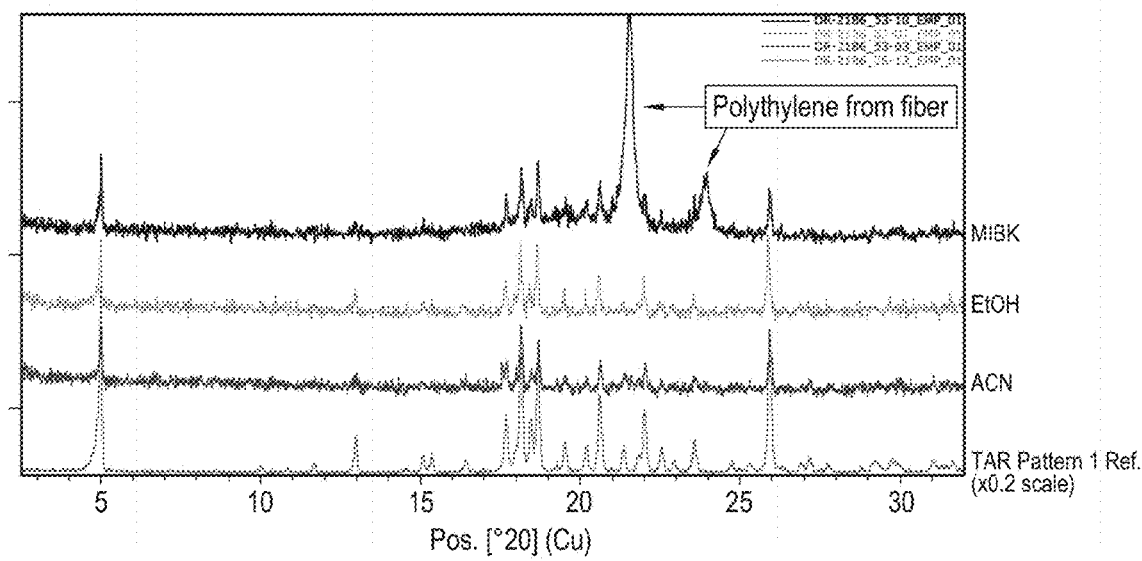

FIG. 120. XRPD Diffractograms of various samples of Tartrate salt (low intensity samples).

Figure 121:
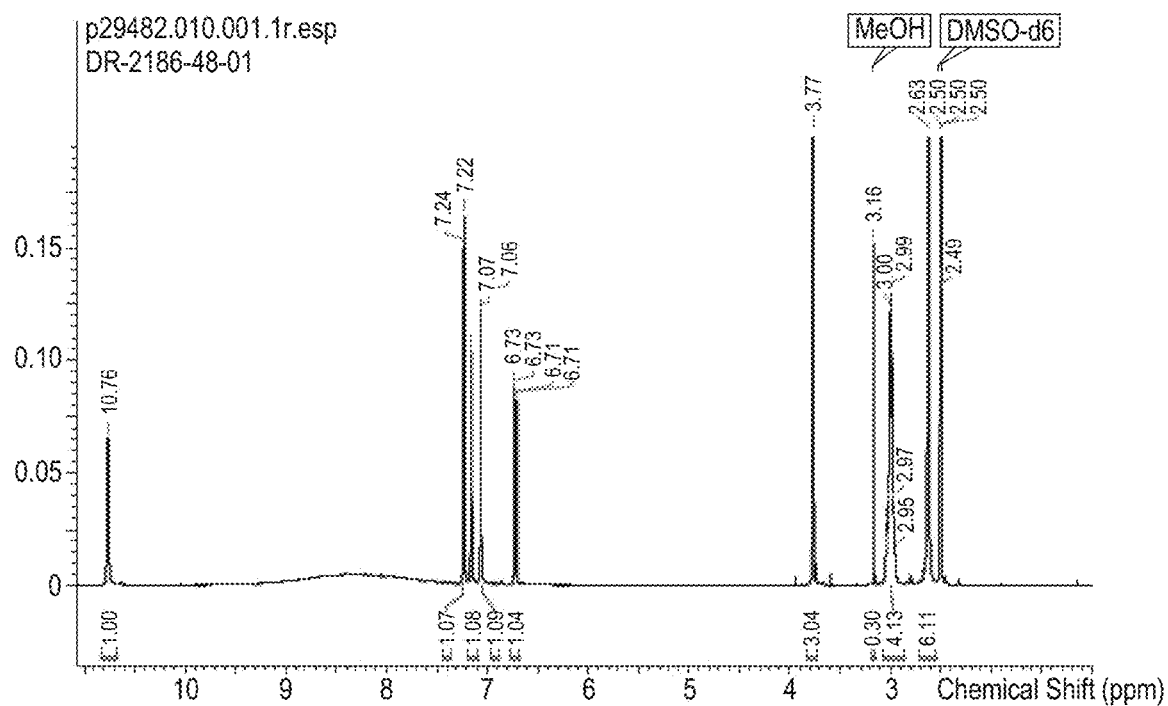

FIG. 121. $^1$H-NMR Spectrum of 5-MeO-DMT Phosphate salt Pattern 1.

Figure 122:
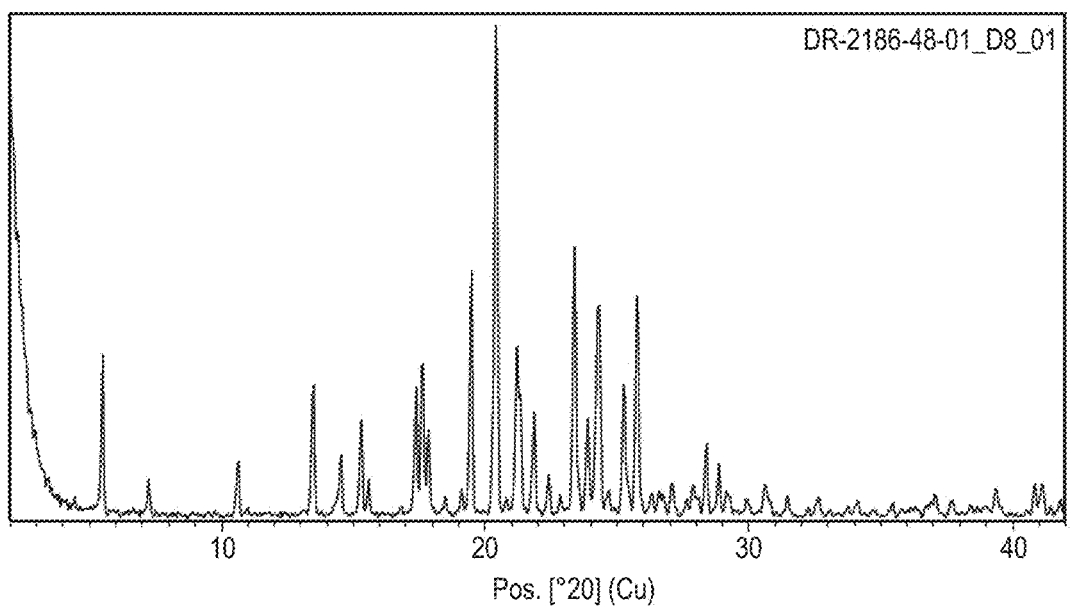

FIG. 122. XRPD Diffractogram of 5-MeO-DMT Phosphate Pattern 1.

Figure 123:
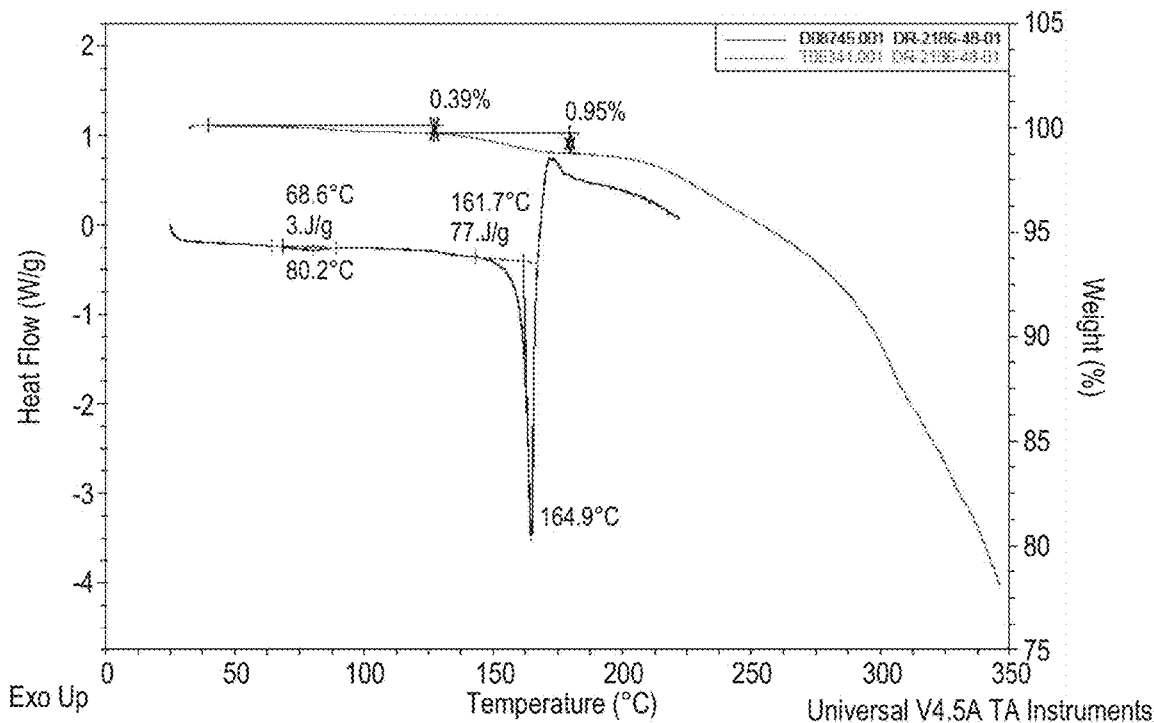

FIG. 123. Thermal analysis (TGA and DSC) of 5-MeO-DMT Phosphate Pattern 1.

Figure 124:
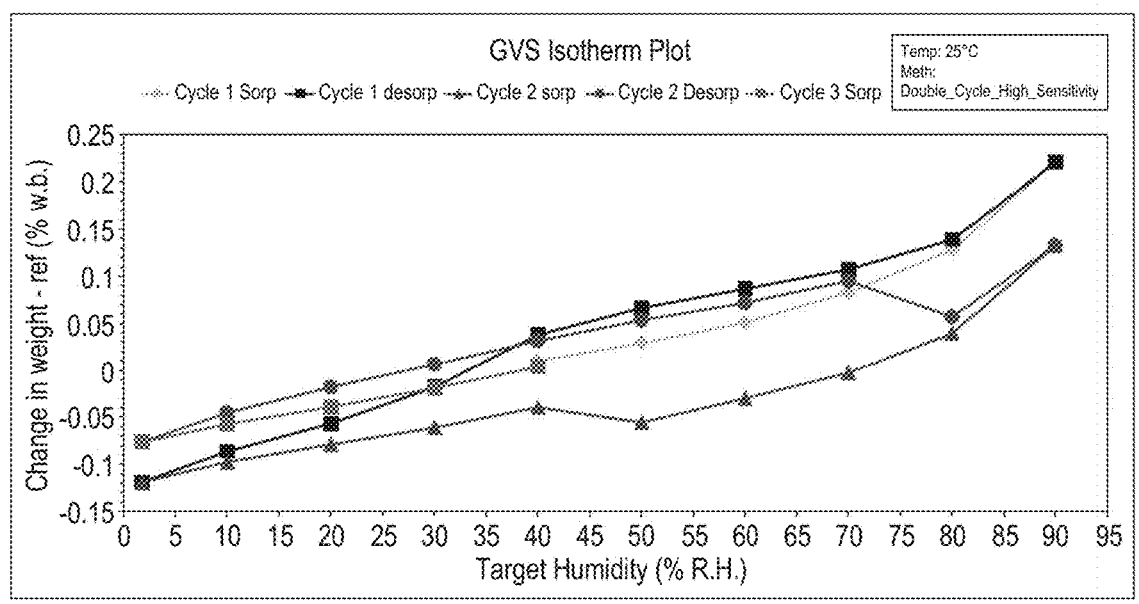

FIG. 124. DVS Isotherm plot of 5-MeO-DMT Phosphate Pattern 1.

Figure 125:
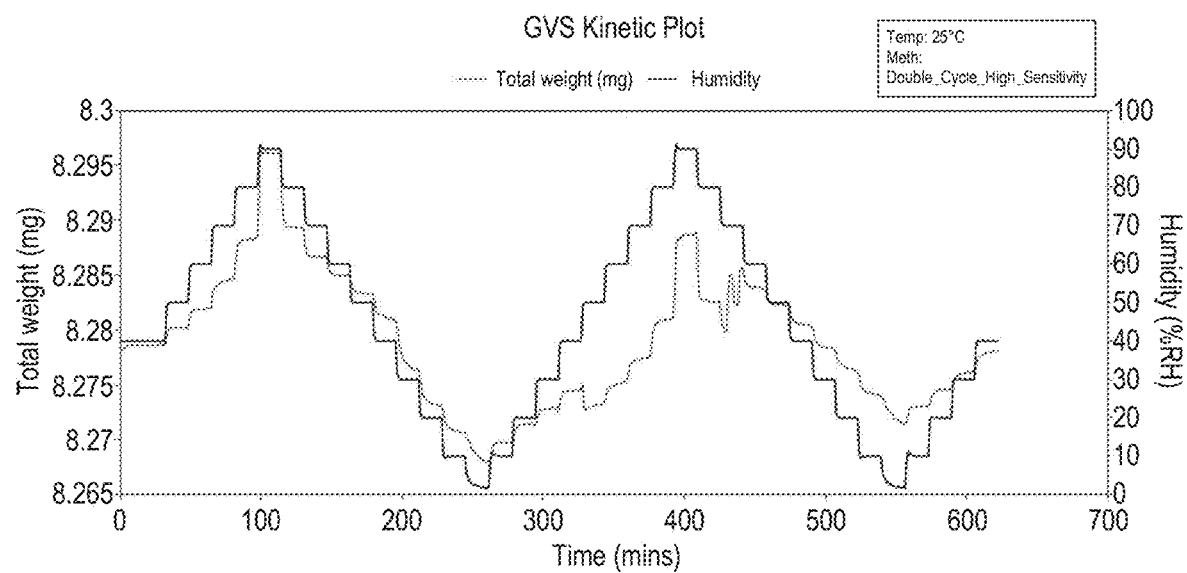

FIG. 125. Sorption kinetic plot of 5-MeO-DMT Phosphate Pattern 1.

Figure 126:
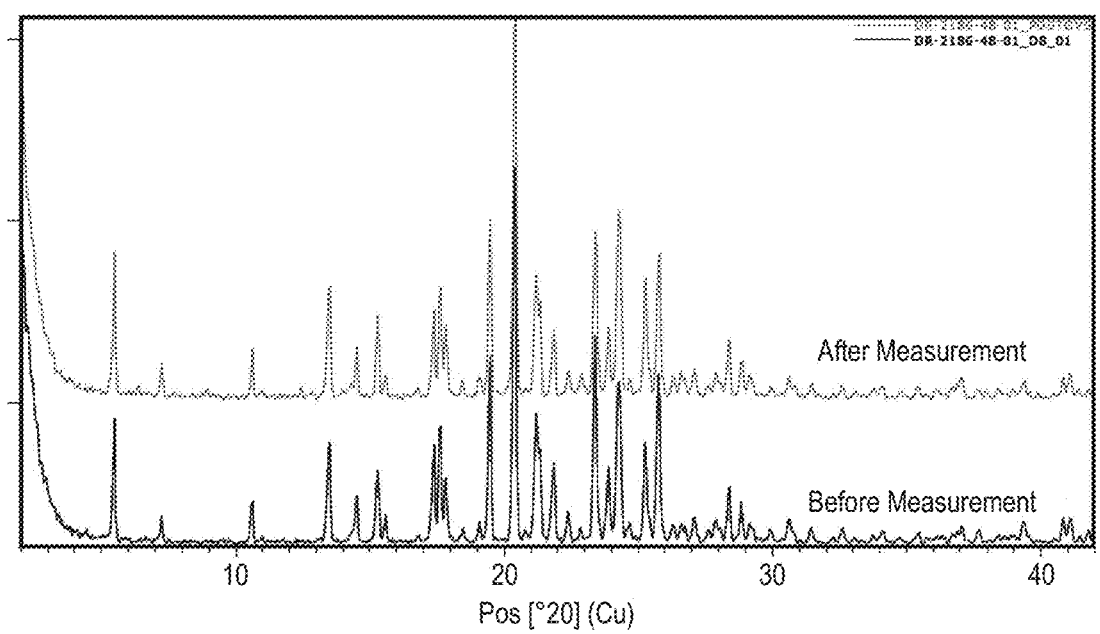

FIG. 126. XRPD Diffractogram comparison of 5-MeO-DMT Phosphate pre- and post-DVS showing the form remains Pattern 1.

Figure 127:
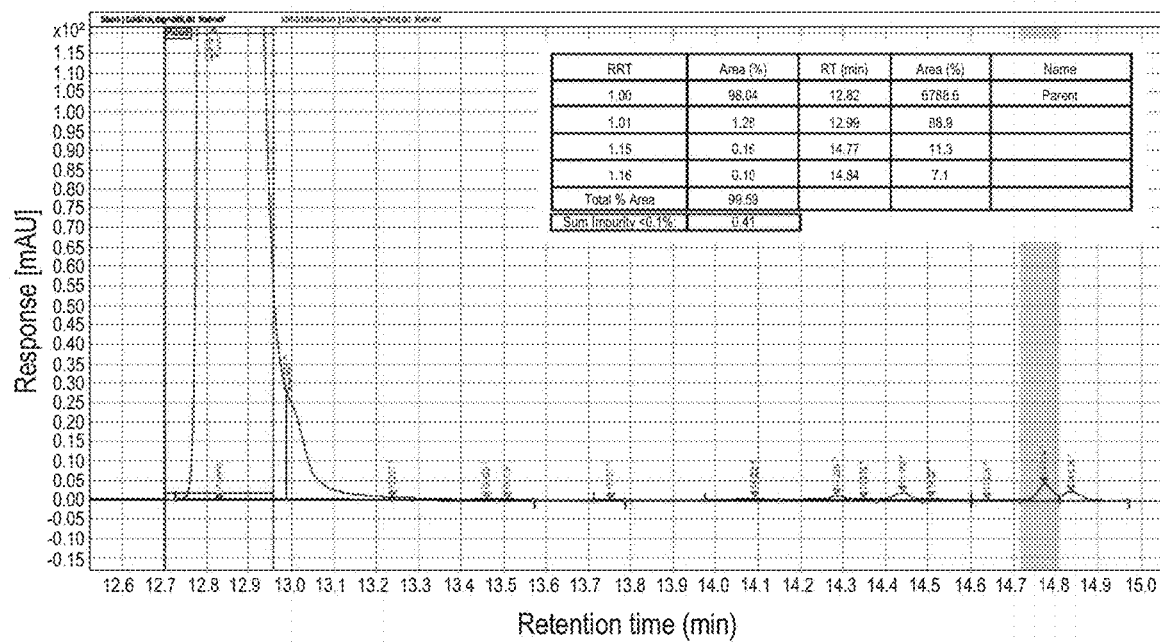

FIG. 127. HPLC chromatogram and purity analysis of 5-MeO-DMT Phosphate Pattern 1.

Figure 128:
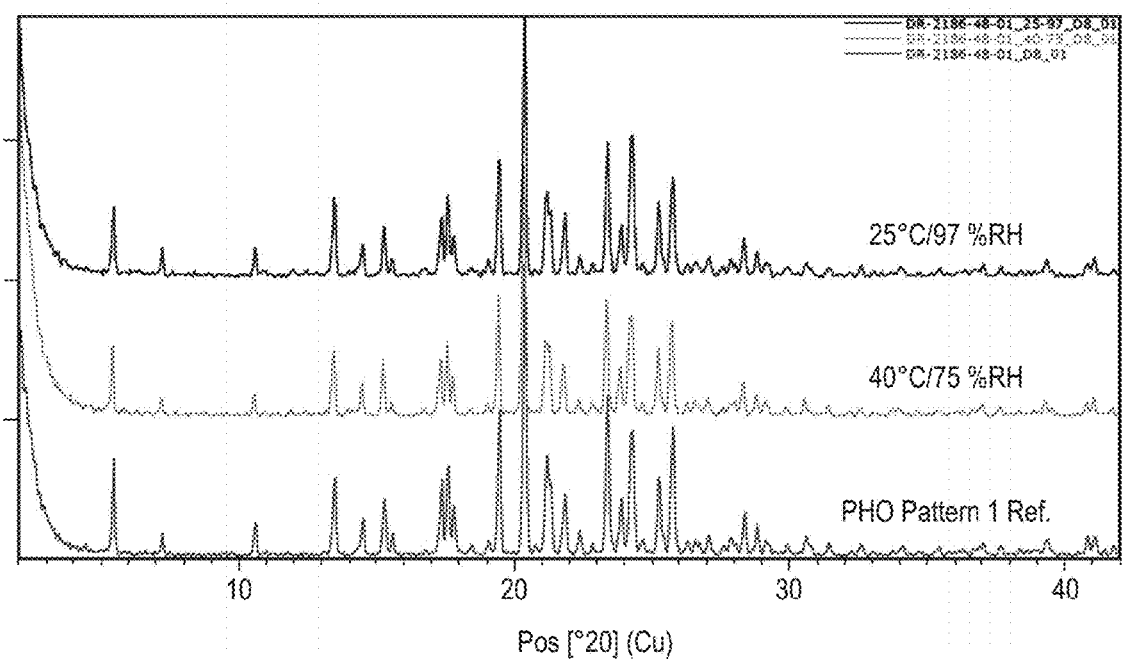

FIG. 128. XRPD diffractogram overlay of 5-MeO-DMT Phosphate Pattern 1 before and after storage at 25° C./97% RH and 40° C./75% RH for 7 days.

Figure 129:
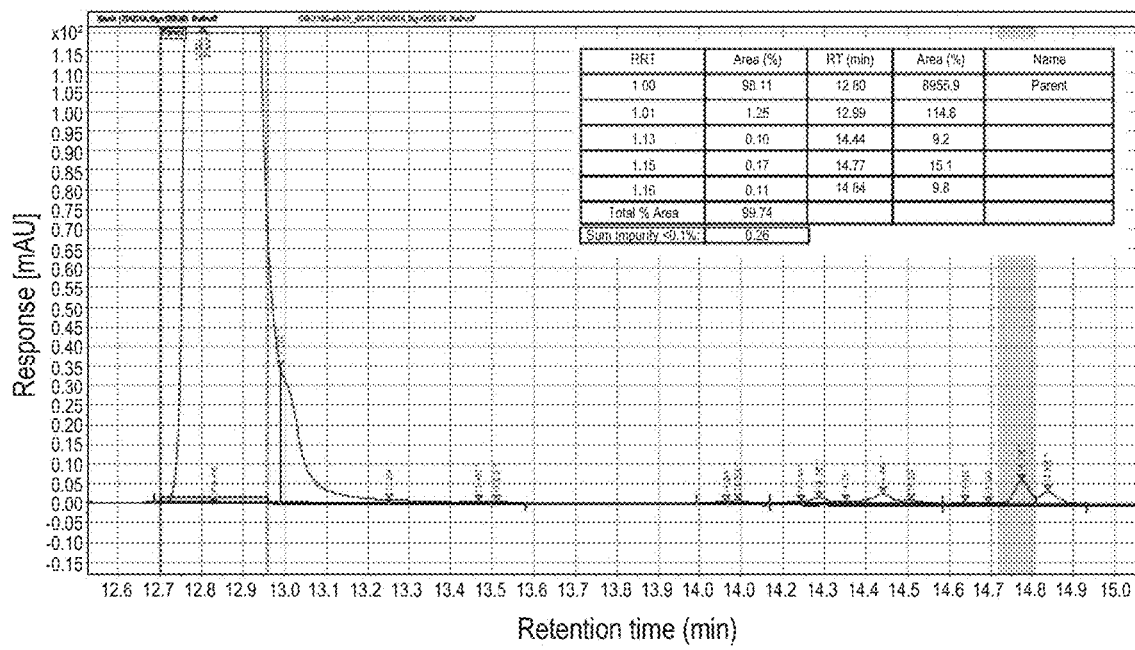

FIG. 129. HPLC chromatogram and purity analysis of 5-MeO-DMT Phosphate Pattern 1 before and after storage at 40° C./75% RH for 7 days.

Figure 130:
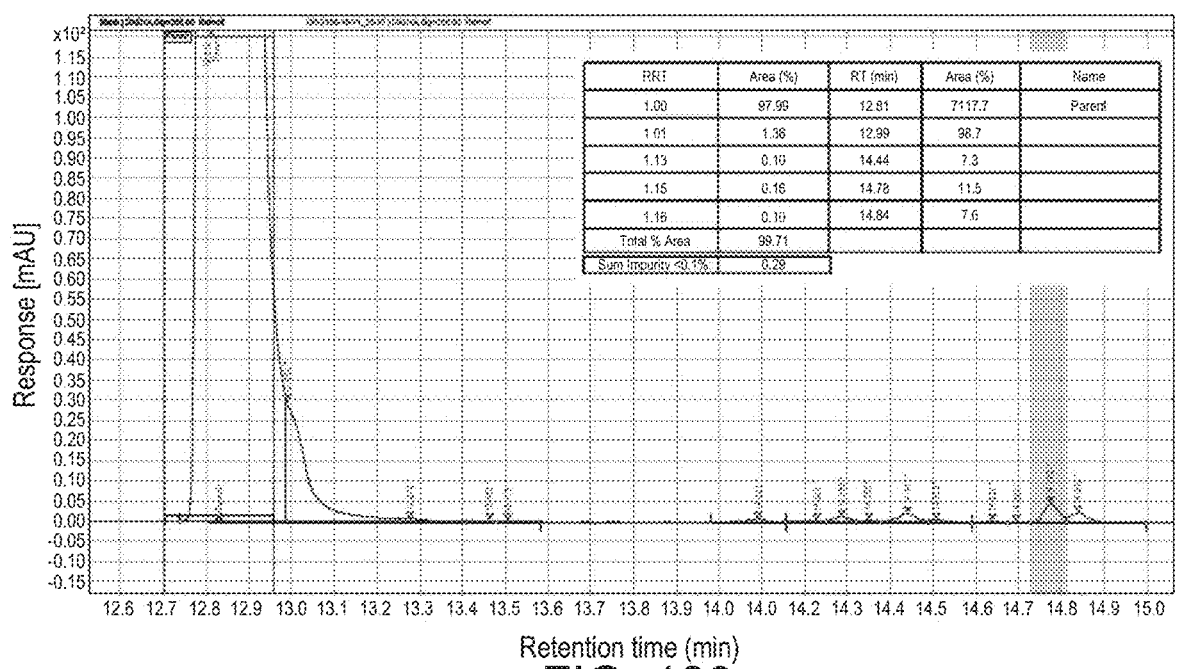

FIG. 130. HPLC chromatogram and purity analysis of 5-MeO-DMT Phosphate Pattern 1 before and after storage at 25° C./97% RH for 7 days.

Figure 131:
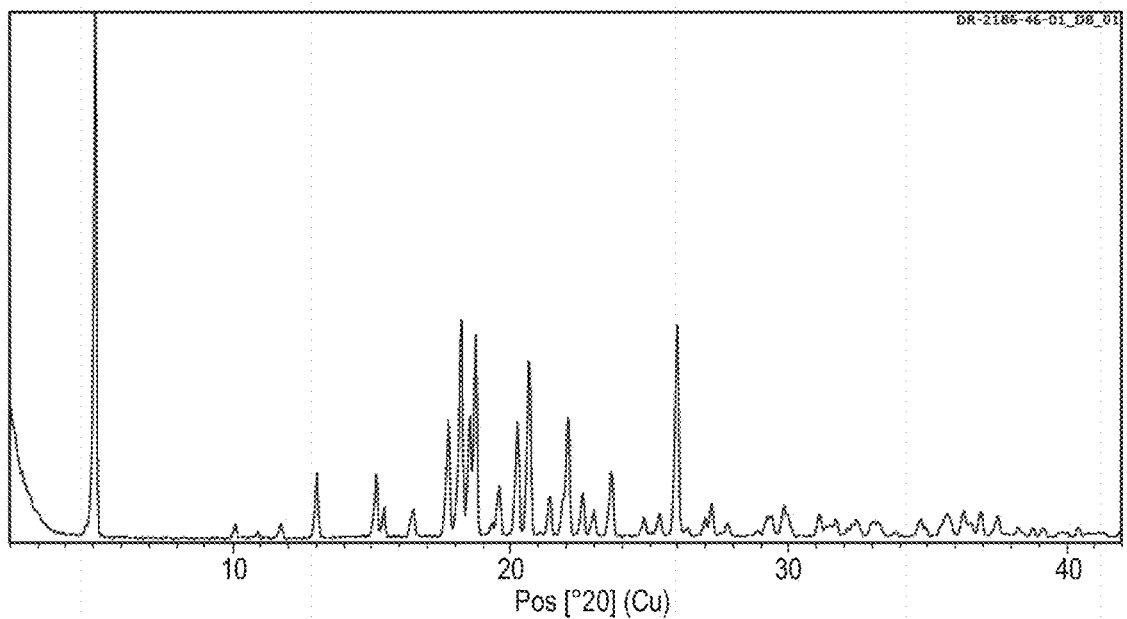

FIG. 131. XRPD diffractogram of 5-MeO-DMT Tartrate Pattern 1.

Figure 132:
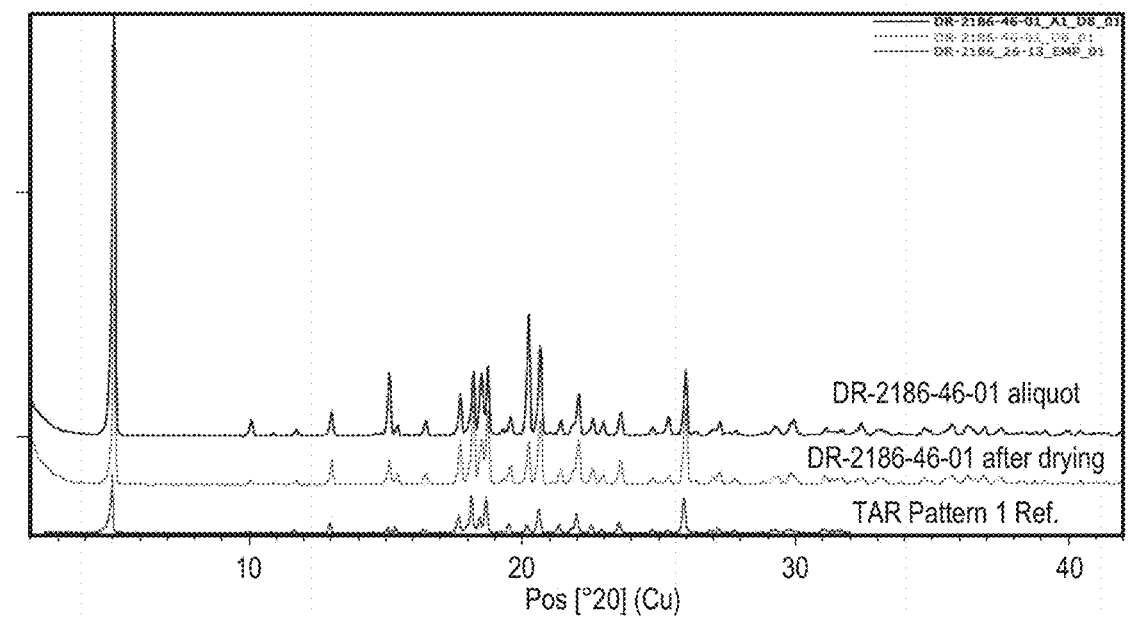

FIG. 132. XRPD diffractogram overlay of 5-MeO-DMT Tartrate Pattern 1.

Figure 133:
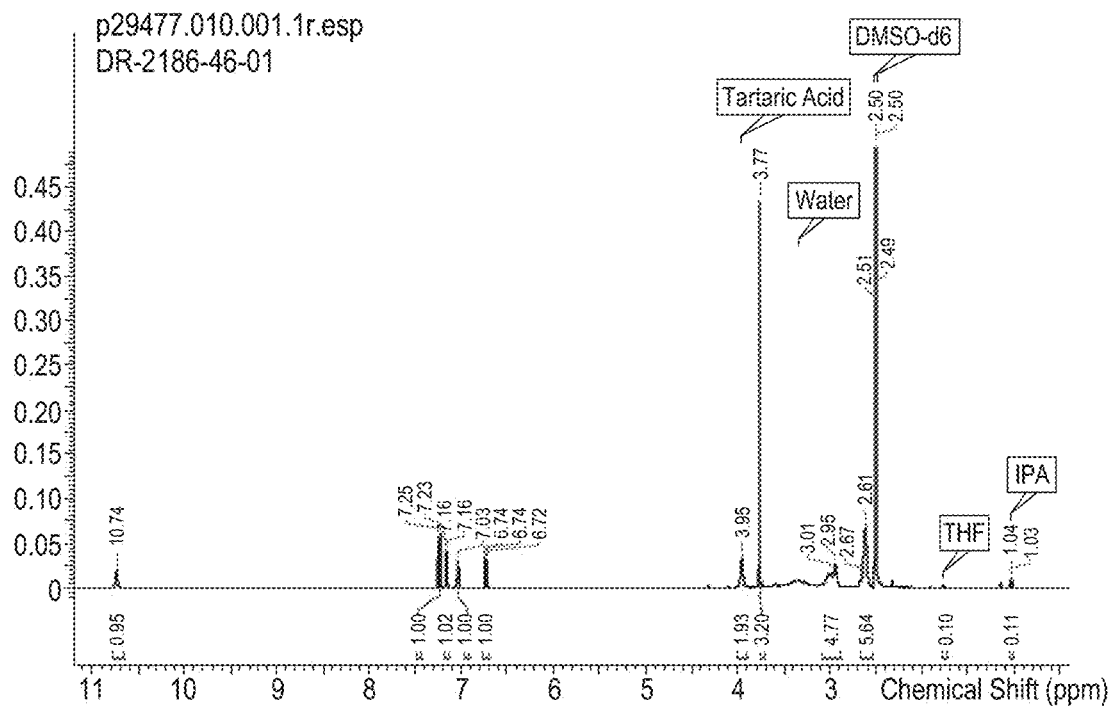

FIG. 133. $^1$H-NMR Spectrum of 5-MeO-DMT Tartrate salt Pattern 1.

Figure 134:
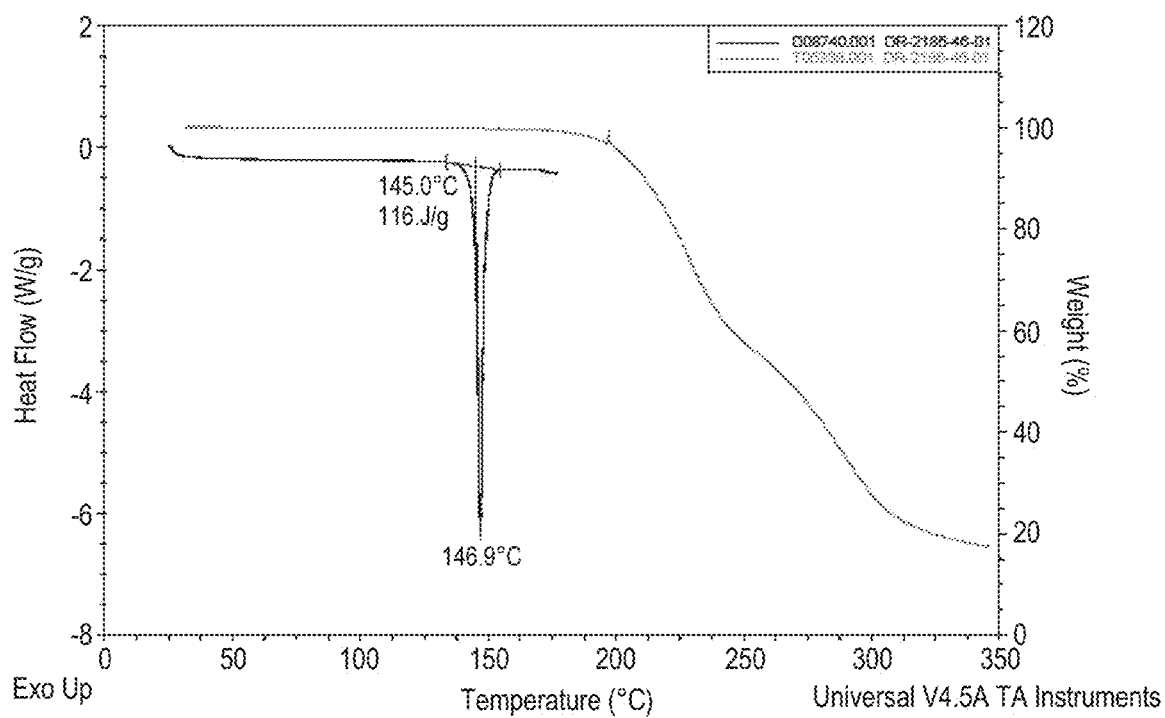

FIG. 134. Thermal analysis (TGA and DSC) of 5-MeO-DMT Tartrate Pattern 1.

Figure 135:
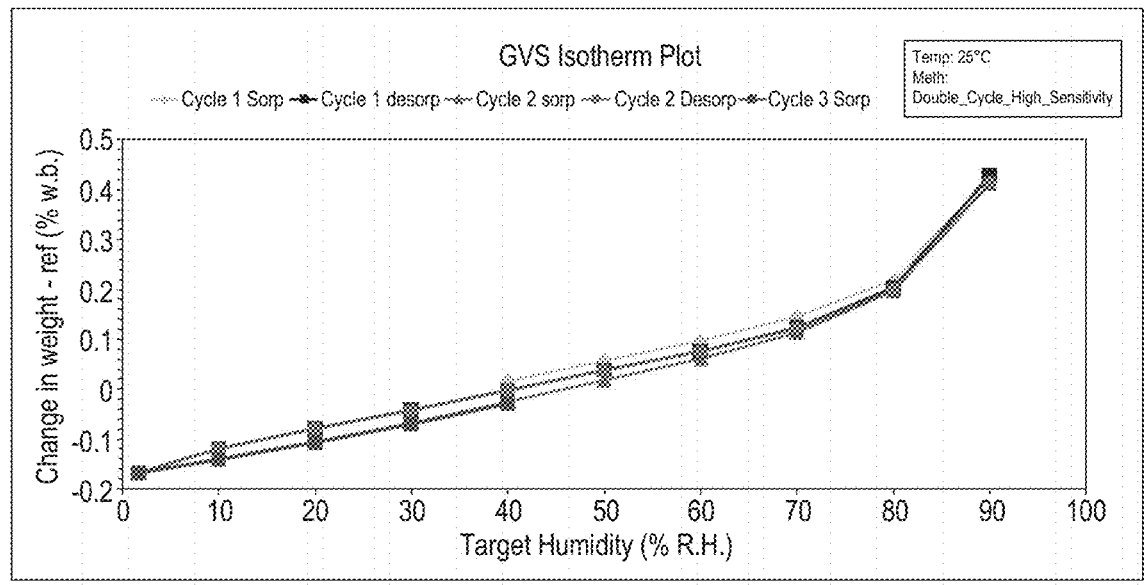

FIG. 135. DVS Isotherm plot of 5-MeO-DMT Tartrate Pattern 1.

Figure 136:
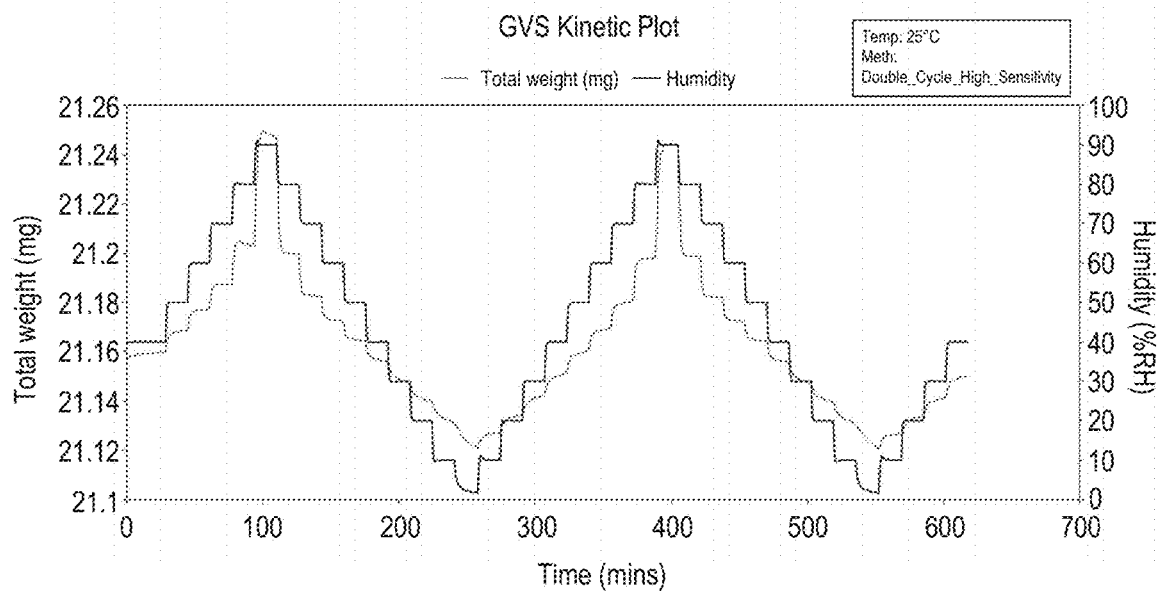

FIG. 136. Sorption kinetic plot of 5-MeO-DMT Tartrate Pattern 1.

Figure 137:
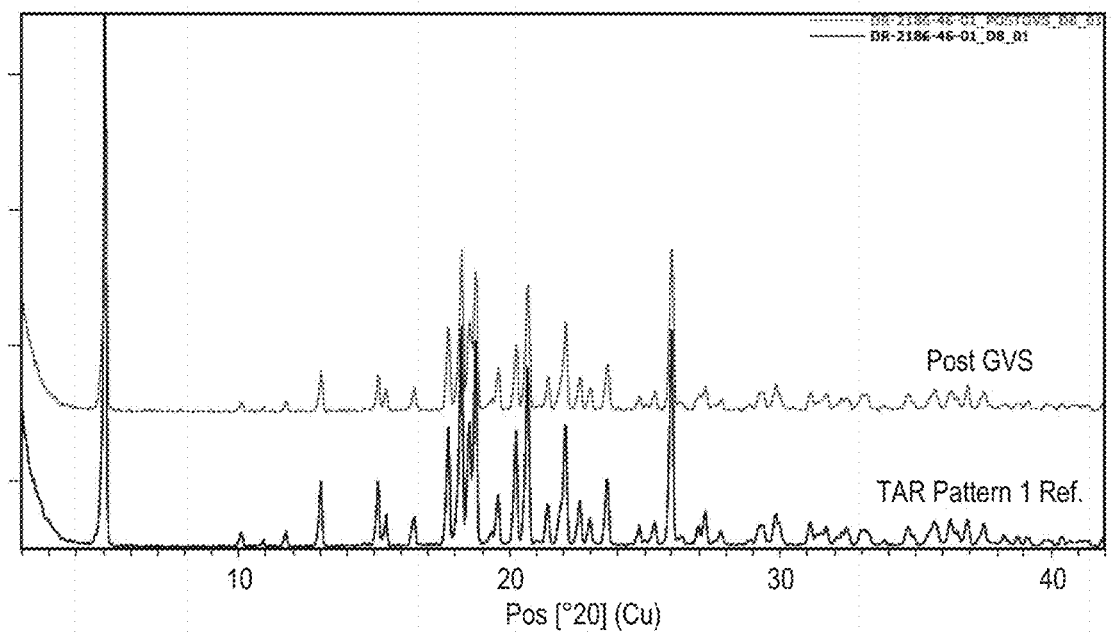

FIG. 137. XRPD diffractogram overlay of 5-MeO-DMT Tartrate Pattern 1 pre- and post-DVS showing the form remains Pattern 1.

Figure 138:
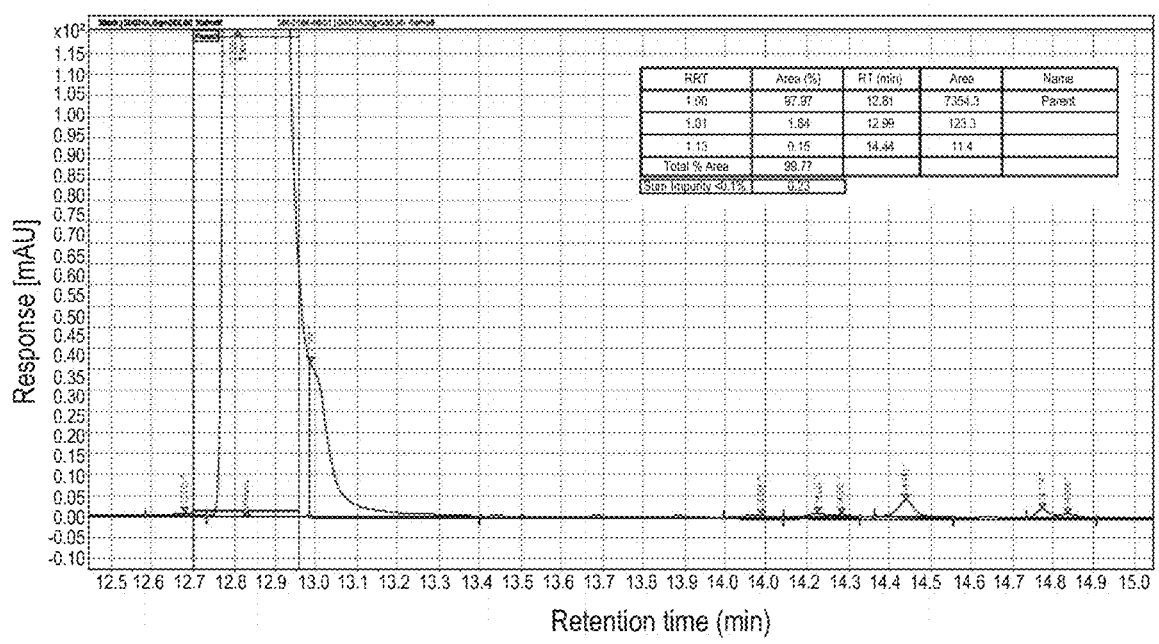

FIG. 138. HPLC chromatogram and purity analysis of 5-MeO-DMT Tartrate Pattern 1.

Figure 139:
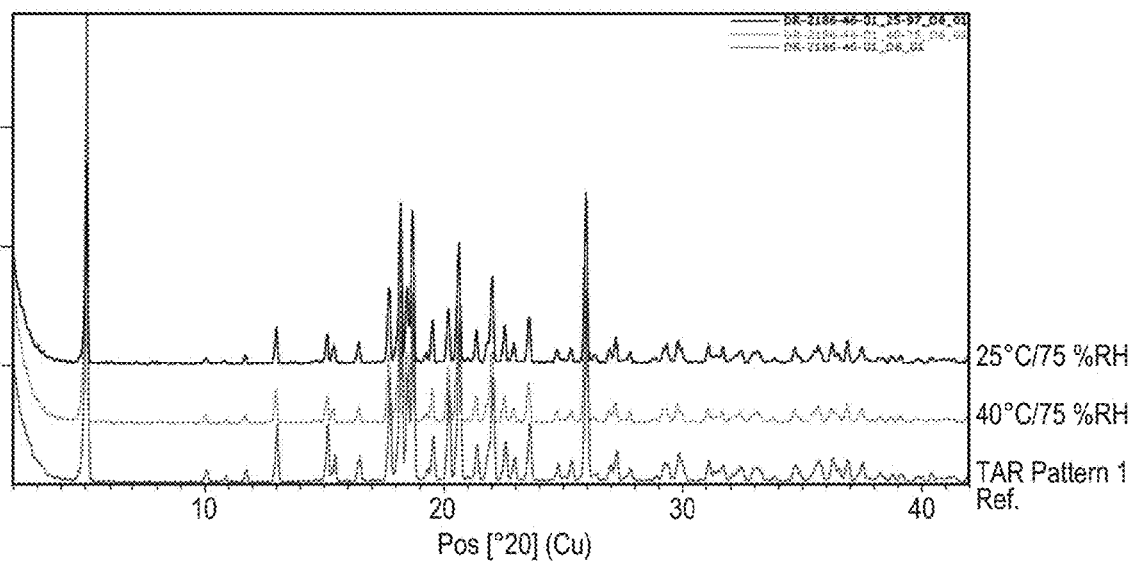

FIG. 139. XRPD diffractogram overlay of 5-MeO-DMT Tartrate Pattern 1 before and after storage at 25° C./97% RH and 40° C./75% RH for 7 days.

Figure 140:
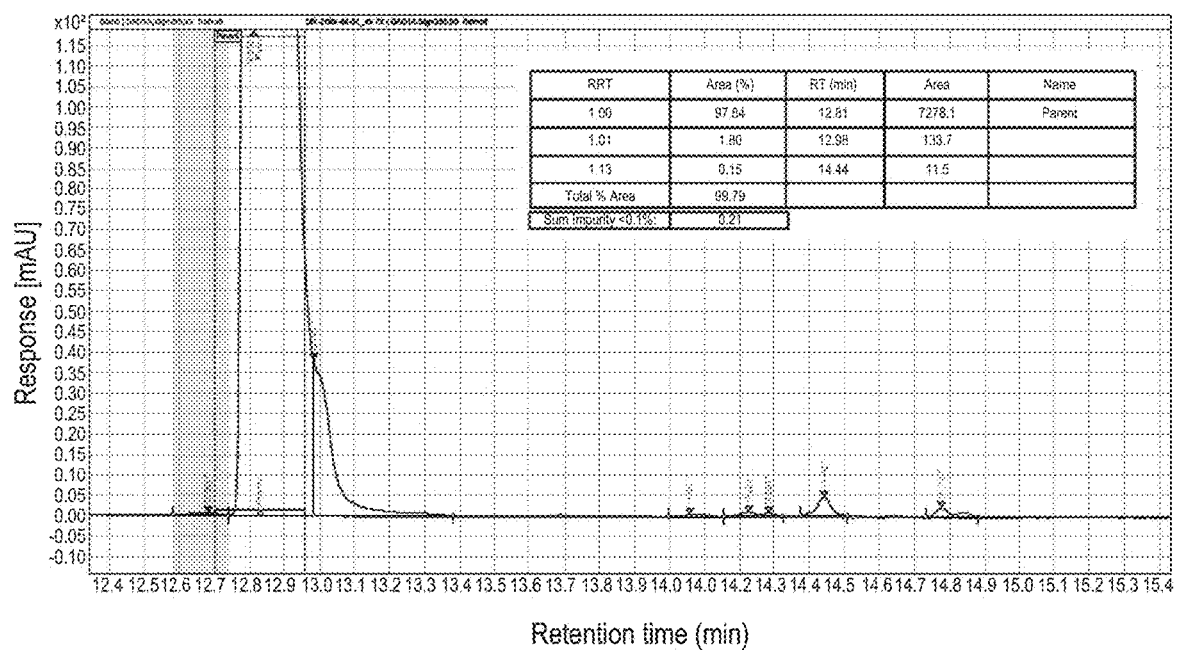

FIG. 140. HPLC chromatogram and purity analysis of 5-MeO-DMT Tartrate Pattern 1 before and after storage at 40° C./75% RH for 7 days.

Figure 141:
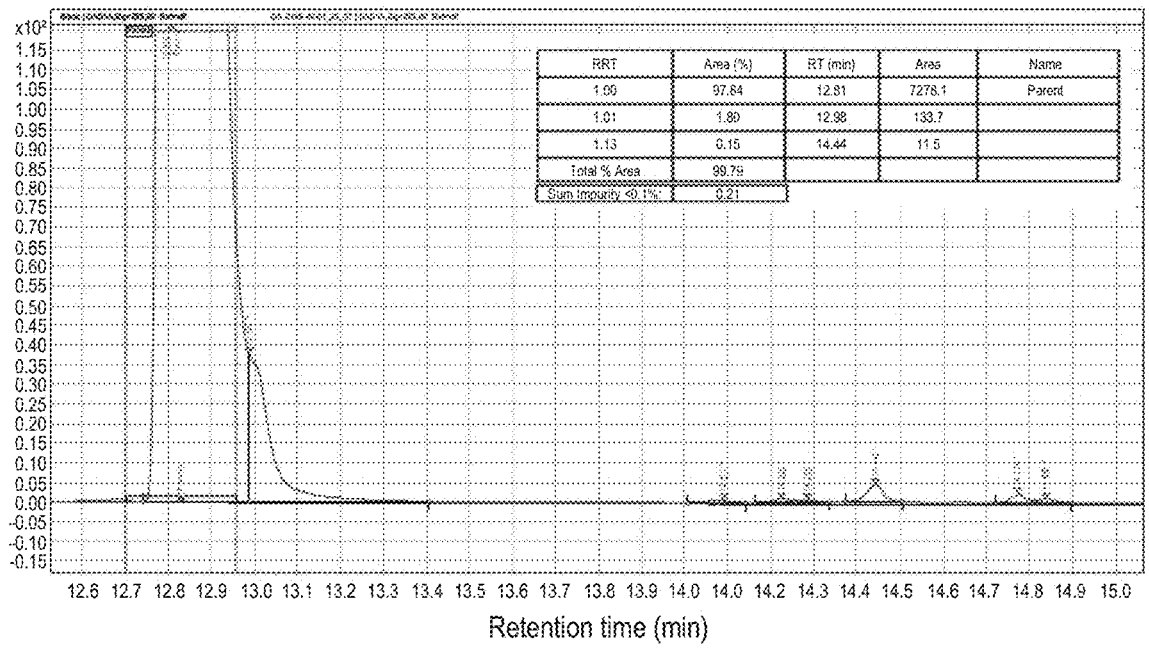

FIG. 141. HPLC chromatogram and purity analysis of 5-MeO-DMT Tartrate Pattern 1 before and after storage at 25° C./97% RH for 7 days.

Figure 142:
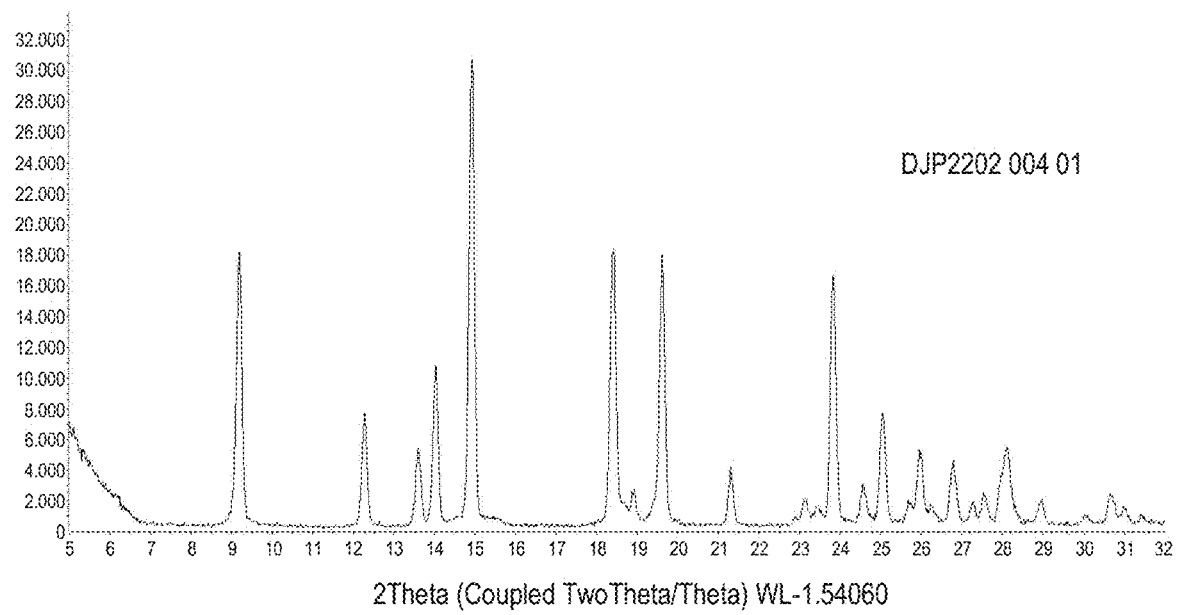

FIG. 142. XRPD Diffractogram of hydrochloride salt lot RPI-014-022.

Figure 143:
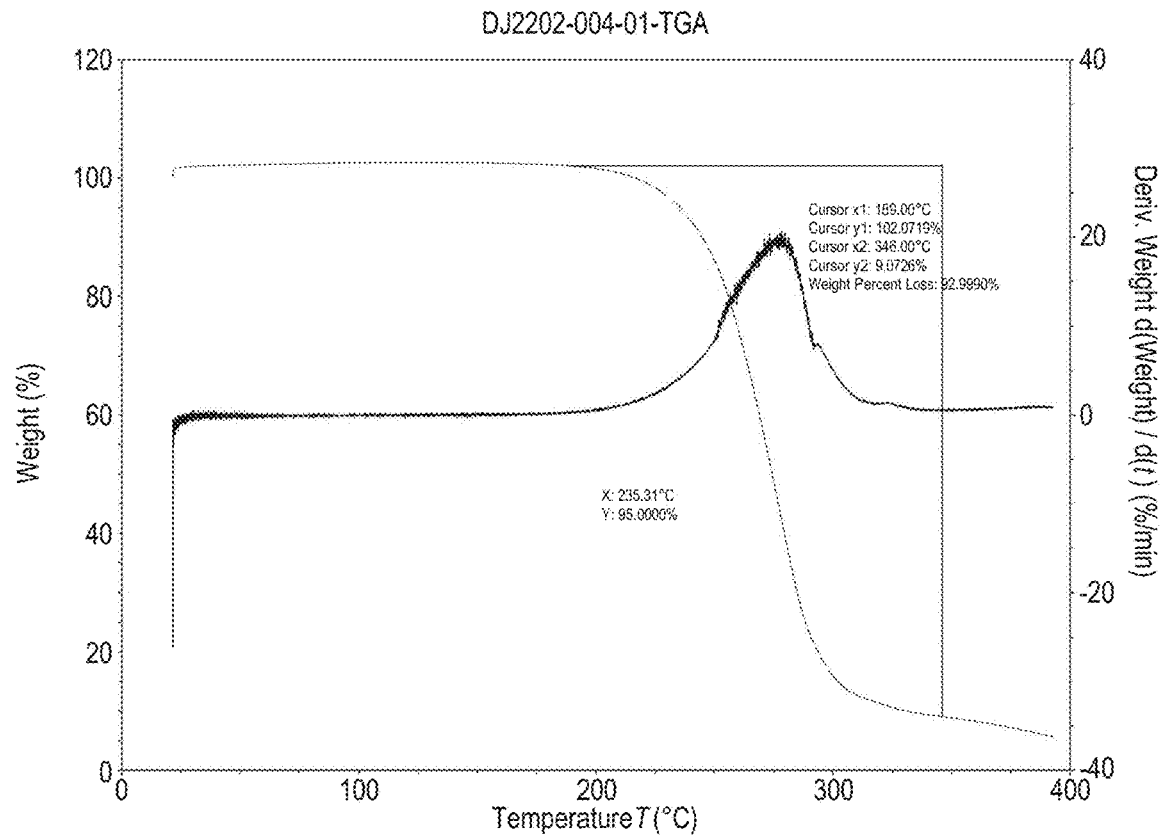

FIG. 143. TGA Thermogram of hydrochloride salt lot RPI-014-022.

Figure 144:
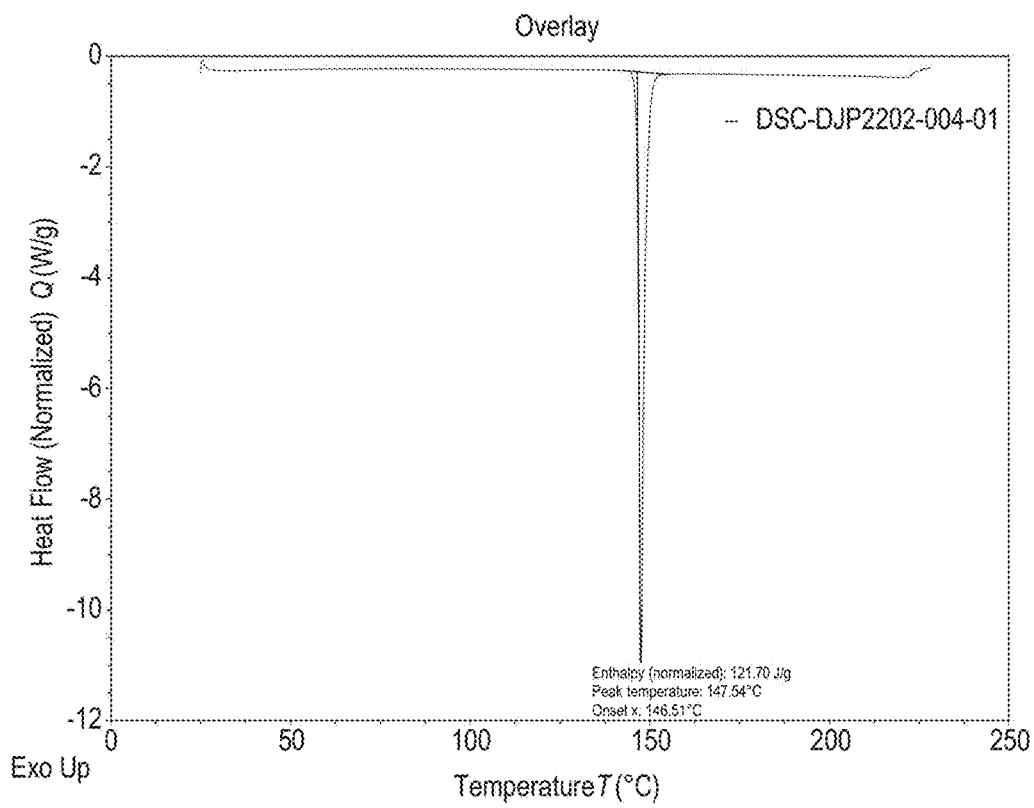

FIG. 144. DSC Thermogram of first heat cycle of hydrochloride salt lot RPI-014-022.

Figure 145:
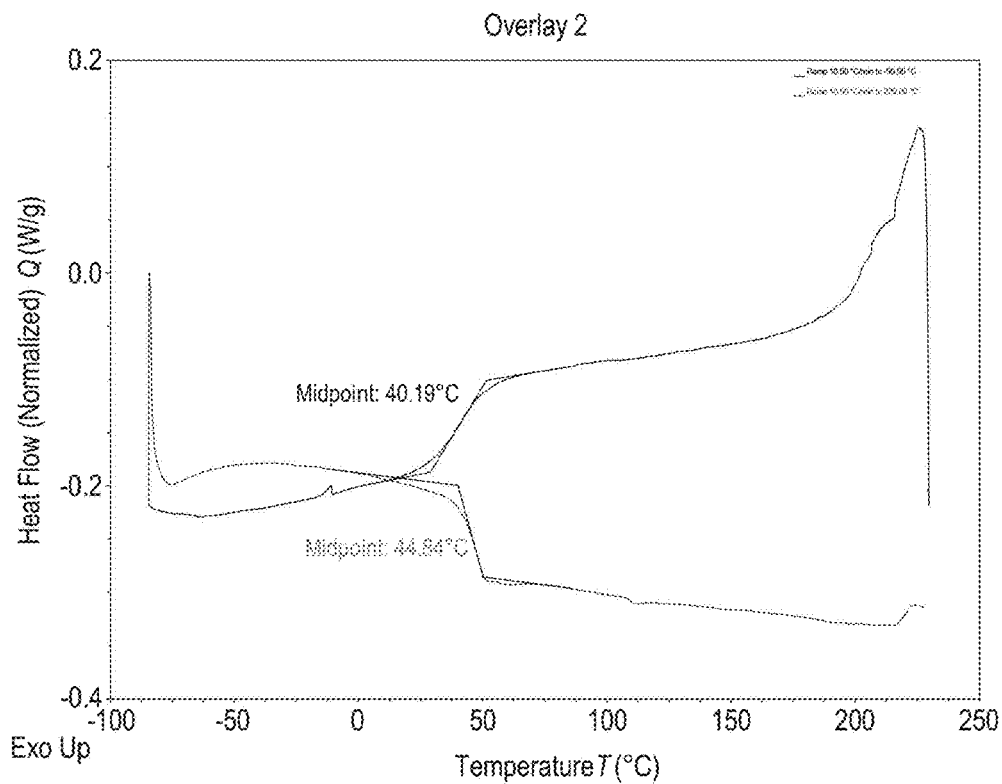

FIG. 145. DSC Thermogram of cool and reheat cycles of hydrochloride salt lot RPI-014-022.

Figure 146:
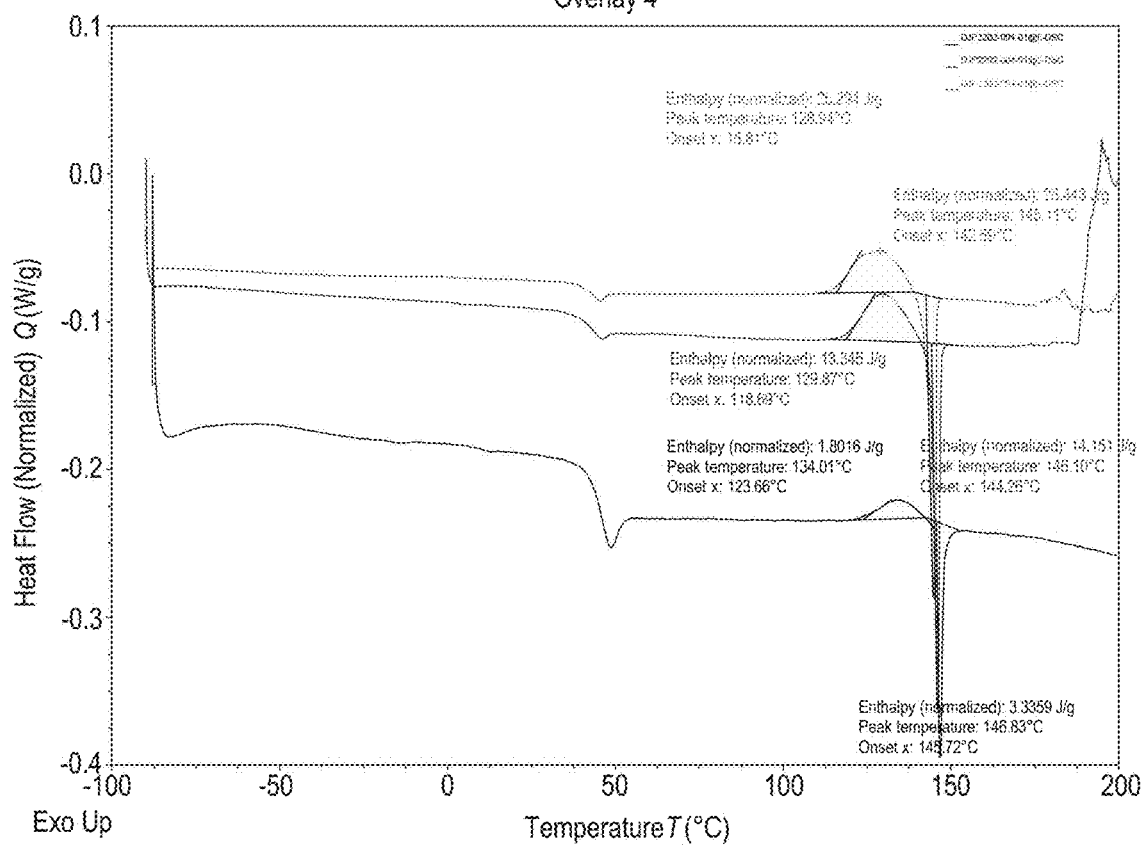

FIG. 146. DSC Thermograms for reheating of hydrochloride lot RPI-014-022 at different heating rates.

Figure 147:
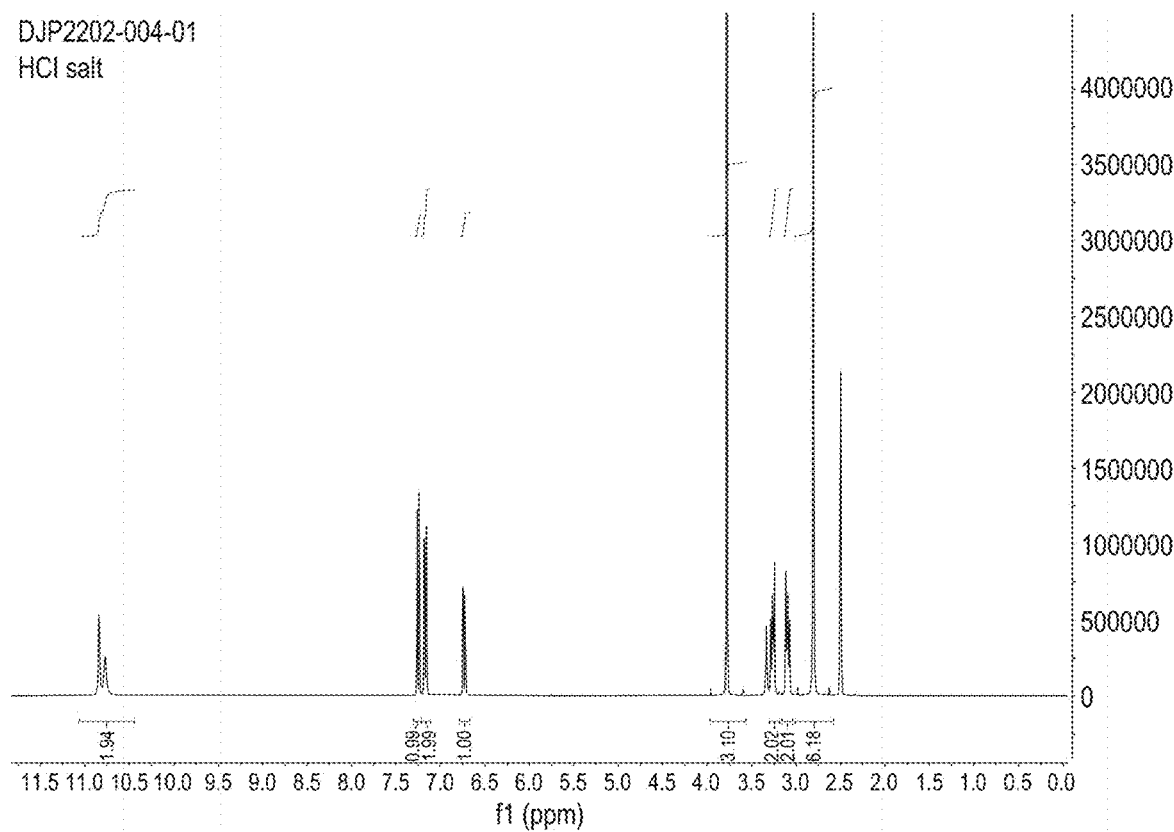

FIG. 147. $^1$H NMR Spectrum of hydrochloride salt lot RPI-014-022.

Figure 148:
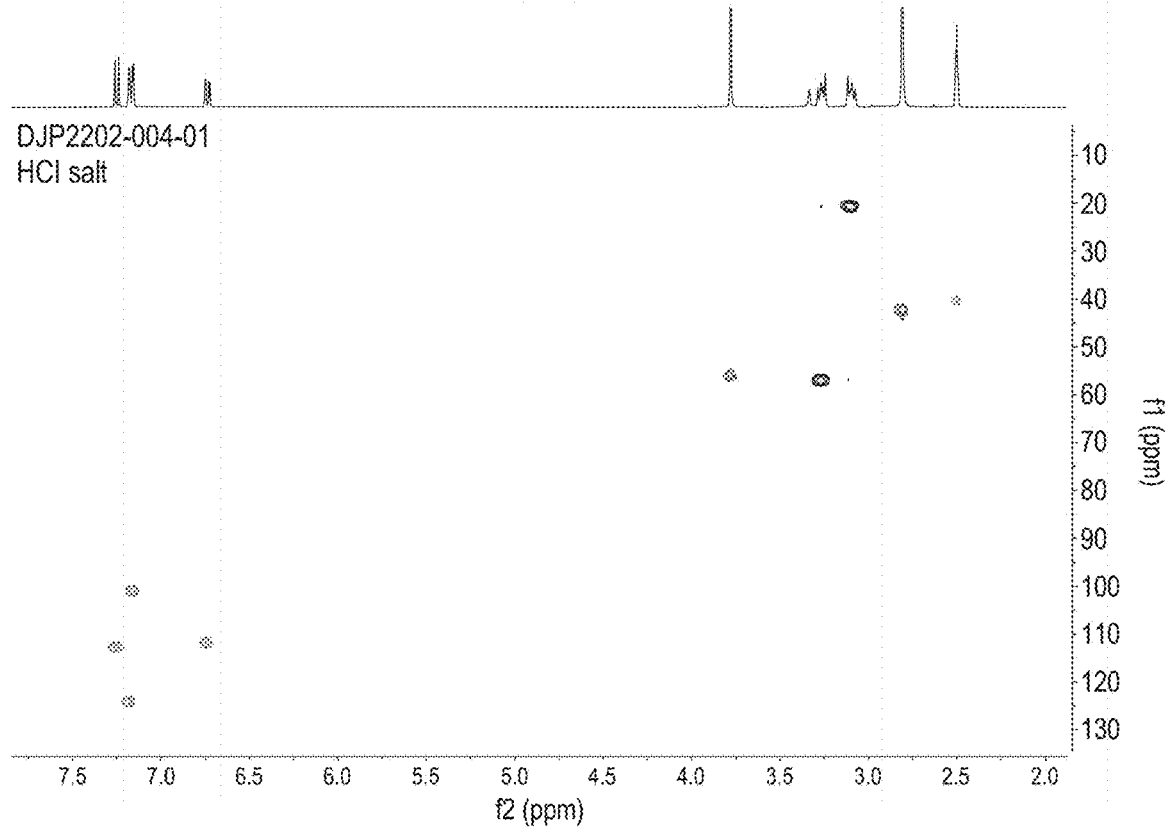

FIG. 148. $^1$H-$^{13}$C HSQC Spectrum of hydrochloride salt lot RPI-014-022.

Figure 149:
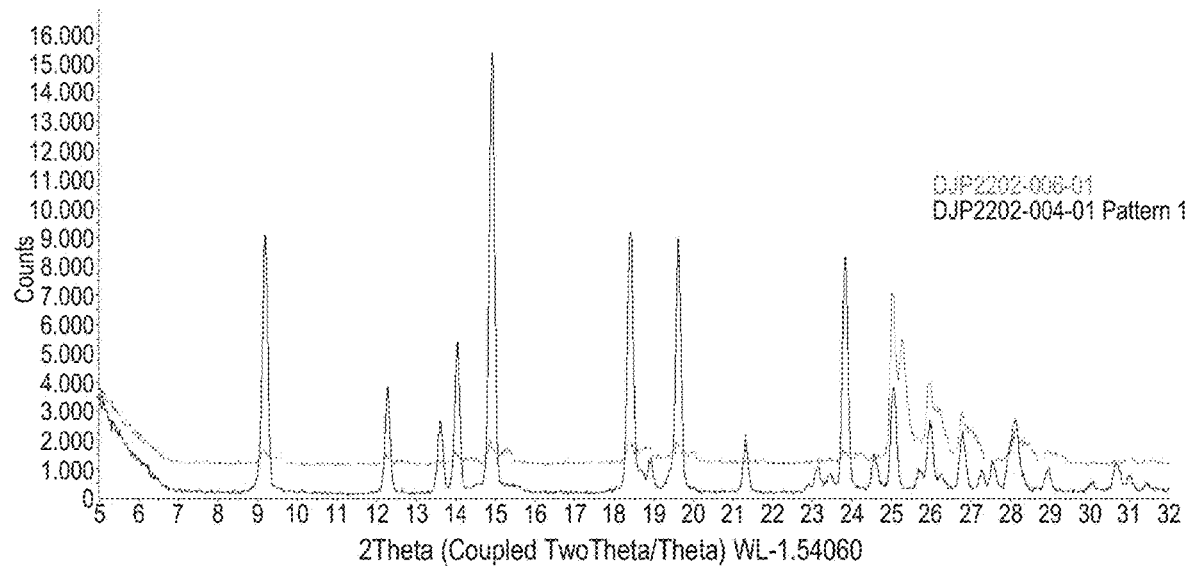

FIG. 149. XRPD Diffractogram of lyophilised hydrochloride salt (red) vs supplied pattern 1 (black).

Figure 150:
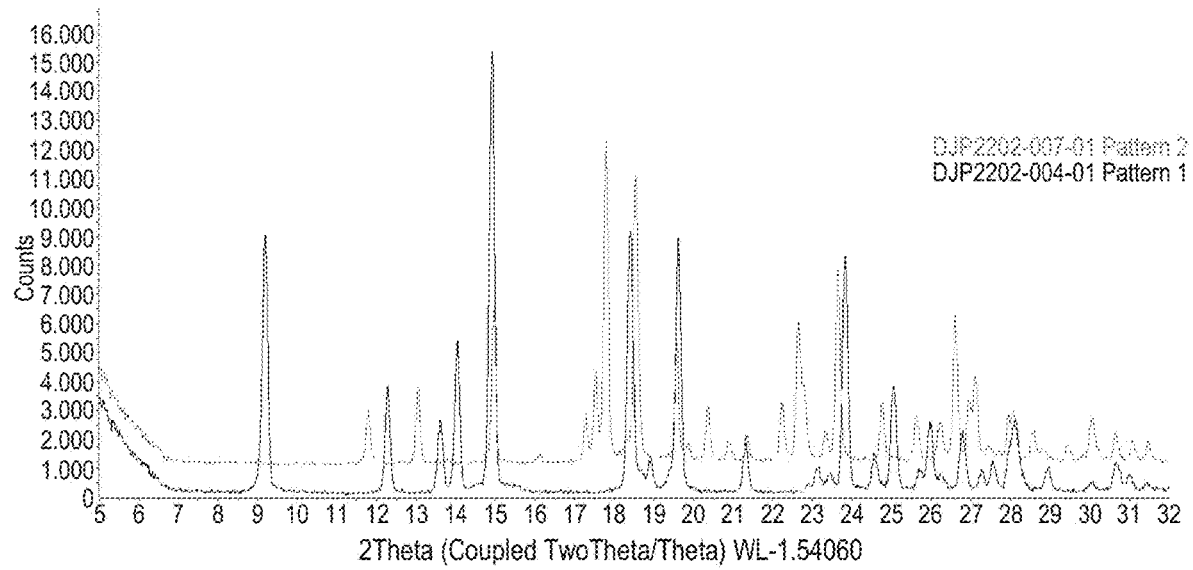

FIG. 150. XRPD Diffractogram of pattern 2 lot DJP2202-007-01 from dioxane (red) compared to pattern 1.

Figure 151:
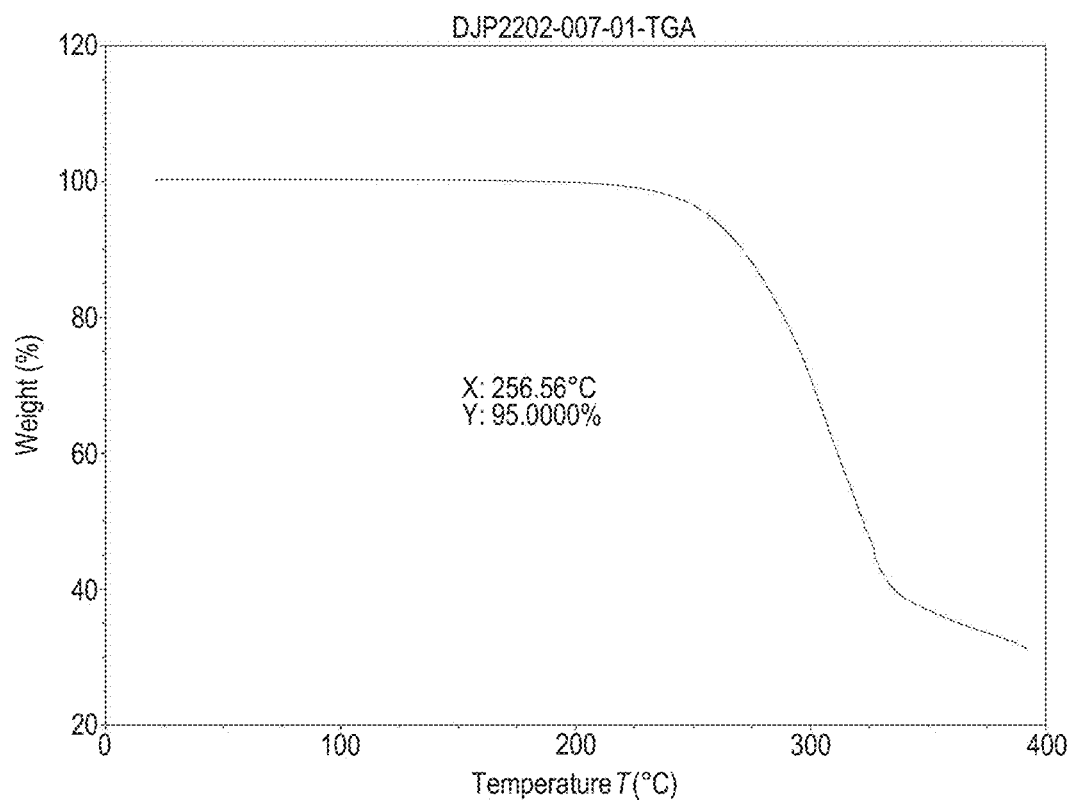

FIG. 151. TGA Thermogram of Hydrochloride pattern 2 lot DJP2202-007-01.

Figure 152:
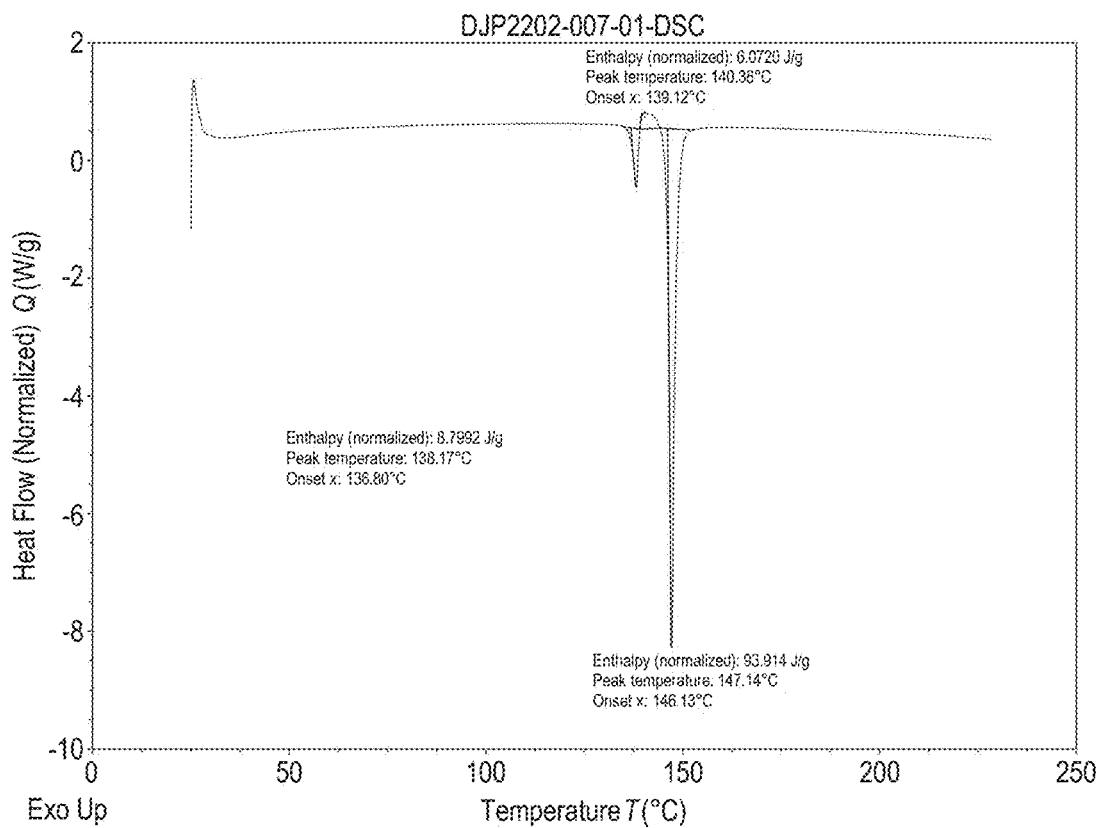

FIG. 152. DSC Thermogram of Hydrochloride pattern 2 lot DJP2202-007-01.

Figure 153:
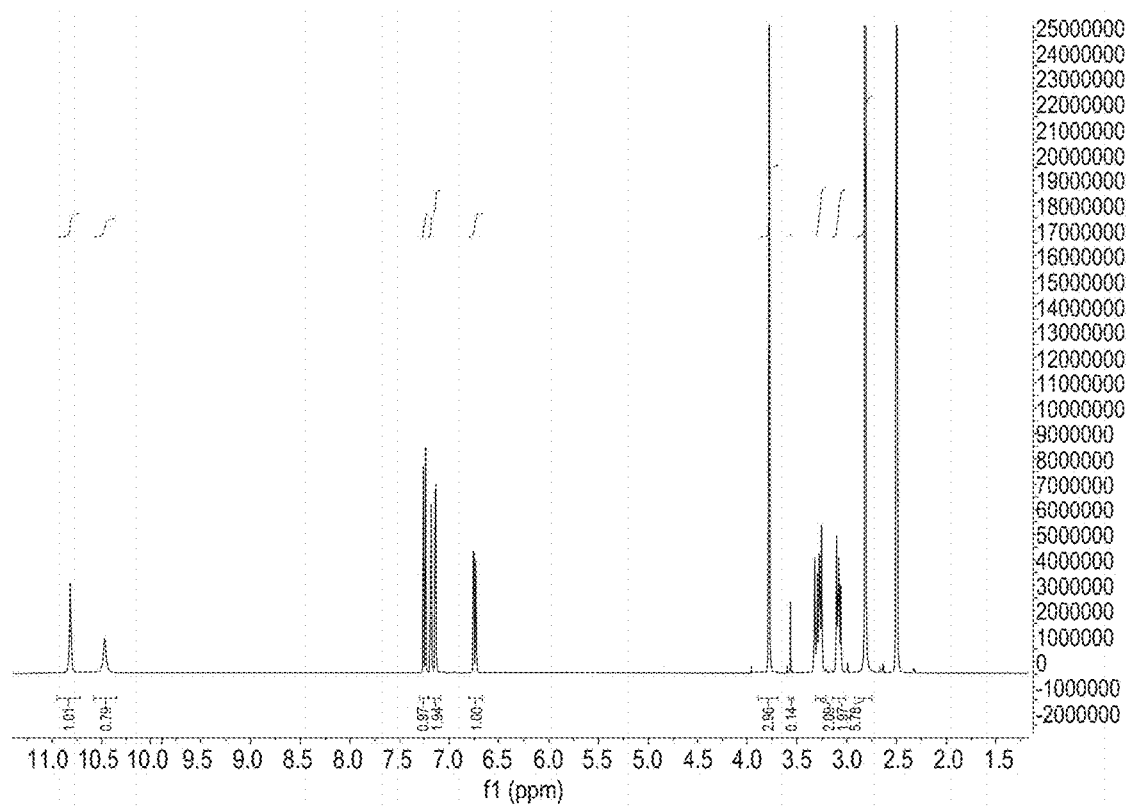

FIG. 153. $^1$H NMR Spectrum of Hydrochloride pattern 2 lot DJP2202-007-01.

Figure 154:
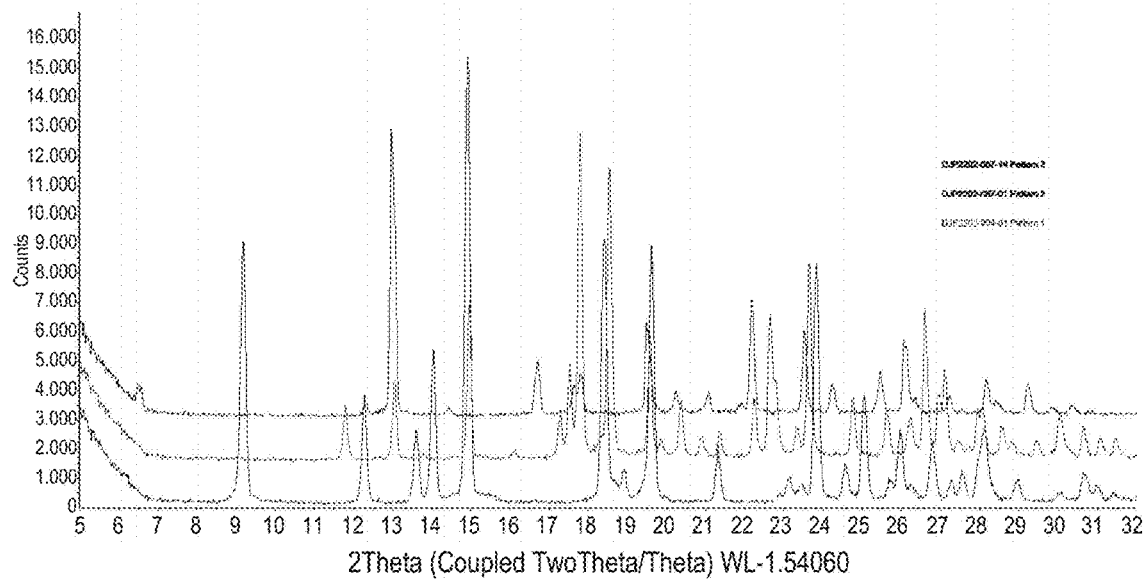

FIG. 154. XRPD Diffractogram of Hydrochloride pattern 3 (blue) and pattern 2 (red) and pattern 1 (black).

Figure 155:
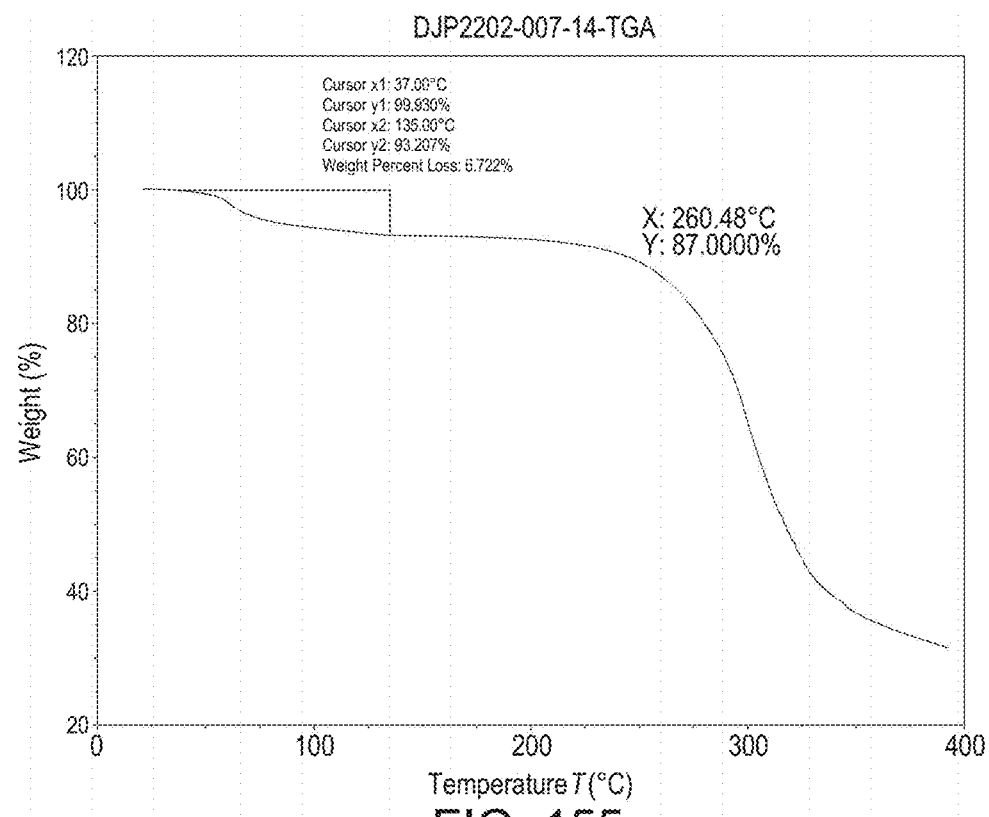

FIG. 155. TGA Thermogram of Hydrochloride pattern 3 lot DJP2202-007-14.

Figure 156:
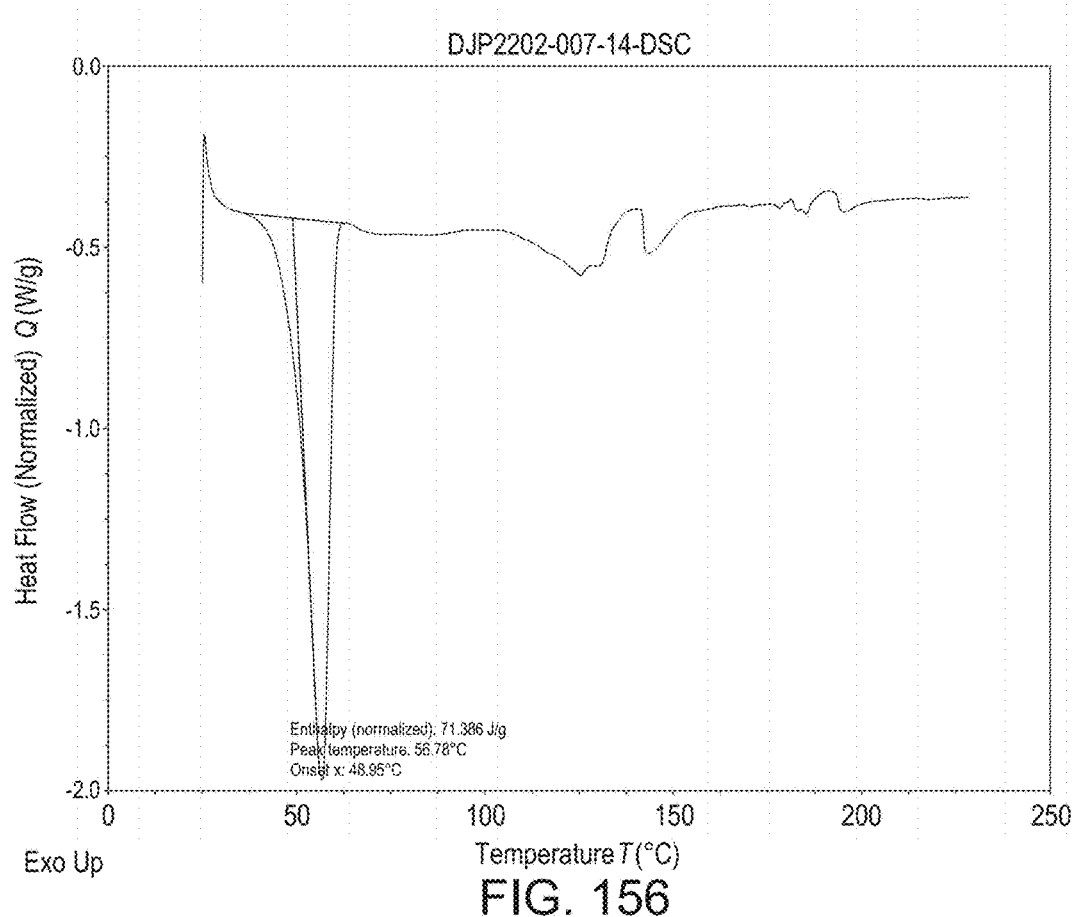

FIG. 156. DSC Thermogram of Hydrochloride pattern 3 lot DJP2202-007-14.

Figure 157:
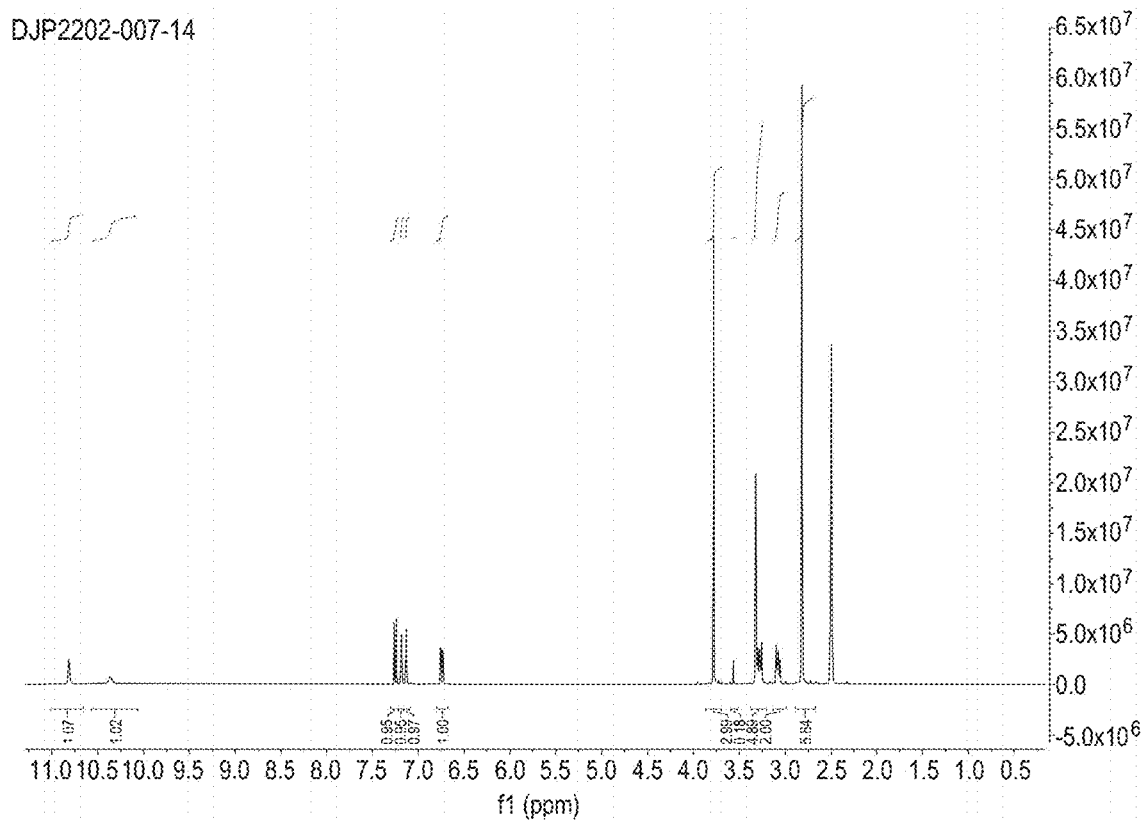

FIG. 157. $^1$H NMR Spectrum of hydrochloride pattern 3 lot DJP2202-007-14.

Figure 158:
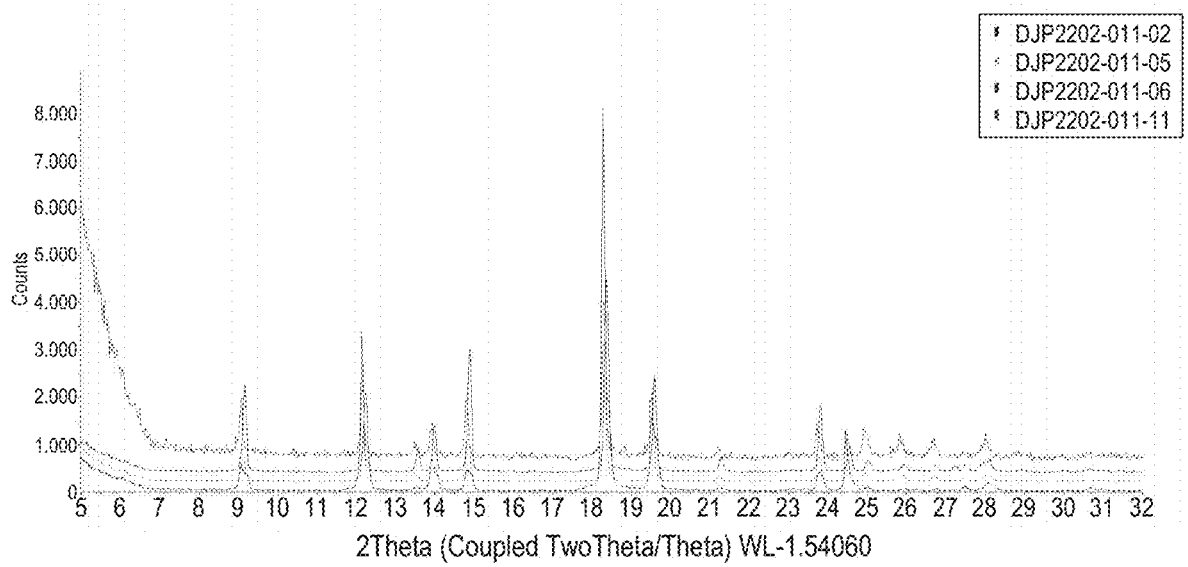

FIG. 158. XRPD Diffractogram of pattern 1 resulting from evaporation of 5-MeO-DMT HCl/solvent combinations: HCl/MEK (green, top), HCl/IPA (blue, immediately below green), HCl/EtOH (red, immediately below blue) and HCl/1-PrOH (black, bottom).

Figure 159:
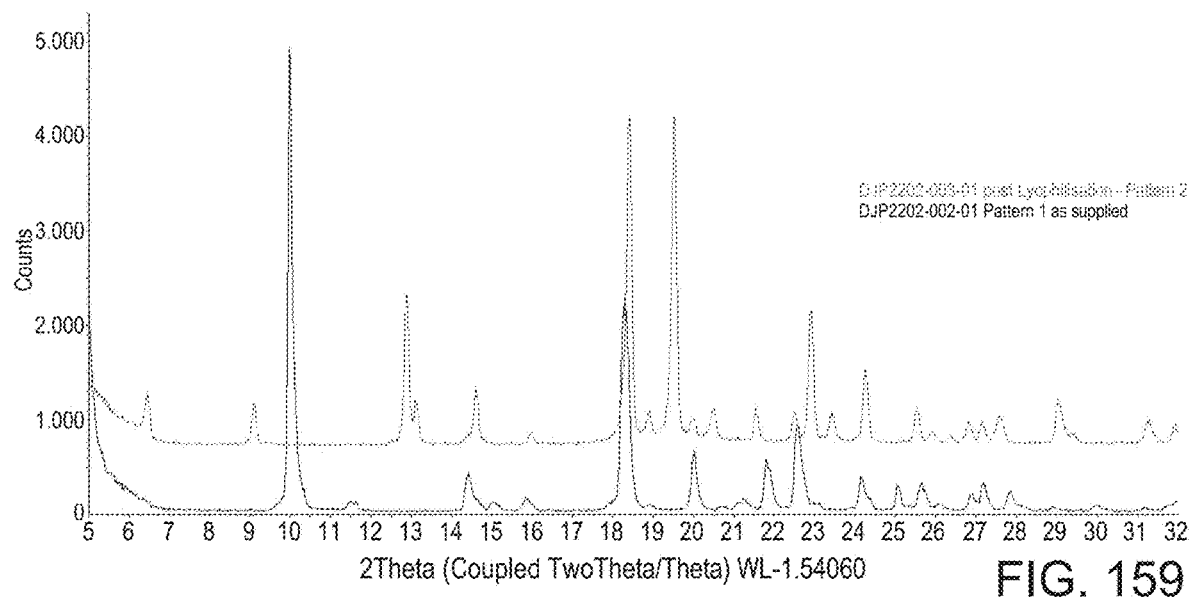

FIG. 159. XRPD Diffractogram of benzoate salt pattern 2 (red) vs supplied pattern 1 (black).

Figure 160:
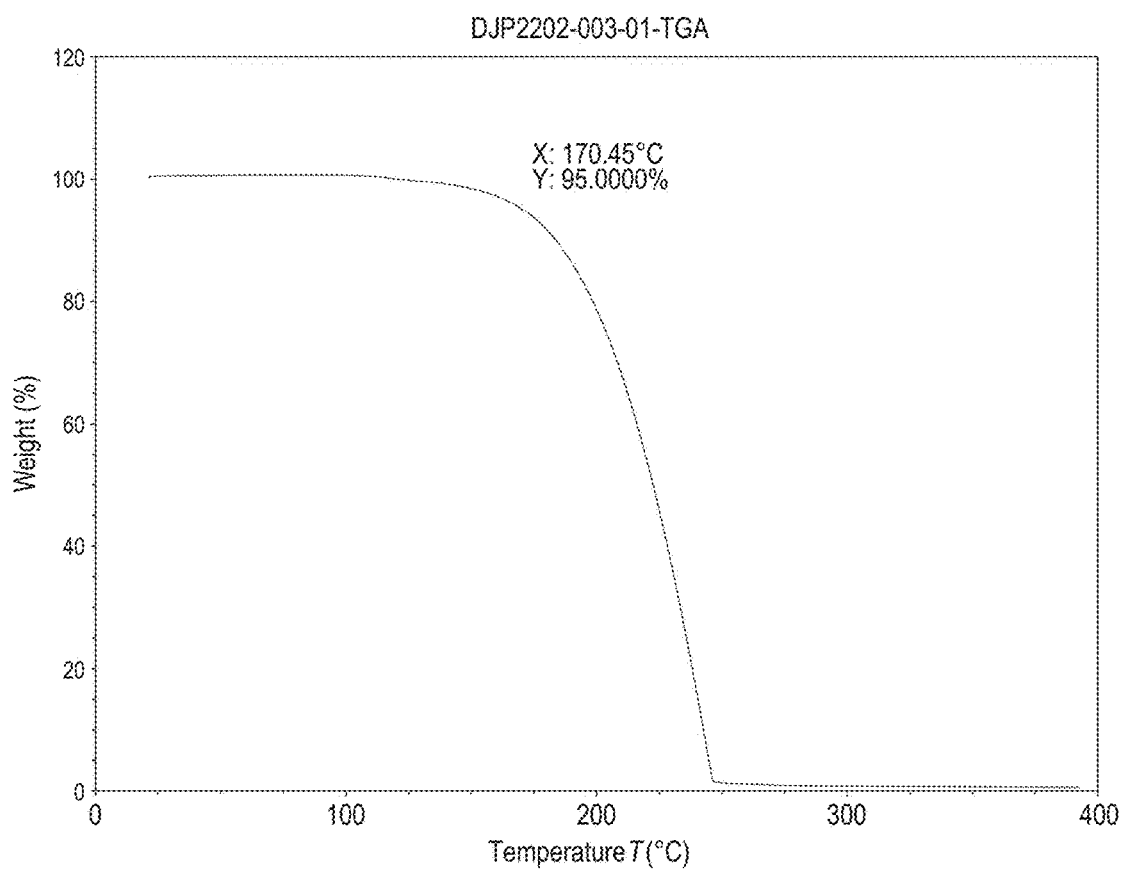

FIG. 160. TGA Thermogram of benzoate salt pattern 2 lot DJP2202-003-01.

Figure 161:
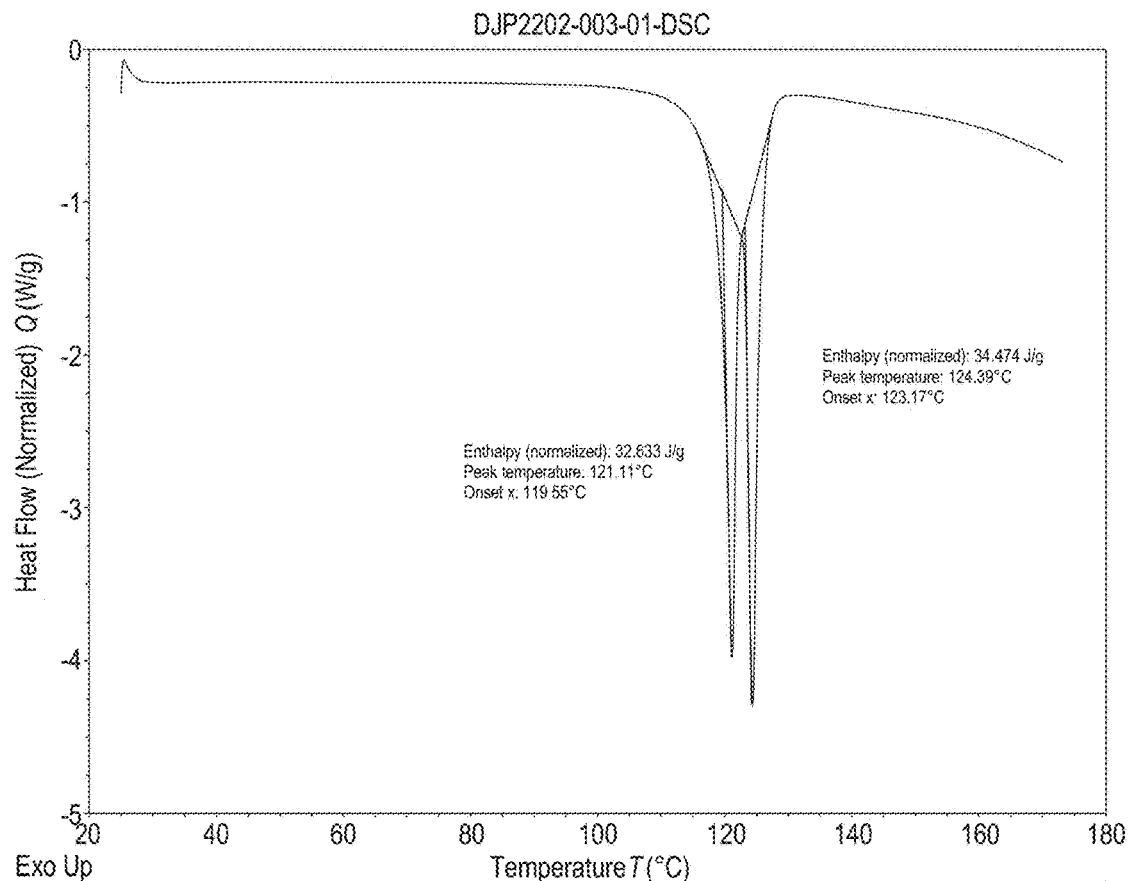

FIG. 161. DSC Thermogram of benzoate salt pattern 2 lot DJP2202-003-01.

Figure 162:
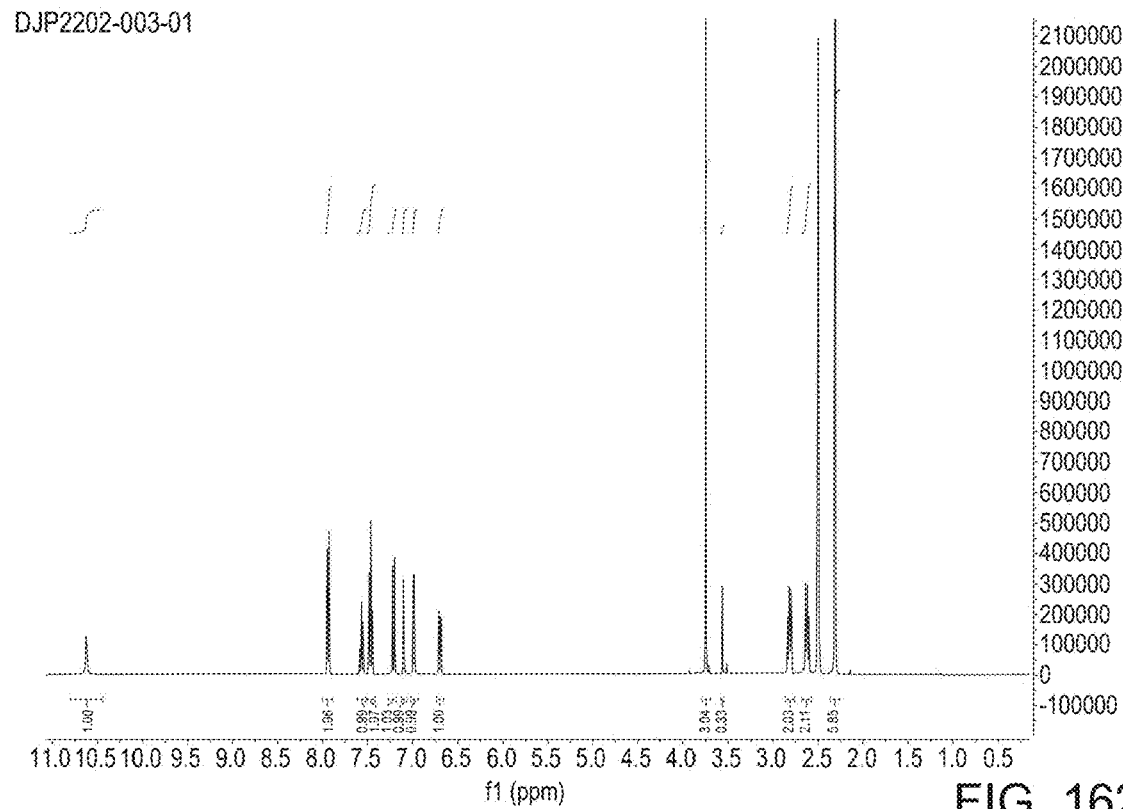

FIG. 162. $^1$H NMR Spectrum of benzoate salt pattern 2 lot DJP2202-003-01.

Figure 163:
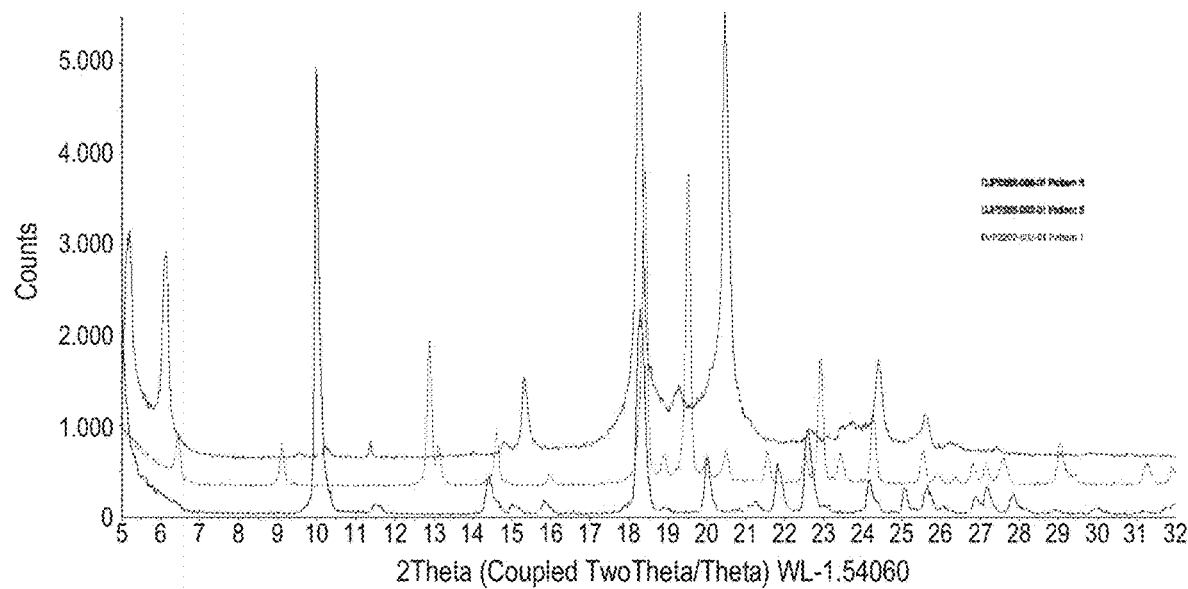

FIG. 163. XRPD Diffractogram of benzoate pattern 3 (blue) compared to pattern 2 (red) and pattern 1 (black).

Figure 164:
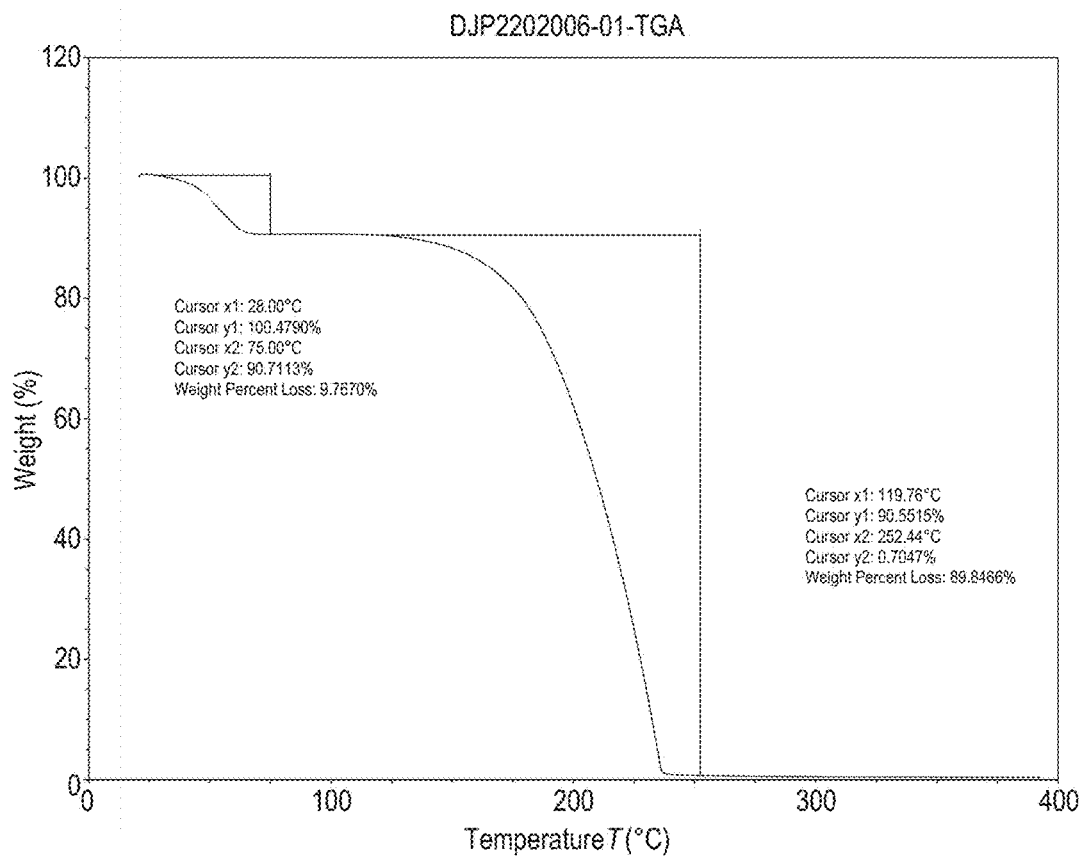

FIG. 164. TGA Thermogram of benzoate salt pattern 3 lot DJP2202-006-01.

Figure 165:
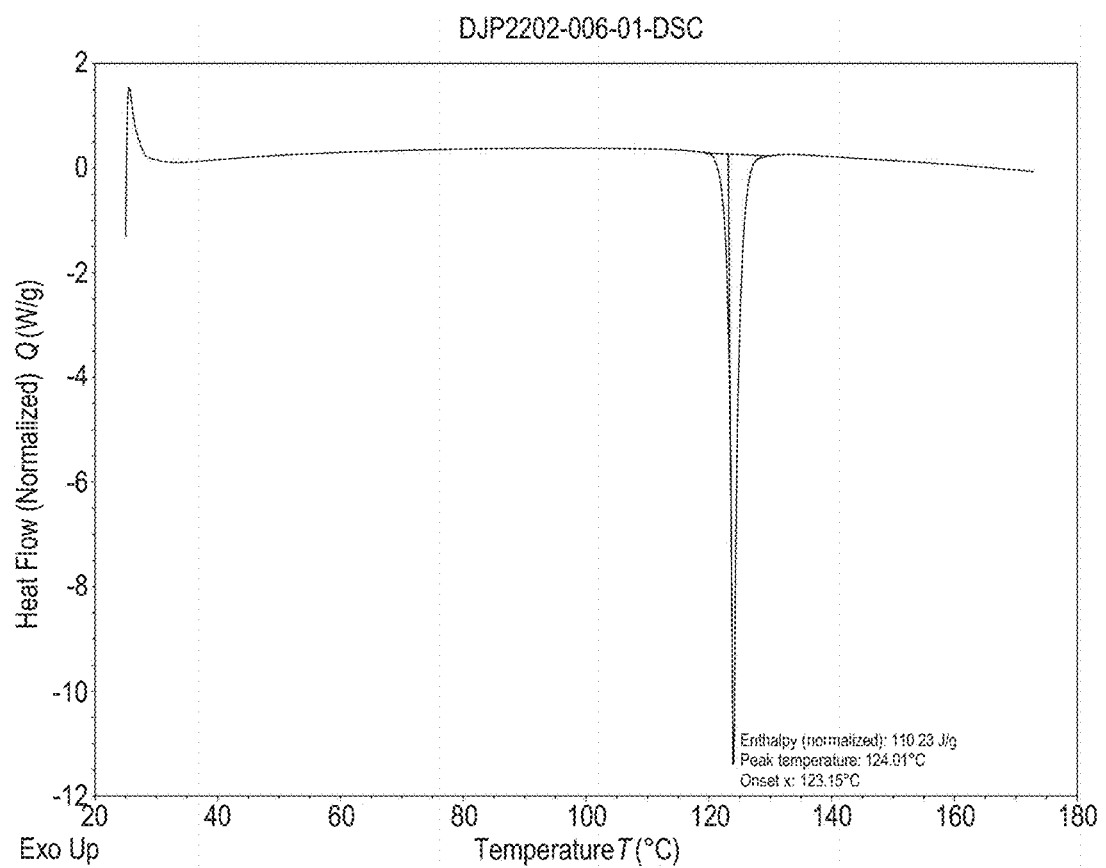

FIG. 165. DSC Thermogram of benzoate salt pattern 3 lot DJP2202-006-01.

Figure 166:
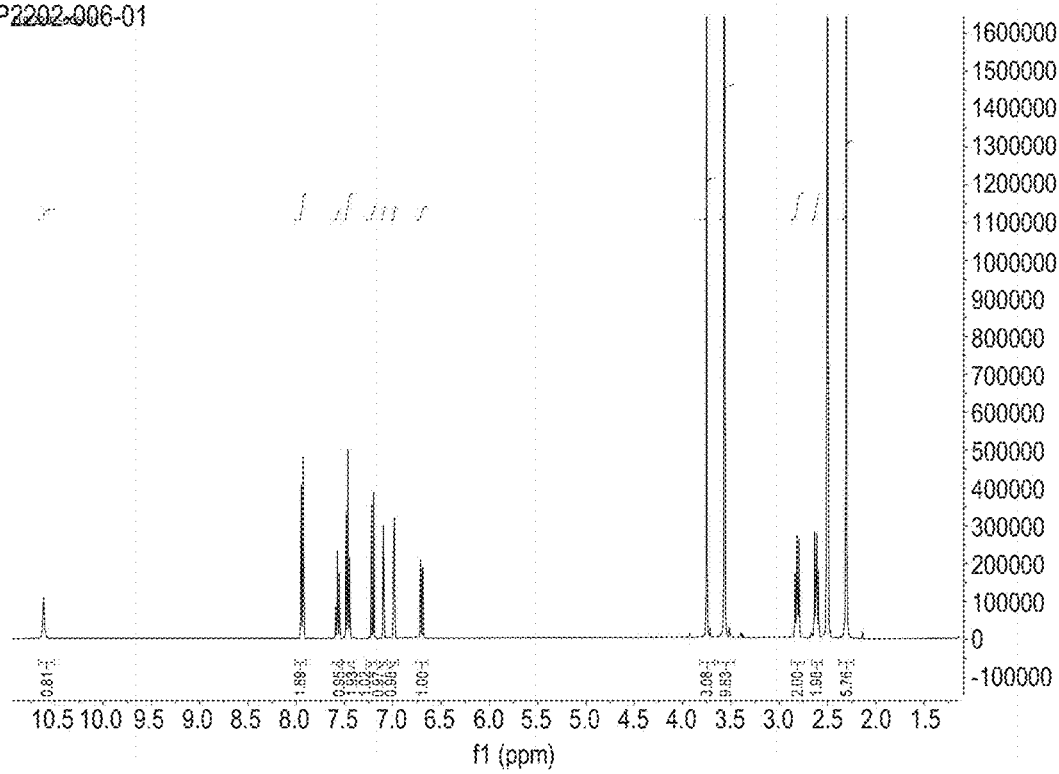

FIG. 166. $^1$H NMR Spectrum of benzoate salt pattern 3 lot DJP2202-006-01.

Figure 167:
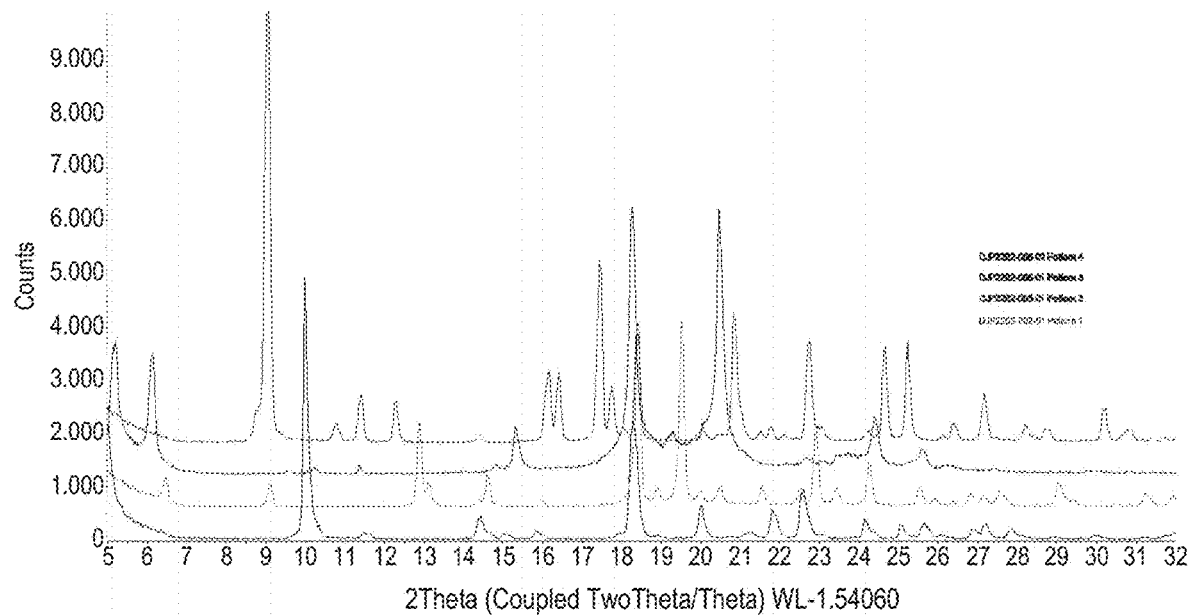

FIG. 167. XRPD Diffractogram of benzoate salt pattern 4 (green) compared to pattern 3 (blue), pattern 2 (red) and pattern 1 (black).

Figure 168:
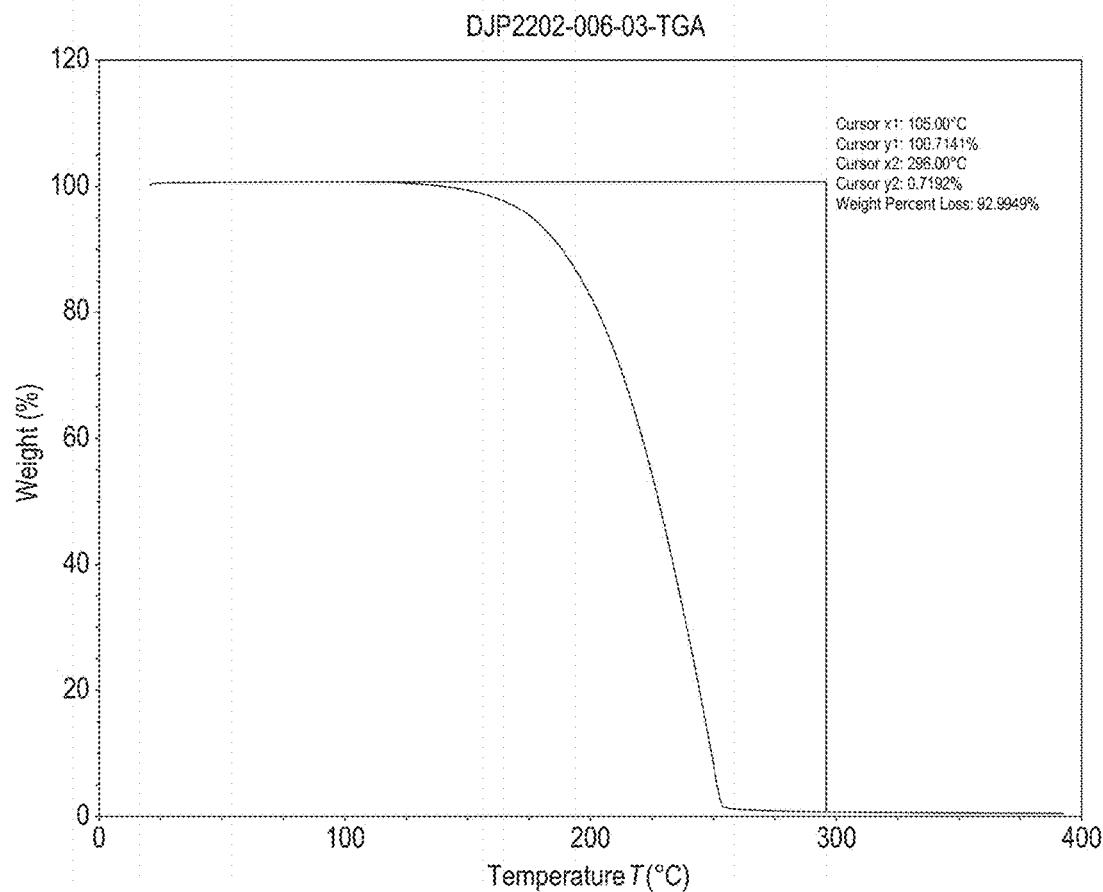

FIG. 168. TGA Thermogram of benzoate salt pattern 4 lot DJP2202-006-03.

Figure 169:
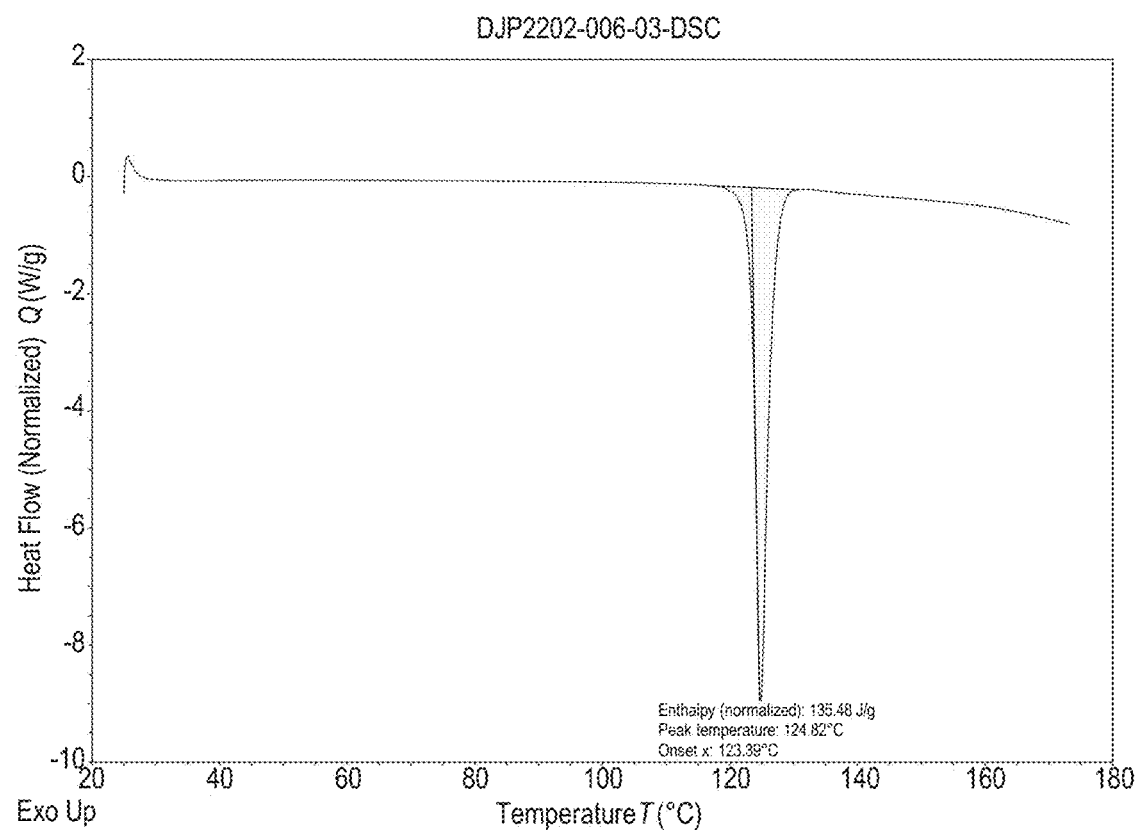

FIG. 169. DSC Thermogram of benzoate salt pattern 4 lot DJP2202-006-03.

Figure 170:
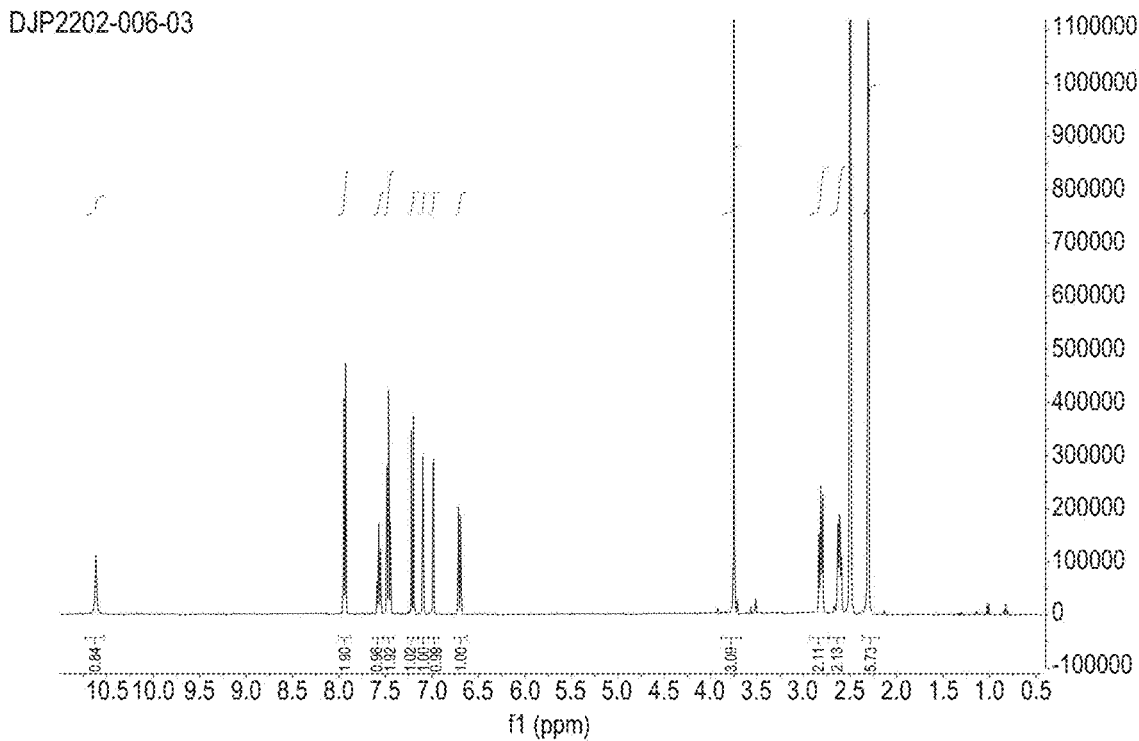

FIG. 170. $^1$H NMR Spectrum of benzoate salt pattern 4 lot DJP2202-006-03.

Figure 171:
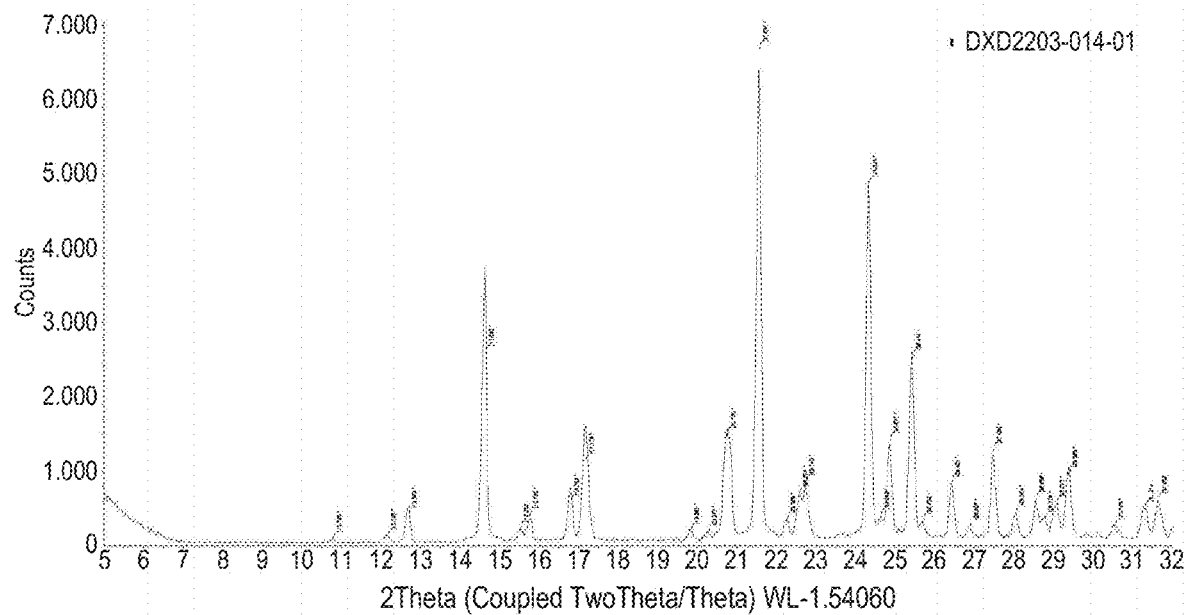

FIG. 171. XRPD Diffractogram of hydrobromide salt pattern 2.

Figure 172:
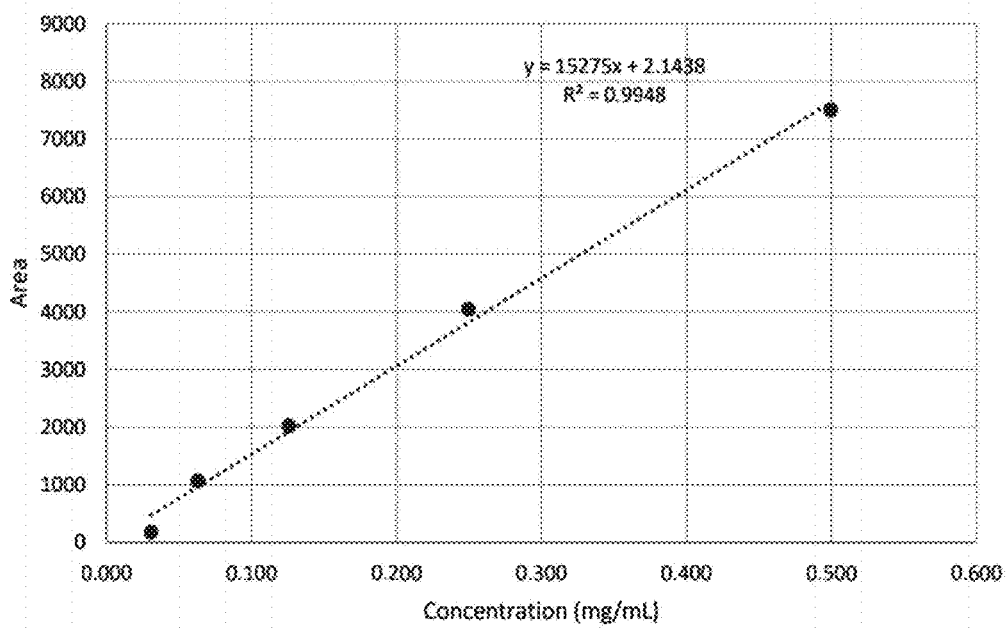

FIG. 172. Calibration curve of free base.

DESCRIPTION OF THE INVENTION

An object of the present invention is to provide 5-MeO-DMT salts. Moreover, another object of the present invention is to provide 5-MeO-DMT salts which neither easily convert into hydrates, even when a pharmaceutical composition comprising a 5-MeO-DMT salt is stored for a long period of time. Hygroscopicity is the phenomenon of attracting and holding water molecules via either adsorption or absorption from the surrounding environment. Pharmaceuticals that pick up less than 0.2% moisture at 80% RH are considered non hygroscopic. Pharmaceuticals that pick up between 0.2% and 2.0% moisture at 80% RH are considered slightly hygroscopic. Pharmaceuticals that pick up between 2.0% and 15.0% moisture at 80% RH are considered moderately hygroscopic. Pharmaceuticals that pick up more than 15.0% moisture at 80% RH are considered very hygroscopic. Hygroscopic substances are difficult to handle and costly and burdensome measures must be taken in order to ensure they are not exposed to moisture during process and formulation. Exposed to moisture, hygroscopic substances can take on water and convert to a hydrous form. This presents several disadvantages. First, the hydrous forms may have the disadvantage of being less bioavailable and less dissoluble than the anhydrous forms. Second, the variation in the amount of hydrous versus anhydrous substance from batch to batch could fail to meet specifications set by drug regulatory agencies. Third, processes like milling may cause the drug substance to adhere to manufacturing equipment which may further result in processing delay, increased operator involvement, increased cost, increased maintenance and lower production yield. Fourth, in addition to problems caused by introduction of moisture during the processing of these hygroscopic substances, the potential for absorbance of moisture during storage and handling would adversely affect the dissolubility of the drug substance. Thus shelf-life of the product could be significantly decreased and/or packaging costs could be significantly increased.

The inventors have surprising discovered that 5-MeO-DMT hydrobromide is a non-hygroscopic salt of 5-MeO-DMT. The tartrate salt of 5-MeO-DMT is moderately hygroscopic, the tosylate salt and the phosphate salt are both slightly hygroscopic.

The inventors have further surprisingly discovered that 5-MeO-DMT hydrobromide, whilst being non-hygroscopic, has high solubility compared to other moderately hygroscopic salts of 5-MeO-DMT for example the benzoate or oxalate salts. The non-hygroscopic, highly soluble HBr salt of 5-MeO-DMT therefore affords the advantage of removing the need for costly and burdensome processing measures, for example the need for low humidity manufacturing environment. The high solubility of the HBr salt of 5-MeO-DMT also facilitates the use of simplified solid formulations without the need for costly solubility enhancement techniques.

The inventors have further surprisingly discovered multiple polymorphic forms of crystalline 5-MeO-DMT hydrobromide, including a form referred to as form/pattern 2 with desirable qualities. The XRPD for this crystalline form can be seen in FIG. 171 and the peaks are tabulated in Tables 21, 21a and 21b.

Example 1: Salt Screen 5-methoxy-N,N-dimethyltryptamine (5-MeO-DMT) was supplied as a HCl salt. In order to preform salt screening experiments, the HCl salt was converted into free base. The crystalline nature of isolated free base was confirmed by XRPD and further analysed by TGA, DSC, $^1$H NMR analyses.

Salt screening studies with 24 selected counter-ions were performed to determine if 5-MeO-DMT free base is amenable to salt formation. On completion of this study, 11 crystalline salts were successfully generated and are displayed in Table 1. Salts were examined by XRPD, TGA, DSC, 1H NMR and some by DVS analyses. Short term physical stability was examined by storage of salts at 40° C./75% RH for three days.

TABLE 1

| Produced crystalline salts |
|---|
| Salt |
| Phosphate |
| Fumarate |
| Oxalate |
| Tartrate |
| Benzenesulfonate |
| Tosylate |
| Hydrobromide |
| Glycolate |
| Ketoglutarate |

TABLE 1-continued

Produced crystalline salts
Salt

Saccharinate
Malate

Instruments

X-Ray Powder Diffraction (XRPD)

XRPD diffractograms were acquired using Bruker D2 Phaser diffractometer equipped with LYNXEYE detector. Samples were prepared using a zero-background sample holder. The samples were scanned from 5 to 32° (2θ) using a step size of 0.02° and a time per step of 0.13 second whilst spinning the sample. Diffractograms were plotted using the EVA program from Bruker.

Thermo—Gravimetric Analysis (TGA)

TGA thermograms were obtained with a TA Instrument Discovery 550 in Al pans. The heating rate used was 10° C./min linear ramp from 25 to 400° C. with a nitrogen purging at a rate of 60 ml/min. TGA thermograms were analysed using TRIOS software.

Differential Scanning Calorimetry (DSC)

DSC analyses were performed on a TA Instrument DSC250 with a Tzero cell purged at constant flow rate of 50 ml min$^{-1}$ with dry nitrogen and a refrigerated cooling system RCS90. The instrument was calibrated using Indium as a standard. A small quantity of the samples was weighed into TA Tzero Aluminium pan with pierced lid. Samples were heating at 10° C./min in heat-cool-reheat method. TRIOS software was used to analyse DSC scans.

Nuclear Magnetic Resonance Spectroscopy (NMR)

The 1H NMR spectra were measured on Bruker NEO spectrometer operating at 400.13 MHz for protons. Samples were dissolved in d6-DMSO. Data were processed using MestReNova×64 software.

Dynamic Vapor Sorption (DVS)

DVS analyses were performed on TA Instrument DVS Q5000. Samples were added to a pre-tared metallised quartz crucible and run at 25° C. from 40% RH to 90% RH, down to zero and back to 40%. This cycle was repeated in increments of 10% RH.

Preparation and Initial Characterisation of Free Base

5-MeO-DMT Hydrochloride salt (2×5 g) was used for preparation of free base.

Free base was isolated from NaHCO$_3$-Ethyl acetate extraction (5.7 g, 67% yield).

5-MeO-DMT free base was characterised by XPRD, TGA, DSC and $^1$H NMR.

X-Ray Powder Diffraction (XRPD)

Figure 1:
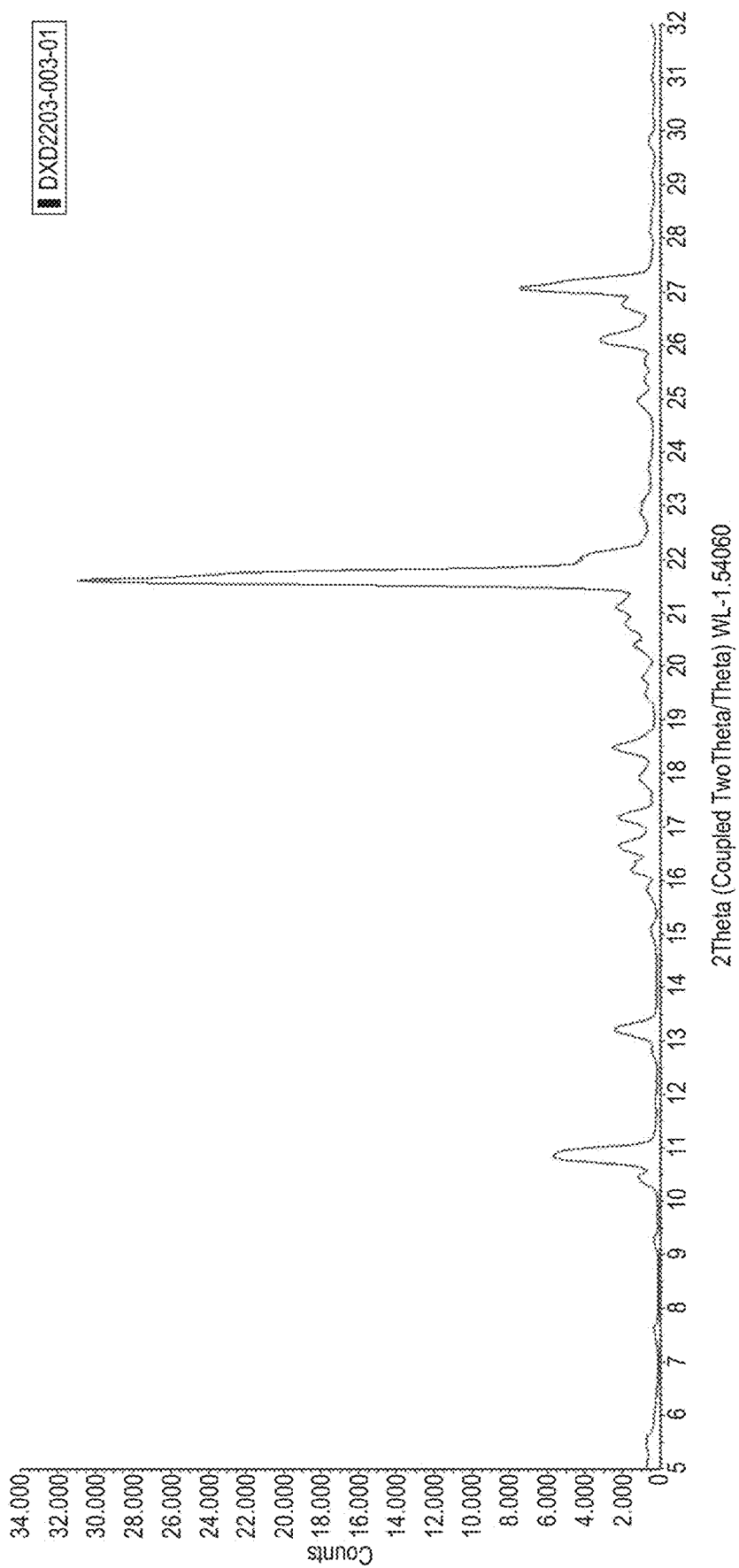
FIG. 1. XRPD Diffractogram of free base, Batch: DXD2203-003-01.

XRPD diffractogram in FIG. 1 displayed crystalline peaks confirming the crystallinity of the free base. This was nominated as free base pattern 1. The XRPD peak data is shown in Table 2.

TABLE 2

XRPD Peak data for free base pattern 1.

| Peak No. | Angle 2 θ | d Value | Rel. Intensity |
|---|---|---|---|
| 1 | 5.464° | 16.160 | 0.010 |
| 2 | 7.588° | 11.641 | 0.006 |
| 3 | 9.294° | 9.507 | 0.008 |
| 4 | 10.450° | 8.459 | 0.037 |
| 5 | 10.867° | 8.135 | 0.201 |
| 6 | 11.867° | 7.451 | 0.002 |
| 7 | 12.779° | 6.922 | 0.009 |
| 8 | 13.217° | 6.693 | 0.083 |
| 9 | 15.062° | 5.878 | 0.011 |
| 10 | 15.833° | 5.593 | 0.019 |
| 11 | 16.251° | 5.450 | 0.041 |
| 12 | 16.644° | 5.322 | 0.069 |
| 13 | 17.192° | 5.154 | 0.070 |
| 14 | 17.933° | 4.942 | 0.027 |
| 15 | 18.478° | 4.798 | 0.080 |
| 16 | 19.480° | 4.553 | 0.017 |
| 17 | 19.802° | 4.480 | 0.020 |
| 18 | 20.402° | 4.349 | 0.036 |
| 19 | 20.814° | 4.264 | 0.051 |
| 20 | 21.106° | 4.206 | 0.071 |
| 21 | 21.652° | 4.101 | 1.000 |
| 22 | 21.971° | 4.042 | 0.141 |
| 23 | 22.976° | 3.868 | 0.019 |
| 24 | 23.686° | 3.753 | 0.008 |
| 25 | 24.958° | 3.565 | 0.030 |
| 26 | 25.340° | 3.512 | 0.015 |
| 27 | 25.705° | 3.463 | 0.013 |
| 28 | 26.111° | 3.410 | 0.101 |
| 29 | 26.764° | 3.328 | 0.058 |
| 30 | 27.082° | 3.290 | 0.258 |
| 31 | 28.120° | 3.171 | 0.006 |
| 32 | 28.439° | 3.136 | 0.005 |
| 33 | 29.176° | 3.058 | 0.005 |
| 34 | 29.811° | 2.995 | 0.010 |
| 35 | 30.329° | 2.945 | 0.005 |
| 36 | 31.067° | 2.876 | 0.005 |

TABLE 2a

XRPD Peak data for free base pattern 1 (2 d.p.).

| Peak No. | Angle 2 θ | d Value | Rel. Intensity |
|---|---|---|---|
| 1 | 5.46° | 16.16 | 0.01 |
| 2 | 7.59° | 11.64 | 0.01 |
| 3 | 9.29° | 9.51 | 0.01 |
| 4 | 10.45° | 8.46 | 0.04 |
| 5 | 10.87° | 8.14 | 0.20 |
| 6 | 11.87° | 7.45 | 0.00 |
| 7 | 12.78° | 6.92 | 0.01 |
| 8 | 13.22° | 6.69 | 0.08 |
| 9 | 15.06° | 5.88 | 0.01 |
| 10 | 15.83° | 5.59 | 0.02 |
| 11 | 16.25° | 5.45 | 0.04 |
| 12 | 16.64° | 5.32 | 0.07 |
| 13 | 17.19° | 5.15 | 0.07 |
| 14 | 17.93° | 4.94 | 0.03 |
| 15 | 18.48° | 4.80 | 0.08 |
| 16 | 19.48° | 4.55 | 0.02 |
| 17 | 19.8° | 4.48 | 0.02 |
| 18 | 20.4° | 4.35 | 0.04 |
| 19 | 20.81° | 4.26 | 0.05 |
| 20 | 21.11° | 4.21 | 0.07 |
| 21 | 21.65° | 4.10 | 1.00 |
| 22 | 21.97° | 4.04 | 0.14 |
| 23 | 22.98° | 3.87 | 0.02 |
| 24 | 23.69° | 3.75 | 0.01 |
| 25 | 24.96° | 3.57 | 0.03 |
| 26 | 25.34° | 3.51 | 0.02 |
| 27 | 25.71° | 3.46 | 0.01 |
| 28 | 26.11° | 3.41 | 0.10 |
| 29 | 26.76° | 3.33 | 0.06 |
| 30 | 27.08° | 3.29 | 0.26 |
| 31 | 28.12° | 3.17 | 0.01 |

TABLE 2a-continued

XRPD Peak data for free base pattern 1 (2 d.p.).

| Peak No. | Angle 2 θ | d Value | Rel. Intensity |
|---|---|---|---|
| 32 | 28.44° | 3.14 | 0.01 |
| 33 | 29.18° | 3.06 | 0.01 |
| 34 | 29.81° | 3.00 | 0.01 |
| 35 | 30.33° | 2.95 | 0.01 |
| 36 | 31.07° | 2.88 | 0.01 |

TABLE 2b

XRPD Peak data for free base pattern 1 (1 d.p.).

| Peak No. | Angle 2 θ | d Value | Rel. Intensity |
|---|---|---|---|
| 1 | 5.5° | 16.2 | 0.0 |
| 2 | 7.6° | 11.6 | 0.0 |
| 3 | 9.3° | 9.5 | 0.0 |
| 4 | 10.5° | 8.5 | 0.0 |
| 5 | 10.9° | 8.1 | 0.2 |
| 6 | 11.9° | 7.5 | 0.0 |
| 7 | 12.8° | 6.9 | 0.0 |
| 8 | 13.2° | 6.7 | 0.1 |
| 9 | 15.1° | 5.9 | 0.0 |
| 10 | 15.8° | 5.6 | 0.0 |
| 11 | 16.3° | 5.5 | 0.0 |
| 12 | 16.6° | 5.3 | 0.1 |
| 13 | 17.2° | 5.2 | 0.1 |
| 14 | 17.9° | 4.9 | 0.0 |
| 15 | 18.5° | 4.8 | 0.1 |
| 16 | 19.5° | 4.6 | 0.0 |
| 17 | 19.8° | 4.5 | 0.0 |
| 18 | 20.4° | 4.3 | 0.0 |
| 19 | 20.8° | 4.3 | 0.1 |
| 20 | 21.1° | 4.2 | 0.1 |
| 21 | 21.7° | 4.1 | 1.0 |
| 22 | 22.0° | 4.0 | 0.1 |
| 23 | 23.0° | 3.9 | 0.0 |
| 24 | 23.7° | 3.8 | 0.0 |
| 25 | 25.0° | 3.6 | 0.0 |
| 26 | 25.3° | 3.5 | 0.0 |
| 27 | 25.7° | 3.5 | 0.0 |
| 28 | 26.1° | 3.4 | 0.1 |
| 29 | 26.8° | 3.3 | 0.1 |
| 30 | 27.1° | 3.3 | 0.3 |
| 31 | 28.1° | 3.2 | 0.0 |
| 32 | 28.4° | 3.1 | 0.0 |
| 33 | 29.2° | 3.1 | 0.0 |
| 34 | 29.8° | 3.0 | 0.0 |
| 35 | 30.3° | 2.9 | 0.0 |
| 36 | 31.1° | 2.9 | 0.0 |

Thermo—Gravimetric Analysis (TGA)

Figure 2:
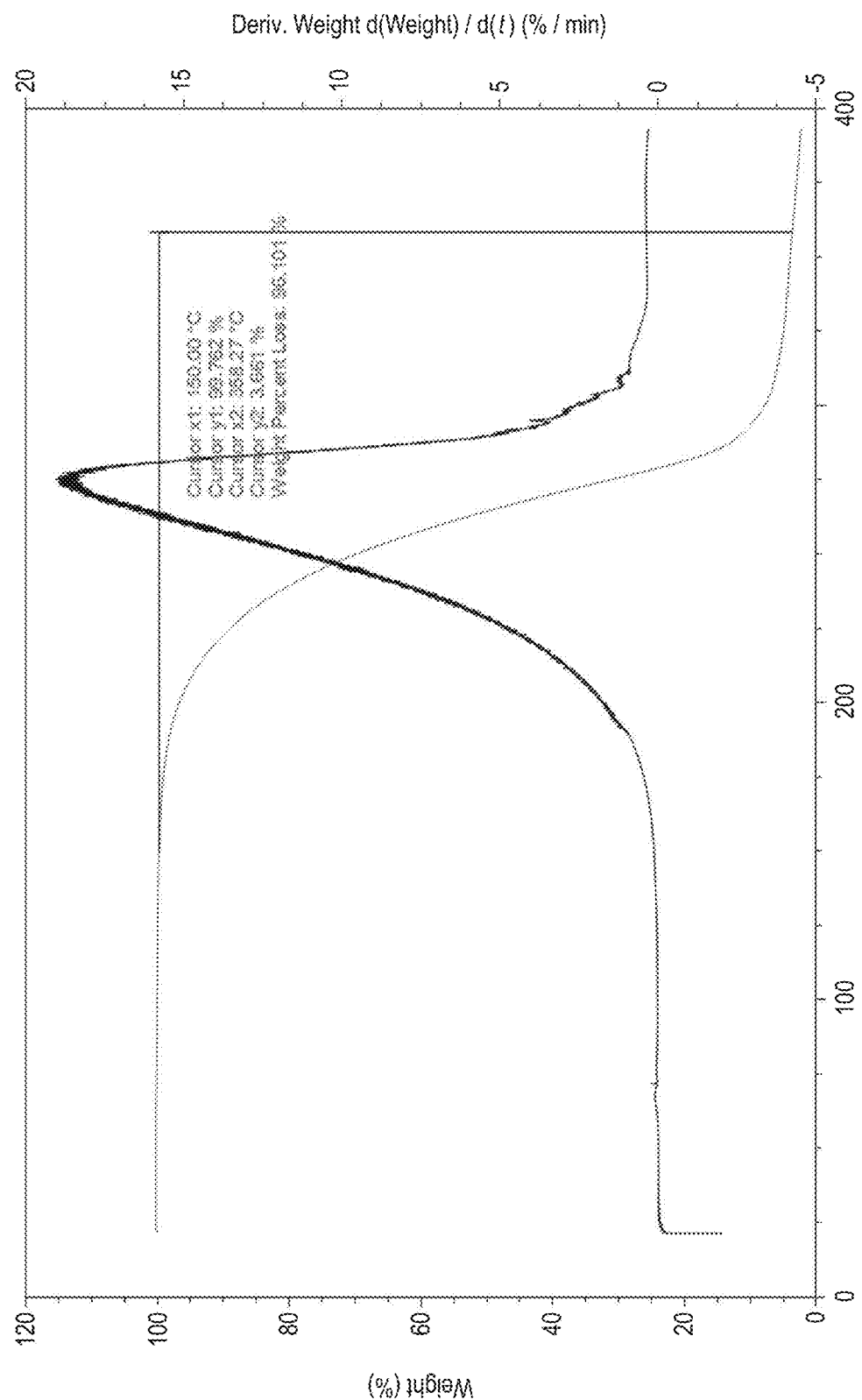
FIG. 2. TGA Thermogram of free base, Batch: DXD2203-003-01.

TGA thermogram of free base in FIG. 2 showed no weight loss between 25 to 150° C. and good thermal stability up to 150° C. followed by a rapid weight loss due to the thermal degradation of the API.

Differential Scanning Calorimetry (DSC)

Figure 3:
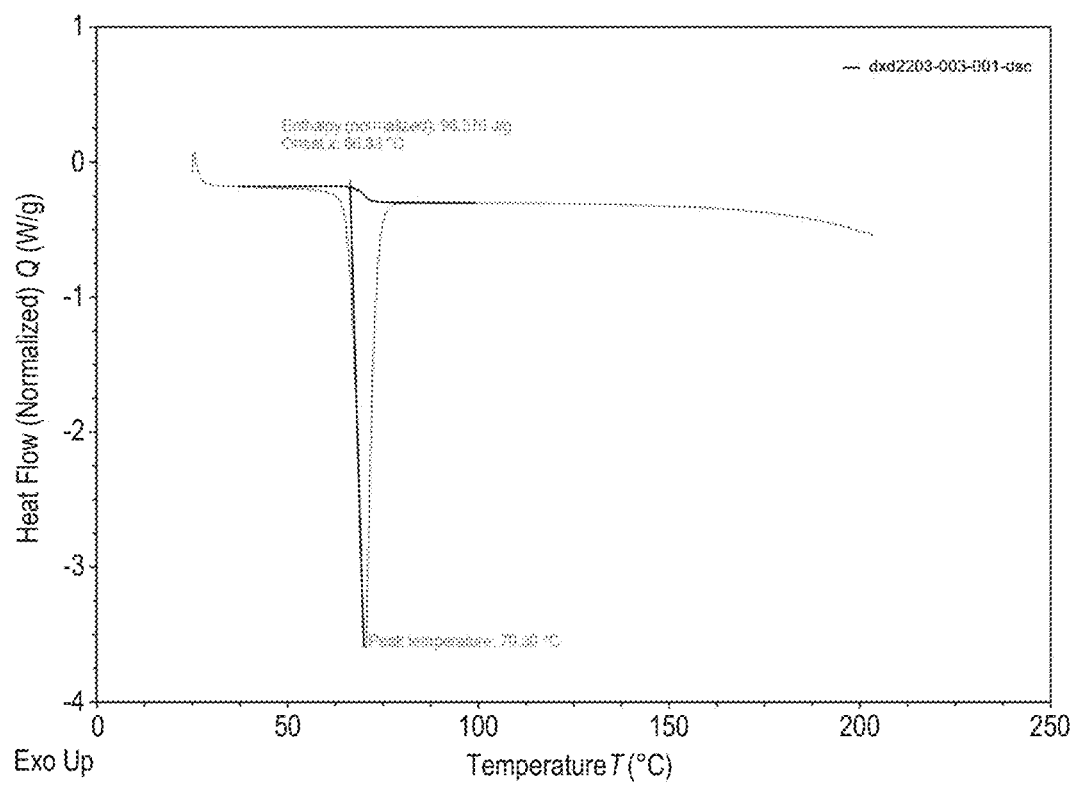
FIG. 3. DSC Thermogram (1st heat) of free base, Batch: DXD2203-003-01.

The first heating ramp displayed a sharp endothermic event with $T_{onst}$ at 66.4° C. and heat of fusion 96.4 J/g, which corresponds to melting of the free base as shown in, or substantially as shown in, FIG. 3.

Figure 4:
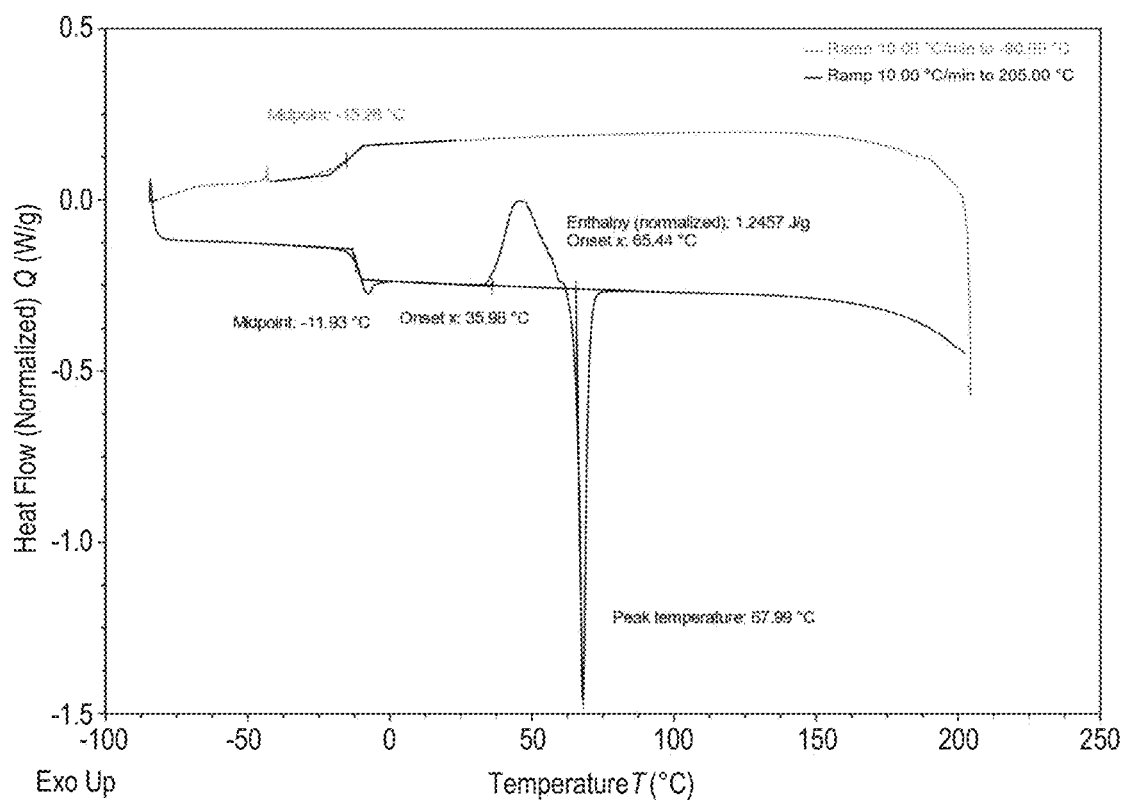
FIG. 4. DSC Thermograms of free base, Batch: DXD2203-003-01, cooling (blue trace), 2nd heat (green trace).

The cooling ramp of 10° C./min from 205° C. to −90° C. displayed a vitrification at around −15.3° C. The 2nd heating ramp showed an endothermic shift in the baseline around −11.9° C. (Tg), followed by recrystallisation exotherm with the onset temperature of 36° C. The sharp endotherm with onset temperature of 65.4° C. corresponds to melting of pattern 1 as demonstrated in FIG. 4.

Nuclear Magnetic Resonance Spectroscopy (NMR)

Figure 5:
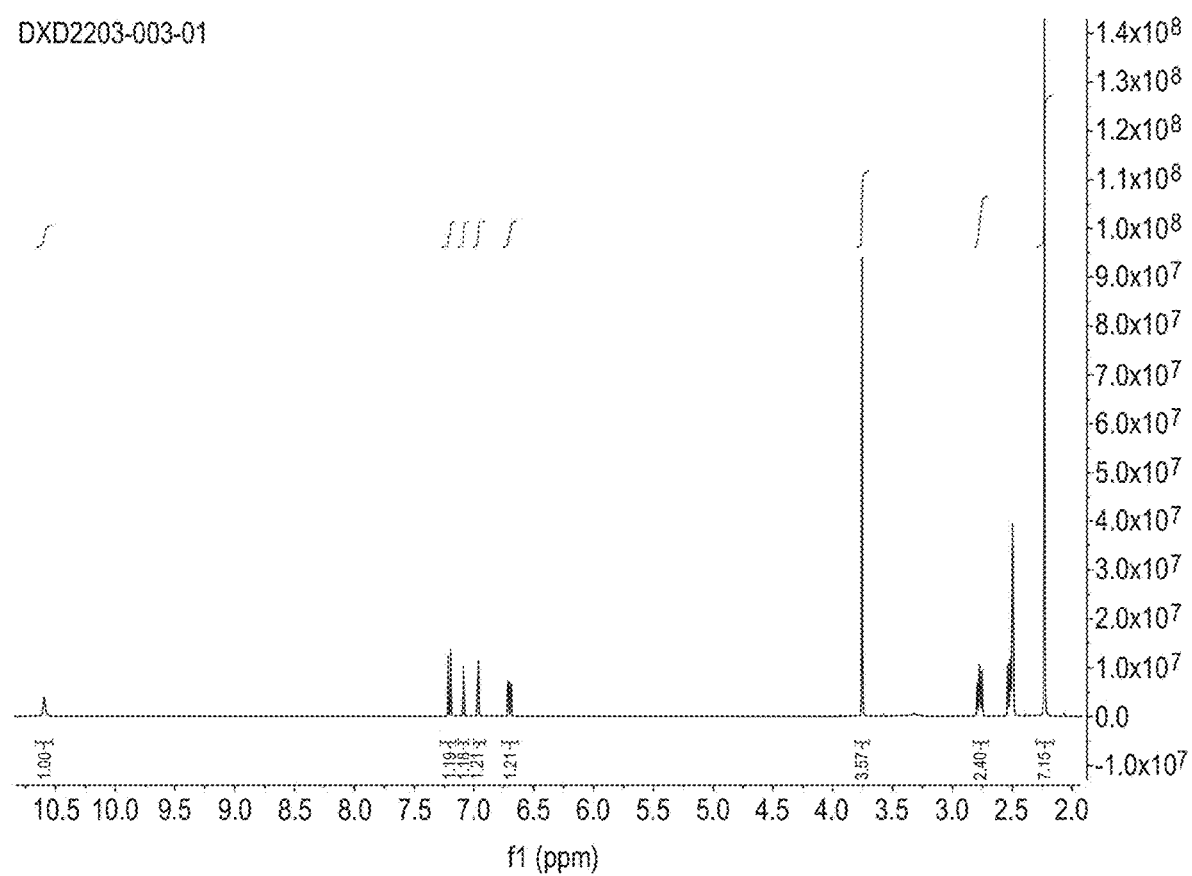
FIG. 5. 1H NMR (d6-DMSO) Spectrum of free base, Batch: DXD2203-003-01.

The $^1$H NMR spectrum of free base in $d_6$-DMSO shown in FIG. 5 provided structure confirmation of the material. There is no obvious evidence of residual solvents present in the sample.

Salt Screen Studies

Salt screens experiments were consisted of combining solutions of the API and 1.05 stochiometric amounts of counter ions.

Selected counter ions for salt studies are tabulated in Table 3.

TABLE 3

Selected counter ions

| | Counter sons - Set 1 |
|---|---|
| 1 | Sulphuric acid 98% |
| 2 | p-Toluene sulphonic acid |
| 3 | Methane sulphonic acid |
| 4 | Benzene sulphonic acid |
| 5 | Maleic acid |
| 6 | Phosphoric acid |
| 7 | Ethane sulphonic acid 70 wt % in water |
| 8 | L-Tartaric acid |
| 9 | Fumaric acid |
| 10 | (2S)-5-oxopyrrolidine-2-carboxylic acid |
| 11 | L-Lactic acid |
| 12 | Citric acid |
| | Counter ions - Set 2 |
| 13 | Hydrobromic acid |
| 14 | Oxalic acid |
| 15 | 2-Hydroxy ethanesulphonic acid |
| 16 | L-Glutamic acid |
| 17 | Ketoglutaric acid |
| 18 | L-Malic acid |
| 19 | Glycolic acid |
| 20 | Adipic acid |
| 21 | Acetic acid |
| 22 | Propionic acid |
| 23 | Hippuric acid |
| 24 | Saccharin |

Free base (2.16 g) was dissolved in 1,4-dioxane (72 ml) at room temperature. Approximately 1 ml of this the stock solution was dispensed to 72 (2 ml) HPLC vials. This preparation was carried out twice for each set of 12 counter ions.

Set 1:

Free Base dioxane solutions were then frozen at −20° C. for 5 hours. After this time frozen samples were lyophilised for approximately 60 hours.

Set 2:

Free Base dioxane solutions were then frozen at −20° C. for 5 hours. After this time frozen samples were lyophilised for 12 hours.

To freeze dried samples approximately 0.5 ml of solvent was added. Solvents used in this study are tabulated in Table 4.

TABLE 4

Solvents used in salt screening experiments

| |
|---|
| Acetone |
| EtOAc |
| MeCN |
| THF |
| IPA |
| 5% water:EtOH |

Acid stock solutions in 1.05 eq. ratio were added to free base samples. Solvents used for preparation of acid stock solutions are summarised in Table 5. Due to poor solubility of L-Glutamic acid in examined solvents, L-Glutamic acid was added as a solid in 1.05 eq. to free base samples.

TABLE 5

Acid stock solutions

| Counter ions-Set 1 | Stock Solvent | Counter ions - Set 2 | Stock Solvent |
|---|---|---|---|
| Sulphuric acid 98% | Water | Hydrobromic acid | Water |
| p-Toluene sulphonic acid | Water | Oxalic acid | Water |
| Methane sulphonic acid | Water | 2-Hydroxy ethanesulphonic acid | Water |
| Benzene sulphonic acid | Water | L-Glutamic acid | N/A |
| Maleic acid | Water | Ketoglutaric acid | Water |
| Phosphoric acid | Water | L-Malic acid | Water |
| Ethane sulphonic acid 70 wt % in water | Water | Glycolic acid | Water |
| L-Tartaric acid | Water | Adipic acid | THF |
| Fumaric acid | 5% Water:EtOH | Acetic acid | Water |
| (2S)-5-oxopyrrolidine-2carboxylic acid | EtOH | Propionic acid | Water |

TABLE 5-continued

Acid stock solutions

| Counter ions-Set 1 | Stock Solvent | Counter ions - Set 2 | Stock Solvent |
|---|---|---|---|
| L-Lactic acid | Water | Hippuric acid | THF:MeOH (1:1; v/v) |
| Citric acid | Water | Saccharin | THF |

No formation of solid phases was observed after mixing acids with API solutions.

Thermal cycling experiment was performed on samples between ambient and 40° C. Temperature was held for 4 hours at each condition. Thermal cycling—Set-1 for 20 hours. Thermal cycling—Set-2 for 24 hours.

Where solids were observed after thermal cycling, these were isolated by centrifuge filtration using Nylon 0.2 micrometre centrifuge filter tubes and analysed by XRPD.

Any new crystalline forms were also analysed by TGA, DSC, $^1$H NMR and DVS analyses.

Remaining solutions were first cooled to 4° C. for 2 hours to promote precipitation. As no precipitation occurred solutions were allowed to evaporate under ambient conditions.

The outcome of experiments is summarised in Table 6 and Table 7, respectively.

TABLE 6

Outcome summary of experiments, Set-1

| Acid | Solvent | Batch | After thermal cycling | After evaporation to dryness |
|---|---|---|---|---|
| Sulphuric acid | Acetone | DXD2203-004-001 | Yellow solution | Yellow glass |
| | EtOAc | DXD2203-004-002 | Dark pink solution | Dark pink glass |
| | MeCN | DXD2203-004-003 | Pink solution | Pink glass |
| | THF | DXD2203-004-004 | Pink solution | Pink glass |
| | IPA | DXD2203-004-005 | Pink solution | Pink glass |
| | 5% water:EtOH | DXD2203-004-006 | Pink solution | Pink glass |
| p-toluene sulphonic acid | Acetone | DXD2203-004-007 | Light yellow solution | Light yellow glass |
| | EtOAc | DXD2203-004-008 | Light yellow solution | Light yellow glass |
| | MeCN | DXD2203-004-009 | Light yellow solution | Light yellow glass |
| | THF | DXD2203-004-010 | Pink solution | Pink glass |
| | IPA | DXD2203- 004-011 | Light yellow solution | Light yellow glass |
| | 5% water:EtOH | DXD2203-004-012 | Pink solution | Pink glass |
| Methane sulphonic acid | Acetone | DXD2203-004-013 | Yellow solution | Yellow glass |
| | EtOAc | DXD2203-004-014 | Pink solution | Pink glass |
| | MeCN | DXD2203-004-015 | Yellow solution | Yellow glass |
| | THF | DXD2203-004-016 | Yellow solution | Yellow glass |
| | IPA | DXD2203-004-017 | Pink solution | Pink glass |
| | 5% water:EtOH | DXD2203-004-018 | Pink solution | Pink glass |
| Benzene sulphonic acid | Acetone | DXD2203-004-019 | Light yellow solution | Light yellow glass |
| | EtOAc | DXD2203-004-020 | Light yellow solution | Light yellow glass |
| | MeCN | DXD2203-004-021 | Light yellow solution | Light yellow glass |
| | THF | DXD2203-004-022 | Light yellow solution | Light yellow glass |
| | IPA | DXD2203-004-023 | Light yellow solution | Light yellow glass |
| | 5% water:EtOH | DXD2203-004-024 | Light yellow solution | Light yellow glass |
| Maleic acid | Acetone | DXD2203-004-025 | Yellow solution | Yellow glass |
| | EtOAc | DXD2203-004-026 | Yellow solution | Yellow glass |
| | MeCN | DXD2203-004-027 | Yellow solution | Yellow glass |
| | THF | DXD2203-004-028 | Yellow solution | Yellow glass |
| | IPA | DXD2203-004-029 | Yellow solution | Yellow glass |
| | 5% water:EtOH | DXD2203-004-030 | Yellow solution | Yellow glass |
| Phosphoric acid | Acetone | DXD2203-004-031 | Light yellow solution | Light yellow glass |
| | EtOAc | DXD2203-004-032 | White precipitate | N/A |
| | MeCN | DXD2203-004-033 | Light yellow solution | Light yellow glass |
| | THF | DXD2203-004-034 | White precipitate | N/A |
| | IPA | DXD2203-004-035 | White precipitate | N/A |
| | 5% water:EtOH | DXD2203-004-036 | Light yellow solution | Light yellow glass |
| Ethane sulphonic acid | Acetone | DXD2203-004-037 | Light yellow solution | Light yellow glass |
| | EtOAc | DXD2203-004-038 | Light yellow solution | Light yellow glass |
| | MeCN | DXD2203-004-039 | Light yellow solution | Light yellow glass |
| | THF | DXD2203-004-040 | Light yellow solution | Light yellow glass |
| | IPA | DXD2203-004-041 | Light yellow solution | Light yellow glass |
| | 5% water:EtOH | DXD2203-004-042 | Light yellow solution | Light yellow glass |

TABLE 6-continued

Outcome summary of experiments, Set-1

| Acid | Solvent | Batch | After thermal cycling | After evaporation to dryness |
|---|---|---|---|---|
| L-tartaric acid | Acetone | DXD2203-004-043 | Light yellow solution | Light yellow glass |
| | EtOAc | DXD2203-004-044 | Light yellow solution | Light yellow glass |
| | MeCN | DXD2203-004-045 | Light yellow solution | Light yellow glass |
| | THF | DXD2203-004-046 | Light yellow solution | Light yellow glass |
| | IPA | DXD2203-004-047 | Light yellow solution | Light yellow glass |
| | 5% water:EtOH | DXD2203-004-048 | Light yellow solution | Light yellow glass |
| Fumaric acid | Acetone | DXD2203-004-049 | White precipitate | N/A |
| | EtOAc | DXD2203-004-050 | White precipitate | N/A |
| | MeCN | DXD2203-004-051 | Light yellow solution | Light yellow glass |
| | THF | DXD2203-004-052 | Light pink solution | Light pink glass |
| | IPA | DXD2203-004-053 | White precipitate | N/A |
| | 5% water:EtOH | DXD2203-004-054 | Light yellow solution | Light yellow glass |
| (2S)-5oxopyrrolidine-2carboxylic acid | Acetone | DXD2203-004-055 | Light yellow solution | Light yellow glass |
| | EtOAc | DXD2203-004-056 | Light yellow solution | Light yellow glass |
| | MeCN | DXD2203-004-057 | Light yellow solution | Light yellow glass |
| | THF | DXD2203-004-058 | Light yellow solution | Light yellow glass |
| | IPA | DXD2203-004-059 | Light yellow solution | Light yellow glass |
| | 5% water:EtOH | DXD2203-004-060 | Light yellow solution | Light yellow glass |
| L-lactic acid | Acetone | DXD2203-004-061 | Light yellow solution | Light yellow glass |
| | EtOAc | DXD2203-004-062 | Light yellow solution | Light yellow glass |
| | MeCN | DXD2203-004-063 | Light yellow solution | Light yellow glass |
| | THF | DXD2203-004-064 | Light yellow solution | Light yellow glass |
| | IPA | DXD2203-004-065 | Light yellow solution | Light yellow glass |
| | 5% water:EtOH | DXD2203-004-066 | Light yellow solution | Light yellow glass |
| Citric acid | Acetone | DXD2203-004-067 | Light yellow solution | Light yellow glass |
| | EtOAc | DXD2203-004-068 | Light yellow solution | Light yellow glass |
| | MeCN | DXD2203-004-069 | Light yellow solution | Light yellow glass |
| | THF | DXD2203-004-070 | Light yellow solution | Light yellow glass |
| | IPA | DXD2203-004-071 | Light yellow solution | Light yellow glass |
| | 5% water:EtOH | DXD2203-004-072 | Light yellow solution | Light yellow glass |

TABLE 7

Outcome summary of experiments. Set-2

| Acid | Solvent | Batch | After thermal cycling | After evaporation to dryness |
|---|---|---|---|---|
| Hydrobromic acid | Acetone | DXD2203-007-01 | Yellow solution | Yellow glass |
| | EtOAc | DXD2203-007-02 | Yellow solution | Yellow glass |
| | MeCN | DXD2203-007-03 | Light pink solution | Light pink glass |
| | THF | DXD2203-007-04 | Light pink solution | Light pink glass |
| | IPA | DXD2203-007-05 | Light pink solution | Light pink glass |
| | 5% water EtOH | DXD2203-007-06 | Light pink solution | Light pink glass |
| Oxalic acid | Acetone | DXD2203-007-07 | Off white precipitate | N/A |
| | EtOAc | DXD2203-007-08 | White precipitate | N/A |
| | MeCN | DXD2203-007-09 | Off white precipitate | N/A |
| | THF | DXD2203-007-10 | Off white precipitate | N/A |
| | IPA | DXD2203-007-11 | Off white precipitate | N/A |
| | 5% water:EtOH | DXD2203-007-12 | Off white precipitate | N/A |
| 2-hydroxy ethanesulfonic acid | Acetone | DXD2203-007-13 | Light yellow solution | Yellow glass |
| | EtOAc | DXD2203-007-14 | Light yellow solution | Yellow glass |
| | MeCN | DXD2203-007-15 | Light pink solution | Light pink glass |
| | THF | DXD2203-007-16 | Light pink solution | Light pink glass |
| | IPA | DXD2203-007-17 | Light pink solution | Light pink glass |
| | 5% water:EtOH | DXD2203-007-18 | Light pink solution | Light pink glass |
| L-glutamic acid | Acetone | DXD2203-007-19 | Light yellow solution + undissolved acid | N/A |
| | EtOAc | DXD2203-007-20 | Light yellow-solution + undissolved acid | N/A |
| | MeCN | DXD2203-007-21 | Light yellow-solution + undissolved acid | N/A |

TABLE 7-continued

Outcome summary of experiments. Set-2

| Acid | Solvent | Batch | After thermal cycling | After evaporation to dryness |
|---|---|---|---|---|
| | THF | DXD2203-007-22 | Light yellow solution + undissolved acid | N/A |
| | IPA | DXD2203-007-23 | Light yellow solution + undissolved acid | N/A |
| | 5% water:EtOH | DXD2203-007-24 | Light yellow solution + undissolved acid | N/A |
| Ketoglutaric acid | Acetone | DXD2203-007-25 | Light yellow solution | Light yellow glass |
| | EtOAc | DXD2203-007-26 | Light yellow solution | Light yellow glass |
| | MeCN | DXD2203-007-27 | Light yellow-solution | Light yellow glass |
| | THF | DXD2203-007-28 | Light yellow-solution | Light yellow glass |
| | IPA | DXD2203-007-29 | Light yellow solution | Light yellow glass |
| | 5% water:EtOH | DXD2203-007-30 | Light yellow solution | Light yellow glass |
| L-malic acid | Acetone | DXD2203-007-31 | Yellow solution | Yellow glass |
| | EtOAc | DXD2203-007-32 | Yellow solution | Yellow glass |
| | MeCN | DXD2203-007-33 | Yellow solution | Yellow glass |
| | THF | DXD2203-007-34 | Yellow solution | Yellow glass |
| | IPA | DXD2203-007-35 | Yellow solution | Yellow glass |
| | 5% water:EtOH | DXD2203-007-36 | Yellow solution | Yellow glass |
| Glycolic acid | Acetone | DXD2203-007-37 | Yellow solution | Yellow glass |
| | EtOAc | DXD2203-007-38 | Yellow solution | Yellow glass |
| | MeCN | DXD2203-007-39 | Yellow solution | Yellow glass |
| | THF | DXD2203-007-40 | Yellow solution | Yellow glass |
| | IPA | DXD2203-007-41 | Yellow solution | Yellow glass |
| | 5% water:EtOH | DXD2203-007-42 | Yellow solution | Yellow glass |
| Adipic acid | Acetone | DXD2203-007-43 | Yellow solution | Yellow glass |
| | EtOAc | DXD2203-007-44 | Off white precipitate | N/A |
| | MeCN | DXD2203-007-45 | Yellow solution | Yellow glass |
| | THF | DXD2203-007-46 | Yellow solution | Yellow glass |
| | IPA | DXD2203-007-47 | Yellow solution | Yellow glass |
| | 5% water:EtOH | DXD2203-007-48 | Yellow solution | Yellow glass |
| Acetic acid | Acetone | DXD2203-007-49 | Light yellow solution | Light yellow glass |
| | EtOAc | DXD2203-007-50 | Yellow solution | Yellow glass |
| | MeCN | DXD2203-007-51 | Yellow solution | Yellow glass |
| | THF | DXD2203-007-52 | Yellow solution | Yellow glass |
| | IPA | DXD2203-007-53 | Yellow solution | Yellow glass |
| | 5% water:EtOH | DXD2203-007-54 | Yellow solution | Yellow glass |
| Propionic acid | Acetone | DXD22 03-007-55 | Light yellow solution | Light yellow glass |
| | EtOAc | DXD2203-007-56 | Yellow solution | Yellow glass |
| | MeCN | DXD2203-007-57 | Yellow solution | Yellow solution |
| | THF | DXD2203-007-58 | Yellow solution | Yellow solution |
| | IPA | DXD2203-007-59 | Yellow solution | Yellow solution |
| | 5% water:EtOH | DXD2203-007-60 | Yellow solution | Yellow solution |
| Hippuric acid | Acetone | DXD2203-007-61 | Light yellow solution | Light yellow glass |
| | EtOAc | DXD2203-007-62 | Light yellow solution | Light yellow glass |
| | MeCN | DXD2203-007-63 | Light yellow solution | Light yellow glass |
| | THF | DXD2203-007-64 | Light yellow solution | Light yellow glass |
| | IPA | DXD2203-007-65 | Light yellow solution | Light yellow glass |
| | 5% water:EtOH | DXD2203-007-66 | Light yellow solution | Light yellow glass |
| Saccharin | Acetone | DXD2203-007-67 | Yellow solution | Light yellow glass |
| | EtOAc | DXD2203-007-68 | Yellow solution | Light yellow glass |
| | MeCN | DXD2203-007-69 | Yellow solution | Light yellow glass |
| | THF | DXD2203-007-70 | Yellow solution | Light yellow glass |
| | IPA | DXD2203-007-71 | Yellow solution | Light yellow glass |
| | 5% water:EtOH | DXD2203-007-72 | Yellow solution | Light yellow glass |

Phosphate Salt

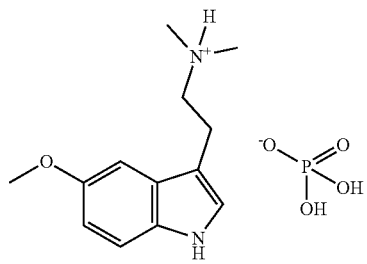

Figure 6:
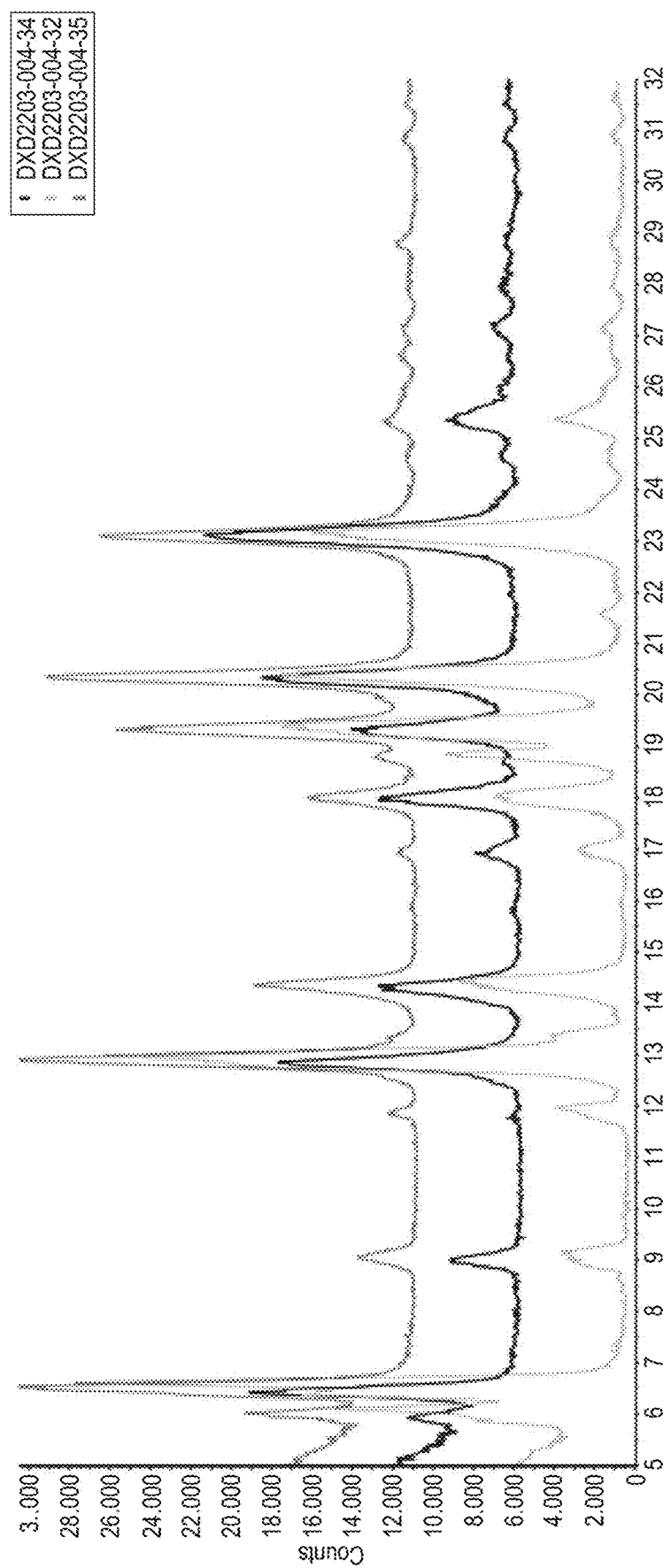
FIG. 6. XRPD Diffractograms of Phosphate salt isolated from IPA (blue trace, top), THF (black trace, middle) and Ethyl Acetate (red trace, bottom).

The Phosphate salt showed the same crystalline XRPD pattern for all three solids isolated from different solvents as displayed in FIG. 6. This crystalline form was nominated as pattern 1 and XRPD peak data are tabulated in Table 8, Table 8a or Table 8b.

TABLE 8

XRPD Peak data for Phosphate pattern 1.

| Peak No. | Angle 2 θ | d Value | Rel. intensity |
|---|---|---|---|
| 1 | 6.012° | 14.690 | 0.296 |
| 2 | 6.529° | 13.527 | 0.961 |
| 3 | 9.045° | 9.769 | 0.142 |
| 4 | 11.855° | 7.459 | 0.061 |
| 5 | 12.888° | 6.863 | 1.000 |
| 6 | 14.357° | 6.165 | 0.404 |
| 7 | 16.929° | 5.233 | 0.042 |
| 8 | 18.004° | 4.923 | 0.253 |
| 9 | 18.809° | 4.714 | 0.087 |
| 10 | 19.319° | 4.591 | 0.748 |
| 11 | 20.353° | 4.360 | 0.922 |
| 12 | 23.104° | 3.847 | 0.795 |
| 13 | 24.607° | 3.615 | 0.012 |
| 14 | 25.343° | 3.512 | 0.068 |
| 15 | 26.625° | 3.345 | 0.036 |
| 16 | 27.128° | 3.284 | 0.025 |
| 17 | 27.982° | 3.136 | 0.018 |
| 18 | 28.784° | 3.099 | 0.039 |
| 19 | 30.815° | 2.899 | 0.032 |
| 20 | 31.505° | 2.837 | 0.016 |

TABLE 8a

XRPD Peak data for Phosphate pattern 1 (2 d.p.).

| Peak No. | Angle 2 θ | d Value | Rel. intensity |
|---|---|---|---|
| 1 | 6.01° | 14.69 | 0.30 |
| 2 | 6.53° | 13.53 | 0.96 |
| 3 | 9.05° | 9.77 | 0.14 |
| 4 | 11.86° | 7.46 | 0.06 |
| 5 | 12.89° | 6.86 | 1.00 |
| 6 | 14.36° | 6.17 | 0.40 |
| 7 | 16.93° | 5.23 | 0.04 |
| 8 | 18.00° | 4.92 | 0.25 |
| 9 | 18.81° | 4.71 | 0.09 |
| 10 | 19.32° | 4.59 | 0.75 |
| 11 | 20.35° | 4.36 | 0.92 |
| 12 | 23.1° | 3.85 | 0.80 |
| 13 | 24.61° | 3.62 | 0.01 |
| 14 | 25.34° | 3.51 | 0.07 |
| 15 | 26.63° | 3.35 | 0.04 |
| 16 | 27.13° | 3.28 | 0.03 |
| 17 | 27.98° | 3.19 | 0.02 |
| 18 | 28.78° | 3.10 | 0.04 |
| 19 | 30.82° | 2.90 | 0.03 |
| 20 | 31.51° | 2.34 | 0.02 |

TABLE 8b

XRPD Peak data for Phosphate pattern 1 (1 d.p.).

| Peak No. | Angle 2 θ | d Value | Rel. intensity |
|---|---|---|---|
| 1 | 6.0° | 14.7 | 0.3 |
| 2 | 6.5° | 13.5 | 1.0 |
| 3 | 9.0° | 9.8 | 0.1 |
| 4 | 11.9° | 7.5 | 0.1 |
| 5 | 12.9° | 6.9 | 1.0 |
| 6 | 14.4° | 6.2 | 0.4 |
| 7 | 16.9° | 5.2 | 0.0 |
| 8 | 18.0° | 4.9 | 0.3 |
| 9 | 18.3° | 4.7 | 0.1 |
| 10 | 19.3° | 4.6 | 0.7 |
| 11 | 20.4° | 4.4 | 0.9 |
| 12 | 23.1° | 3.8 | 0.8 |
| 13 | 24.6° | 3.6 | 0.0 |
| 14 | 25.3° | 3.5 | 0.1 |
| 15 | 26.6° | 3.3 | 0.0 |
| 16 | 27.1° | 3.3 | 0.0 |
| 17 | 28.0° | 3.2 | 0.0 |
| 18 | 28.3° | 3.1 | 0.0 |
| 19 | 30.8° | 2.9 | 0.0 |
| 20 | 31.5° | 2.8 | 0.0 |

Figure 7:
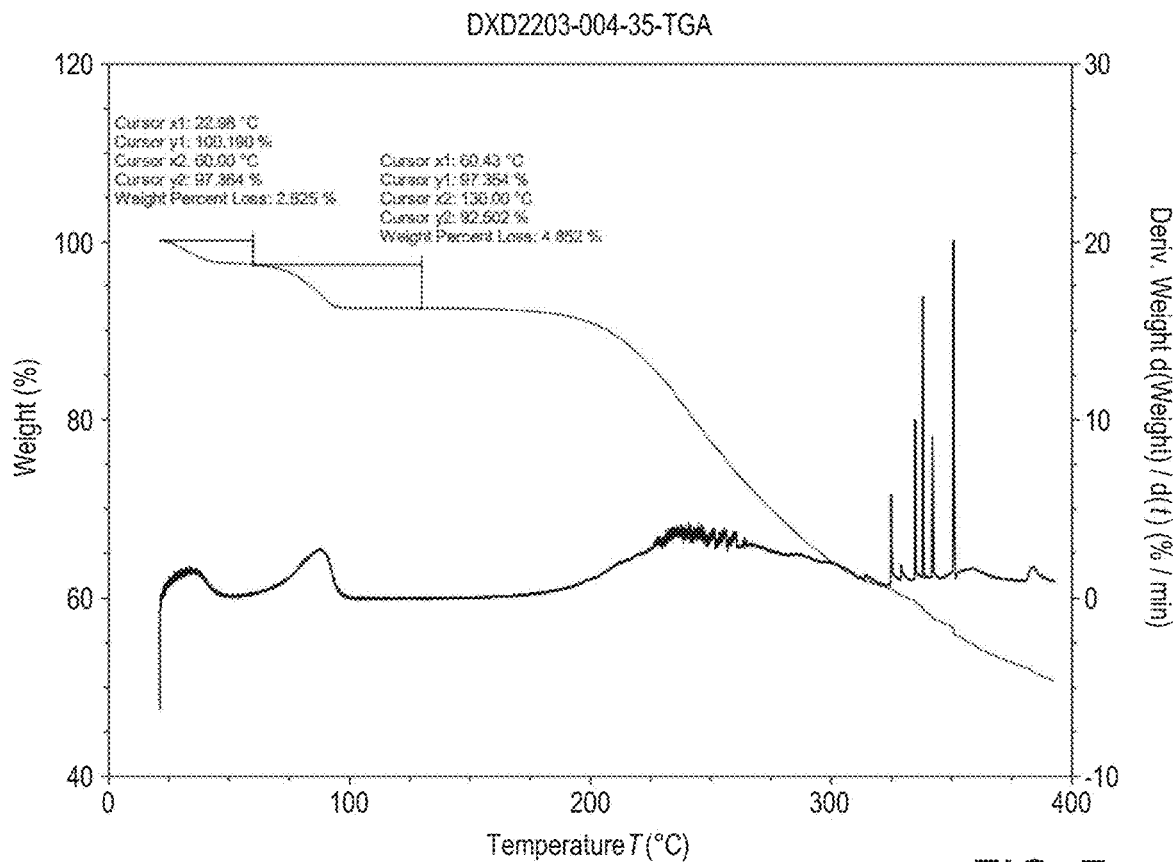
FIG. 7. TGA Thermogram of Phosphate salt, Batch: DXD2203-04-35.

The TGA thermogram of Phosphate salt presented in FIG. 7 displayed a two-step weight loss before the thermal decomposition. From ambient temperature to 60° C. the weight loss of 2.8%, which corresponds to loss of IPA (~0.15 eq) from surface of particles. The second weight loss of 4.9% between 60 to 130° C. is due to dehydration of ~0.9 eq of water.

Figure 8:
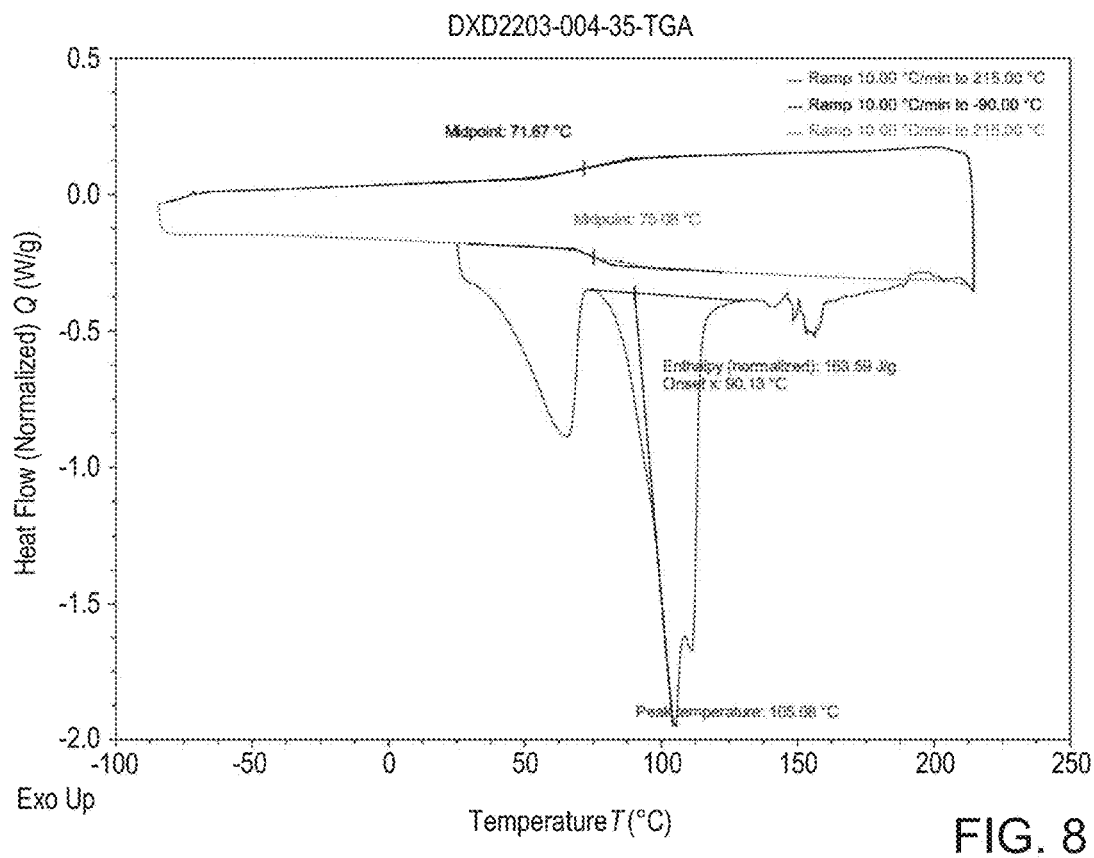
FIG. 8. Heat-cool-reheat DSC thermogram of Phosphate salt, 1st heating (blue trace), cooling ramp (green trace) and 2nd heating (red trace), Batch: DXD2203-004-35.

The 1st heating DSC thermogram in FIG. 8 displayed a broad endotherm corresponding to desolvation/dehydration process. The melting endothermic event of the Phosphate salt with $T_{onst}$ around 90.1° C. and heat of fusion 163.6 J/g is followed by the thermal degradation of the material. The cooling ramp of 10° C./min from 215° C. to −90° C. displayed a vitrification around 71.7° C. and the 2nd heat cycle the glass transition around 75.1° C.

Figure 9:
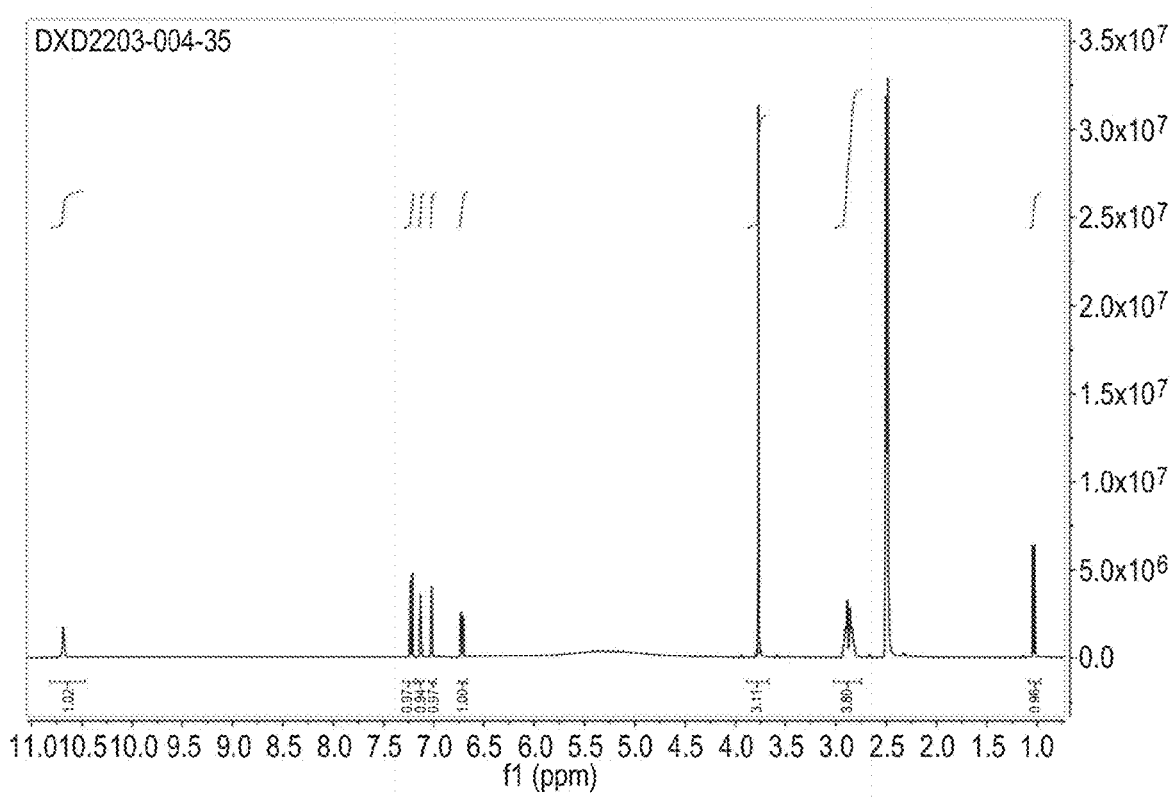
FIG. 9. 1H NMR (d6-DMSO) Spectrum of Phosphate salt, Batch: DXD2203-004-35

The $^1$H NMR spectrum of Phosphate salt in $d_6$-DMSO solvent is shown in FIG. 9. Proton chemical shift changes when compared to $^1$H NMR spectrum of free base indicate salt formation. Approximately 0.16 eq of IPA solvent was observed.

Figure 10:
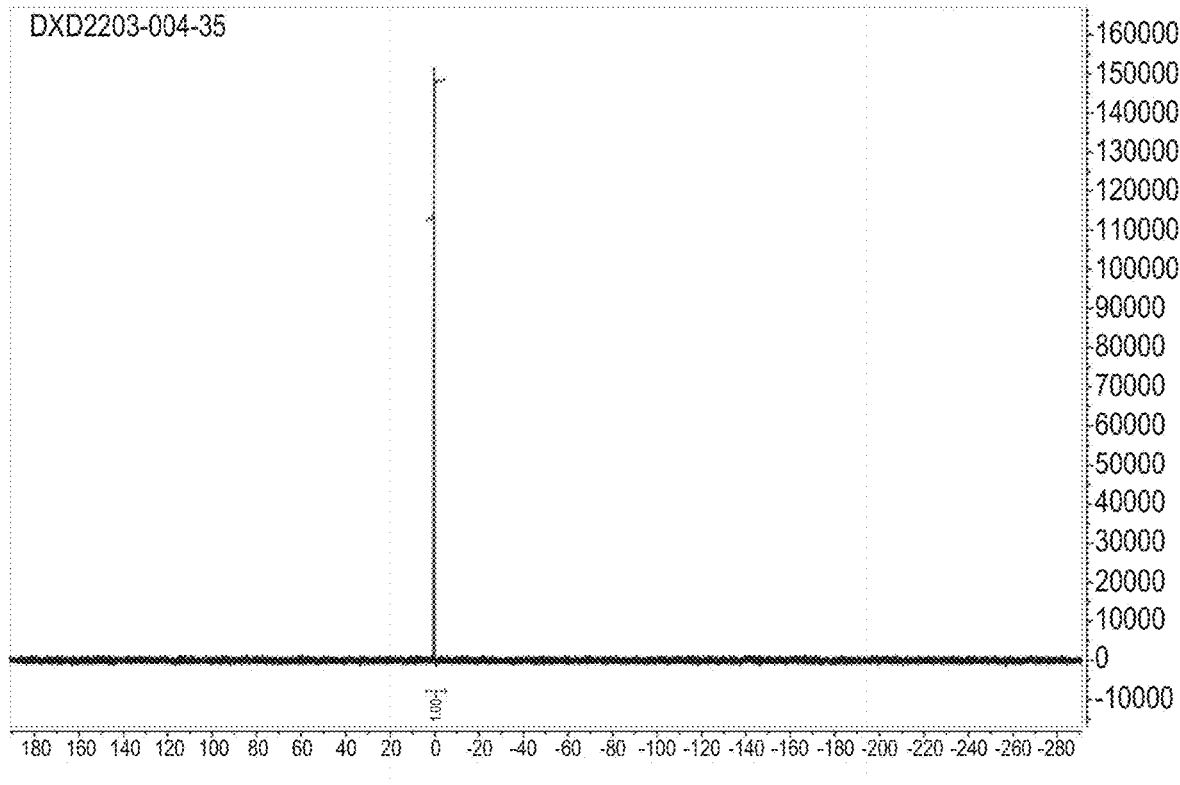
FIG. 10. 31P NMR (d6-DMSO) Spectrum of Phosphate salt, Batch: DXD2203-004-35

The $^{31}$P NMR spectrum of Phosphate salt in $d_6$-DMSO shows a singlet peak at around 0 ppm, confirming the presence of phosphoric acid as displayed in FIG. 10.

Figure 11:
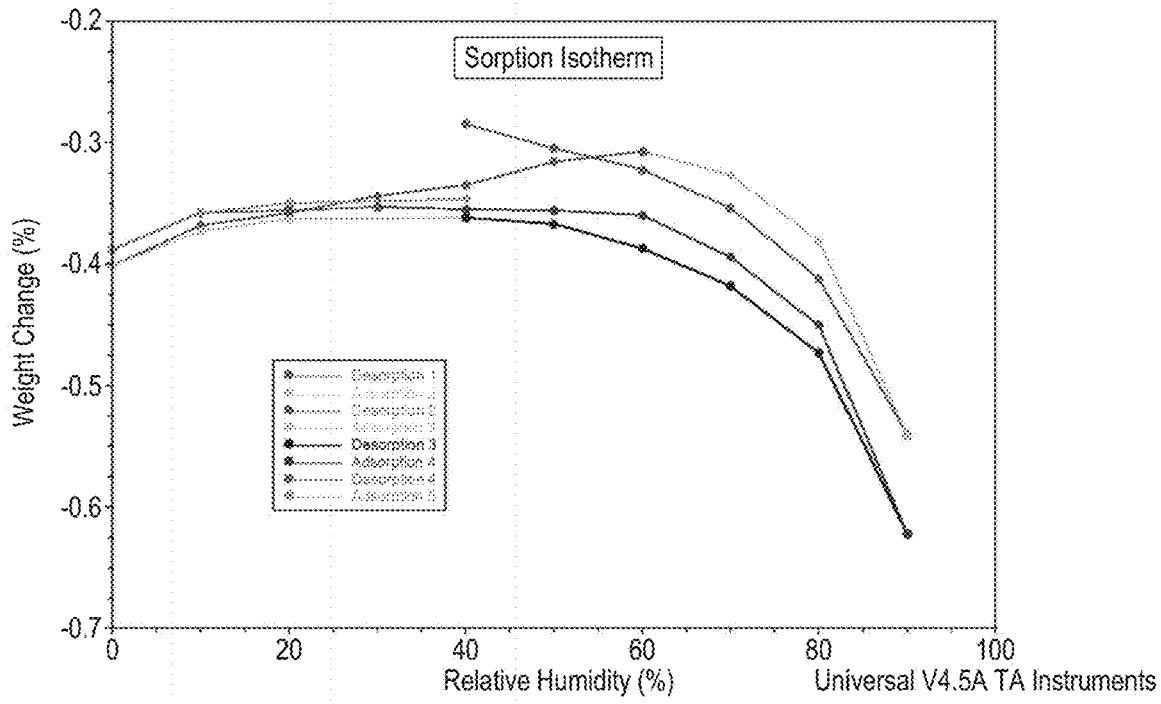
FIG. 11. DVS Isotherm plot of Phosphate salt, Batch: DXD2203-004-35.

DVS analysis was performed using a small sample mass due to material constraints. The sample shows no evidence of form change and only shows evidence of the material drying out. It would be wise to repeat this experiment if more material becomes available. FIG. 11 displays DVS Isotherm plot of Phosphate salt.

Figure 12:
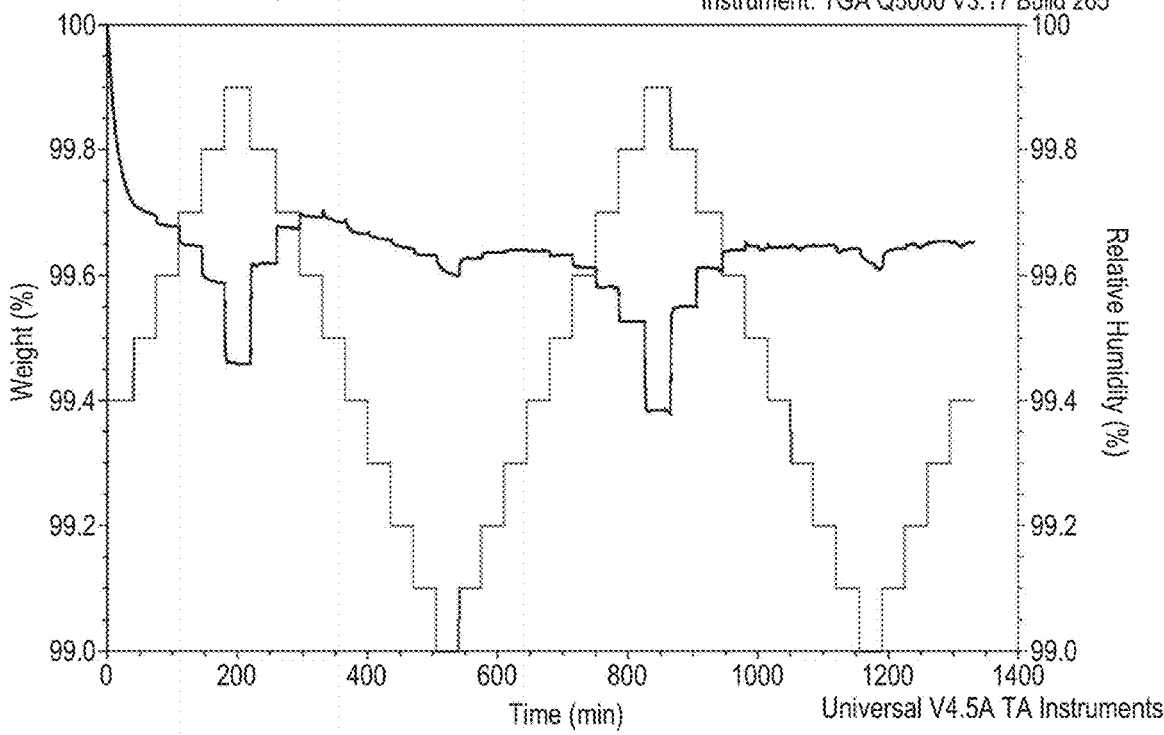
FIG. 12. DVS Kinetic plot of Phosphate salt, Batch: DXD2203-004-35.

The DVS kinetic plot of Phosphate salt DXD220-004-35 is shown in FIG. 12. It can be seen from the XRPD diffractogram in FIG. 13 that the post DVS Phosphate salt is missing peaks at around 5.9, 11.9 and 18.8 2θ when compared to the input material as indicated by arrows. Also, the post DVS sample displayed a new shoulder at around 12.6 and 19.9 2θ, respectively as indicated by asterisks, which are not characteristics of free base.

In one embodiment, there is provided 5-MeO-DMT phosphate. In one embodiment, there is provided a pharmaceutical composition comprising 5-MeO-DMT phosphate. In one embodiment, there is provided crystalline 5-MeO-DMT phosphate, or a pharmaceutical composition comprising crystalline 5-MeO-DMT phosphate, as characterised by one or more of:

An XRPD pattern as shown in, or substantially as shown in, FIG. 6;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty peaks in an XRPD diffractogram as detailed in Table 8, Table 8a or Table 8b;

One or more, two or more, three or more, four or more, five or more peaks in an XRPD diffractogram with a relative intensity of over 0.1, 0.2, 0.3, 0.4, 0.5, 0.6, 0.7, 0.8 or 0.9 as detailed in Table 8, Table 8a or Table 8b;

A TGA thermogram as shown in, or substantially as shown in, FIG. 7;

A weight loss of 2.8% between ambient temperature and 60° C., as measured by TGA thermogram;

A weight loss of between 1.5 to 3.5% between ambient temperature and 60° C., as measured by TGA thermogram;

A weight loss of 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4 or 3.5% between ambient temperature and 60° C., as measured by TGA thermogram;

A weight loss of 4.9% between 60 to 130° C., as measured by TGA thermogram;

A weight loss of between 3.5 to 6.5% between 60 to 130° C., as measured by TGA thermogram;

A weight loss of 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4 or 6.5% between 60 and 130° C., as measured by TGA thermogram;

A DSC thermogram as shown in, or substantially as shown in, FIG. 8;

A melting endothermic event with an onset of around 90.1° C. and a heat of fusion of 163.6 J/g, as measured in a DSC thermogram;

A melting endothermic event with an onset of around 85 to 95° C. and a heat of fusion of around 155 to 170 J/g, as measured in a DSC thermogram;

A melting endothermic event with an onset of around 85, 86, 87, 88, 89, 90, 91, 92, 93, 94 or 95° C. and a heat of fusion of around 155, 156, 157, 158, 159, 160, 161, 162, 163, 164, 165, 166, 167, 168, 169 or 170 J/g, as measured in a DSC thermogram;

A vitrification around 71.7° C., as measured in a DSC thermogram with a cooling ramp of 10° C./min from 215° C. to −90° C.;

A vitrification around 65-75° C., as measured in a DSC thermogram with a cooling ramp of 10° C./min from 215° C. to −90° C.;

A vitrification around 65, 66, 67, 68, 69, 70, 71, 72, 73, 74 or 75° C., as measured in a DSC thermogram with a cooling ramp of 10° C./min from 215° C. to −90° C.;

A glass transition around 75.1° C., as measured in a DSC thermogram with a cooling ramp of 10° C./min from 215° C. to −90° C.;

A glass transition around 70-80° C., as measured in a DSC thermogram with a cooling ramp of 10° C./min from 215° C. to −90° C.;

A glass transition around 70, 71, 72, 73, 74, 75, 76, 77, 78, 79 or 80° C., as measured in a DSC thermogram with a cooling ramp of 10° C./min from 215° C. to −90° C.;

A $^1$H NMR spectrum as shown in, or substantially as shown in, FIG. 9;

A $^{31}$P NMR spectrum as shown in, or substantially as shown in, FIG. 10;

A DVS isotherm as shown in, or substantially as shown in, FIG. 11; and/or

A DVS kinetic plot as shown in, or substantially as shown in, FIG. 12.

Figure 13:
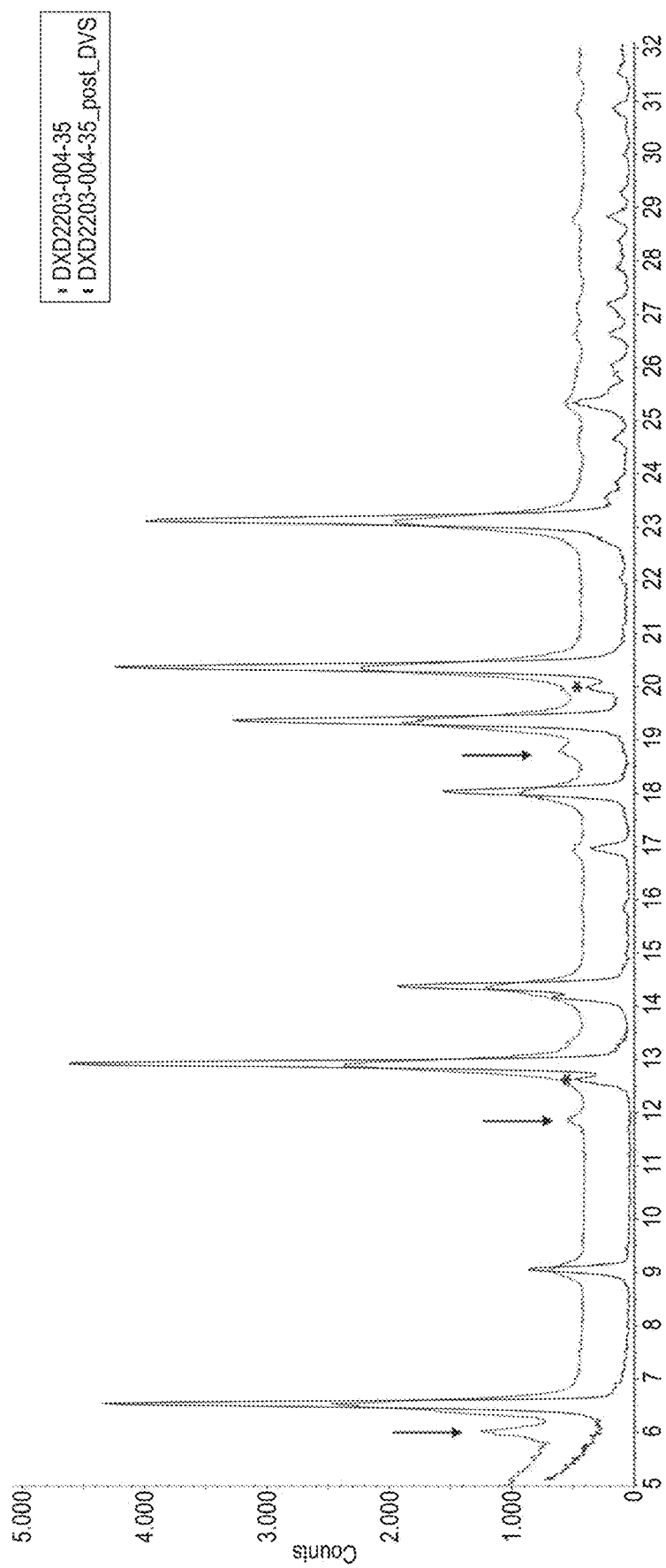
FIG. 13. XRPD Diffractograms of Phosphate salt, Batch: DXD2203-004-35 (red trace, top) and post-DVS (black trace, bottom).

In one embodiment, there is provided crystalline 5-MeO-DMT phosphate, or a pharmaceutical composition comprising crystalline 5-MeO-DMT phosphate, as characterised by an XRPD pattern as shown in, or substantially as shown in, FIG. 13.

Fumarate Salt

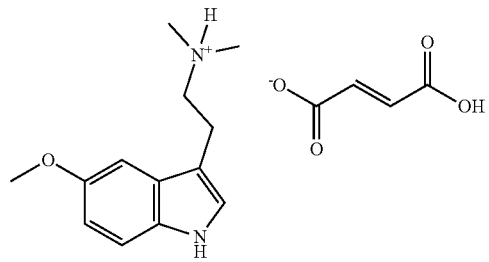

Figure 14:
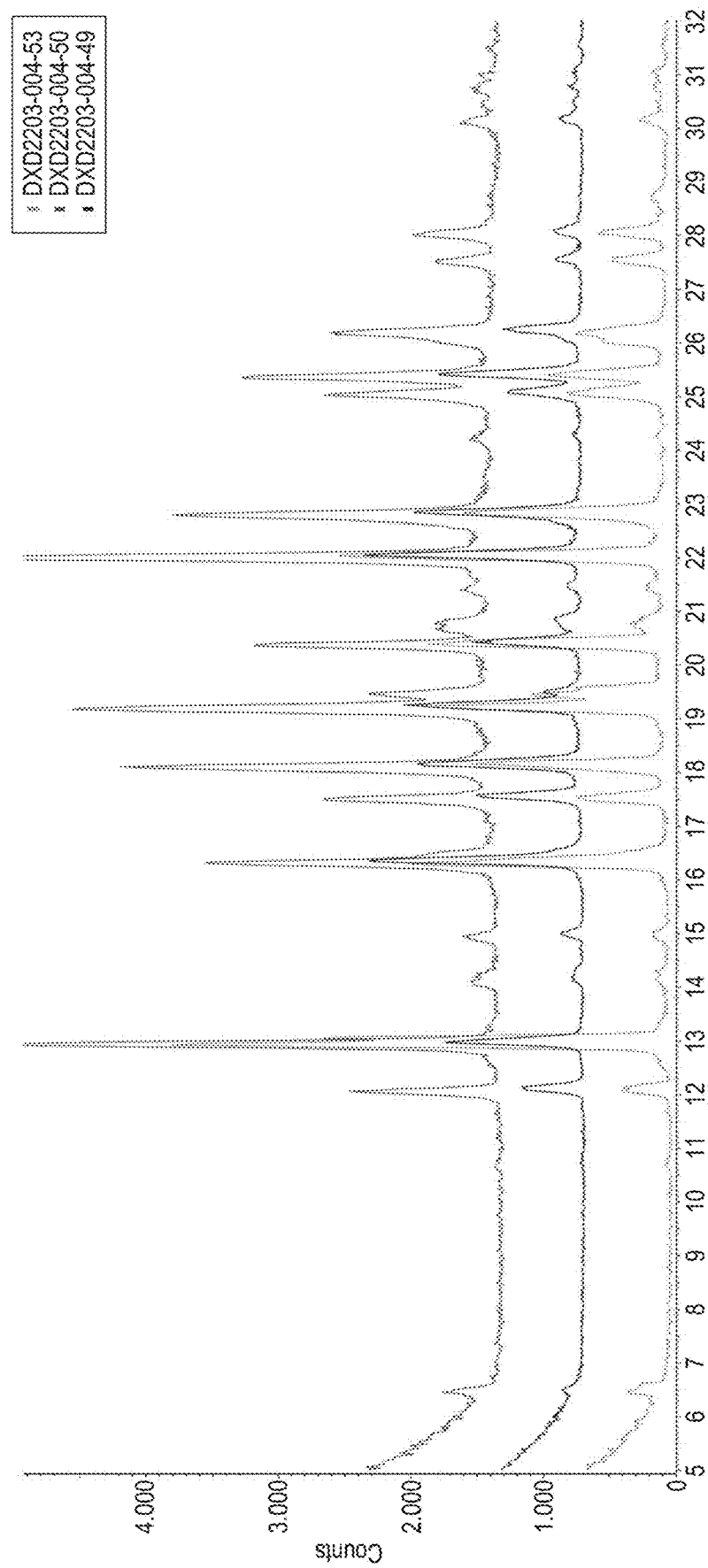
FIG. 14. XRPD Diffractograms of Fumarate salt isolated from Ethyl Acetate (red trace, top), Acetone (black trace, middle) and IPA (blue trace, bottom).

The XRPD results shown in FIG. 14 confirmed the crystallinity of Fumarate salt. All three isolated samples from different solvents displayed the same crystalline pattern. This was nominated as pattern 1 with XRPD data peak presented in Table 9, Table 9a or Table 9b.

TABLE 9

XRPD data peak for Fumarate pattern 1.

| Peak No. | Angle 2 θ | d Value | Rel. intensity |
| --- | --- | --- | --- |
| 1 | 5.911° | 14.940 | 0.015 |
| 2 | 6.459° | 13.673 | 0.073 |
| 3 | 10.694° | 8.266 | 0.012 |
| 4 | 12.107° | 7.305 | 0.104 |
| 5 | 12.981° | 6.815 | 1.000 |
| 6 | 14.203° | 6.231 | 0.021 |
| 7 | 14.975° | 5.911 | 0.034 |
| 8 | 16.304° | 5.432 | 0.673 |
| 9 | 17.532° | 5.055 | 0.233 |
| 10 | 18.166° | 4.879 | 0.498 |
| 11 | 19.220° | 4.614 | 0.604 |
| 12 | 19.443° | 4.561 | 0.345 |
| 13 | 20.396° | 4.351 | 0.598 |
| 14 | 20.783° | 4.271 | 0.073 |
| 15 | 21.487° | 4.132 | 0.037 |
| 16 | 22.052° | 4.028 | 0.859 |
| 17 | 22.834° | 3.891 | 0.523 |
| 18 | 24.255° | 3.667 | 0.015 |
| 19 | 25.064° | 3.550 | 0.243 |
| 20 | 25.410° | 3.502 | 0.310 |
| 21 | 26.116° | 3.409 | 0.200 |
| 22 | 27.542° | 3.236 | 0.135 |
| 23 | 28.051° | 3.178 | 0.174 |
| 24 | 28.709° | 3.107 | 0.035 |
| 25 | 30.166° | 2.960 | 0.071 |
| 26 | 30.482° | 2.930 | 0.024 |
| 27 | 30.764° | 2.904 | 0.031 |
| 28 | 31.022° | 2.880 | 0.034 |
| 29 | 31.555° | 2.833 | 0.008 |

TABLE 9a

XRPD data peak for Fumarate pattern 1 (2 d.p.).

| Peak No. | Angle 2 θ | d Value | Rel. intensity |
|---|---|---|---|
| 1 | 5.91° | 14.94 | 0.02 |
| 2 | 6.46° | 13.67 | 0.07 |
| 3 | 10.69° | 8.27 | 0.01 |
| 4 | 12.11° | 7.31 | 0.10 |
| 5 | 12.98° | 6.82 | 1.00 |
| 6 | 14.20° | 6.23 | 0.02 |
| 7 | 14.98° | 5.91 | 0.03 |
| 8 | 16.30° | 5.43 | 0.67 |
| 9 | 17.53° | 5.06 | 0.23 |
| 10 | 18.17° | 4.88 | 0.50 |
| 11 | 19.22° | 4.61 | 0.60 |
| 12 | 19.45° | 4.56 | 0.35 |
| 13 | 20.40° | 4.35 | 0.60 |
| 14 | 20.78° | 4.27 | 0.07 |
| 15 | 21.49° | 4.13 | 0.04 |
| 16 | 22.05° | 4.03 | 0.86 |
| 17 | 22.83° | 3.89 | 0.52 |
| 18 | 24.26° | 3.67 | 0.02 |
| 19 | 25.06° | 3.55 | 0.24 |
| 20 | 25.41° | 3.50 | 0.31 |
| 21 | 26.12° | 3.41 | 0.20 |
| 22 | 27.54° | 3.24 | 0.14 |
| 23 | 28.05° | 3.18 | 0.17 |
| 24 | 28.71° | 3.11 | 0.04 |
| 25 | 30.17° | 2.96 | 0.07 |
| 26 | 30.48° | 2.93 | 0.02 |
| 27 | 30.76° | 2.90 | 0.03 |
| 28 | 31.02° | 2.88 | 0.03 |
| 29 | 31.56° | 2.83 | 0.01 |

TABLE 9b

XRPD data peak for Fumarate pattern 1 (1 d.p.).

| Peak No. | Angle 2 θ | d Value | Rel. intensity |
|---|---|---|---|
| 1 | 5.9° | 14.9 | 0.0 |
| 2 | 6.5° | 13.7 | 0.1 |
| 3 | 10.7° | 8.3 | 0.0 |
| 4 | 12.1° | 7.3 | 0.1 |
| 5 | 13.0° | 6.8 | 1.0 |
| 6 | 14.2° | 6.2 | 0.0 |
| 7 | 15.0° | 5.9 | 0.0 |
| 8 | 16.3° | 5.4 | 0.7 |
| 9 | 17.5° | 5.1 | 0.2 |
| 10 | 18.2° | 4.9 | 0.5 |
| 11 | 19.2° | 4.6 | 0.6 |
| 12 | 19.4° | 4.6 | 0.3 |
| 13 | 20.4° | 4.4 | 0.6 |
| 14 | 20.8° | 4.3 | 0.1 |
| 15 | 21.5° | 4.1 | 0.0 |
| 16 | 22.1° | 4.0 | 0.9 |
| 17 | 22.8° | 3.9 | 0.5 |
| 18 | 24.3° | 3.7 | 0.0 |
| 19 | 25.1° | 3.6 | 0.2 |
| 20 | 25.4° | 3.5 | 0.3 |
| 21 | 26.1° | 3.4 | 0.2 |
| 22 | 27.5° | 3.2 | 0.1 |
| 23 | 28.1° | 3.2 | 0.2 |
| 24 | 28.7° | 3.1 | 0.0 |
| 25 | 30.2° | 3.0 | 0.1 |
| 26 | 30.5° | 2.9 | 0.0 |
| 27 | 30.8° | 2.9 | 0.0 |
| 28 | 31.0° | 2.9 | 0.0 |
| 29 | 31.6° | 2.8 | 0.0 |

Figure 15:
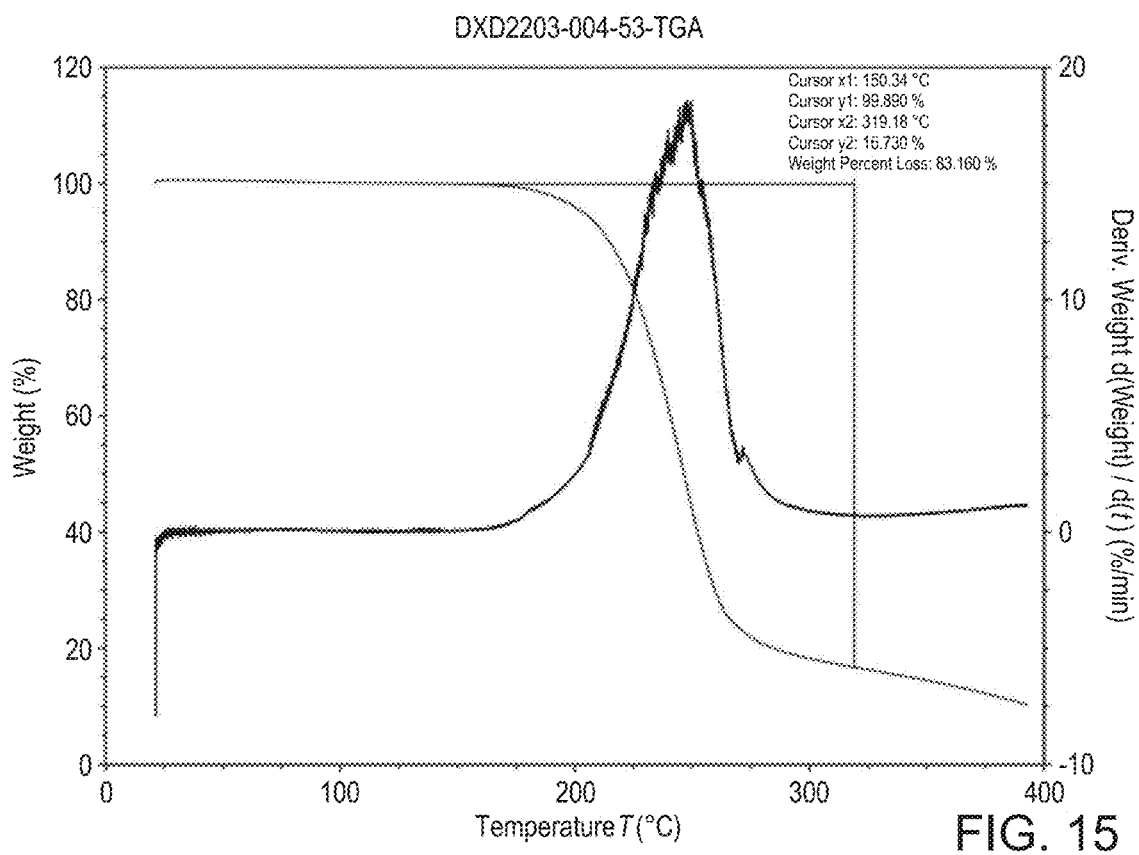
FIG. 15. TGA Thermogram of Fumarate salt, Batch: DXD2203-004-53.

The TGA thermogram of Fumarate salt presented in FIG. 15, displayed no presence of residual solvents and good thermal stability up to 150° C.

The 1st heating DSC data showed two small endothermic events around 93.7° C. and 134.0° C. respectively, corresponding to solid-state transformations. The sharp endotherm with $T_{onst}$ around 176.5° C. and heat of fusion 92.3 J/g corresponds to melting, followed by the thermal degradation of the Fumarate salt as demonstrated in FIG. 16.

Figure 17:
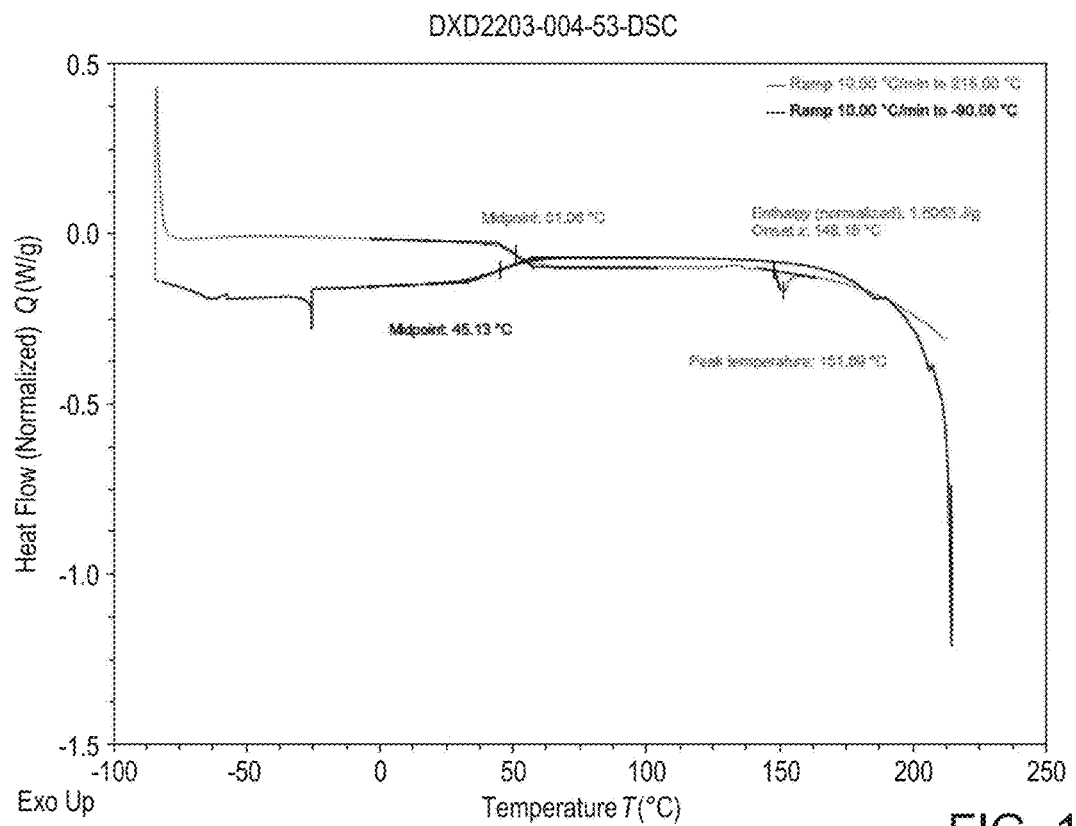
FIG. 17. DSC Thermograms of Fumarate salt, cooling (green trace) and 2nd heating (blue trace).

The 10° C./min cooling ramp from 215° C. to −90° C. displayed a vitrification around 45.1° C. and the 2nd heating cycle exhibited a glass transition around 51.1° C. as shown in, or substantially as shown in, FIG. 17.

Figure 18:
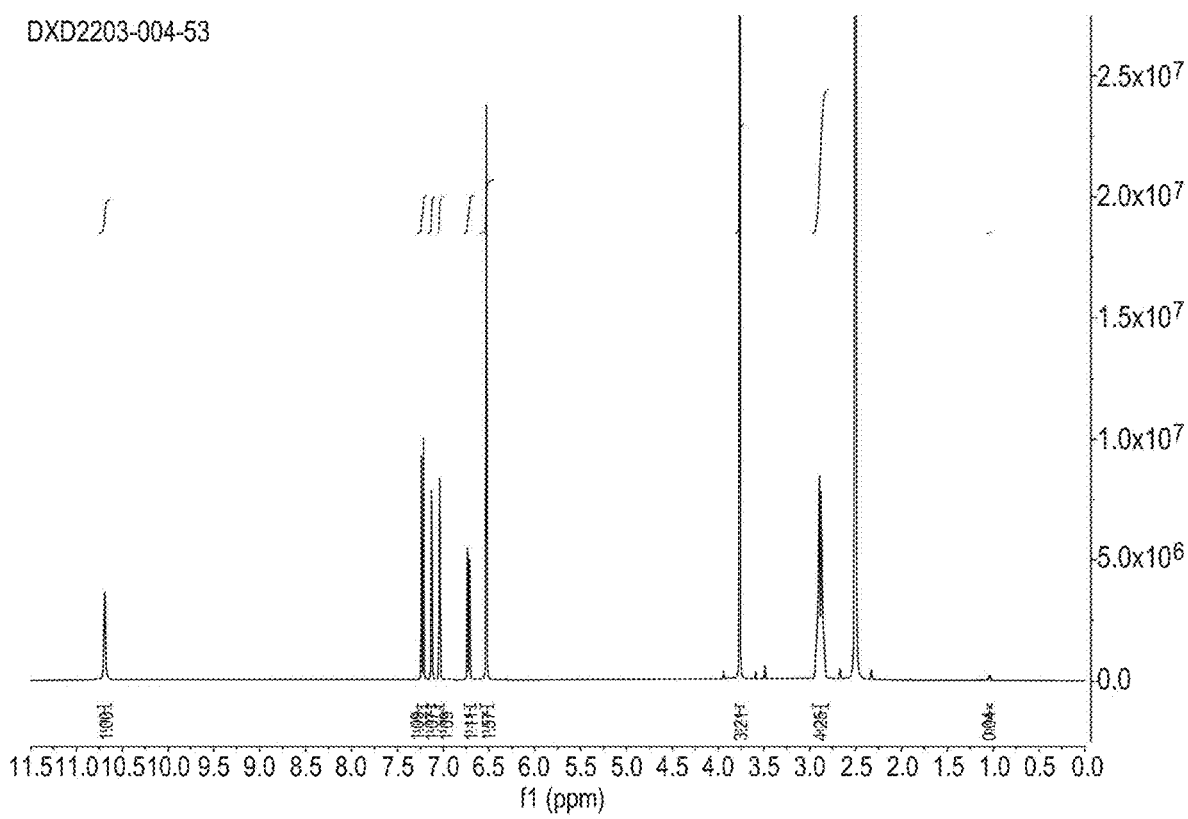
FIG. 18. 1H NMR (d6-DMSO) Spectrum of Fumarate salt, Batch: DXD2203-004-53.

The $^1$H NMR spectrum of Fumarate salt in $d_6$-DMSO shown in FIG. 18 displayed around 1.4 eq of fumaric acid present as well as traces of IPA solvent.

Figure 16:
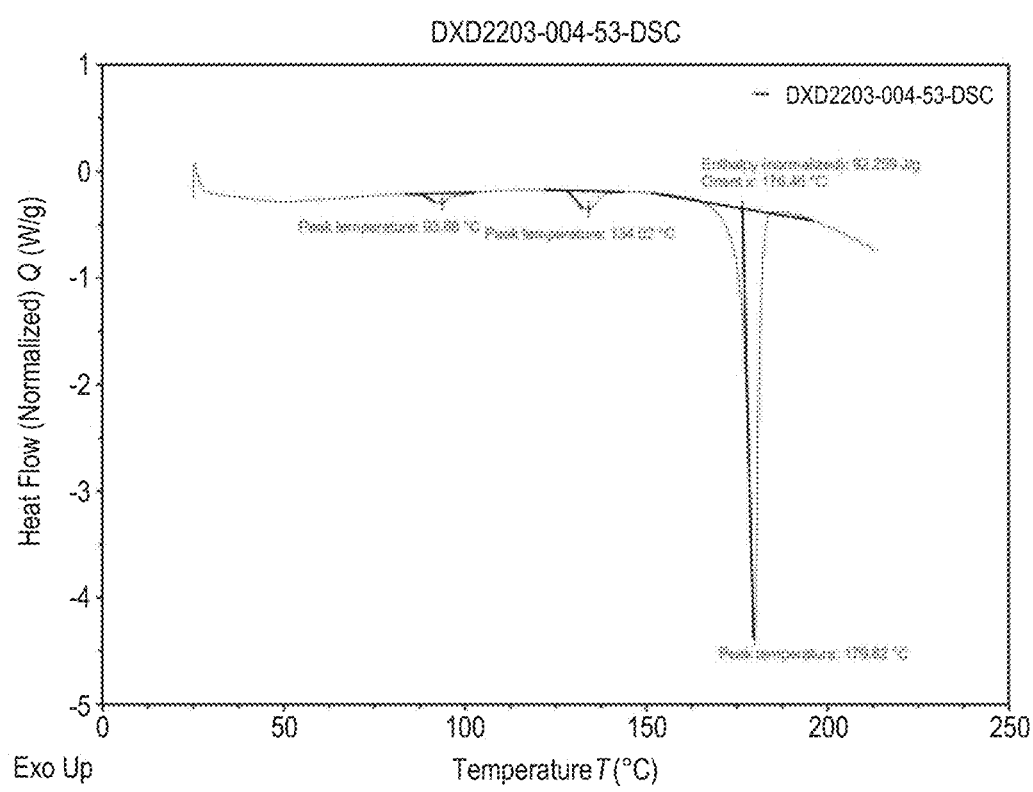
FIG. 16. DSC Thermogram (1st heating) of Fumarate salt, Batch: DXD2203-004-53.

In one embodiment, there is provided 5-MeO-DMT fumarate. In one embodiment, there is provided a pharmaceutical composition comprising 5-MeO-DMT fumarate. In one embodiment, there is provided crystalline 5-MeO-DMT fumarate, or a pharmaceutical composition comprising crystalline 5-MeO-DMT fumarate, as characterised by one or more of:

An XRPD pattern as shown in, or substantially as shown in, FIG. 14;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, or twenty nine peaks in an XRPD diffractogram as detailed in Table 9, Table 9a or Table 9b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 9, Table 9a or Table 9b;

A TGA thermogram as shown in, or substantially as shown in, FIG. 15;

A DSC thermogram as shown in, or substantially as shown in, FIG. 16;

Two small endothermic events around 93.7° C. and 134.0° C. respectively as measured in a DSC thermogram;

Two small endothermic events around 85-100° C. and 130-140° C. respectively as measured in a DSC thermogram;

Two small endothermic events around 85, 86, 87, 88, 89, 90, 91, 92, 93, 94, 95, 96, 97, 98, 99 or 100° C. and 130, 131, 132, 133, 134, 135, 136, 137, 138, 139 or 140° C. respectively as measured in a DSC thermogram;

A sharp endotherm with an onset of around 176.5° C. and heat of fusion 92.3 J/g as measured in a DSC thermogram;

A sharp endotherm with an onset of around 165-185° C. and heat of fusion about 88-100 J/g as measured in a DSC thermogram;

A sharp endotherm with an onset of around 165, 166, 167, 168, 169, 170, 171, 172, 173, 174, 175, 176, 177, 178, 179, 180, 181, 182, 183, 184, or 185° C. and heat of fusion about 88, 89, 90, 91, 92, 93, 94, 95, 96, 97, 98, 99, or 100 J/g as measured in a DSC thermogram;

A vitrification around 45.1° C., as measured in a DSC thermogram with a cooling ramp of 10° C./min from 215° C. to −90° C.;

A vitrification around 40-50° C., as measured in a DSC thermogram with a cooling ramp of 10° C./min from 215° C. to −90° C.;

A vitrification around 40, 41, 42, 43, 44, 45, 46, 47, 48, 49 or 50° C., as measured in a DSC thermogram with a cooling ramp of 10° C./min from 215° C. to −90° C.;

A glass transition around 51.1° C., as measured in a DSC thermogram with a cooling ramp of 10° C./min from 215° C. to −90° C.;

A glass transition around 45-55° C., as measured in a DSC thermogram with a cooling ramp of 10° C./min from 215° C. to −90° C.;

A glass transition around 45, 46, 47, 48, 49, 50, 51, 52, 53, 54 or 55° C., as measured in a DSC thermogram with a cooling ramp of 10° C./min from 215° C. to −90° C.; and/or A 1H NMR spectrum as shown in, or substantially as shown in, FIG. 18.

Oxalate Salt

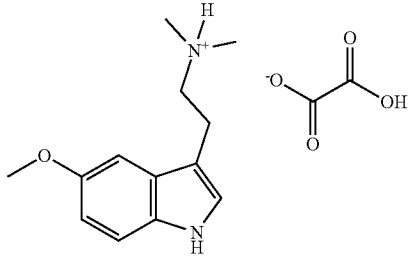

Figure 19:
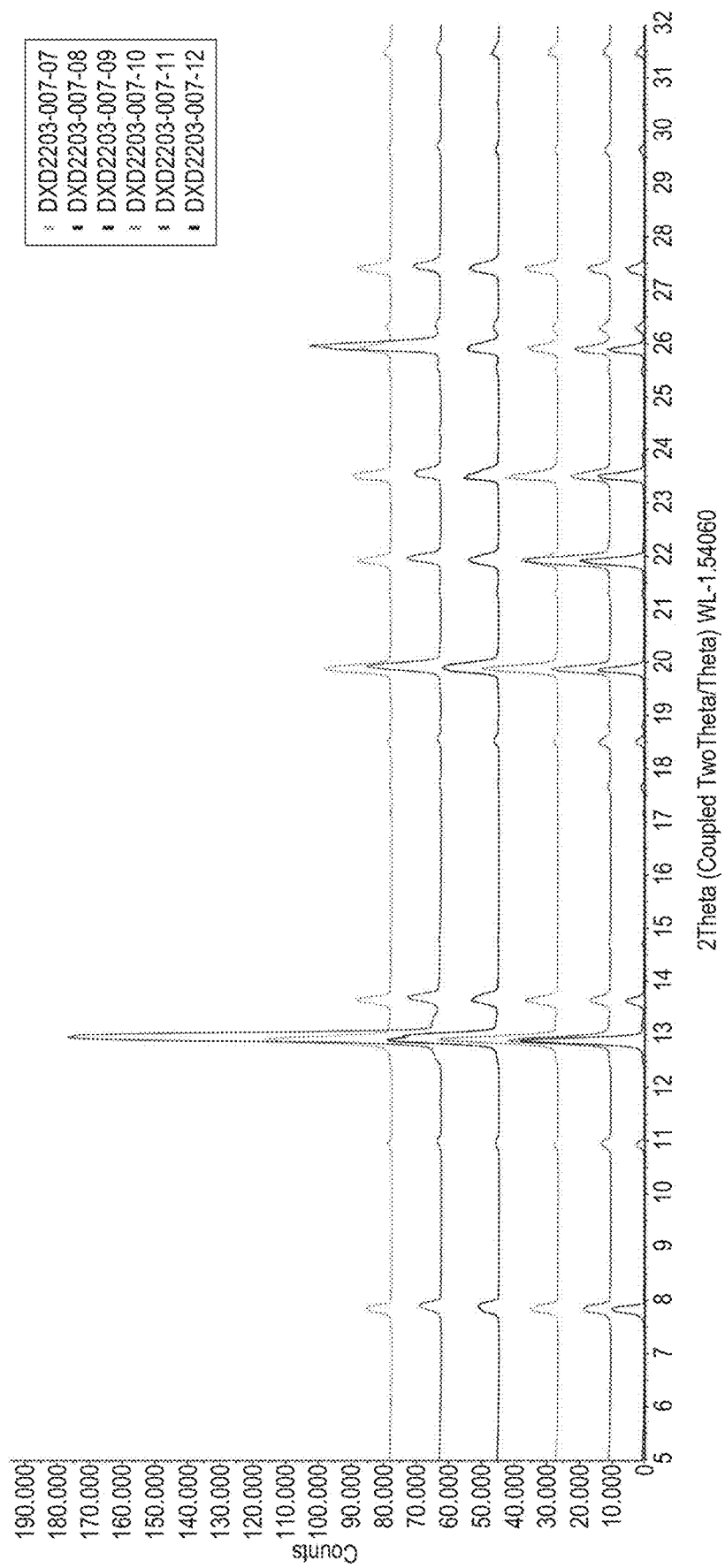
FIG. 19. XRPD Diffractograms of Oxalate salt isolated from (from top to bottom of the XRPD) acetone (pink trace), ethyl acetate (brown trace), acetonitrile (black trace), THF (red trace), IPA (blue trace) and 5% water: ethanol (green trace).

XRPD diffractograms of Oxalate salt displayed the same crystalline solid form for all samples as shown in, or substantially as shown in, FIG. 19. This was nominated as pattern 1 with XRPD data peak presented in Table 10, 10a and 10b.

TABLE 10

XRPD Peak data for Oxalate pattern 1.

| Peak No. | Angle 2 θ | d Value | Rel. intensity |
|---|---|---|---|
| 1 | 7.923° | 11.150 | 0.062 |
| 2 | 10.999° | 8.037 | 0.012 |
| 3 | 11.688° | 7.565 | 0.002 |
| 4 | 12.963° | 6.824 | 1.000 |
| 5 | 13.697° | 6.460 | 0.095 |
| 6 | 14.779° | 5.989 | 0.005 |
| 7 | 16.600° | 5.336 | 0.001 |
| 8 | 17.217° | 5.146 | 0.002 |
| 9 | 17.777° | 4.985 | 0.004 |
| 10 | 18.284° | 4.843 | 0.001 |
| 11 | 18.570° | 4.774 | 0.010 |
| 12 | 18.861° | 4.701 | 0.003 |
| 13 | 20.147° | 4.404 | 0.005 |
| 14 | 19.928° | 4.452 | 0.214 |
| 15 | 21.360° | 4.157 | 0.004 |
| 16 | 21.967° | 4.043 | 0.100 |
| 17 | 23.560° | 3.773 | 0.077 |
| 18 | 23.933° | 3.715 | 0.003 |
| 19 | 24.348° | 3.653 | 0.003 |
| 20 | 25.159° | 3.537 | 0.002 |
| 21 | 25.573° | 3.481 | 0.010 |
| 22 | 25.961° | 3.429 | 0.377 |
| 23 | 26.348° | 3.380 | 0.015 |
| 24 | 26.605° | 3.348 | 0.001 |
| 25 | 27.458° | 3.246 | 0.080 |
| 26 | 27.960° | 3.189 | 0.001 |
| 27 | 29.719° | 3.004 | 0.011 |
| 28 | 30.525° | 2.926 | 0.005 |
| 29 | 31.562° | 2.832 | 0.015 |

TABLE 10a

XRPD Peak data for Oxalate pattern 1 (2 d.p.).

| Peak No. | Angle 2 θ | d Value | Rel. intensity |
|---|---|---|---|
| 1 | 7.92° | 11.15 | 0.06 |
| 2 | 11.00° | 8.04 | 0.01 |
| 3 | 11.69° | 7.57 | 0.00 |
| 4 | 12.96° | 6.82 | 1.00 |
| 5 | 13.7° | 6.46 | 0.10 |
| 6 | 14.78° | 5.99 | 0.01 |
| 7 | 16.60° | 5.34 | 0.00 |
| 8 | 17.22° | 5.15 | 0.00 |
| 9 | 17.78° | 4.99 | 0.00 |
| 10 | 18.28° | 4.85 | 0.00 |
| 11 | 18.57° | 4.77 | 0.01 |
| 12 | 18.86° | 4.70 | 0.00 |
| 13 | 20.15° | 4.40 | 0.01 |
| 14 | 19.93° | 4.45 | 0.21 |
| 15 | 21.36° | 4.16 | 0.00 |
| 16 | 21.97° | 4.04 | 0.10 |
| 17 | 23.56° | 3.77 | 0.08 |
| 18 | 23.93° | 3.72 | 0.00 |
| 19 | 24.35° | 3.65 | 0.00 |
| 20 | 25.16° | 3.54 | 0.00 |
| 21 | 25.57° | 3.48 | 0.01 |
| 22 | 25.96° | 3.43 | 0.38 |
| 23 | 26.35° | 3.38 | 0.02 |
| 24 | 26.61° | 3.35 | 0.00 |
| 25 | 27.46° | 3.25 | 0.08 |
| 26 | 27.96° | 3.19 | 0.00 |
| 27 | 29.72° | 3.00 | 0.01 |
| 28 | 30.53° | 2.93 | 0.01 |
| 29 | 31.56° | 2.83 | 0.02 |

TABLE 10b

XRPD Peak data for Oxalate pattern 1 (1 d.p.).

| Peak No. | Angle 2 θ | d Value | Rel. intensity |
|---|---|---|---|
| 1 | 7.9° | 11.2 | 0.1 |
| 2 | 11.0° | 8.0 | 0.0 |
| 3 | 11.7° | 7.6 | 0.0 |
| 4 | 13.0° | 6.8 | 1.0 |
| 5 | 13.7° | 6.5 | 0.1 |
| 6 | 14.8° | 6.0 | 0.0 |
| 7 | 16.6° | 5.3 | 0.0 |
| 8 | 17.2° | 5.1 | 0.0 |
| 9 | 17.8° | 5.0 | 0.0 |
| 10 | 18.3° | 4.8 | 0.0 |
| 11 | 18.6° | 4.8 | 0.0 |
| 12 | 18.9° | 4.7 | 0.0 |
| 13 | 20.1° | 4.4 | 0.0 |
| 14 | 19.9° | 4.5 | 0.2 |
| 15 | 21.4° | 4.2 | 0.0 |
| 16 | 22.0° | 4.0 | 0.1 |
| 17 | 23.6° | 3.3 | 0.1 |
| 18 | 23.9° | 3.7 | 0.0 |
| 19 | 24.3° | 3.7 | 0.0 |
| 20 | 25.2° | 3.5 | 0.0 |
| 21 | 25.6° | 3.5 | 0.0 |
| 22 | 26.0° | 3.4 | 0.4 |
| 23 | 26.3° | 3.4 | 0.0 |
| 24 | 26.6° | 3.3 | 0.0 |
| 25 | 27.5° | 3.2 | 0.1 |
| 26 | 28.0° | 3.2 | 0.0 |
| 27 | 29.7° | 3.0 | 0.0 |
| 28 | 30.5° | 2.9 | 0.0 |
| 29 | 31.6° | 2.8 | 0.0 |

Figure 20:
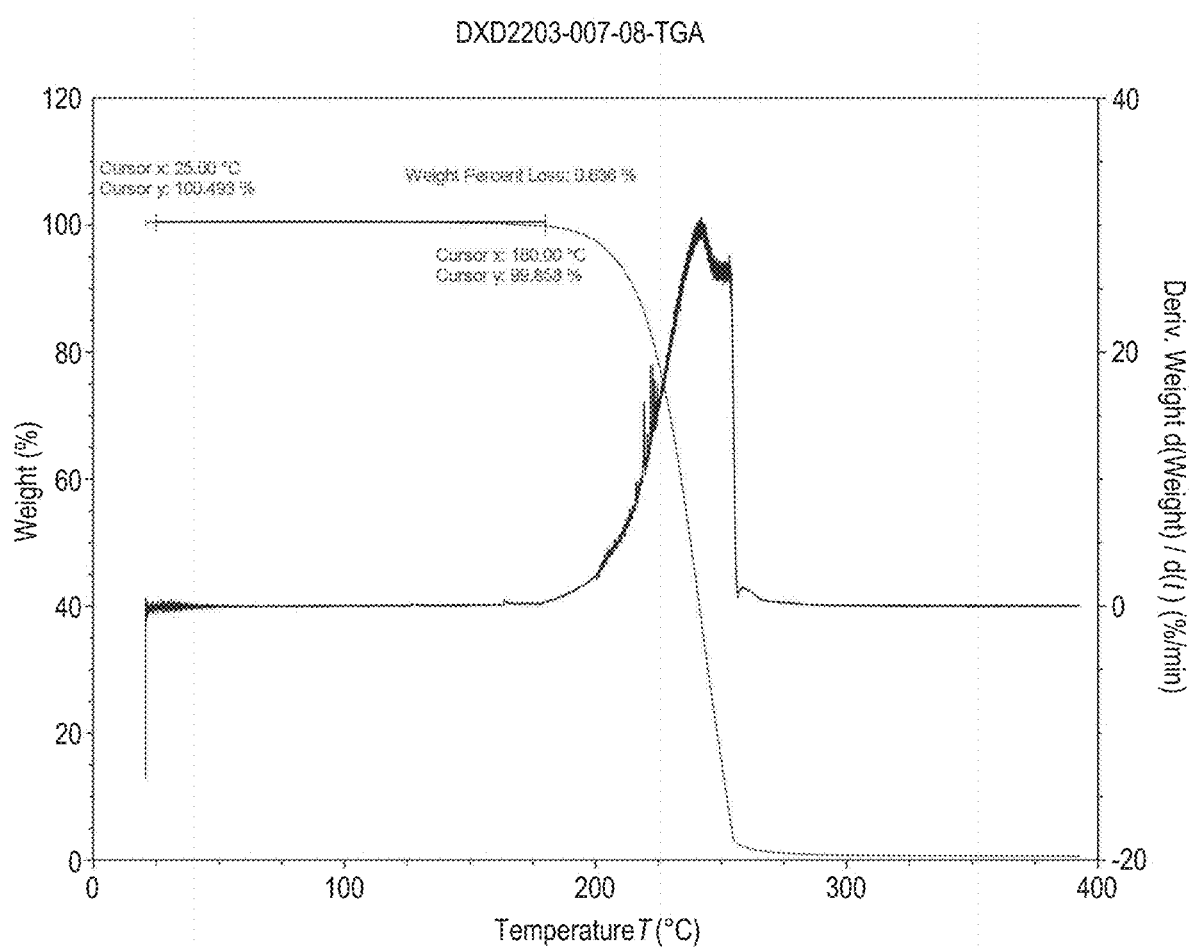
FIG. 20. TGA Thermogram of Oxalate salt, Batch: DXD2203-007-08.

TGA analysis of the Oxalate salt shows 0.6% weight loss between 25-180° C. (~0.02 moles EtOAc) followed by a single step thermal degradation as shown in, or substantially as shown in, FIG. 20. The 1st heating DSC thermogram displayed a single melting endotherm with $T_{onst}$ around 176.1° C., followed by the decomposition of the material.

Figure 21:
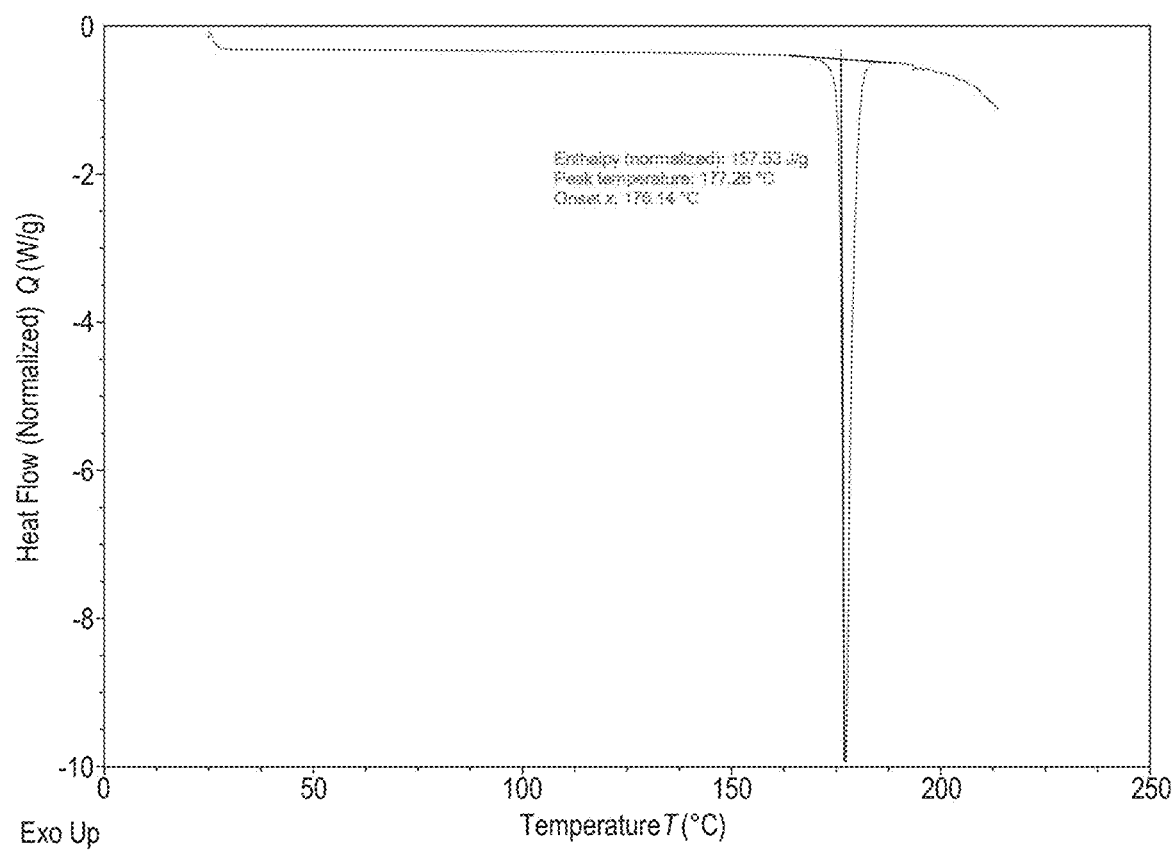
FIG. 21. DSC Thermogram (1st heating) of Oxalate salt, Batch: DXD2203-007-08.
Figure 22:
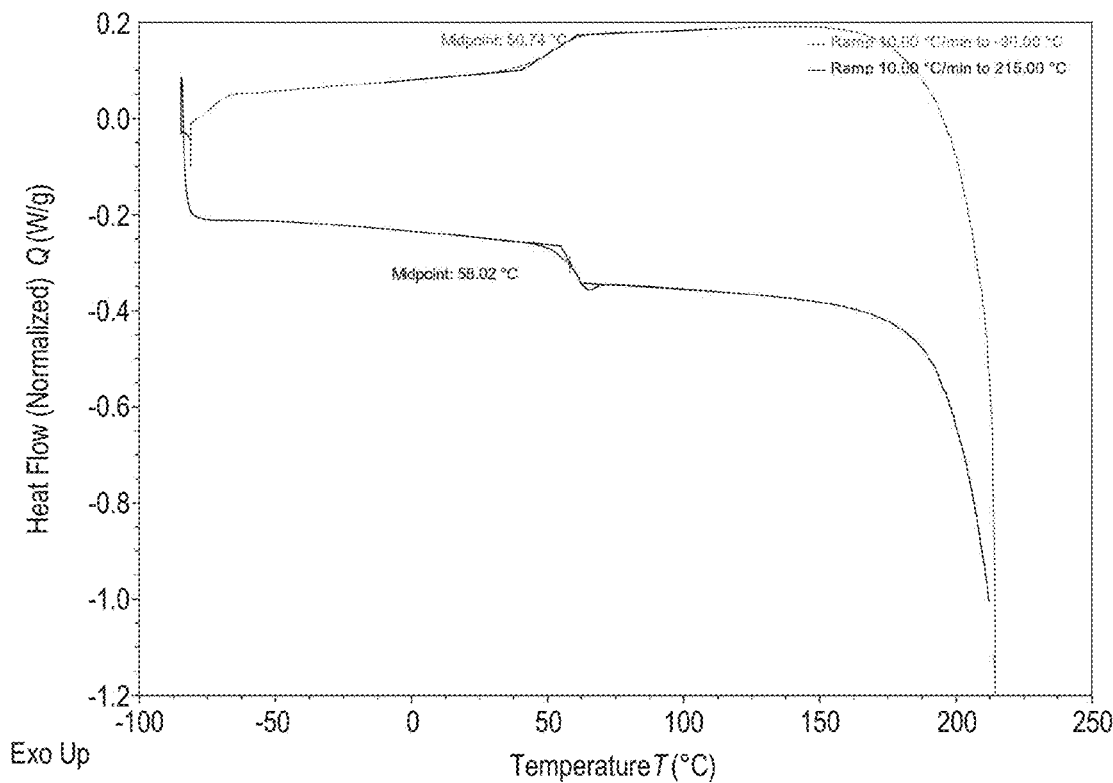
FIG. 22. DSC Thermograms of Oxalate salt, cooling (blue trace) and 2nd heating (green trace).

The enthalpy associated with the endothermic peak is 157.5 J/g as shown in, or substantially as shown in, FIG. 21. DSC thermograms of Oxalate salt showed a vitrification around 50.7° C. upon cooling and glass transition at 58.0° C. during the 2nd heating cycle as shown in, or substantially as shown in, FIG. 22.

Figure 23:
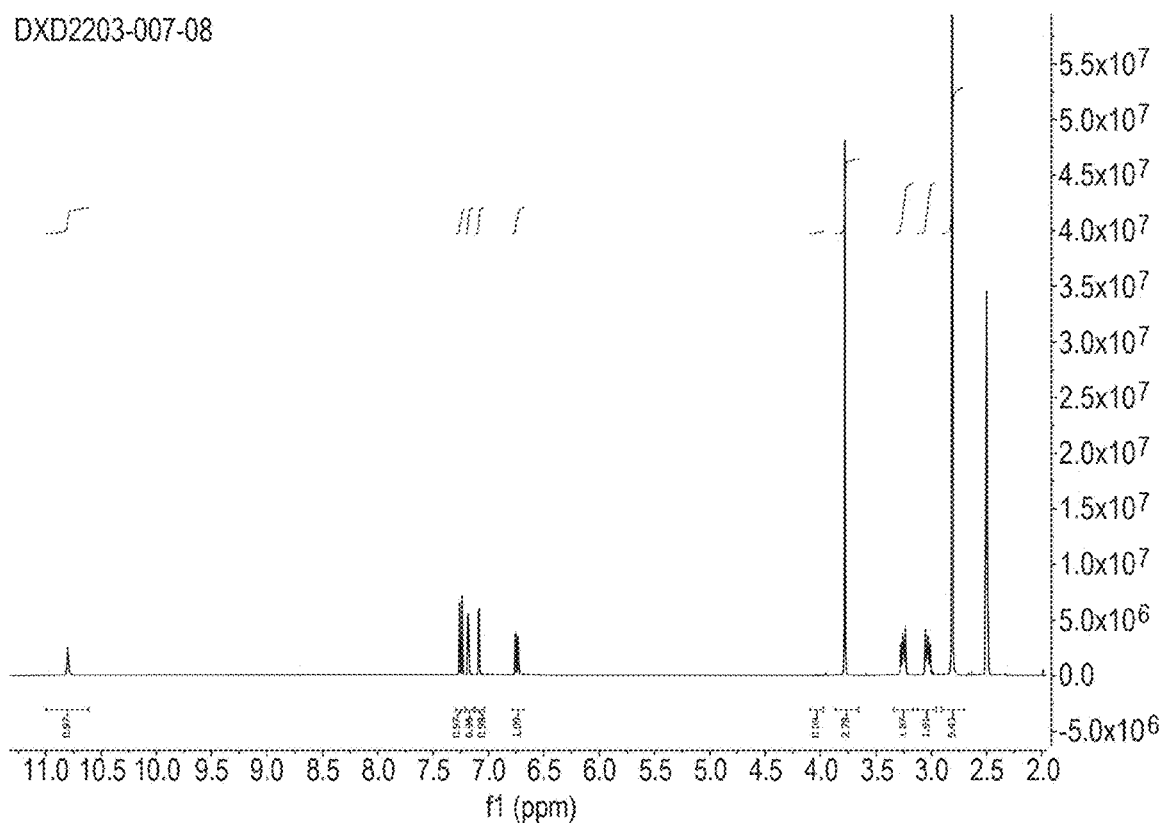
FIG. 23. 1H NMR (d6-DMSO) Spectrum of Oxalate salt, Batch: DXD2203-007-08.

Proton chemical shift changes in NMR (d$_6$-DMSO) spectrum indicate Oxalate salt formation. Traces of EtOAc were also detected in the spectrum as shown in, or substantially as shown in, FIG. 23.

Figure 24:
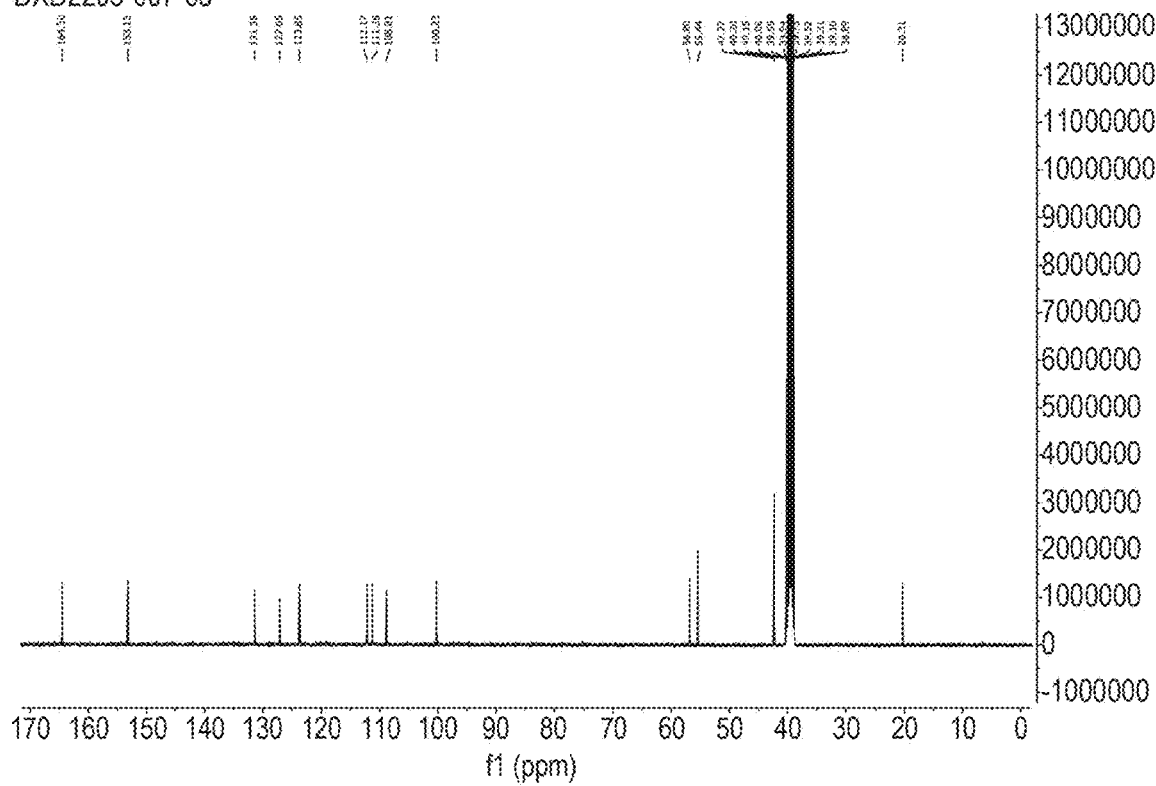
FIG. 24. 13C NMR (d6-DMSO) Spectrum of Oxalate salt, Batch: DXD2203-007-08.
Figure 25:
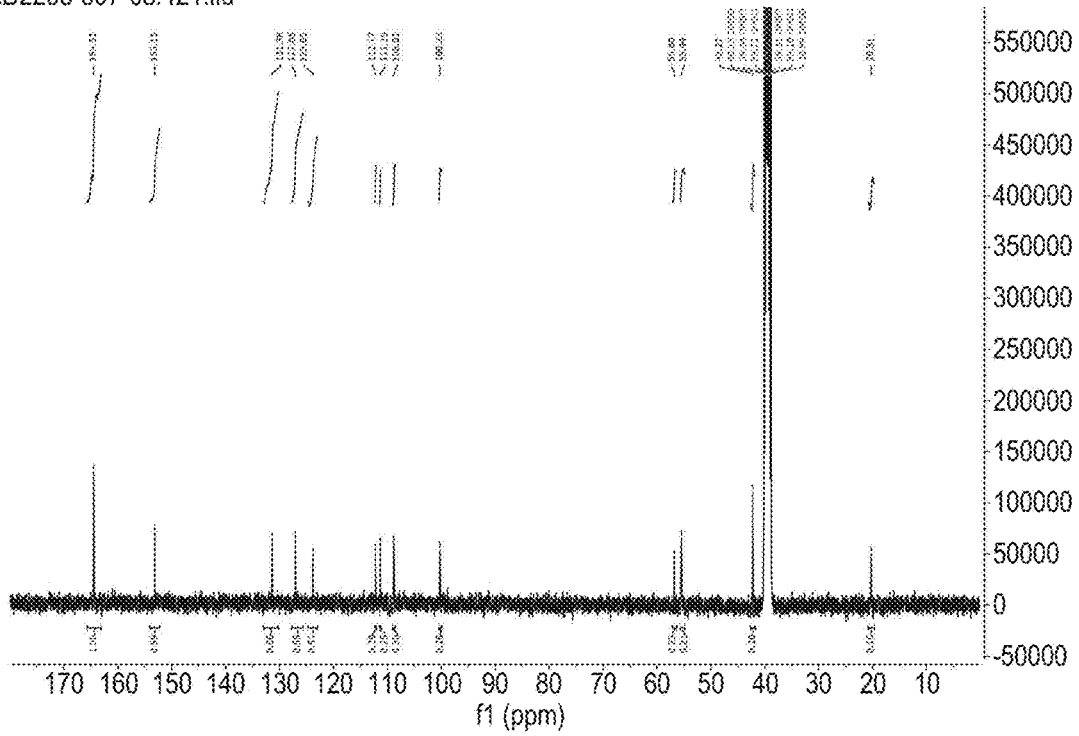
FIG. 25. Quantitative 13C NMR (d6-DMSO) Spectrum of Oxalate salt, Batch: DXD2203-007-08.
Figure 26:
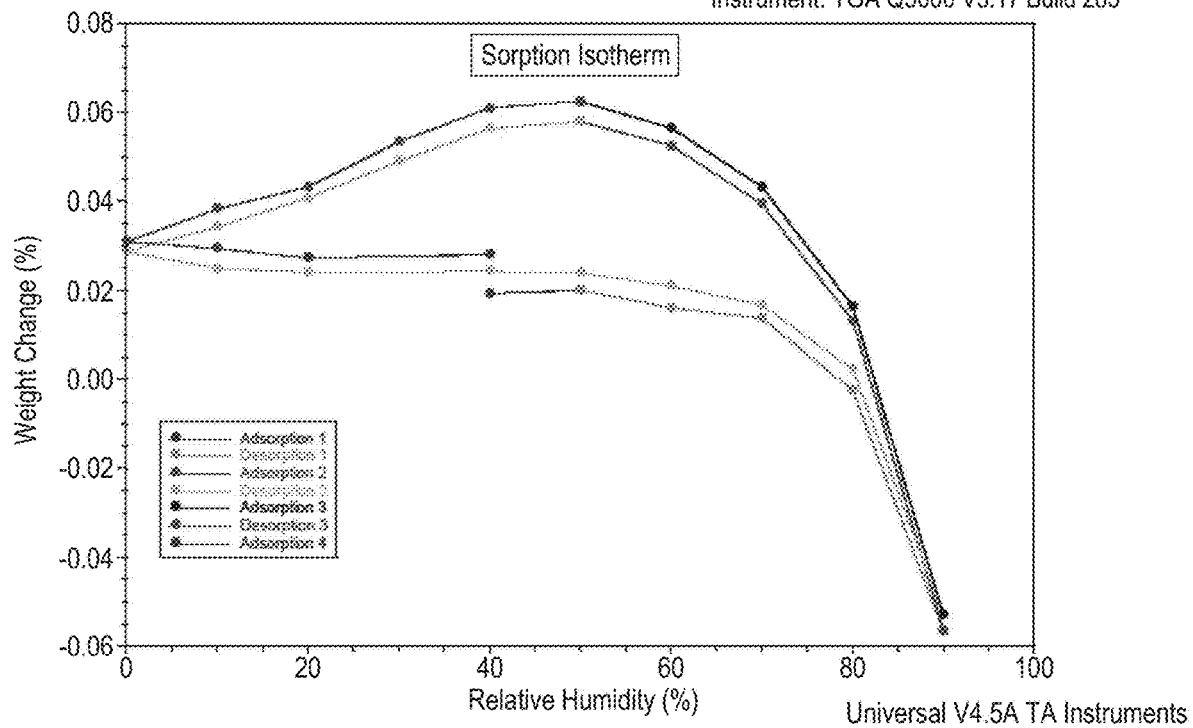
FIG. 26. DVS Isotherm plot of Oxalate salt, Batch: DXD2203-007-07.
Figure 27:
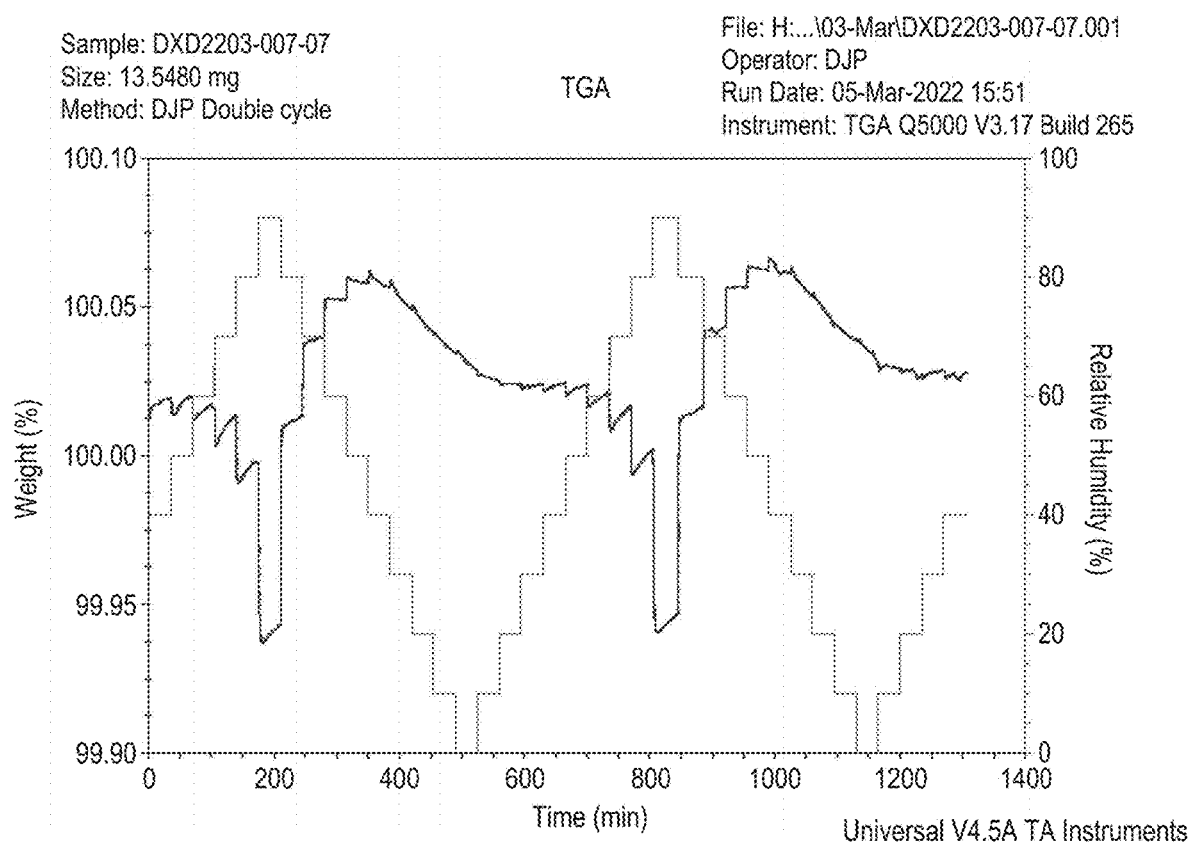
FIG. 27. Sorption kinetic plot of Oxalate salt, Batch: DXD2203-007-07.
Figure 28:
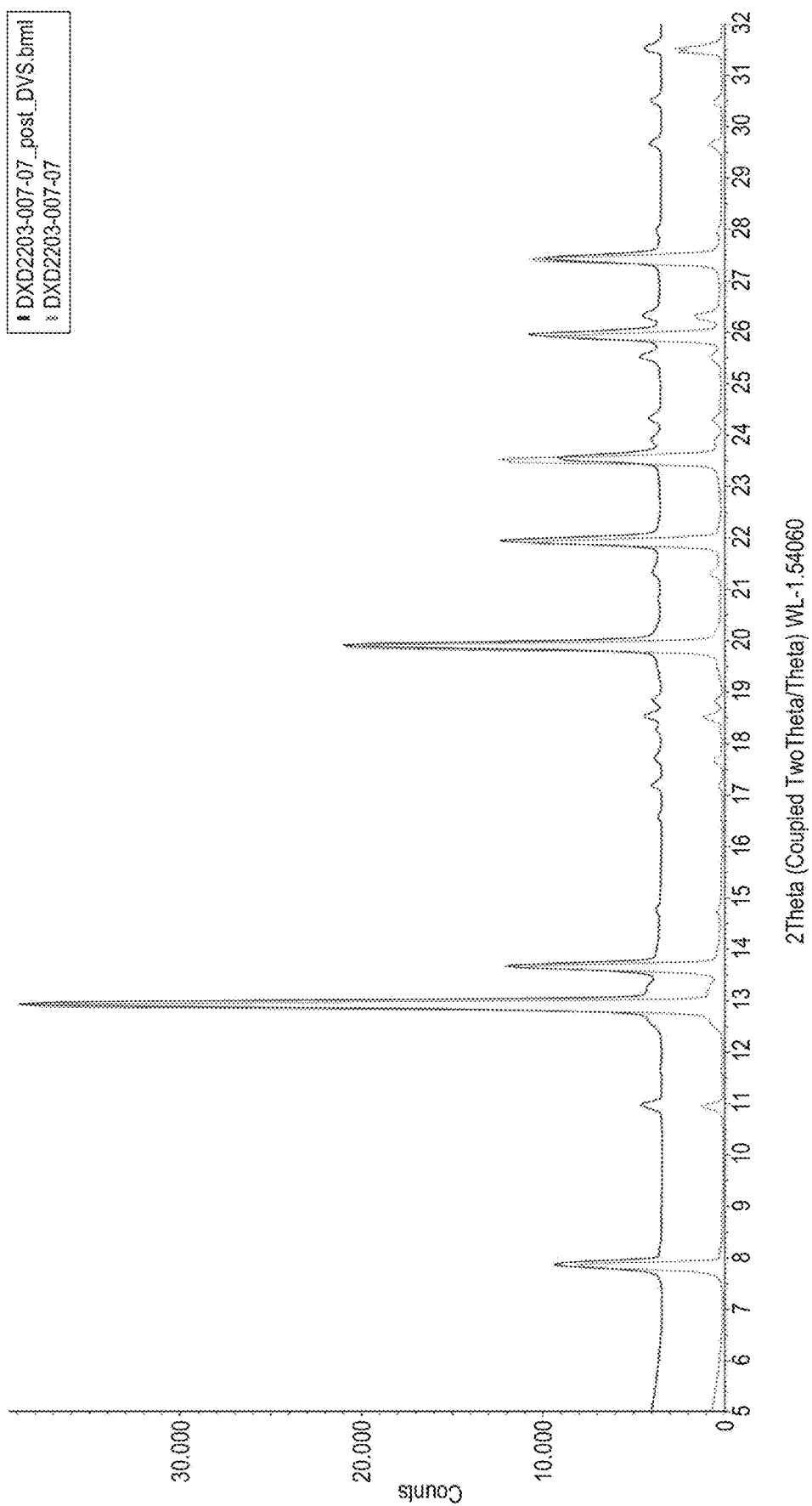
FIG. 28. XRPD Diffractograms of Oxalate salt, Batch: DXD2203-007-07 (red trace, bottom) and post-DVS (black trace, top).

$^{13}$C NMR spectrum of Oxalate salt in d$_6$-DMSO presented in FIG. 24, showed a signal for carbon at 164 ppm, confirming the presence of the oxalic acid. The quantitative $^{13}$C NMR spectrum of Oxalate salt in d$_6$-DMSO is presented in FIG. 25. The signal for carbon at 164 ppm, confirming the presence of ~1 eq of the oxalic acid. DVS Analysis of the Oxalate salt lot DXD2203-007-07 was performed and the isotherm plot is shown in FIG. 26. The DVS kinetic plot of the Oxalate salt lot DXD2203-007-07 is displayed in FIG. 27 and showed no evidence of a form change. XRPD analysis performed on post DVS Oxalate salt showed that no change in the crystalline form occurred during the DVS experiment as demonstrated in FIG. 28.

In one embodiment, there is provided 5-MeO-DMT oxalate. In one embodiment, there is provided a pharmaceutical composition comprising 5-MeO-DMT oxalate. In one embodiment, there is provided crystalline 5-MeO-DMT oxalate, or a pharmaceutical composition comprising crystalline 5-MeO-DMT oxalate, as characterised by one or more of:

An XRPD pattern as shown in, or substantially as shown in, FIG. 19;
One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, or twenty nine peaks in an XRPD diffractogram as detailed in Table 10, Table 10a or Table 10b;
One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 10, Table 10a or Table 10b;
A TGA thermogram as shown in, or substantially as shown in, FIG. 20;
A weight loss of around 0.6% between 25-180° C., as measured by TGA thermogram;
A weight loss of around 0.1-1.0% between 25-180° C., as measured by TGA thermogram;
A weight loss of around 0.1, 0.2, 0.3, 0.4, 0.5, 0.6, 0.7, 0.8, 0.9 or 1.0% between 25-180° C., as measured by TGA thermogram;
A DSC thermogram as shown in, or substantially as shown in, FIG. 21;
A melting endothermic event with an onset of around 176.1° C. and an enthalpy of 157.5 J/g, as measured in a DSC thermogram;
A melting endothermic event with an onset of around 170-180° C. and an enthalpy of 152-162 J/g, as measured in a DSC thermogram;
A melting endothermic event with an onset of around 170, 171, 172, 173, 174, 175, 176, 177, 178, 179 or 180° C.
and an enthalpy of around 152, 153, 154, 155, 156, 157, 158, 159, 160, 161 or 162 J/g, as measured in a DSC thermogram;
A vitrification around 50.7° C., as measured in a DSC thermogram with a cooling ramp of 10° C./min from 215° C. to −90° C.;
A vitrification around 45-55° C., as measured in a DSC thermogram with a cooling ramp of 10° C./min from 215° C. to −90° C.;
A vitrification around 45, 46, 47, 48, 49, 50, 51, 52, 53, 54 or 55° C., as measured in a DSC thermogram with a cooling ramp of 10° C./min from 215° C. to −90° C.;
A glass transition around 58.0° C., as measured in a DSC thermogram with a cooling ramp of 10° C./min from 215° C. to −90° C.;
A glass transition around 53-63° C., as measured in a DSC thermogram with a cooling ramp of 10° C./min from 215° C. to −90° C.;
A glass transition around 53, 54, 55, 56, 57, 58, 59, 60, 61, 62 or 63° C., as measured in a DSC thermogram with a cooling ramp of 10° C./min from 215° C. to −90° C.;
A $^1$H NMR spectrum as shown in, or substantially as shown in, FIG. 23;
A $^{13}$C NMR spectrum as shown in, or substantially as shown in, FIG. 24;
A $^{13}$C NMR spectrum as shown in, or substantially as shown in, FIG. 25;
A DVS isotherm as shown in, or substantially as shown in, FIG. 26;
A DVS kinetic plot as shown in, or substantially as shown in, FIG. 27; and/or
An XRPD pattern as shown in, or substantially as shown in, FIG. 28.

Adipate Salt

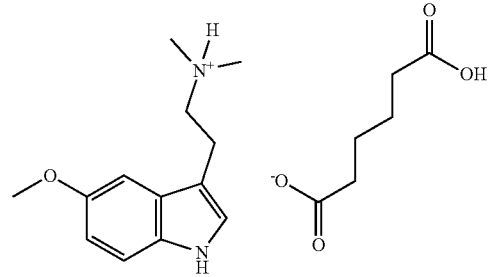

Figure 29:
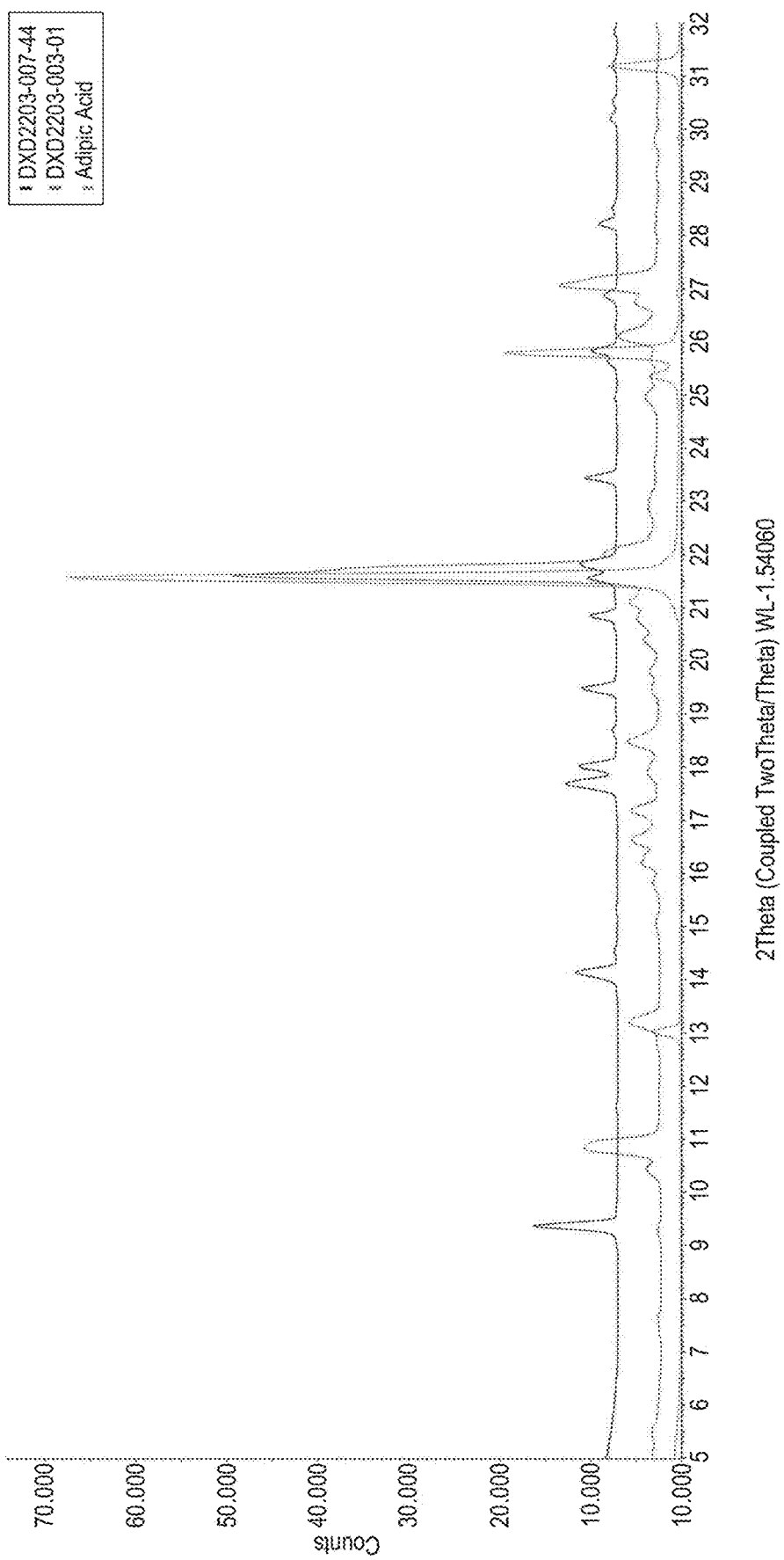
FIG. 29. XRPD Diffractograms of Batch: DXD2203-007-44 isolated from ethyl acetate (black trace, top), free base (blue trace, middle) and adipic acid (red trace, bottom).

XRPD diffractogram of isolated solid from ethyl acetate displayed a crystalline pattern which does not correspond to free base pattern 1 or adipic acid as shown in, or substantially as shown in, FIG. 29. Later analysis indicated this to be a free form and as such nominated as pattern 2.

TABLE 11

XRPD Peak data for DXD2203-007-44, pattern 2.

| Peak No. | Angle 2 θ | d Value | Rel. Intensity |
|---|---|---|---|
| 1 | 9.368° | 9.433 | 1.000 |
| 2 | 14.136° | 6.260 | 0.493 |
| 3 | 14.535° | 6.089 | 0.039 |
| 4 | 17.694° | 5.009 | 0.611 |
| 5 | 18.017° | 4.919 | 0.448 |
| 6 | 18.692° | 4.743 | 0.052 |
| 7 | 19.490° | 4.551 | 0.414 |

TABLE 11-continued

XRPD Peak data for DXD2203-007-44, pattern 2.

| Peak No. | Angle 2 θ | d Value | Rel. Intensity |
|---|---|---|---|
| 8 | 20.846° | 4.258 | 0.309 |
| 9 | 21.557° | 4.119 | 0.338 |
| 10 | 21.831° | 4.068 | 0.433 |
| 11 | 23.433° | 3.793 | 0.368 |
| 12 | 24.948° | 3.566 | 0.027 |
| 13 | 25.633° | 3.473 | 0.117 |
| 14 | 25.831° | 3.446 | 0.308 |
| 15 | 26.875° | 3.315 | 0.157 |
| 16 | 28.213° | 3.161 | 0.214 |
| 17 | 28.503° | 3.129 | 0.058 |
| 18 | 30.224° | 2.955 | 0.079 |
| 19 | 30.499° | 2.929 | 0.052 |
| 20 | 31.203° | 2.864 | 0.054 |
| 21 | 31.867° | 2.806 | 0.033 |

TABLE 11a

XRPD Peak data for DXD2203-007-44, pattern 2 (2 d.p.).

| Peak No. | Angle 2 θ | d Value | Rel. Intensity |
|---|---|---|---|
| 1 | 9.37° | 9.43 | 1.00 |
| 2 | 14.14° | 6.26 | 0.49 |
| 3 | 14.54° | 6.09 | 0.04 |
| 4 | 17.69° | 5.01 | 0.61 |
| 5 | 18.02° | 4.92 | 0.45 |
| 6 | 18.69° | 4.74 | 0.05 |
| 7 | 19.49° | 4.55 | 0.41 |
| 8 | 20.85° | 4.26 | 0.31 |
| 9 | 21.56° | 4.12 | 0.34 |
| 10 | 21.83° | 4.07 | 0.43 |
| 11 | 23.43° | 3.79 | 0.37 |
| 12 | 24.95° | 3.57 | 0.03 |
| 13 | 25.63° | 3.47 | 0.12 |
| 14 | 25.83° | 3.45 | 0.31 |
| 15 | 26.88° | 3.32 | 0.16 |
| 16 | 28.21° | 3.16 | 0.21 |
| 17 | 28.50° | 3.13 | 0.06 |
| 18 | 30.22° | 2.96 | 0.08 |
| 19 | 30.50° | 2.93 | 0.05 |
| 20 | 31.20° | 2.86 | 0.05 |
| 21 | 31.87° | 2.81 | 0.03 |

TABLE 11b

XRPD Peak data for DXD2203-007-44, pattern 2 (1 d.p.).

| Peak No. | Angle 2 θ | d Value | Rel. Intensity |
|---|---|---|---|
| 1 | 9.4° | 9.4 | 1.0 |
| 2 | 14.1° | 6.3 | 0.5 |
| 3 | 14.5° | 6.1 | 0.0 |
| 4 | 17.7° | 5.0 | 0.6 |
| 5 | 18.0° | 4.9 | 0.4 |
| 6 | 18.7° | 4.7 | 0.1 |
| 7 | 19.5° | 4.6 | 0.4 |
| 8 | 20.8° | 4.3 | 0.3 |
| 9 | 21.6° | 4.1 | 0.3 |
| 10 | 21.8° | 4.1 | 0.4 |
| 11 | 23.4° | 3.8 | 0.4 |
| 12 | 24.9° | 3.6 | 0.0 |
| 13 | 25.6° | 3.5 | 0.1 |
| 14 | 25.8° | 3.4 | 0.3 |
| 15 | 26.9° | 3.3 | 0.2 |
| 16 | 28.2° | 3.2 | 0.2 |
| 17 | 28.5° | 3.1 | 0.1 |
| 18 | 30.2° | 3.0 | 0.1 |
| 19 | 30.5° | 2.9 | 0.1 |
| 20 | 31.2° | 2.9 | 0.1 |
| 21 | 31.9° | 2.8 | 0.0 |

Figure 30:
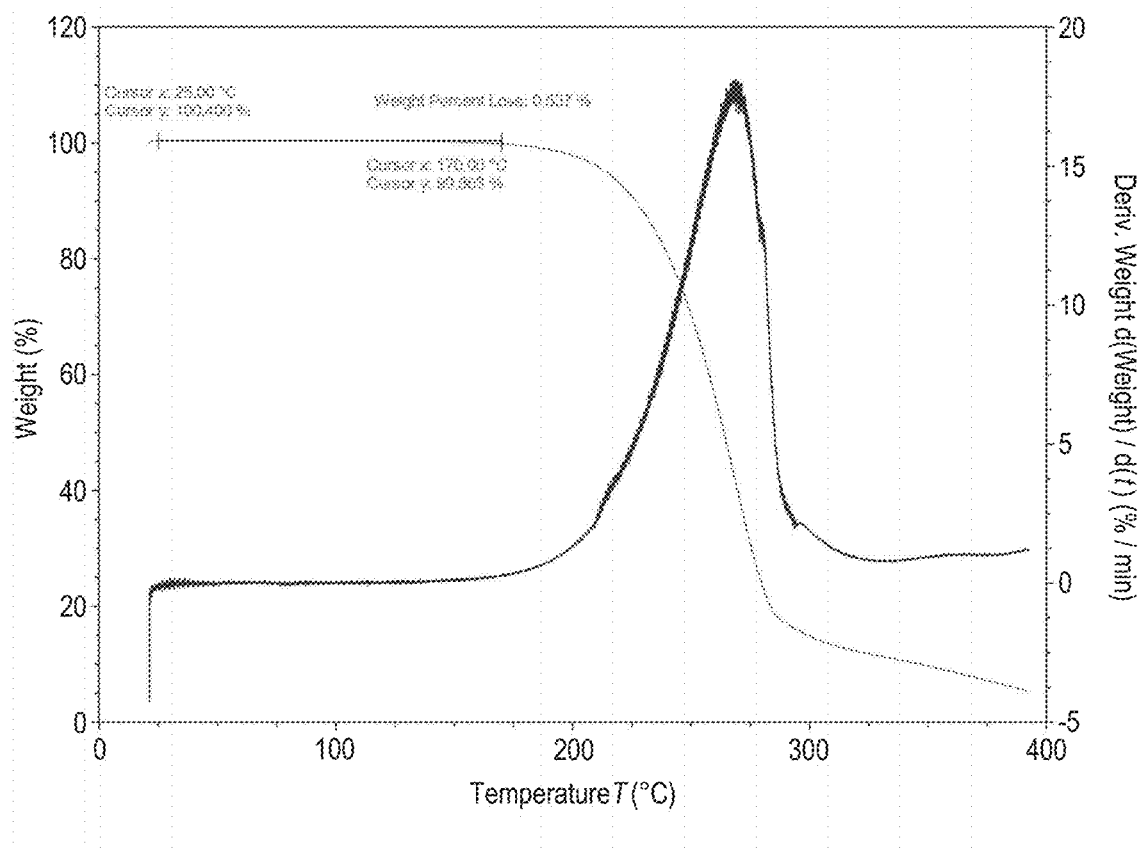
FIG. 30. TGA Thermogram of Batch: DXD2203-007-44.

The TGA thermograph displayed in FIG. 30 showed a weight loss of 0.5% between 25-170° C., (~0.03 moles EtOAc) followed by the thermal degradation of the material.

Figure 31:
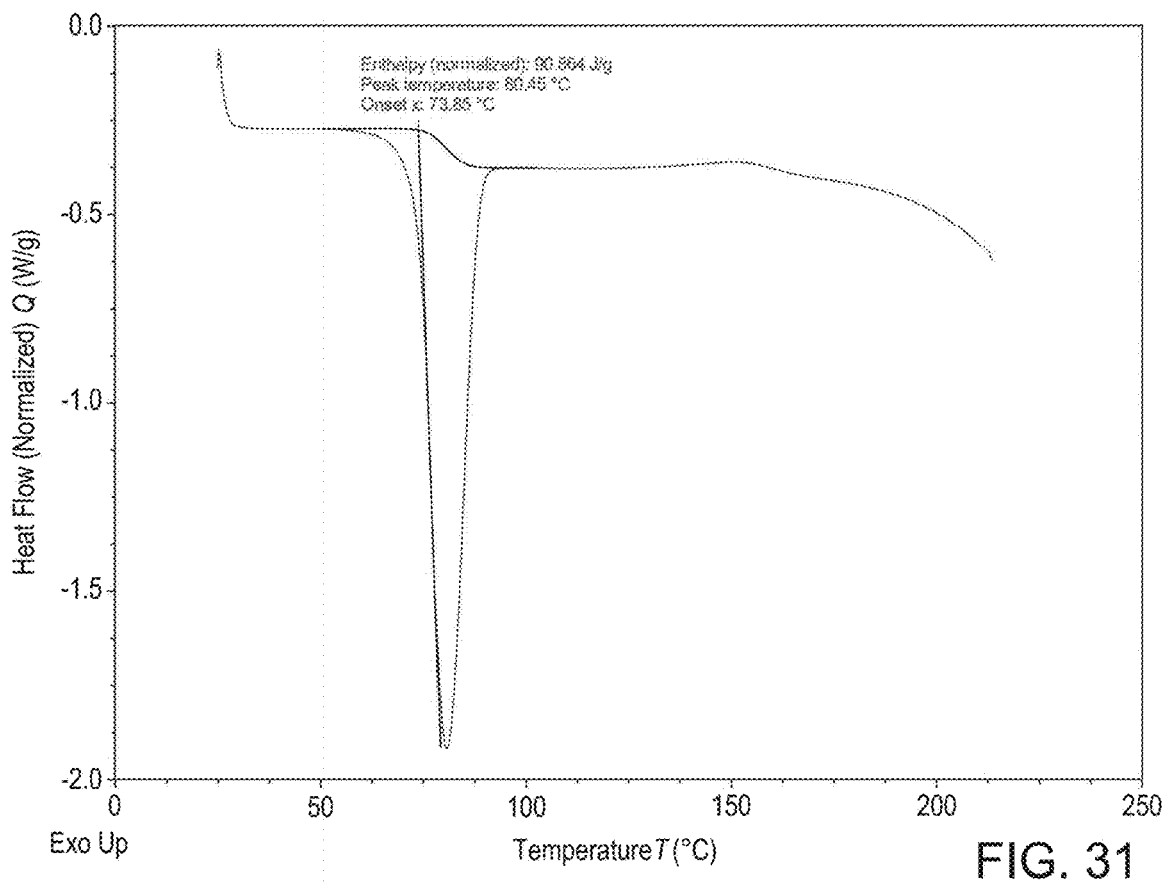
FIG. 31. DSC Thermogram (1st heating) of Batch: DXD2203-007-44.

The 1$^{st}$ heating DSC thermogram shown in FIG. 31, displayed a broad endotherm with onset temperature of 73.9° C. and heat of fusion 90.9 J/g corresponding to the melt of the material.

Figure 32:
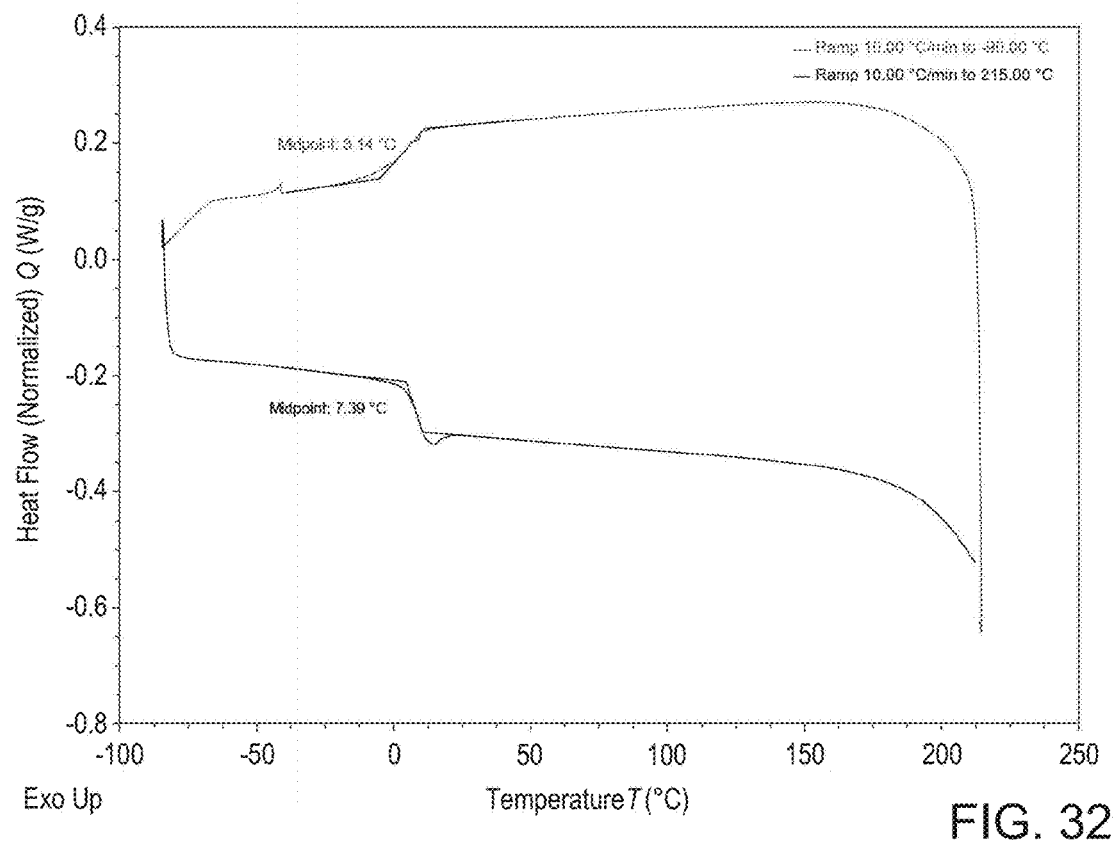
FIG. 32. DSC Thermograms of Batch: DXD2203-007-44, cooling (blue trace) and 2nd heating (green trace).

As shown in, or substantially as shown in, FIG. 32, the cooling ramp from 215° C. to −90° C. at 10° C./min displayed a vitrification at around 3.1° C. The glass transition at around 7.4° C. was observed during the 2$^{nd}$ heating ramp.

Figure 33:
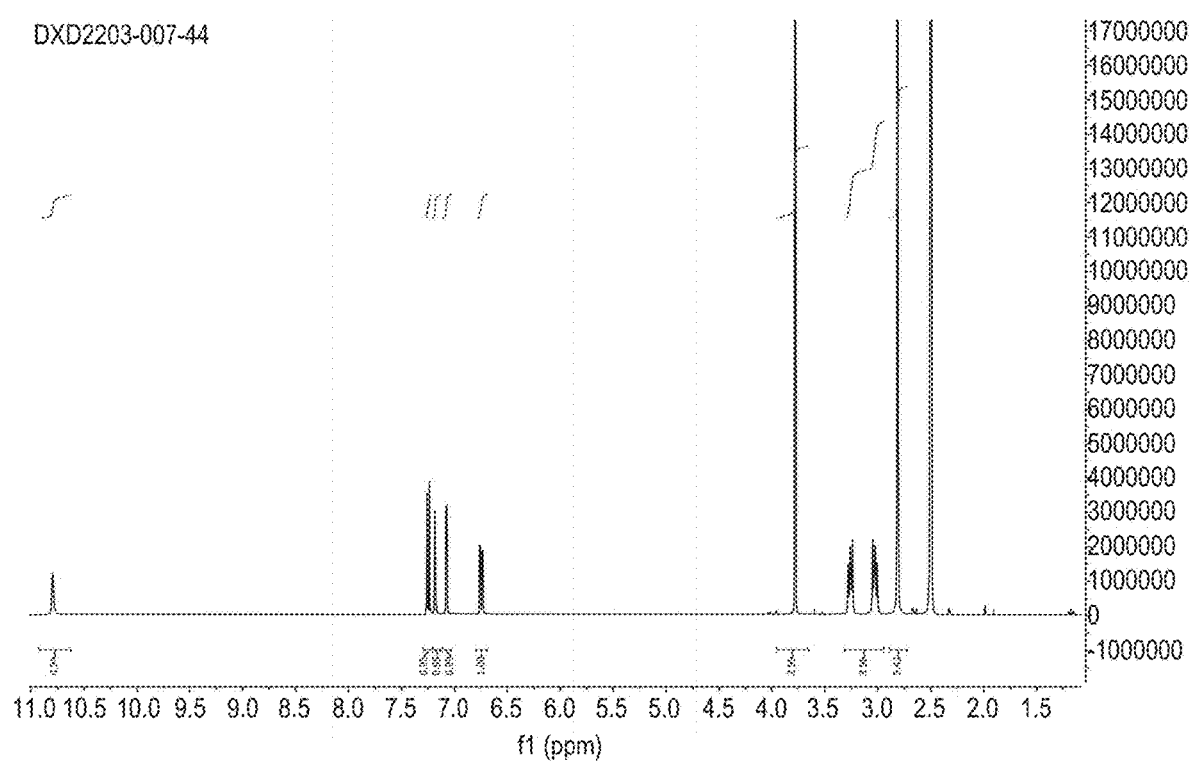
FIG. 33. 1H NMR (d6-DMSO) Spectrum of Batch: DXD2203-007-44.

$^{1}$H NMR spectrum (d$_{6}$-DMSO) of DXD2203-007-44 solid displayed in FIG. 33 showed traces of ethyl acetate and no presence of adipic acid. This suggests that isolated material is a free base of different crystalline form as the XRPD pattern of DXD2203-007-44 does not match with the input (DXD2203003-01). This was nominated as pattern 2 of free base.

However, it is interesting to note the significant difference in glass transitions. As mentioned previously, free base pattern 1 displayed Tg around −11.9° C. during the second heating cycle, whereas free base pattern 2 showed Tg around 7.4° C.

In one embodiment, there is provided 5-MeO-DMT adipate. In one embodiment, there is provided a pharmaceutical composition comprising 5-MeO-DMT adipate. In one embodiment, there is provided crystalline 5-MeO-DMT adipate, or a pharmaceutical composition comprising crystalline 5-MeO-DMT adipate, as characterised by one or more of:

An XRPD pattern as shown in, or substantially as shown in, FIG. 29;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, or twenty one peaks in an XRPD diffractogram as detailed in Table 11, Table 11a or Table 11b;

One or more, two or more, three or more, four or more, or five or more peaks in an XRPD diffractogram with a relative intensity of over 0.1, 0.2, 0.3, 0.4, 0.5, 0.6, 0.7, 0.8 or 0.9 as detailed in Table 11, Table 11a or Table 11b;

A TGA thermogram as shown in, or substantially as shown in, FIG. 30;

A weight loss of 0.5% between 25-170° C., as measured by TGA thermogram;

A weight loss of around 0.1-1.0% between 25-170° C., as measured by TGA thermogram;

A weight loss of around 0.1, 0.2, 0.3, 0.4, 0.5, 0.6, 0.7, 0.8, 0.9 or 1.0% between 25-170° C., as measured by TGA thermogram;

A DSC thermogram as shown in, or substantially as shown in, FIG. 31 or 32;

A melting endothermic event with an onset of around 73.9° C. and an enthalpy of 90.9 J/g, as measured in a DSC thermogram;

A melting endothermic event with an onset of around 68-80° C. and an enthalpy of around 85-95 J/g, as measured in a DSC thermogram;

A melting endothermic event with an onset of around 68, 69, 70, 71, 72, 73, 74, 75, 76, 77, 78, 79 or 80° C. and an enthalpy of around 85, 86, 87, 88, 89, 90, 91, 92, 93, 94 or 95 J/g, as measured in a DSC thermogram;

A vitrification around 3.1° C., as measured in a DSC thermogram with a cooling ramp of 10° C./min from 215° C. to −90° C.;

A vitrification around 0-10° C., as measured in a DSC thermogram with a cooling ramp of 10° C./min from 215° C. to −90° C.;

A vitrification around 0, 1, 2, 3, 4, 5, 6, 7, 8, 9 or 10° C., as measured in a DSC thermogram with a cooling ramp of 10° C./min from 215° C. to −90° C.;

A glass transition around 7.4° C., as measured in a DSC thermogram with a cooling ramp of 10° C./min from 215° C. to −90° C.;

A glass transition around 2-12° C., as measured in a DSC thermogram with a cooling ramp of 10° C./min from 215° C. to −90° C.;

A glass transition around 2, 3, 4, 5, 6, 7, 8, 9, 10, 11 or 12° C., as measured in a DSC thermogram with a cooling ramp of 10° C./min from 215° C. to −90° C.; and/or A $^1$H NMR spectrum as shown in, or substantially as shown in, FIG. 33.

Solvent—Anti-Solvent Experiments

Amorphous salts produced by a slow evaporation to dryness at RT (DXD2203-004 and DXD2203-007) were used for solvent/anti-solvent experiments.

Approximately 1 ml of solvent was added to amorphous salt and samples were placed to 40° C. chamber for one hour. After this time clear solutions were allowed to cool down to room temperature and antisolvent (approximately 2 ml) was added dropwise. Solvent/anti-solvent systems used are tabulated in Table 12.

In some cases, precipitates were formed during cooling solutions to the room temperature. Saccharinate amorphous salt did not dissolve after one hour at 40° C. and the IPA solvent was allowed to evaporate.

Produced solids were isolated by centrifuge filtration using Nylon 0.2 micrometre centrifuge filter tubes and analysed by XRPD.

Any new crystalline forms were also analysed by TGA, DSC, $^1$H NMR and DVS analyses.

TABLE 12

Solvent/Anti-solvent experiments.

| Salt | Batch | Solvent | Anti-solvent |
| --- | --- | --- | --- |
| Tartrate | DXD2203-009-08 | IPA | hexane |
|  | DXD2203-009-09 | THF | hexane |
|  | DXD2203-009-12 | EtOH (40° C.) | N/A |
|  | DXD2203-009-13 | THF (40° C.) | N/A |
| Fumarate | DXD2203-009-10 | THF | hexane |
|  | DXD2203-009-11 | THF (40° C.) | N/A |
| Benzenesulfonate | DXD2203-009-20 | IPA | hexane |
| Tosylate | DXD2203-009-21 | IPA | Hexane |
| Saccharinate | DXD2203-010-01 | IPA | N/A |

TABLE 12-continued

Solvent/Anti-solvent experiments.

| Salt | Batch | Solvent | Anti-solvent |
| --- | --- | --- | --- |
| Hydrobromide | DXD2203-010-02 | MeOH | MTBE |
|  | DXD2203-010-08 | DMF | toluene |
|  | DXD2203-010-09 | MeCN | toluene |
| Glycolate | DXD2203-010-03 | IPAC (40° C.) | N/A |
| Ketoglutarate | DXD2203-010-04 | EtOH | MTBE |
|  | DXD2203-010-06 | MeOH | MTBE |
| Malate | DXD2203-010-05 | EtOH | MTBE |
|  | DXD2203-010-07 | IPAC | MTBE |

Tartrate Salt

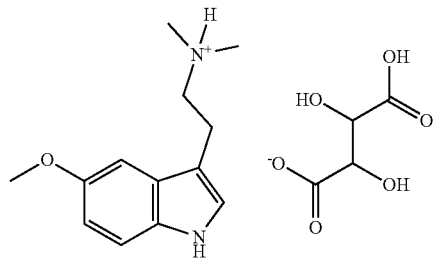

Figure 34:
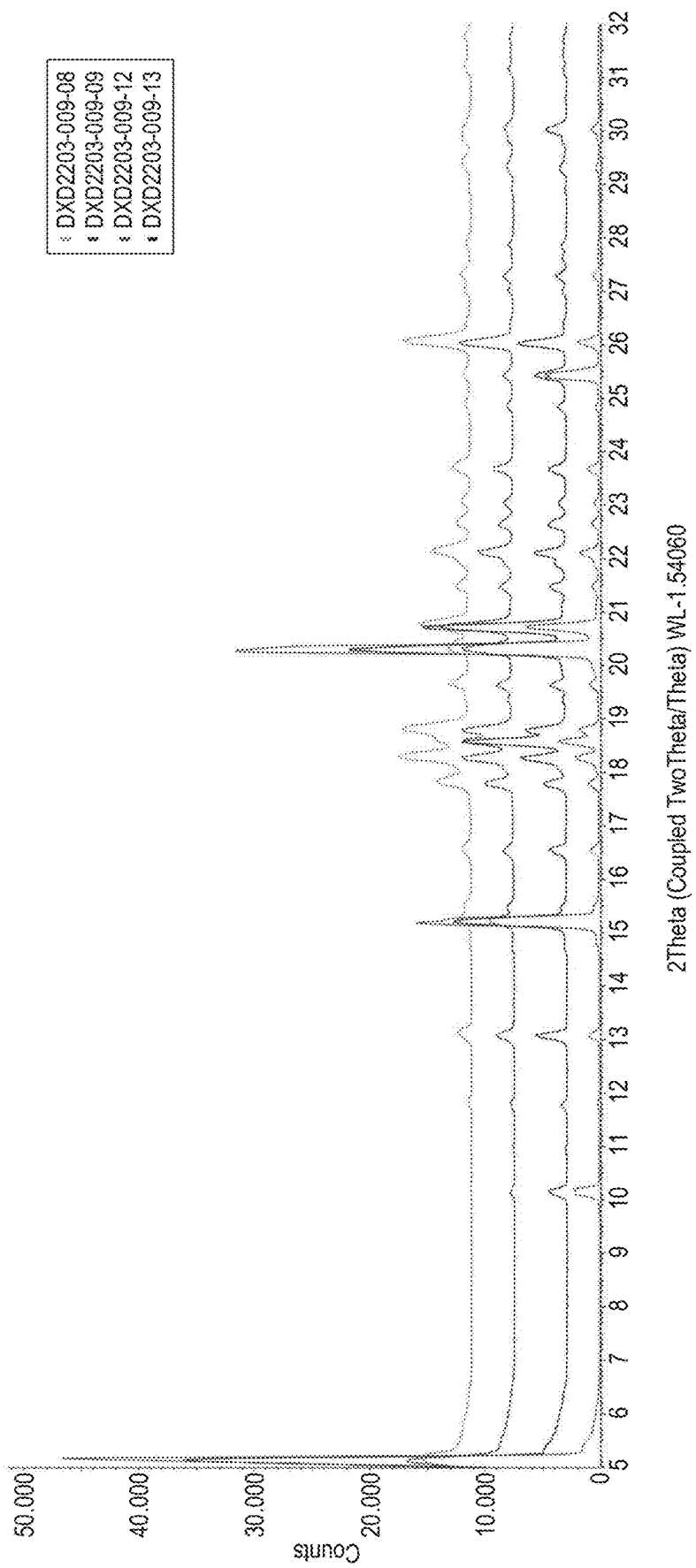
FIG. 34. XRPD Diffractograms (from top to bottom) of Tartrate salt isolated from IPA/hexane (green trace), THF/hexane (blue trace), THF at 40° C. (black trace) and ethanol at 40° C. (red trace).

XRPD diffractograms of Tartrate salt showed that same crystalline solid form was isolated from all solvent systems as demonstrated in FIG. 34. This was nominated as pattern 1 with XRPD peak data displayed in Table 13, Table 13a or Table 13b.

TABLE 13

XRPD Peak data for Tartrate pattern 1.

| Peak No. | Angle 2θ | d Value | Rel. Intensity |
| --- | --- | --- | --- |
| 1 | 10.147° | 8.711 | 0.045 |
| 2 | 10.987° | 8.046 | 0.012 |
| 3 | 11.794° | 7.497 | 0.050 |
| 4 | 13.080° | 6.763 | 0.246 |
| 5 | 14.786° | 5.986 | 0.015 |
| 6 | 15.214° | 5.819 | 0.331 |
| 7 | 15.464° | 5.725 | 0.093 |
| 8 | 16.534° | 5.357 | 0.138 |
| 9 | 17.793° | 4.981 | 0.374 |
| 10 | 18.267° | 4.853 | 0.692 |
| 11 | 18.579° | 4.772 | 0.687 |
| 12 | 18.785° | 4.720 | 0.684 |
| 13 | 19.360° | 4.581 | 0.044 |
| 14 | 19.630° | 4.519 | 0.187 |
| 15 | 20.311° | 4.369 | 0.683 |
| 16 | 20.730° | 4.281 | 1.000 |
| 17 | 21.467° | 4.136 | 0.161 |
| 18 | 22.125° | 4.015 | 0.461 |
| 19 | 22.639° | 3.924 | 0.179 |
| 20 | 23.041° | 3.857 | 0.114 |
| 21 | 23.679° | 3.754 | 0.258 |
| 22 | 24.856° | 3.579 | 0.079 |
| 23 | 25.431° | 3.500 | 0.135 |
| 24 | 26.034° | 3.420 | 0.749 |
| 25 | 26.368° | 3.377 | 0.042 |
| 26 | 27.029° | 3.296 | 0.068 |
| 27 | 27.299° | 3.264 | 0.130 |
| 28 | 27.870° | 3.199 | 0.064 |

TABLE 13-continued

XRPD Peak data for Tartrate pattern 1.

| Peak No. | Angle 2 θ | d Value | Rel. Intensity |
|---|---|---|---|
| 29 | 28.937° | 3.083 | 0.024 |
| 30 | 29.311° | 3.045 | 0.088 |
| 31 | 30.009° | 2.975 | 0.121 |
| 32 | 31.153° | 2.869 | 0.067 |
| 33 | 31.707° | 2.820 | 0.047 |

TABLE 13a

XRPD Peak data for Tartrate pattern 1 (2 d.p.).

| Peak No. | Angle 2 θ | d Value | Rel. Intensity |
|---|---|---|---|
| 1 | 10.15° | 8.71 | 0.05 |
| 2 | 10.99° | 8.05 | 0.01 |
| 3 | 11.79° | 7.50 | 0.05 |
| 4 | 13.08° | 6.76 | 0.25 |
| 5 | 14.79° | 5.99 | 0.02 |
| 6 | 15.21° | 5.82 | 0.33 |
| 7 | 15.46° | 5.73 | 0.09 |
| 8 | 16.53° | 5.36 | 0.14 |
| 9 | 17.79° | 4.98 | 0.37 |
| 10 | 18.27° | 4.85 | 0.69 |
| 11 | 18.58° | 4.77 | 0.69 |
| 12 | 18.79° | 4.72 | 0.68 |
| 13 | 19.36° | 4.58 | 0.04 |
| 14 | 19.63° | 4.52 | 0.19 |
| 15 | 20.31° | 4.37 | 0.68 |
| 16 | 20.73° | 4.28 | 1.00 |
| 17 | 21.47° | 4.14 | 0.16 |
| 18 | 22.13° | 4.02 | 0.46 |
| 19 | 22.64° | 3.92 | 0.18 |
| 20 | 23.04° | 3.86 | 0.11 |
| 21 | 23.68° | 3.75 | 0.26 |
| 22 | 24.86° | 3.58 | 0.08 |
| 23 | 25.43° | 3.50 | 0.14 |
| 24 | 26.03° | 3.42 | 0.75 |
| 25 | 26.37° | 3.38 | 0.04 |
| 26 | 27.03° | 3.30 | 0.07 |
| 27 | 27.30° | 3.26 | 0.13 |
| 28 | 27.87° | 3.20 | 0.06 |
| 29 | 28.94° | 3.08 | 0.02 |
| 30 | 29.31° | 3.05 | 0.09 |
| 31 | 30.01° | 2.98 | 0.12 |
| 32 | 31.15° | 2.87 | 0.07 |
| 33 | 31.71° | 2.82 | 0.05 |

TABLE 13b

XRPD Peak data for Tartrate pattern 1 (1 d.p.).

| Peak No. | Angle 2 θ | d Value | Rel. Intensity |
|---|---|---|---|
| 1 | 10.1° | 8.7 | 0.0 |
| 2 | 11.0° | 8.0 | 0.0 |
| 3 | 11.8° | 7.5 | 0.1 |
| 4 | 13.1° | 6.8 | 0.2 |
| 5 | 14.8° | 6.0 | 0.0 |
| 6 | 15.2° | 5.8 | 0.3 |
| 7 | 15.5° | 5.7 | 0.1 |
| 8 | 16.5° | 5.4 | 0.1 |
| 9 | 17.8° | 5.0 | 0.4 |
| 10 | 18.3° | 4.9 | 0.7 |
| 11 | 18.6° | 4.8 | 0.7 |
| 12 | 18.8° | 4.7 | 0.7 |
| 13 | 19.4° | 4.6 | 0.0 |
| 14 | 19.6° | 4.5 | 0.2 |
| 15 | 20.3° | 4.4 | 0.7 |
| 16 | 20.7° | 4.3 | 1.0 |
| 17 | 21.5° | 4.1 | 0.2 |
| 18 | 22.1° | 4.0 | 0.5 |
| 19 | 22.6° | 3.9 | 0.2 |
| 20 | 23.0° | 3.9 | 0.1 |
| 21 | 23.7° | 3.8 | 0.3 |
| 22 | 24.9° | 3.6 | 0.1 |
| 23 | 25.4° | 3.5 | 0.1 |
| 24 | 26.0° | 3.4 | 0.7 |
| 25 | 26.4° | 3.4 | 0.0 |
| 26 | 27.0° | 3.3 | 0.1 |
| 27 | 27.3° | 3.3 | 0.1 |
| 28 | 27.9° | 3.2 | 0.1 |
| 29 | 28.9° | 3.1 | 0.0 |
| 30 | 29.3° | 3.0 | 0.1 |
| 31 | 30.0° | 3.0 | 0.1 |
| 32 | 31.2° | 2.9 | 0.1 |
| 33 | 31.7° | 2.8 | 0.0 |

The TGA thermogram of Tartrate salt showed 1% of weight loss between 25-170° C. (~0.05 moles THF) and good thermal stability up to around 170° C. as displayed in FIG. 35.

Figure 36:
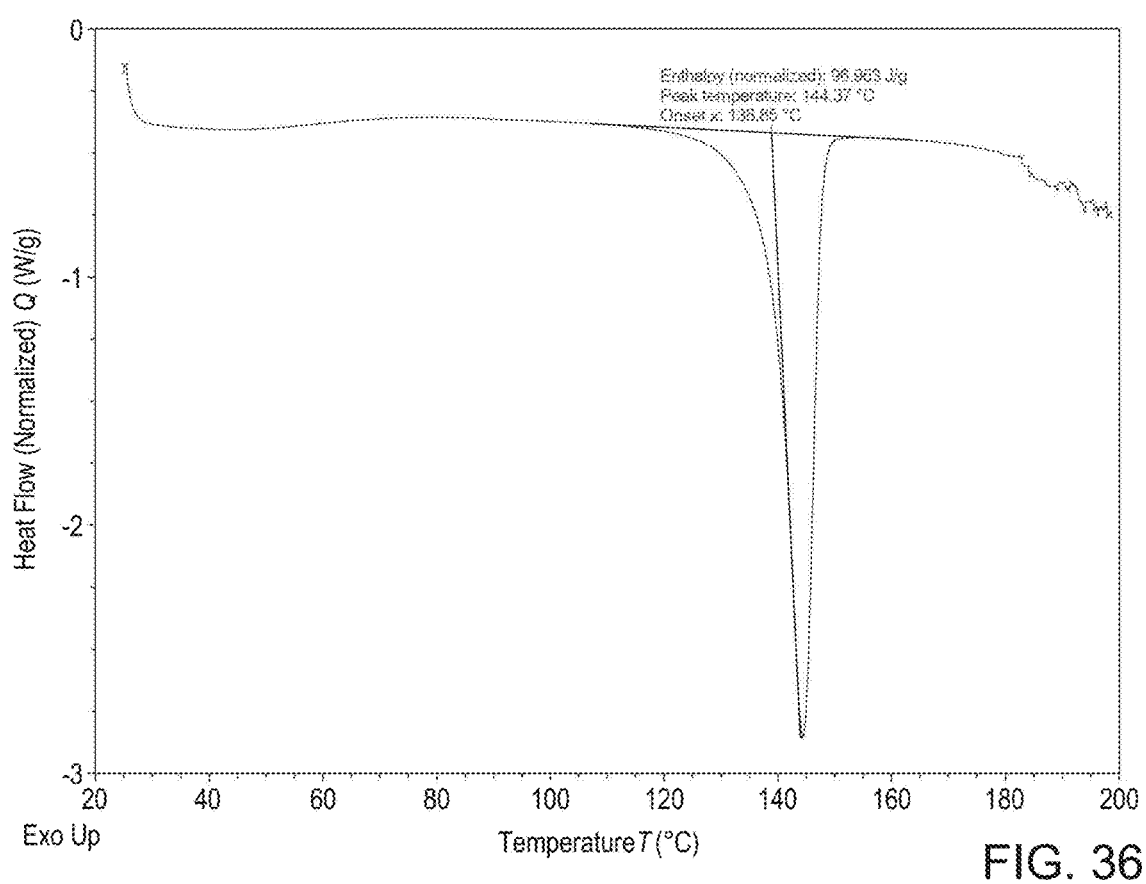
FIG. 36. DSC Thermogram (1st heating) of Tartrate salt, Batch: DXD2203-009-09.

The $1^{st}$ heating cycle DSC thermogram of Tartrate salt displayed a single endothermic event with onset temperature around 138.9° C. and heat of fusion 97.0 J/g as shown in, or substantially as shown in, FIG. 36 which correspond to the melting of the Tartrate salt.

Figure 37:
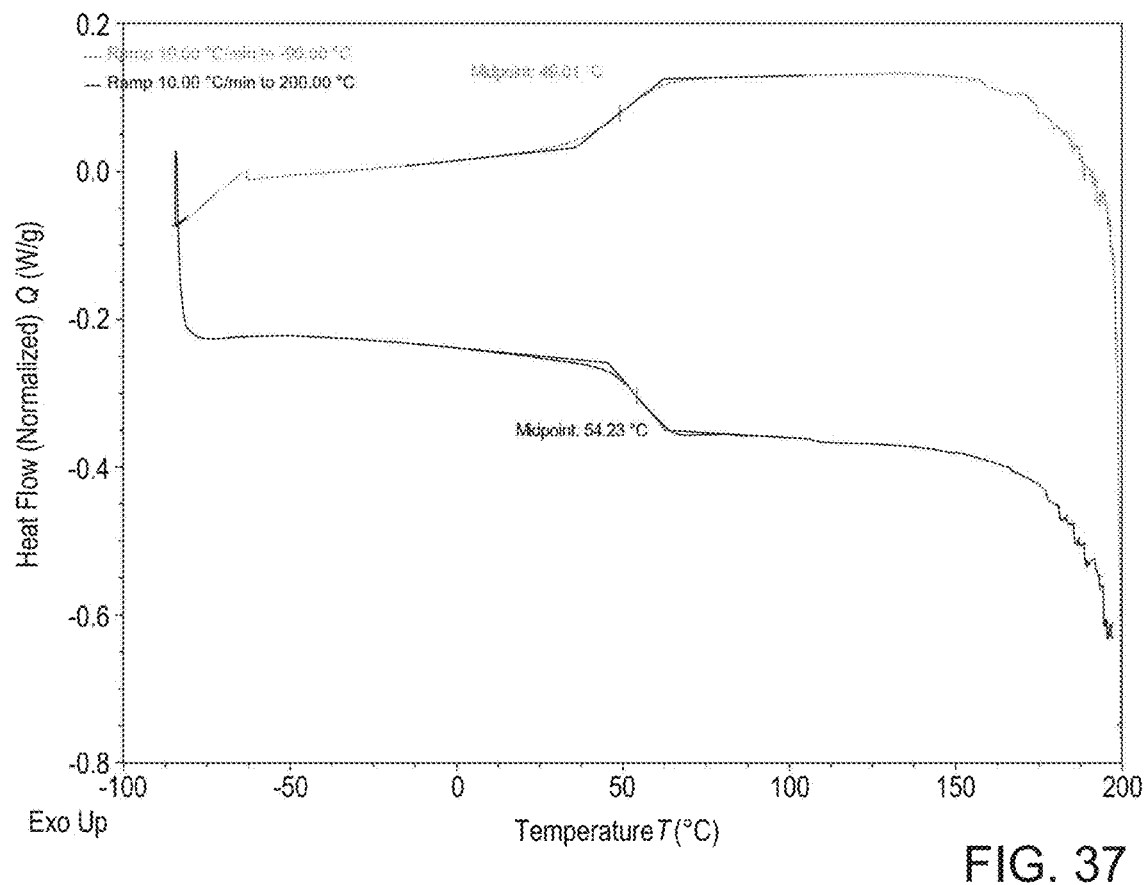
FIG. 37. DSC Thermograms of Tartrate salt, cooling (blue trace) and 2nd heating (green trace).

The cooling ramp from 200° C. to −90° C. at 10° C./min showed a vitrification at around 49.0° C. and the $2^{nd}$ heating cycle displayed a glass transition of 54.2° C. as shown in, or substantially as shown in, FIG. 37.

Figure 38:
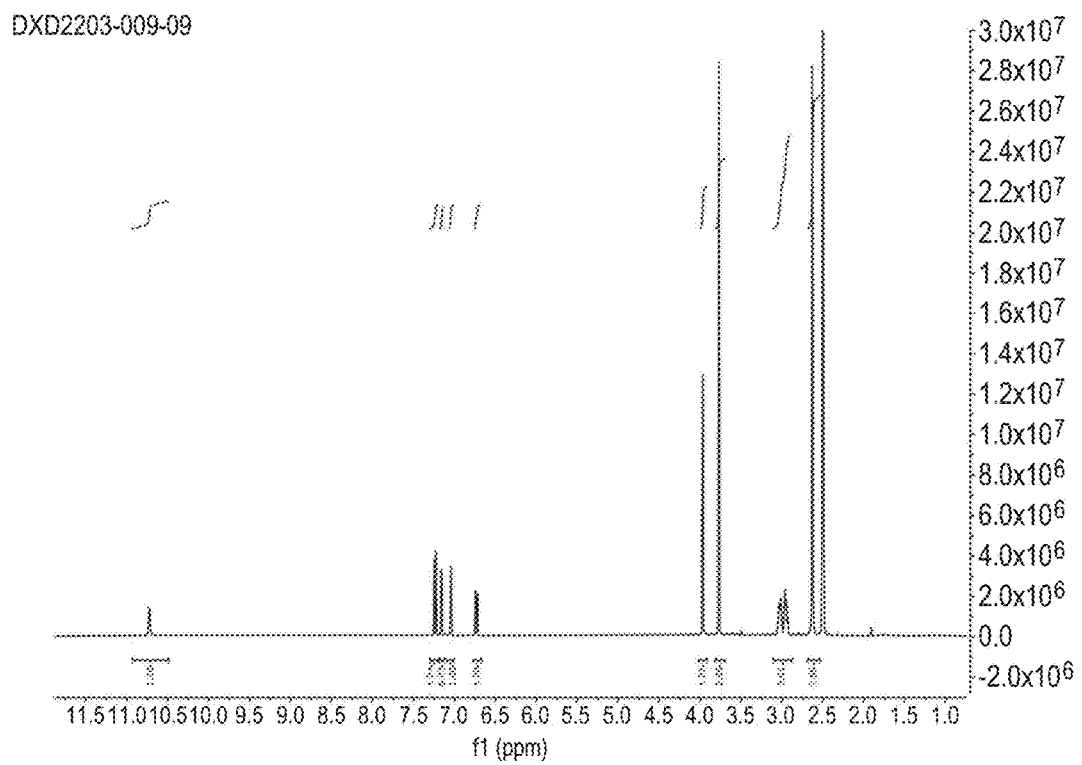
FIG. 38. 1H NMR (d6-DMSO) Spectrum of Tartrate salt, Batch: DXD2203-009-09.
Figure 39:
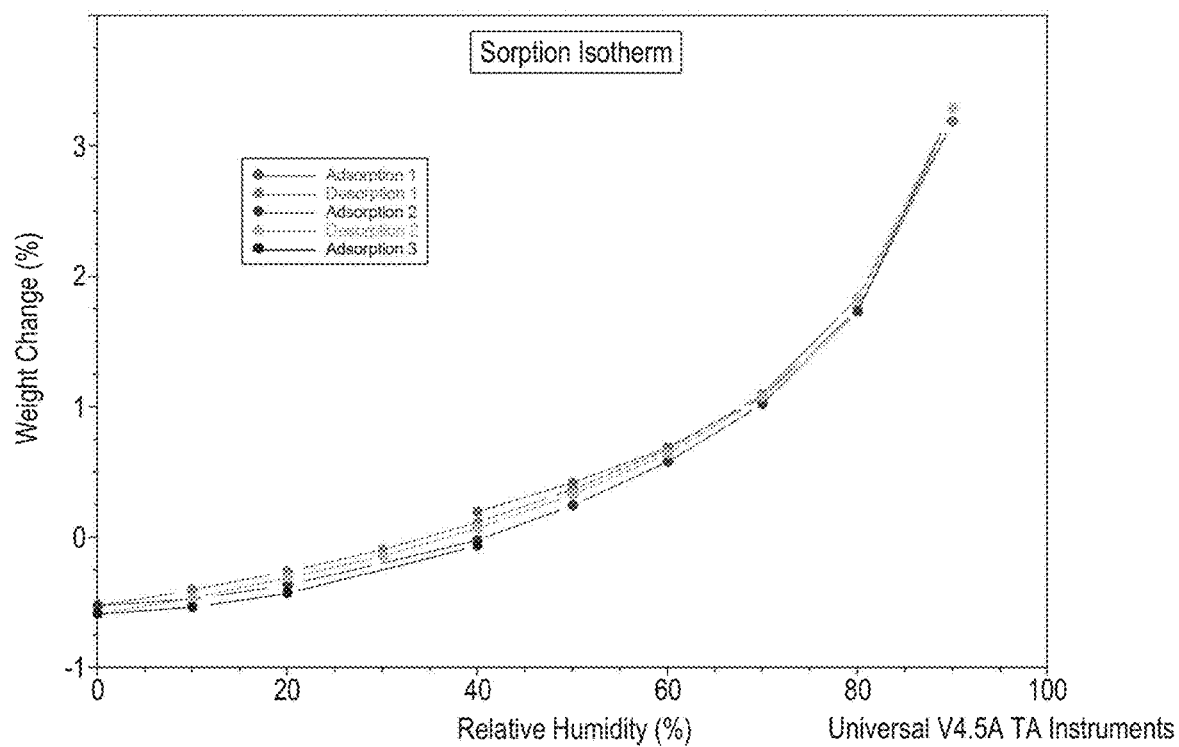
FIG. 39 shows the DVS isotherm plot for Tartrate salt.
Figure 40:
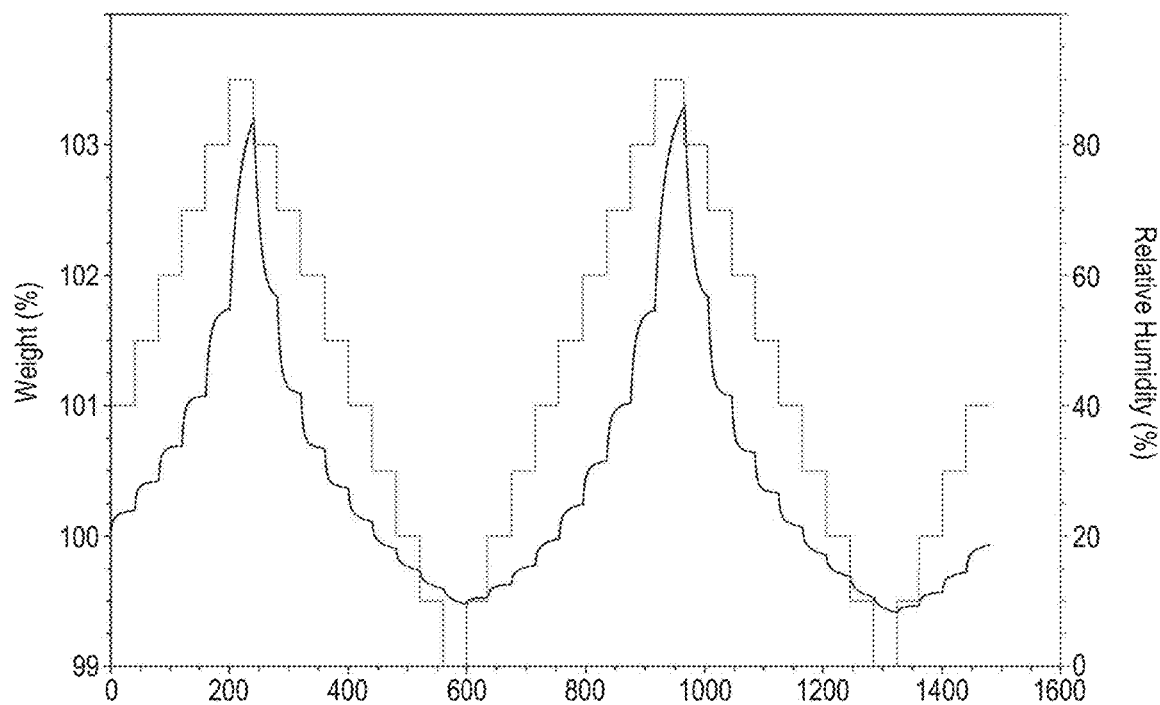
FIG. 40. Sorption kinetic plot of Tartrate salt, Batch: DXD2203-009-08.

$^1$H NMR spectrum of Tartrate salt in $d_6$-DMSO presented in FIG. 38, displayed around 0.9 eq of tartaric acid present and traces of THF. The $^1$H NMR result confirmed the formation of Tartrate salt. The total water uptake between 0% RH and 90% RH at 25° C. was observed to be approximately 3.3% w/w (moderately hygroscopic). Adsorption/desorption profiles are reversible and overlap, which indicates that sorption of moisture at higher humidity does not affect the internal structure of Tartrate salt. The XRPD post DVS analyses showed that Tartrate salt did not undergo any solid form transformation when exposed to moisture and remained the same crystalline solid form as demonstrated in FIG. 41.

Figure 35:
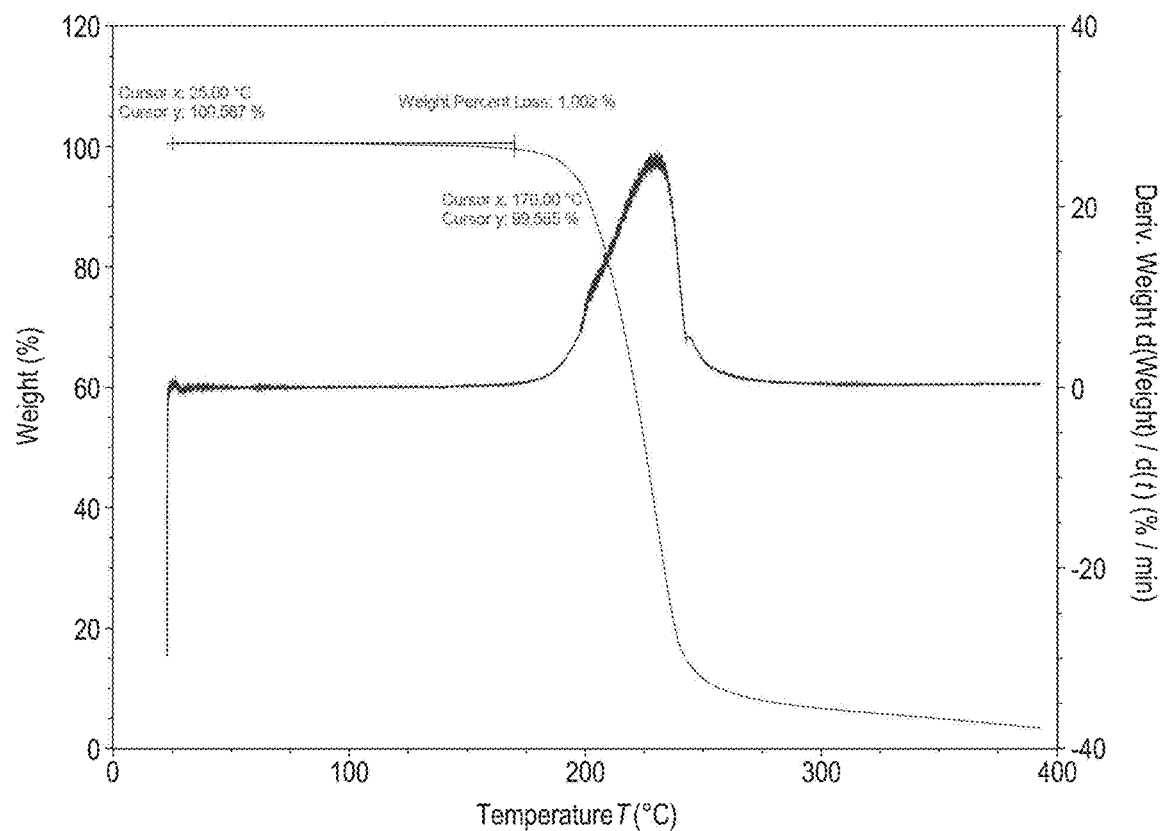
FIG. 35. TGA Thermogram of Tartrate salt, Batch: DXD2203-009-09.

In one embodiment, there is provided 5-MeO-DMT tartrate. In one embodiment, there is provided a pharmaceutical composition comprising 5-MeO-DMT tartrate. In one embodiment, there is provided crystalline 5-MeO-DMT tartrate, or a pharmaceutical composition comprising crystalline 5-MeO-DMT tartrate, as characterised by one or more of:

An XRPD pattern as shown in, or substantially as shown in, FIG. 34;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, or thirty three peaks in an XRPD diffractogram as detailed in Table 13, Table 13a or Table 13b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 13, Table 13a or Table 13b;

A TGA thermogram as shown in, or substantially as shown in, FIG. 35;

A weight loss of 1% between 25-170° C., as measured by TGA thermogram;

A weight loss of around 0.1-1.0% between 25-170° C., as measured by TGA thermogram;

A weight loss of around 0.1, 0.2, 0.3, 0.4, 0.5, 0.6, 0.7, 0.8, 0.9 or 1.0% between 25-170° C., as measured by TGA thermogram;

A DSC thermogram as shown in, or substantially as shown in, FIG. 36 or FIG. 37;

A melting endothermic event with an onset of around 138.9° C. and an enthalpy of 97.0 J/g, as measured in a DSC thermogram;

A melting endothermic event with an onset of around 130-145° C. and an enthalpy of around 92-102 J/g, as measured in a DSC thermogram;

A melting endothermic event with an onset of around 130, 131, 132, 133, 134, 135, 136, 137, 138, 139, 140, 141, 142, 143, 144 or 145° C. and an enthalpy of around 92, 93, 94, 95, 96, 97, 98, 99, 100, 101 or 102 J/g, as measured in a DSC thermogram;

A vitrification around 49° C., as measured in a DSC thermogram with a cooling ramp of 10° C./min from 200° C. to −90° C.;

A vitrification around 45-55° C., as measured in a DSC thermogram with a cooling ramp of 10° C./min from 200° C. to −90° C.;

A vitrification around 45, 46, 47, 48, 49, 50, 51, 52, 53, 54 or 55° C., as measured in a DSC thermogram with a cooling ramp of 10° C./min from 200° C. to −90° C.;

A glass transition around 54.2° C., as measured in a DSC thermogram with a cooling ramp of 10° C./min from 200° C. to −90° C.;

A glass transition around 50-60° C., as measured in a DSC thermogram with a cooling ramp of 10° C./min from 200° C. to −90° C.;

A glass transition around 50, 51, 52, 53, 54, 55, 56, 57, 58, 59 or 60° C., as measured in a DSC thermogram with a cooling ramp of 10° C./min from 200° C. to −90° C.;

A total water uptake between 0% RH and 90% RH at 25° C. of approximately 3.3% w/w;

A $^1$H NMR spectrum as shown in, or substantially as shown in, FIG. 38; and/or

Figure 41:
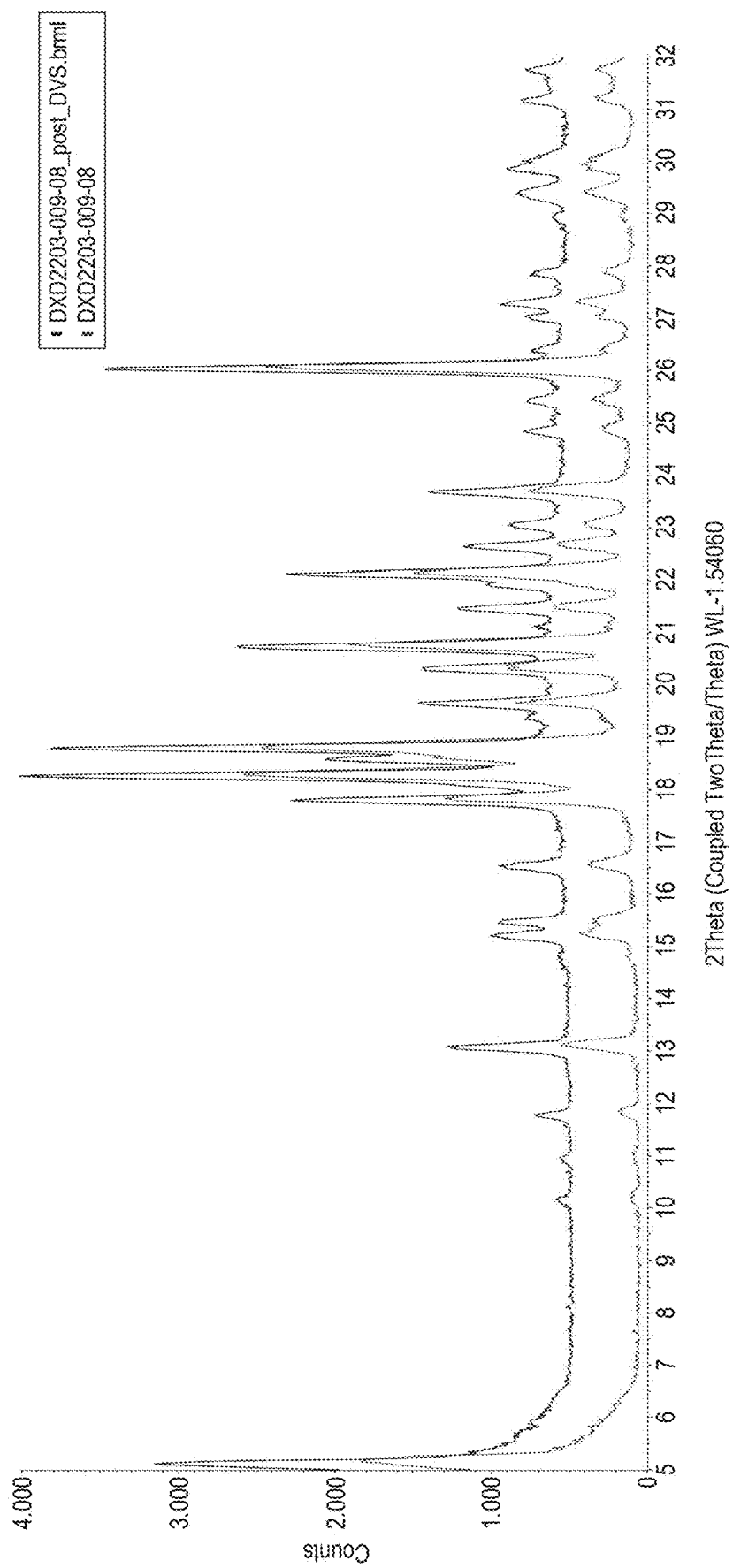
FIG. 41. XRPD Diffractograms of Tartrate salt, Batch: DXD2203-009-08 (red trace) post DVS (black trace).

An XRPD pattern as shown in, or substantially as shown in, FIG. 41.

Benzenesulfonate Salt

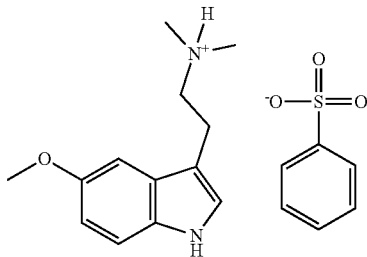

Figure 42:
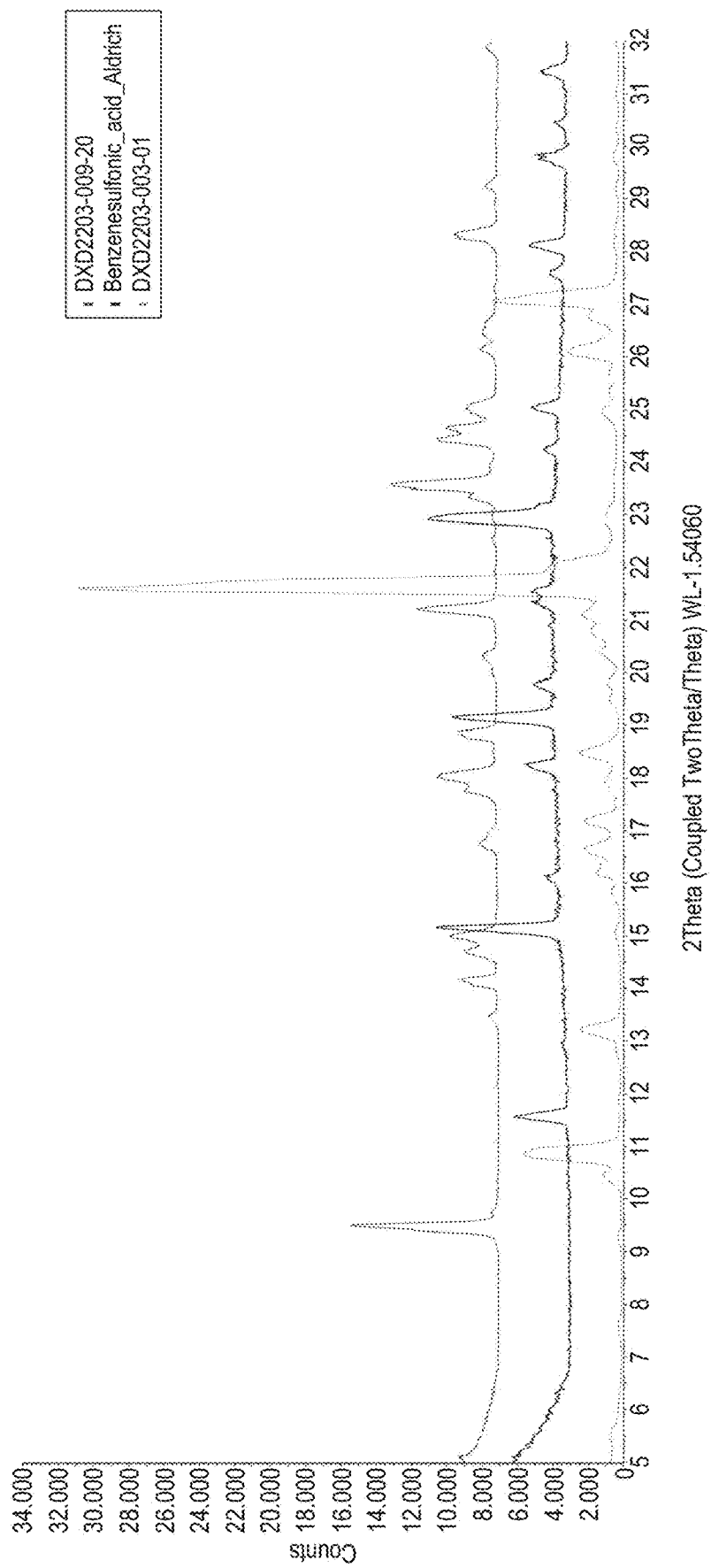
FIG. 42. XRPD Diffractograms of Benzenesulfonate salt isolated from IPA/hexane (red trace), Benzenesulfonic acid (black trace) and Free Base (blue trace).

The XRPD pattern of Benzenesulfonate salt is shown in FIG. 42. It displayed peaks at different 2 theta values when compared to Benzenesulfonic acid and Free Base, thus confirming the salt formation. This was nominated as pattern 1 with XRPD peak data shown in Table 14, Table 14a or Table 14b.

TABLE 14

XRPD Peak data for Benzenesulfonate pattern 1.

| Peak No. | Angle 2 θ | d Value | Rel. Intensity |
|---|---|---|---|
| 1 | 8.579° | 10.298 | 0.006 |
| 2 | 9.490° | 9.312 | 1.000 |
| 3 | 9.738° | 9.076 | 0.051 |
| 4 | 12.189° | 7.255 | 0.006 |
| 5 | 13.449° | 6.578 | 0.064 |
| 6 | 14.164° | 6.248 | 0.260 |
| 7 | 14.703° | 6.020 | 0.225 |
| 8 | 14.997° | 5.903 | 0.315 |
| 9 | 16.791° | 5.276 | 0.105 |
| 10 | 17.770° | 4.987 | 0.213 |
| 11 | 18.035° | 4.915 | 0.393 |
| 12 | 18.506° | 4.791 | 0.025 |
| 13 | 18.872° | 4.698 | 0.266 |
| 14 | 20.035° | 4.428 | 0.024 |
| 15 | 20.332° | 4.364 | 0.092 |
| 16 | 21.215° | 4.185 | 0.535 |
| 17 | 21.954° | 4.045 | 0.014 |
| 18 | 22.526° | 3.944 | 0.025 |
| 19 | 22.964° | 3.870 | 0.023 |
| 20 | 23.338° | 3.809 | 0.175 |
| 21 | 23.571° | 3.771 | 0.704 |
| 22 | 23.911° | 3.719 | 0.039 |
| 23 | 24.435° | 3.640 | 0.389 |
| 24 | 24.655° | 3.608 | 0.331 |
| 25 | 25.050° | 3.552 | 0.188 |
| 26 | 26.152° | 3.405 | 0.104 |
| 27 | 26.536° | 3.356 | 0.083 |
| 28 | 26.962° | 3.304 | 0.015 |
| 29 | 27.316° | 3.262 | 0.017 |
| 30 | 28.333° | 3.147 | 0.295 |
| 31 | 28.900° | 3.087 | 0.010 |
| 32 | 29.249° | 3.051 | 0.076 |
| 33 | 29.621° | 3.013 | 0.007 |
| 34 | 30.064° | 2.970 | 0.013 |
| 35 | 30.564° | 2.923 | 0.011 |
| 36 | 31.017° | 2.881 | 0.010 |
| 37 | 31.901° | 2.803 | 0.054 |

TABLE 14a

XRPD Peak data for Benzenesulfonate pattern 1 (2 d.p.).

| Peak No. | Angle 2 θ | d Value | Rel. Intensity |
|---|---|---|---|
| 1 | 8.58° | 10.30 | 0.01 |
| 2 | 9.49° | 9.31 | 1.00 |
| 3 | 9.74° | 9.08 | 0.05 |
| 4 | 12.19° | 7.26 | 0.01 |
| 5 | 13.45° | 6.58 | 0.06 |
| 6 | 14.16° | 6.25 | 0.26 |
| 7 | 14.70° | 6.02 | 0.23 |
| 8 | 15.00° | 5.90 | 0.32 |
| 9 | 16.79° | 5.28 | 0.11 |
| 10 | 17.77° | 4.99 | 0.21 |
| 11 | 18.04° | 4.92 | 0.39 |
| 12 | 18.51° | 4.79 | 0.03 |
| 13 | 18.87° | 4.70 | 0.27 |
| 14 | 20.04° | 4.43 | 0.02 |
| 15 | 20.33° | 4.36 | 0.09 |
| 16 | 21.22° | 4.19 | 0.54 |
| 17 | 21.95° | 4.05 | 0.01 |
| 18 | 22.53° | 3.94 | 0.03 |
| 19 | 22.96° | 3.87 | 0.02 |
| 20 | 23.34° | 3.81 | 0.18 |
| 21 | 23.57° | 3.77 | 0.70 |
| 22 | 23.91° | 3.72 | 0.04 |
| 23 | 24.44° | 3.64 | 0.39 |
| 24 | 24.66° | 3.61 | 0.33 |
| 25 | 25.05° | 3.55 | 0.19 |
| 26 | 26.15° | 3.41 | 0.10 |
| 27 | 26.54° | 3.36 | 0.08 |
| 28 | 26.96° | 3.30 | 0.02 |
| 29 | 27.32° | 3.26 | 0.02 |
| 30 | 28.33° | 3.15 | 0.30 |
| 31 | 28.90° | 3.09 | 0.01 |
| 32 | 29.25° | 3.05 | 0.08 |
| 33 | 29.62° | 3.01 | 0.01 |
| 34 | 30.06° | 2.97 | 0.01 |
| 35 | 30.56° | 2.92 | 0.01 |
| 36 | 31.02° | 2.88 | 0.01 |
| 37 | 31.90° | 2.80 | 0.05 |

TABLE 14b

XRPD Peak data for Benzenesulfonate pattern 1 (1 d.p.).

| Peak No. | Angle 2 θ | d Value | Rel. Intensity |
|---|---|---|---|
| 1 | 8.6° | 10.3 | 0.0 |
| 2 | 9.5° | 9.3 | 1.0 |
| 3 | 9.7° | 9.1 | 0.1 |
| 4 | 12.2° | 7.3 | 0.0 |
| 5 | 13.4° | 6.6 | 0.1 |
| 6 | 14.2° | 6.2 | 0.3 |
| 7 | 14.7° | 6.0 | 0.2 |
| 8 | 15.0° | 5.9 | 0.3 |
| 9 | 16.8° | 5.3 | 0.1 |
| 10 | 17.8° | 5.0 | 0.2 |
| 11 | 18.0° | 4.9 | 0.4 |
| 12 | 18.5° | 4.8 | 0.0 |
| 13 | 18.9° | 4.7 | 0.3 |
| 14 | 20.0° | 4.4 | 0.0 |
| 15 | 20.3° | 4.4 | 0.1 |
| 16 | 21.2° | 4.2 | 0.5 |
| 17 | 22.0° | 4.0 | 0.0 |
| 18 | 22.5° | 3.9 | 0.0 |
| 19 | 23.0° | 3.9 | 0.0 |
| 20 | 23.3° | 3.8 | 0.2 |
| 21 | 23.6° | 3.8 | 0.7 |
| 22 | 23.9° | 3.7 | 0.0 |
| 23 | 24.4° | 3.6 | 0.4 |
| 24 | 24.7° | 3.6 | 0.3 |
| 25 | 25.1° | 3.6 | 0.2 |
| 26 | 26.2° | 3.4 | 0.1 |
| 27 | 26.5° | 3.4 | 0.1 |
| 28 | 27.0° | 3.3 | 0.0 |
| 29 | 27.3° | 3.3 | 0.0 |
| 30 | 28.3° | 3.1 | 0.3 |
| 31 | 28.9° | 3.1 | 0.0 |
| 32 | 29.2° | 3.1 | 0.1 |
| 33 | 29.6° | 3.0 | 0.0 |
| 34 | 30.1° | 3.0 | 0.0 |
| 35 | 30.6° | 2.9 | 0.0 |
| 36 | 31.0° | 2.9 | 0.0 |
| 37 | 31.9° | 2.8 | 0.1 |

Figure 43:
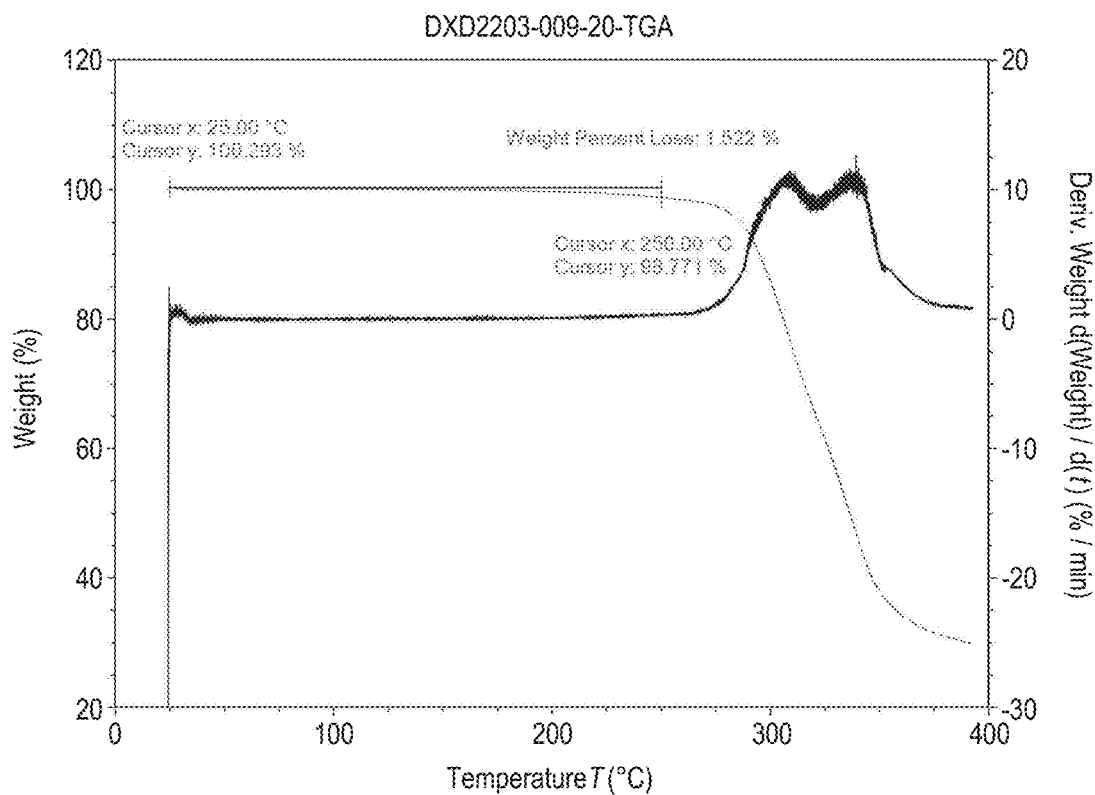
FIG. 43. TGA Thermogram of Benzenesulfonate salt, Batch: DXD2203-009-20.

The TGA thermogram of Benzenesulfonate salt is shown in FIG. 43. It showed a good thermal stability up to 250° C. The observed weight loss of 1.5% between 25-250° C. corresponding to around 0.1 moles of IPA.

The DSC analysis of the Benzenesulfonate salt was performed. The $1^{st}$ heating thermogram in FIG. 44 displayed a broad endothermic event with $T_{onst}$ around 76.2° C. and heat of fusion 66.5 J/g due to the melting of the Benzenesulfonate salt. A weak exothermic event around 140° C. was also observed.

Figure 45:
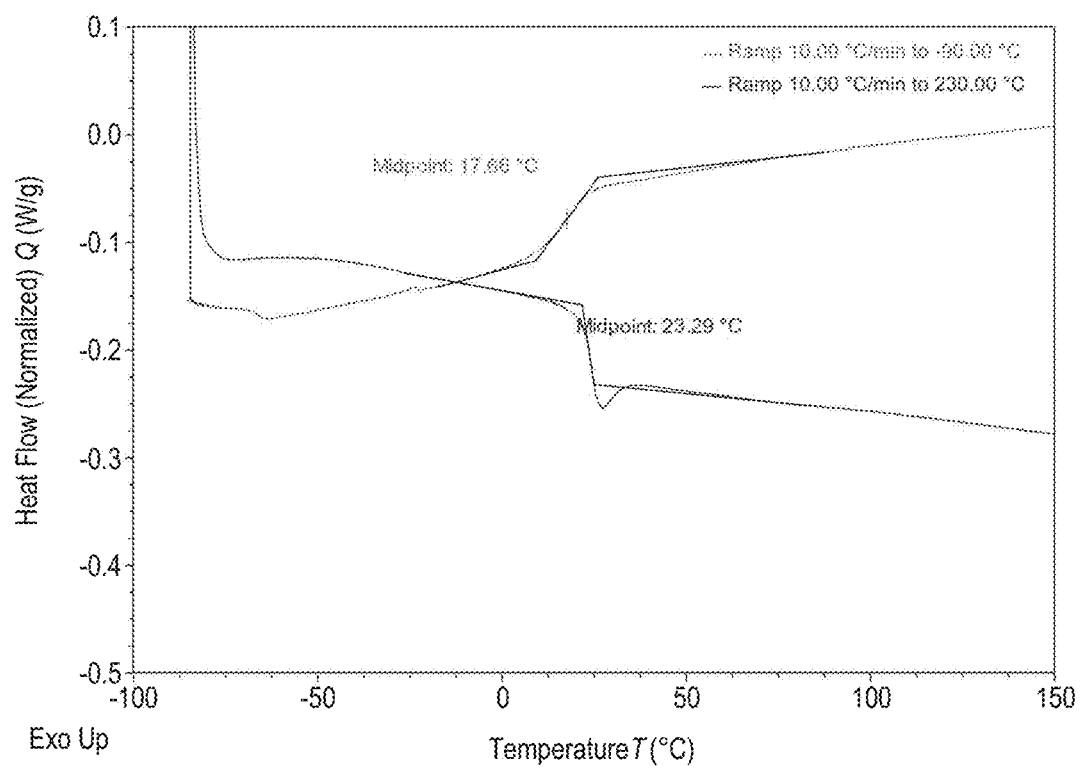
FIG. 45. DSC Thermograms of Benzenesulfonate salt, cooling (blue trace) and 2nd heating (green trace).

The cooling ramp and the $2^{nd}$ heating DSC thermograms in FIG. 45 displayed a vitrification around 17.7° C. and glass transition around 23.3° C., respectively.

Figure 46:
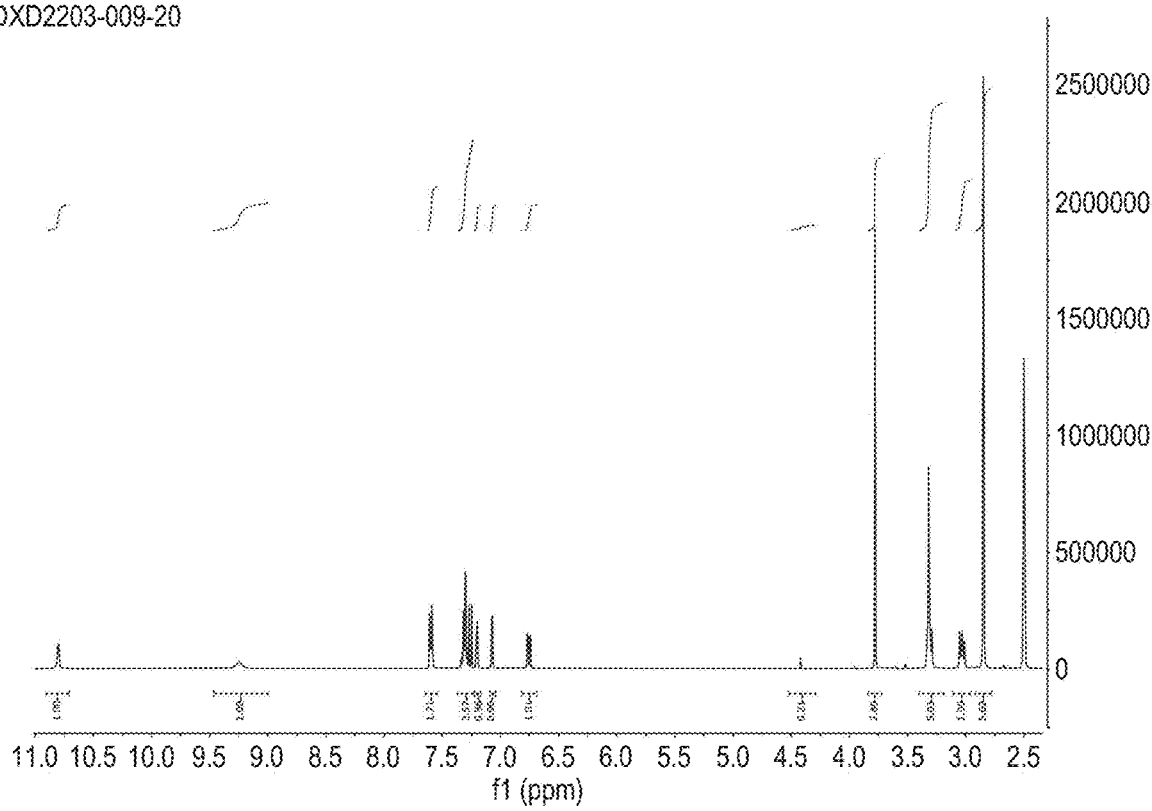
FIG. 46. 1H NMR (d6-DMSO) Spectrum of Benzenesulfonate salt, Batch: DXD2203-009-20.

$^1$H NMR spectrum of Benzenesulfonate salt in $d_6$-DMSO shown in FIG. 46 confirmed presence of 1.0 eq of benzene sulfonic acid. Residual traces of IPAC were also observed in the spectrum.

Figure 47:
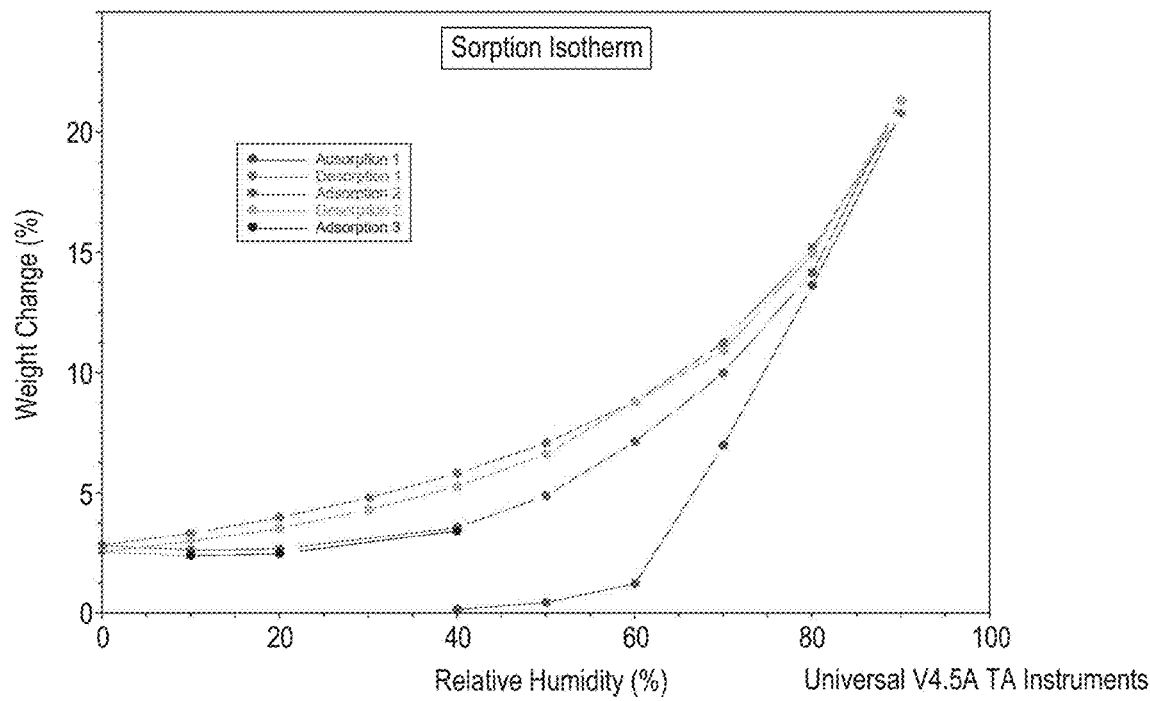
FIG. 47. DVS Isotherm plot of Benzenesulfonate salt, Batch: DXD2203-009-20.

The FIG. 47 shows the DVS isotherm plot for Benzenesulfonate salt. The first sorption isotherm showed hysteresis between 40-80% RH. Firstly, a slight water uptake up to 60% RH (1.2% w/w) was observed. When the salt was exposed to 70% RH and 80% RH it exhibited moisture absorption of 7% and 14% w/w, respectively and then the salt begins to deliquesce. The total moisture uptake between 0% RH and 90% RH at 25° C. was observed to be approximately 21% w/w in both cycles.

Figure 48:
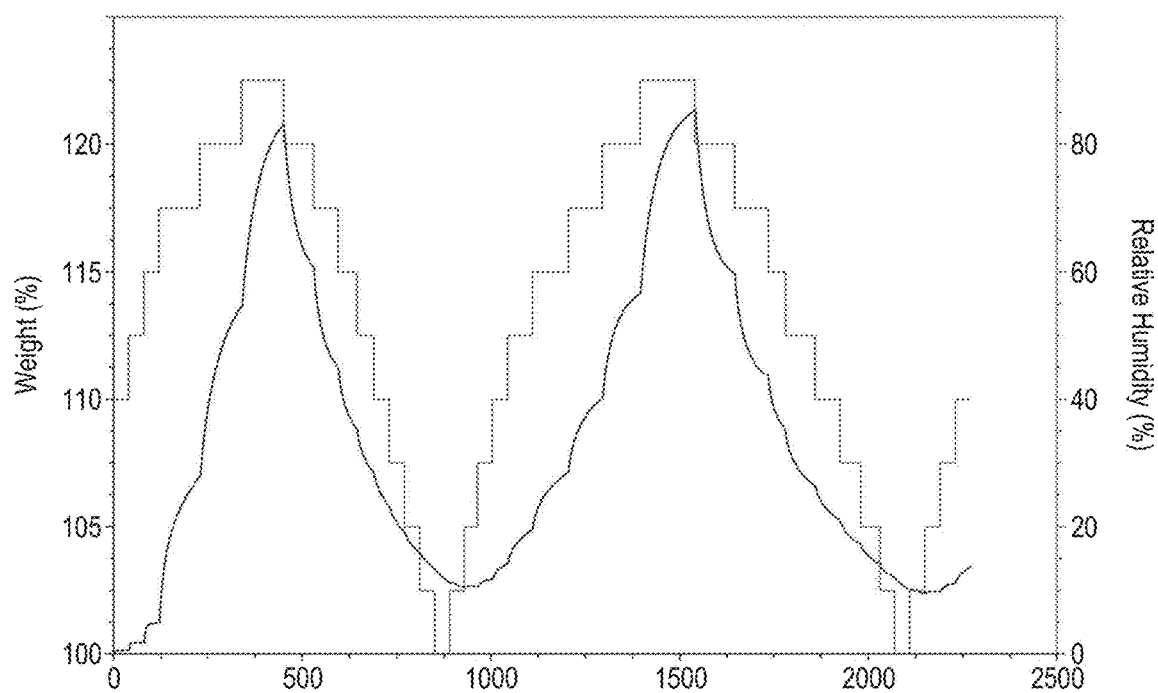
FIG. 48. Sorption kinetic plot of Benzenesulfonate salt, Batch: DXD2203-009-20.

The DVS kinetic plot of Benzenesulfonate salt is presented in FIG. 48. Due to deliquescence of Benzenesulfonate salt during the DVS experiment, XRPD analyses were not performed on post DVS sample.

Figure 44:
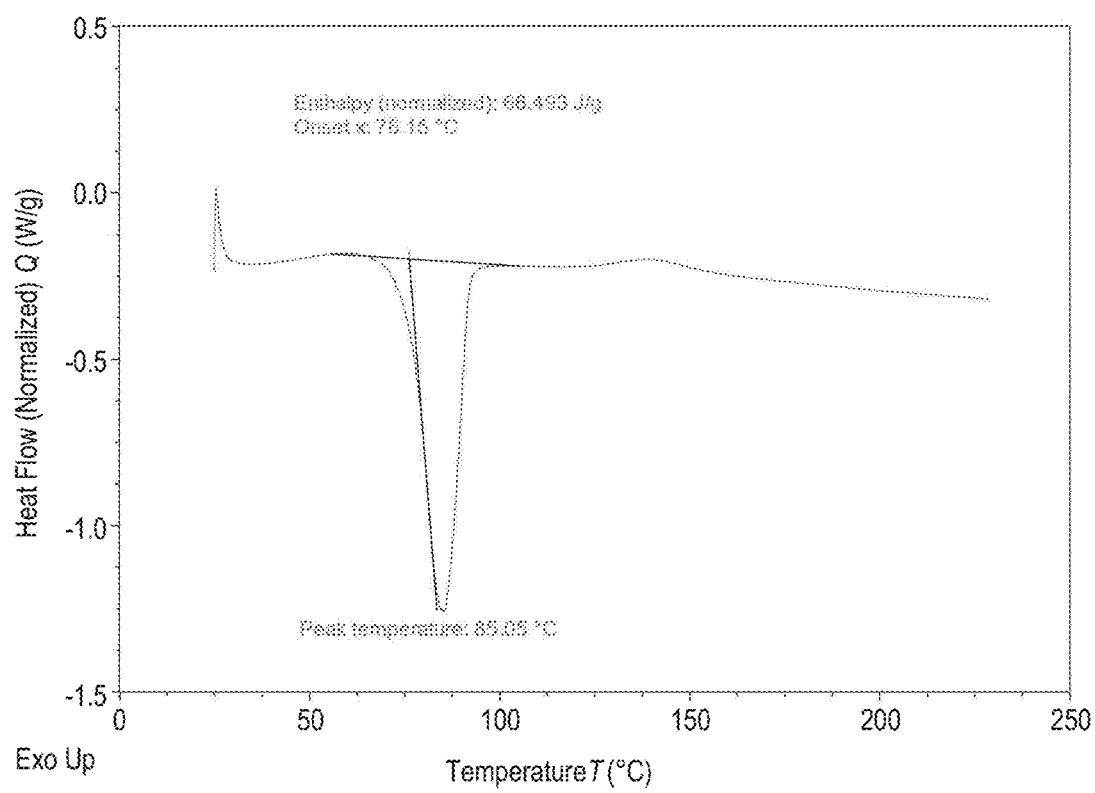
FIG. 44. DSC Thermogram (1st heating) of Benzenesulfonate salt, Batch: DXD2203-009-20.

In one embodiment, there is provided 5-MeO-DMT benzenesulfonate. In one embodiment, there is provided a pharmaceutical composition comprising 5-MeO-DMT benzenesulfonate. In one embodiment, there is provided crystalline 5-MeO-DMT benzenesulfonate, or a pharmaceutical composition comprising crystalline 5-MeO-DMT benzenesulfonate, as characterised by one or more of:

An XRPD pattern as shown in, or substantially as shown in, FIG. 42;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, thirty three or more, thirty four or more, thirty five or more, thirty six or more, or thirty seven peaks in an XRPD diffractogram as detailed in Table 14, Table 14a or Table 14b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 14, Table 14a or Table 14b;

A TGA thermogram as shown in, or substantially as shown in, FIG. 43;

A weight loss of 1.5% between 25-250° C., as measured by TGA thermogram;

A weight loss of around 1.0-2.0% between 25-250° C., as measured by TGA thermogram;

A weight loss of around 1.0, 1.1, 1.2, 1.3, 1.4, 1.5, 1.6, 1.7, 1.8, 1.9 or 2.0% between 25-250° C., as measured by TGA thermogram;

A DSC thermogram as shown in, or substantially as shown in, FIG. 44 or FIG. 45;

A melting endothermic event with an onset of around 76.2° C. and an enthalpy of 66.5 J/g, as measured in a DSC thermogram;

A melting endothermic event with an onset of around 70-80° C. and an enthalpy of around 60-70 J/g, as measured in a DSC thermogram;

A melting endothermic event with an onset of around 70, 71, 72, 73, 74, 75, 76, 77, 78, 79 or 80° C. and an enthalpy of around 60, 61, 62, 63, 64, 65, 66, 67, 68, 69 or 70 J/g, as measured in a DSC thermogram;

A weak exothermic event at around 140° C. as measured in a DSC thermogram;

A weak exothermic event at around 135-145° C. as measured in a DSC thermogram;

A weak exothermic event at around 135, 136, 137, 138, 139, 140, 141, 142, 143, 144 or 145° C. as measured in a DSC thermogram;

A vitrification around 17.7° C., as measured in a DSC thermogram with a cooling ramp of 10° C./min from 230° C. to −90° C.;

A vitrification around 12-22° C., as measured in a DSC thermogram with a cooling ramp of 10° C./min from 230° C. to −90° C.;

A vitrification around 12, 13, 14, 15, 16, 17, 18, 19, 20, 21 or 22° C., as measured in a DSC thermogram with a cooling ramp of 10° C./min from 230° C. to −90° C.;

A glass transition around 23.3° C., as measured in a DSC thermogram with a cooling ramp of 10° C./min from 230° C. to −90° C.;

A glass transition around 18-28° C., as measured in a DSC thermogram with a cooling ramp of 10° C./min from 230° C. to −90° C.;

A glass transition around 18, 19, 20, 21, 22, 23, 24, 25, 26, 27 or 28° C., as measured in a DSC thermogram with a cooling ramp of 10° C./min from 230° C. to −90° C.;

A ¹H NMR spectrum as shown in, or substantially as shown in, FIG. 46;

A DVS isotherm plot as shown in, or substantially as shown in, FIG. 47; and/or A DVS kinetic plot as shown in, or substantially as shown in, FIG. 48.

Tosylate Salt

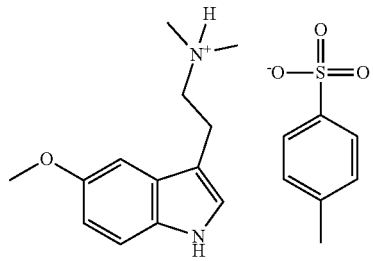

Figure 49:
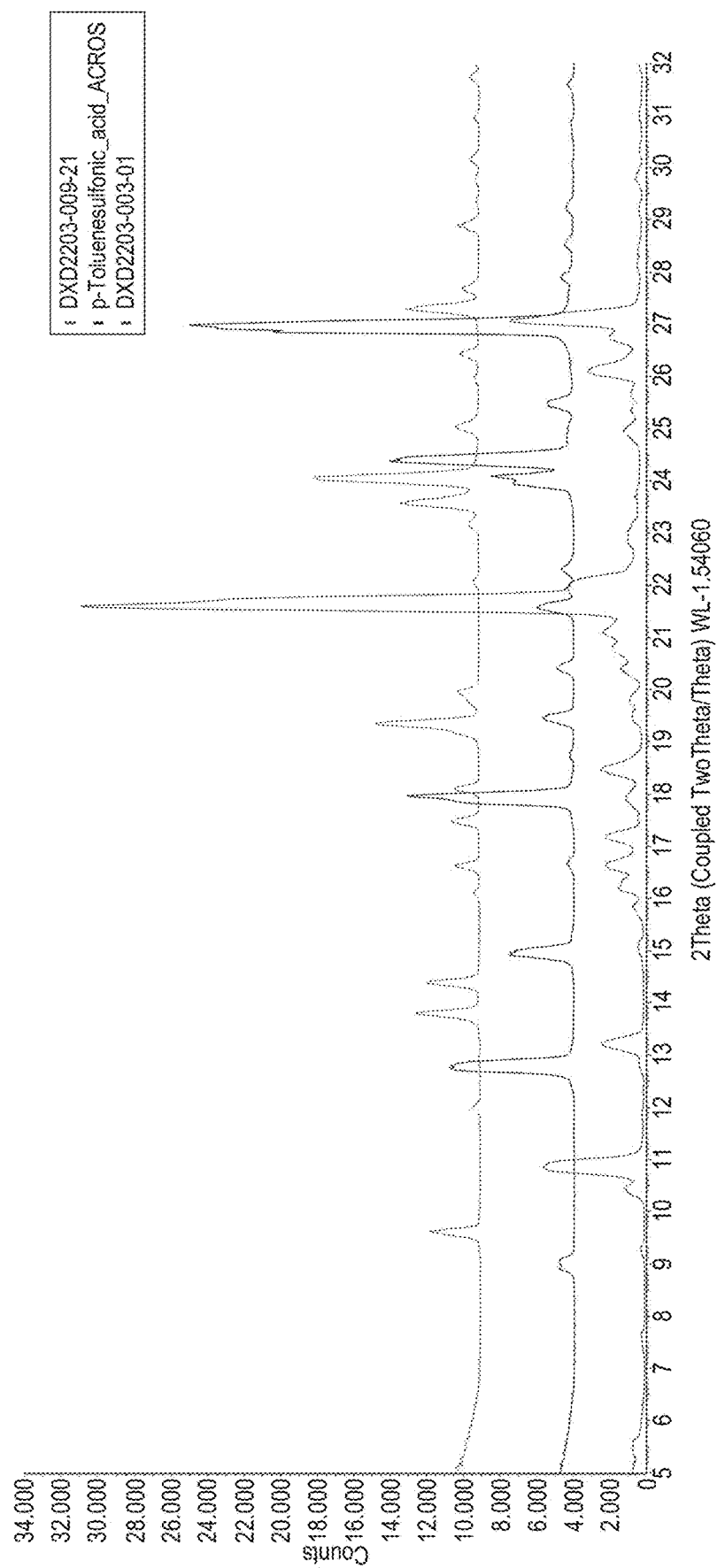
FIG. 49. XRPD Diffractograms of Tosylate salt isolated from IPA/Hexane (red trace, top), p-toluene sulfonic acid (black trace, middle) and Free Base (blue trace, bottom).

As shown in, or substantially as shown in, FIG. 49, the crystalline form of Tosylate salt has a distinctively different XRPD pattern when compared to the free base and p-toluenesulfonic acid confirming the salt formation. This was nominated as pattern 1 with XRPD peak data presented in Table 15, Table 15a or Table 15b.

TABLE 15

XRPD Peak data for Tosylate pattern 1.

| Peak No. | Angle 2 θ | d Value | Rel. Intensity |
|---|---|---|---|
| 1 | 9.609° | 9.197 | 0.296 |
| 2 | 12.001° | 7.369 | 0.041 |
| 3 | 12.934° | 6.839 | 0.007 |
| 4 | 13.798° | 6.413 | 0.386 |
| 5 | 14.391° | 6.150 | 0.315 |
| 6 | 16.105° | 5.499 | 0.034 |
| 7 | 16.625° | 5.328 | 0.138 |
| 8 | 17.489° | 5.067 | 0.157 |
| 9 | 18.114° | 4.893 | 0.142 |
| 10 | 19.342° | 4.585 | 0.622 |
| 11 | 19.945° | 4.448 | 0.119 |
| 12 | 22.076° | 4.023 | 0.034 |
| 13 | 23.161° | 3.837 | 0.057 |
| 14 | 23.571° | 3.771 | 0.472 |
| 15 | 24.054° | 3.697 | 1.000 |
| 16 | 25.037° | 3.554 | 0.130 |
| 17 | 25.979° | 3.427 | 0.023 |
| 18 | 26.435° | 3.369 | 0.107 |
| 19 | 27.302° | 3.264 | 0.420 |
| 20 | 27.712° | 3.216 | 0.097 |
| 21 | 28.880° | 3.089 | 0.123 |
| 22 | 29.371° | 3.039 | 0.013 |
| 23 | 29.769° | 2.999 | 0.026 |
| 24 | 30.161° | 2.961 | 0.046 |
| 25 | 30.981° | 2.884 | 0.032 |
| 26 | 31.738° | 2.817 | 0.048 |

TABLE 15a

XRPD Peak data for Tosylate pattern 1 (2 d.p.).

| Peak No. | Angle 2 θ | d Value | Rel. Intensity |
|---|---|---|---|
| 1 | 9.61° | 9.20 | 0.30 |
| 2 | 12.00° | 7.37 | 0.04 |
| 3 | 12.93° | 6.84 | 0.01 |
| 4 | 13.80° | 6.41 | 0.39 |
| 5 | 14.39° | 6.15 | 0.32 |
| 6 | 16.11° | 5.50 | 0.03 |
| 7 | 16.63° | 5.33 | 0.14 |
| 8 | 17.49° | 5.07 | 0.16 |
| 9 | 18.11° | 4.89 | 0.14 |
| 10 | 19.34° | 4.59 | 0.62 |
| 11 | 19.95° | 4.45 | 0.12 |

TABLE 15a-continued

XRPD Peak data for Tosylate pattern 1 (2 d.p.).

| Peak No. | Angle 2 θ | d Value | Rel. Intensity |
|---|---|---|---|
| 12 | 22.08° | 4.02 | 0.03 |
| 13 | 23.16° | 3.84 | 0.06 |
| 14 | 23.57° | 3.77 | 0.47 |
| 15 | 24.05° | 3.70 | 1.00 |
| 16 | 25.04° | 3.55 | 0.13 |
| 17 | 25.98° | 3.43 | 0.02 |
| 18 | 26.44° | 3.37 | 0.11 |
| 19 | 27.30° | 3.26 | 0.42 |
| 20 | 27.71° | 3.22 | 0.10 |
| 21 | 28.88° | 3.09 | 0.12 |
| 22 | 29.37° | 3.04 | 0.01 |
| 23 | 29.77° | 3.00 | 0.03 |
| 24 | 30.16° | 2.96 | 0.05 |
| 25 | 30.98° | 2.88 | 0.03 |
| 26 | 31.74° | 2.82 | 0.05 |

TABLE 15b

XRPD Peak data for Tosylate pattern 1 (1 d.p.).

| Peak No. | Angle 2 θ | d Value | Rel. Intensity |
|---|---|---|---|
| 1 | 9.6° | 9.2 | 0.3 |
| 2 | 12.0° | 7.4 | 0.0 |
| 3 | 12.9° | 6.8 | 0.0 |
| 4 | 13.8° | 6.4 | 0.4 |
| 5 | 14.4° | 6.2 | 0.3 |
| 6 | 16.1° | 5.5 | 0.0 |
| 7 | 16.6° | 5.3 | 0.1 |
| 8 | 17.5° | 5.1 | 0.2 |
| 9 | 18.1° | 4.9 | 0.1 |
| 10 | 19.3° | 4.6 | 0.6 |
| 11 | 19.9° | 4.4 | 0.1 |
| 12 | 22.1° | 4.0 | 0.0 |
| 13 | 23.2° | 3.8 | 0.1 |
| 14 | 23.6° | 3.8 | 0.5 |
| 15 | 24.1° | 3.7 | 1.0 |
| 16 | 25.0° | 3.6 | 0.1 |
| 17 | 26.0° | 3.4 | 0.0 |
| 18 | 26.4° | 3.4 | 0.1 |
| 19 | 27.3° | 3.3 | 0.4 |
| 20 | 27.7° | 3.2 | 0.1 |
| 21 | 28.9° | 3.1 | 0.1 |
| 22 | 29.4° | 3.0 | 0.0 |
| 23 | 29.8° | 3.0 | 0.0 |
| 24 | 30.2° | 3.0 | 0.0 |
| 25 | 31.0° | 2.9 | 0.0 |
| 26 | 31.7° | 2.8 | 0.0 |

The TGA thermogram of Tosylate salt displayed a weight loss of 1.0% between 25-230° C. (0.1 moles IPA) followed by the thermal degradation as shown in, or substantially as shown in, FIG. 50.

Figure 51:
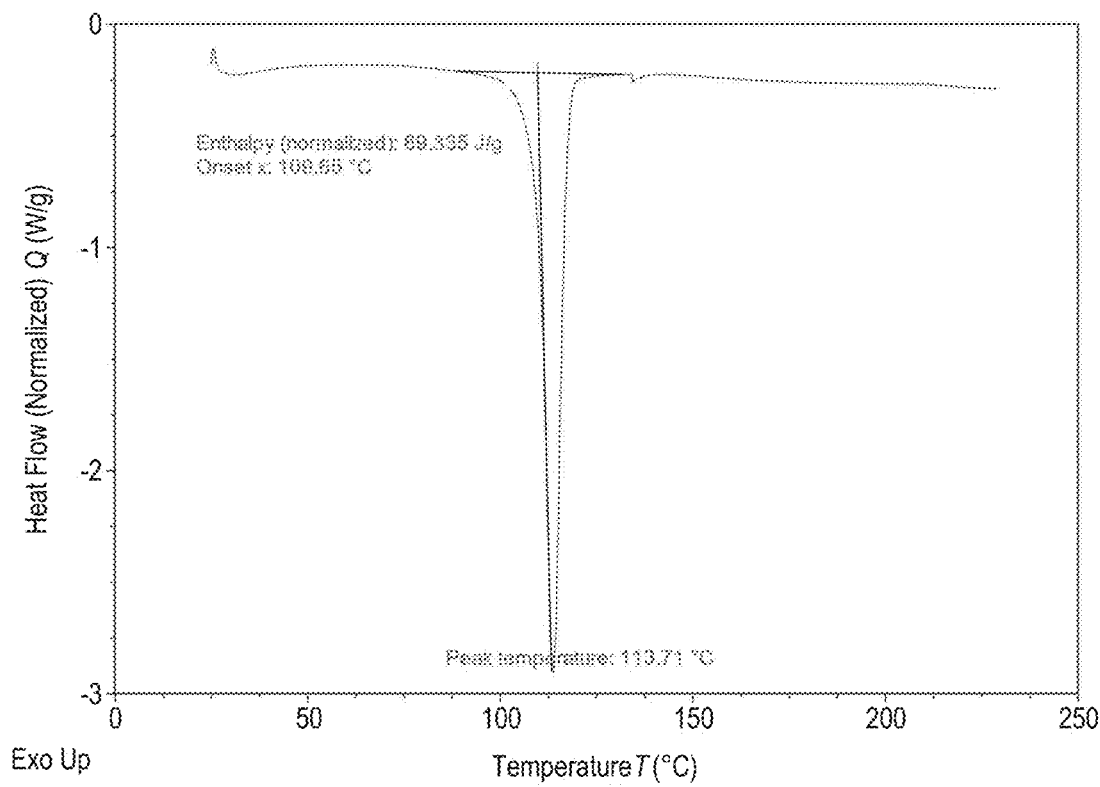
FIG. 51. DSC Thermogram (1st heating) of Tosylate salt, Batch: DXD2203-009-21.

The 1$^{st}$ heating DSC thermogram of Tosylate salt presented in FIG. 51, exhibited a single endothermic event with the onset temperature of 109.7° C. and heat of fusion of 89.3 J/g corresponding to the melting.

Figure 52:
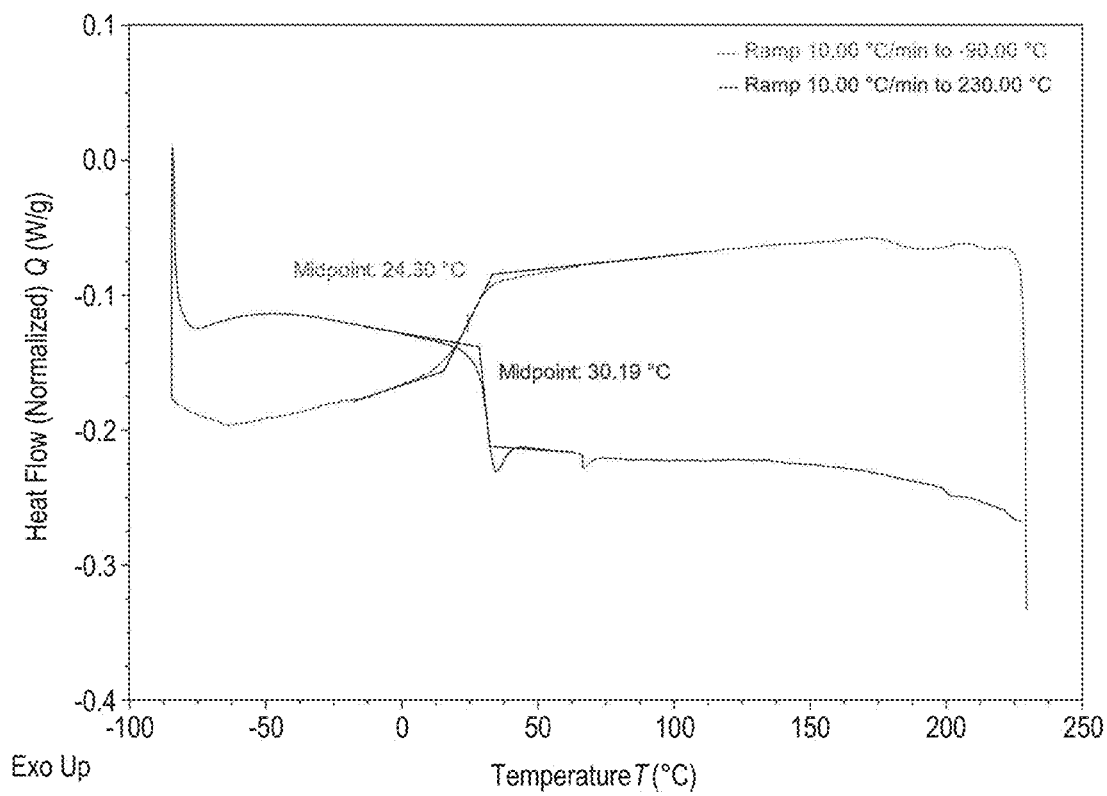
FIG. 52. DSC Thermograms of Tosylate salt, cooling (blue trace) and 2nd heating (green trace).

As presented in FIG. 52, the DSC thermograms of Tosylate salt upon cooling and 2$^{nd}$ heating displayed a vitrification and a glass transition around 24.3 and 30.2° C., respectively.

Figure 53:
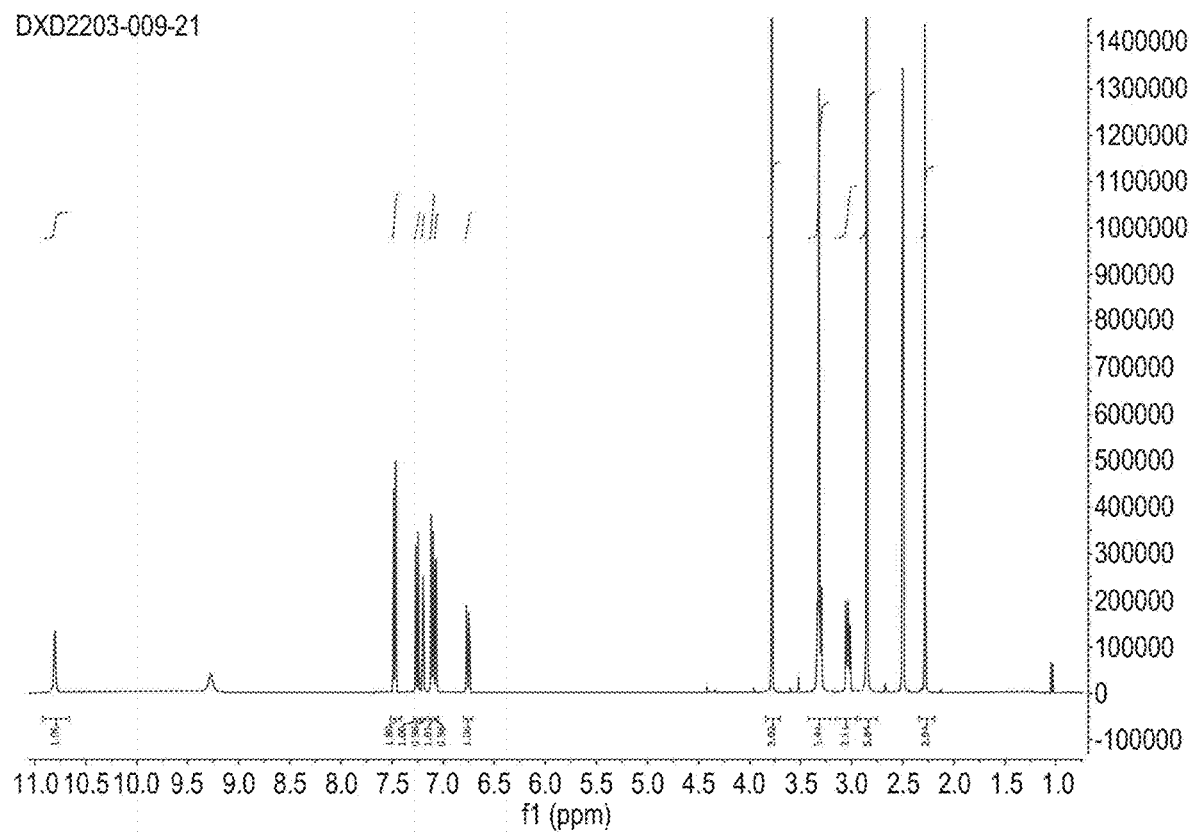
FIG. 53. 1H NMR (d6-DMSO) Spectrum of Tosylate salt, Batch: DXD2203-009-21.

$^1$H NMR spectrum in d$_6$-DMSO of Tosylate salt presented in FIG. 53 displayed the proton signals corresponding to the p-toluene sulfonic acid which were integrated as 1.0 eq. Traces of IPA were detected in the spectrum.

Evaluation of the DVS results obtained for Tosylate salt shows that the material is slightly hygroscopic with a water uptake of approximately 1.9% w/w between 0% RH and 90% RH at 25° C. The material takes up moisture reversibly without hysteresis which indicates that sorption at higher humidity does not affect the internal structure of the Tartrate salt as shown in, or substantially as shown in, FIG. 54.

Figure 55:
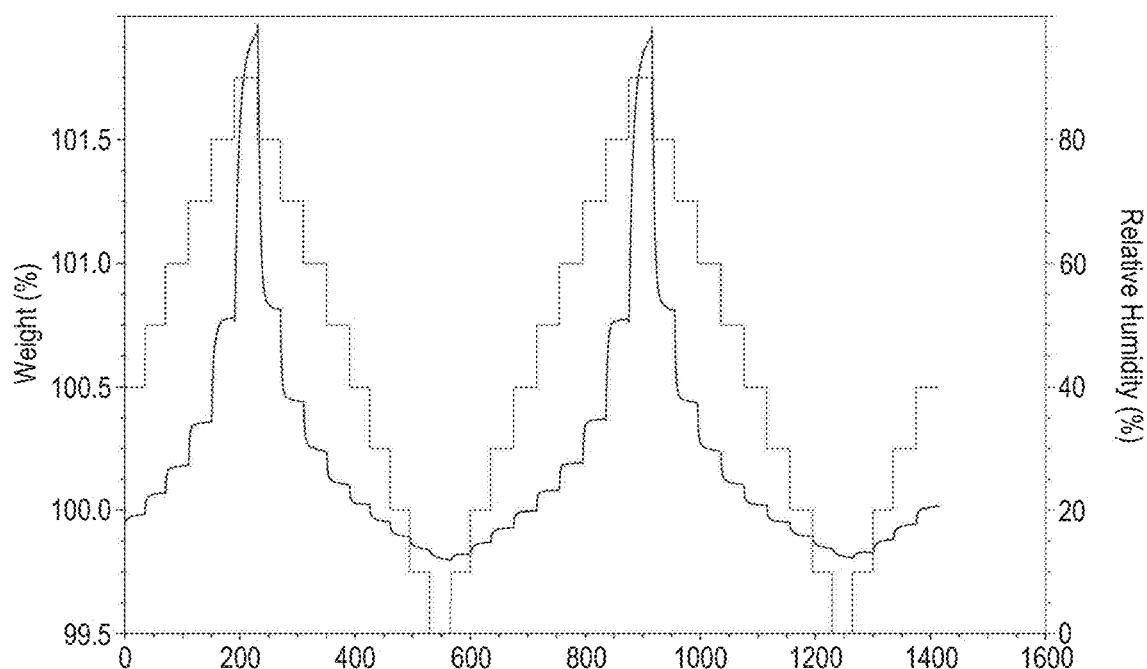
FIG. 55. Sorption kinetic plot of Tosylate salt, Batch: DXD2203-009-21.

The DVS kinetic plot of Tosylate salt is displayed in FIG. 55.

Figure 56:
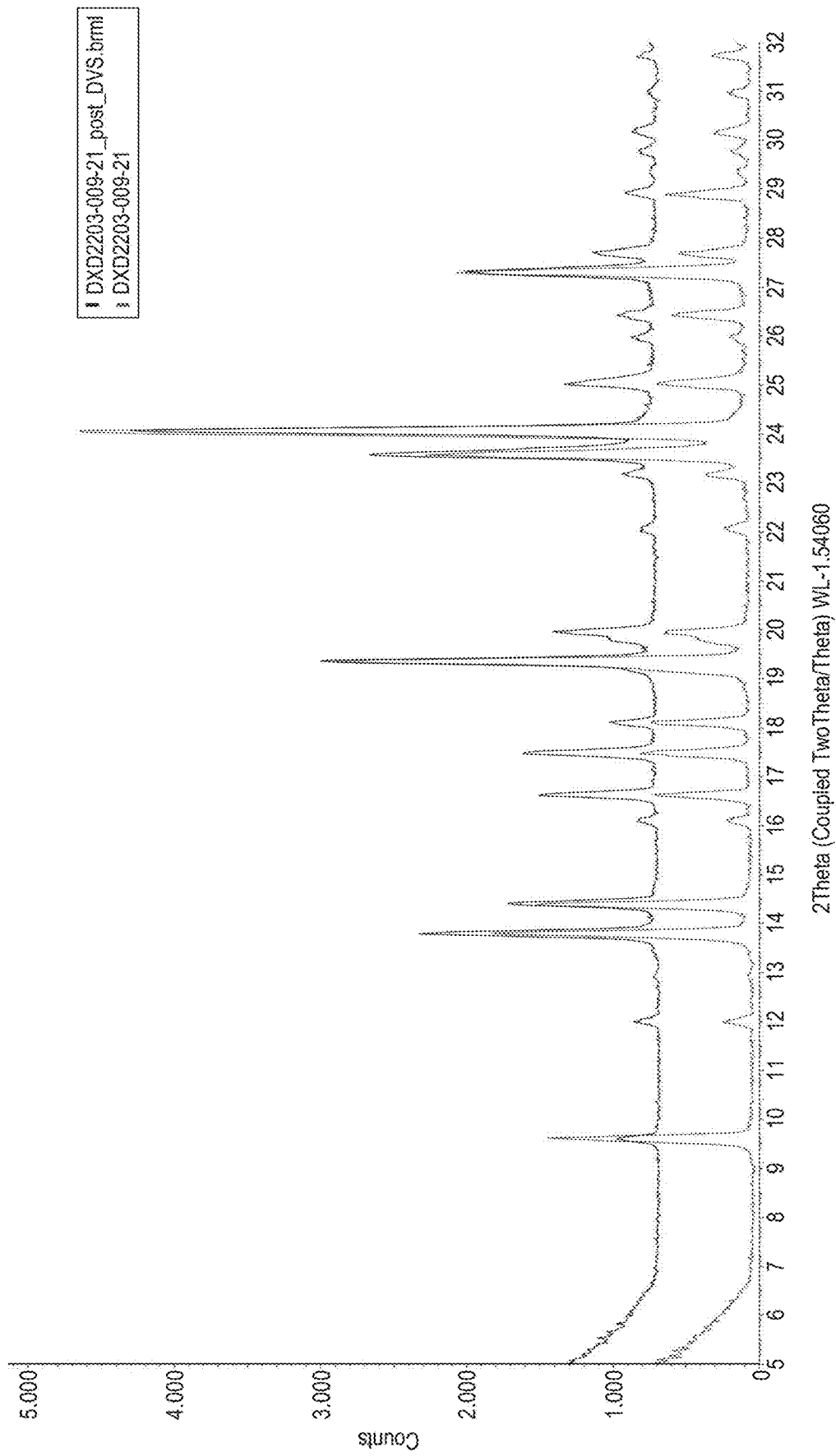
FIG. 56. XRPD Diffractograms of Tosylate salt, Batch: DXD2203-009-21 (red trace) and post DVS (black trace).

It can be seen from the XRPD diffractogram in FIG. 56 that the Tosylate salt did not undergo any solid-state changes during the DVS experiment as the XRPD pattern of post DVS sample remained unchanged.

Figure 50:
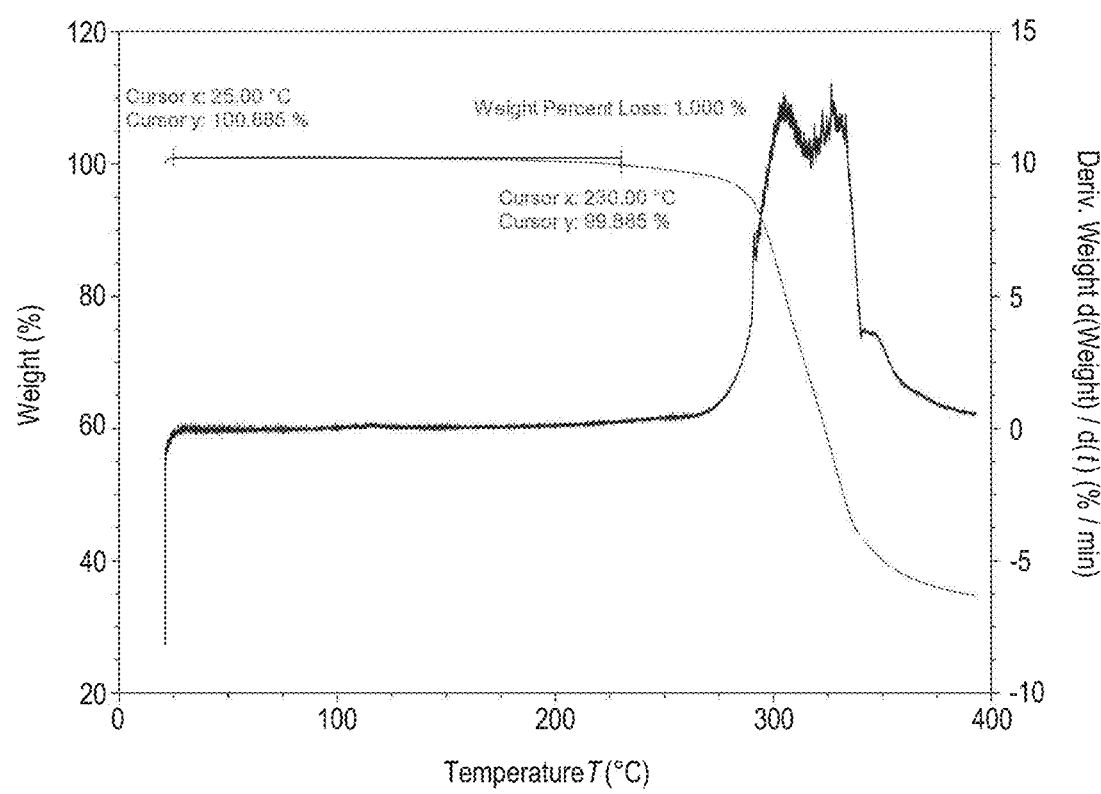
FIG. 50. TGA Thermogram of Tosylate salt, Batch: DXD2203-009-21.
Figure 54:
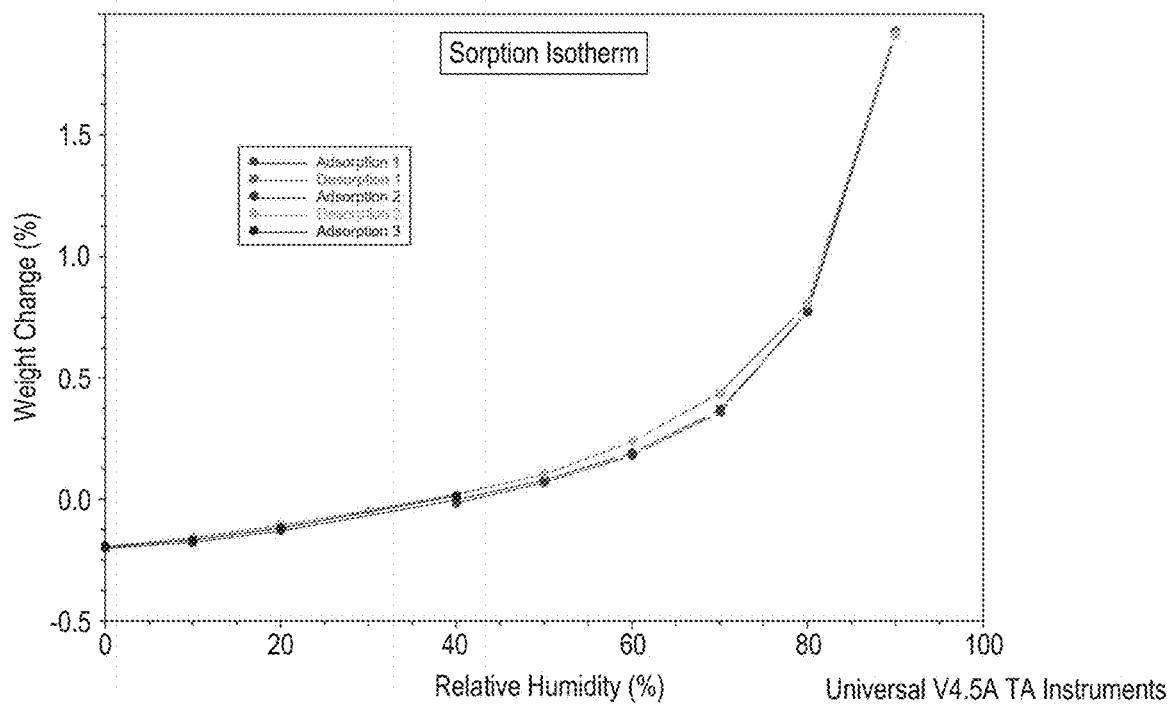
FIG. 54. DVS Isotherm plot of Tosylate salt, Batch: DXD2203-009-21.

In one embodiment, there is provided 5-MeO-DMT tosylate. In one embodiment, there is provided a pharmaceutical composition comprising 5-MeO-DMT tosylate. In one embodiment, there is provided crystalline 5-MeO-DMT tosylate, or a pharmaceutical composition comprising crystalline 5-MeO-DMT tosylate, as characterised by one or more of:

An XRPD pattern as shown in, or substantially as shown in, FIG. 49 or 56;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, or twenty six peaks in an XRPD diffractogram as detailed in Table 15, Table 15a or Table 15b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 15, Table 15a or Table 15b;

A TGA thermogram as shown in, or substantially as shown in, FIG. 50;

A weight loss of 1.0% between 25-230° C., as measured by TGA thermogram;

A weight loss of around 0.5-1.5% between 25-230° C., as measured by TGA thermogram;

A weight loss of around 0.5, 0.6, 0.7, 0.8, 0.9, 1.0, 1.1, 1.2, 1.3, 1.4 or 1.5% between 25-230° C., as measured by TGA thermogram;

A DSC thermogram as shown in, or substantially as shown in, FIG. 52;

A melting endothermic event with an onset of around 109.7° C. and an enthalpy of 89.3 J/g, as measured in a DSC thermogram;

A melting endothermic event with an onset of around 105-115° C. and an enthalpy of around 85-95 J/g, as measured in a DSC thermogram;

A melting endothermic event with an onset of around 105, 106, 107, 108, 109, 110, 111, 112, 113, 114 or 115° C. and an enthalpy of around 85, 86, 87, 88, 89, 90, 91, 92, 93, 94 or 95 J/g, as measured in a DSC thermogram;

A vitrification around 24.3° C., as measured in a DSC thermogram with a cooling ramp of 10° C./min from 230° C. to −90° C.;

A vitrification around 20-30° C., as measured in a DSC thermogram with a cooling ramp of 10° C./min from 230° C. to −90° C.;

A vitrification around 20, 21, 22, 23, 24, 25, 26, 27, 28, 29 or 30° C., as measured in a DSC thermogram with a cooling ramp of 10° C./min from 230° C. to −90° C.;

A glass transition around 30.2° C., as measured in a DSC thermogram with a cooling ramp of 10° C./min from 230° C. to −90° C.;

A glass transition around 25-35° C., as measured in a DSC thermogram with a cooling ramp of 10° C./min from 230° C. to −90° C.;

A glass transition around 25, 26, 27, 28, 29, 30, 31, 32, 33, 34 or 35° C., as measured in a DSC thermogram with a cooling ramp of 10° C./min from 230° C. to −90° C.;

A $^1$H NMR spectrum as shown in, or substantially as shown in, FIG. 53;

A total water uptake between 0% RH and 90% RH at 25° C. of approximately 1.9% w/w;

A total water uptake between 0% RH and 90% RH at 25° C. of approximately 1.5-2.5% w/w;

A total water uptake between 0% RH and 90% RH at 25° C. of approximately 1.5, 1.6, 1.7, 1.8, 1.9, 2.0, 2.1, 2.2, 2.3, 2.4 or 2.5% w/w;

A DVS isotherm plot as shown in, or substantially as shown in, FIG. 54; and/or

A DVS kinetic plot as shown in, or substantially as shown in, FIG. 55.

Hydrobromide Salt

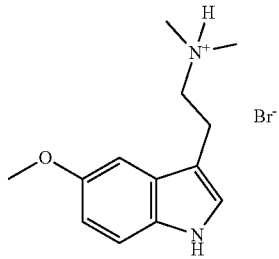

Figure 57:
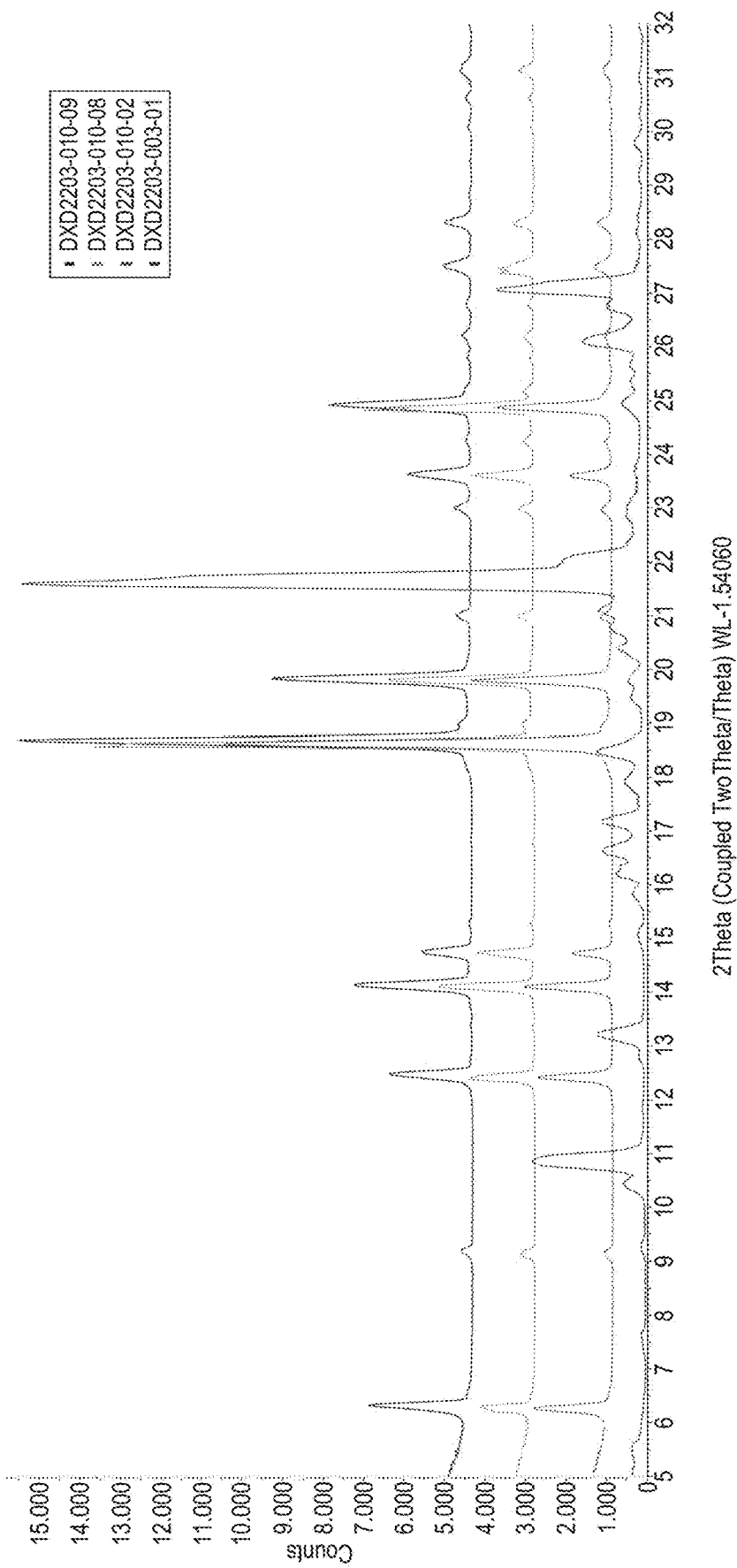
FIG. 57. XRPD Diffractograms (from top to bottom) of Hydrobromide salt isolated from acetonitrile/toluene (black trace), DMF/toluene (red trace), methanol/MTBE (green trace) and Free Base (blue trace).

XRPD diffractograms of Hydrobromide salt displayed same crystalline patterns for all three solvent/anti-solvent systems used as demonstrated in FIG. 57. The XRPD diffractograms of Hydrobromide salt showed a distinct diffraction profile when compared to free base, confirming the salt formation. This was nominated as pattern 1 with XRPD peak data shown in Tables 16, 16a or 16b.

TABLE 16

XRPD Peak data for Hydrobromide pattern 1.

| Peak No. | Angle 2 θ | d Value | Rel. Intensity |
|---|---|---|---|
| 1 | 6.202° | 14.238 | 0.187 |
| 2 | 9.099° | 9.711 | 0.022 |
| 3 | 12.115° | 7.299 | 0.004 |
| 4 | 12.359° | 7.156 | 0.192 |
| 5 | 13.322° | 6.641 | 0.002 |
| 6 | 14.046° | 6.300 | 0.229 |
| 7 | 14.667° | 6.035 | 0.104 |
| 8 | 15.219° | 5.817 | 0.007 |
| 9 | 16.722° | 5.297 | 0.002 |
| 10 | 18.566° | 4.775 | 1.000 |
| 11 | 18.780° | 4.721 | 0.030 |
| 12 | 19.740° | 4.494 | 0.361 |
| 13 | 20.937° | 4.239 | 0.026 |
| 14 | 22.900° | 3.880 | 0.026 |
| 15 | 23.540° | 3.776 | 0.106 |
| 16 | 24.169° | 3.679 | 0.016 |
| 17 | 24.824° | 3.584 | 0.299 |
| 18 | 25.714° | 3.462 | 0.005 |
| 19 | 26.109° | 3.410 | 0.014 |
| 20 | 26.746° | 3.331 | 0.007 |
| 21 | 27.427° | 3.249 | 0.042 |
| 22 | 28.245° | 3.157 | 0.036 |
| 23 | 28.771° | 3.101 | 0.002 |
| 24 | 30.020° | 2.974 | 0.004 |
| 25 | 30.556° | 2.923 | 0.006 |
| 26 | 31.132° | 2.871 | 0.020 |

TABLE 16a

XRPD Peak data for Hydrobromide pattern 1. (2 d.p.)

| Peak No. | Angle 2 θ | d Value | Rel. Intensity |
|---|---|---|---|
| 1 | 6.20° | 14.24 | 0.19 |
| 2 | 9.10° | 9.71 | 0.02 |
| 3 | 12.12° | 7.30 | 0.00 |
| 4 | 12.36° | 7.16 | 0.19 |
| 5 | 13.32° | 6.64 | 0.00 |
| 6 | 14.05° | 6.30 | 0.23 |
| 7 | 14.67° | 6.04 | 0.10 |
| 8 | 15.22° | 5.82 | 0.01 |
| 9 | 16.72° | 5.30 | 0.00 |
| 10 | 18.57° | 4.78 | 1.00 |
| 11 | 18.78° | 4.72 | 0.03 |
| 12 | 19.74° | 4.49 | 0.36 |
| 13 | 20.94° | 4.24 | 0.03 |
| 14 | 22.90° | 3.88 | 0.03 |
| 15 | 23.54° | 3.78 | 0.11 |
| 16 | 24.17° | 3.68 | 0.02 |
| 17 | 24.82° | 3.58 | 0.30 |
| 18 | 25.71° | 3.46 | 0.01 |
| 19 | 26.11° | 3.41 | 0.01 |
| 20 | 26.75° | 3.33 | 0.01 |
| 21 | 27.43° | 3.25 | 0.04 |
| 22 | 28.25° | 3.16 | 0.04 |
| 23 | 28.77° | 3.10 | 0.00 |
| 24 | 30.02° | 2.97 | 0.00 |
| 25 | 30.56° | 2.92 | 0.01 |
| 26 | 31.13° | 2.87 | 0.02 |

TABLE 16b

XRPD Peak data for Hydrobromide pattern 1 (1 d.p.).

| Peak No. | Angle 2 θ | d Value | Rel. intensity |
|---|---|---|---|
| 1 | 6.2° | 14.2 | 0.2 |
| 2 | 9.1° | 9.7 | 0.0 |
| 3 | 12.1° | 7.3 | 0.0 |
| 4 | 12.4° | 7.2 | 0.2 |
| 5 | 13.3° | 6.6 | 0.0 |
| 6 | 14.0° | 6.3 | 0.2 |
| 7 | 14.7° | 6.0 | 0.1 |
| 8 | 15.2° | 5.8 | 0.0 |
| 9 | 16.7° | 5.3 | 0.0 |
| 10 | 18.6° | 4.8 | 1.0 |
| 11 | 18.8° | 4.7 | 0.0 |
| 12 | 19.7° | 4.5 | 0.4 |
| 13 | 20.9° | 4.2 | 0.0 |
| 14 | 22.9° | 3.9 | 0.0 |
| 15 | 23.5° | 3.8 | 0.1 |
| 16 | 24.2° | 3.7 | 0.0 |
| 17 | 24.8° | 3.6 | 0.3 |
| 18 | 25.7° | 3.5 | 0.0 |
| 19 | 26.1° | 3.4 | 0.0 |

TABLE 16b-continued

XRPD Peak data for
Hydrobromide pattern 1 (1 d.p.).

| Peak No. | Angle 2 θ | d Value | Rel. intensity |
|---|---|---|---|
| 20 | 26.7° | 3.3 | 0.0 |
| 21 | 27.4° | 3.7 | 0.0 |
| 22 | 28.2° | 3.2 | 0.0 |
| 23 | 28.8° | 3.1 | 0.0 |
| 24 | 30.0° | 3.0 | 0.0 |
| 25 | 30.6° | 2.9 | 0.0 |
| 26 | 31.1° | 2.9 | 0.0 |

Figure 58:
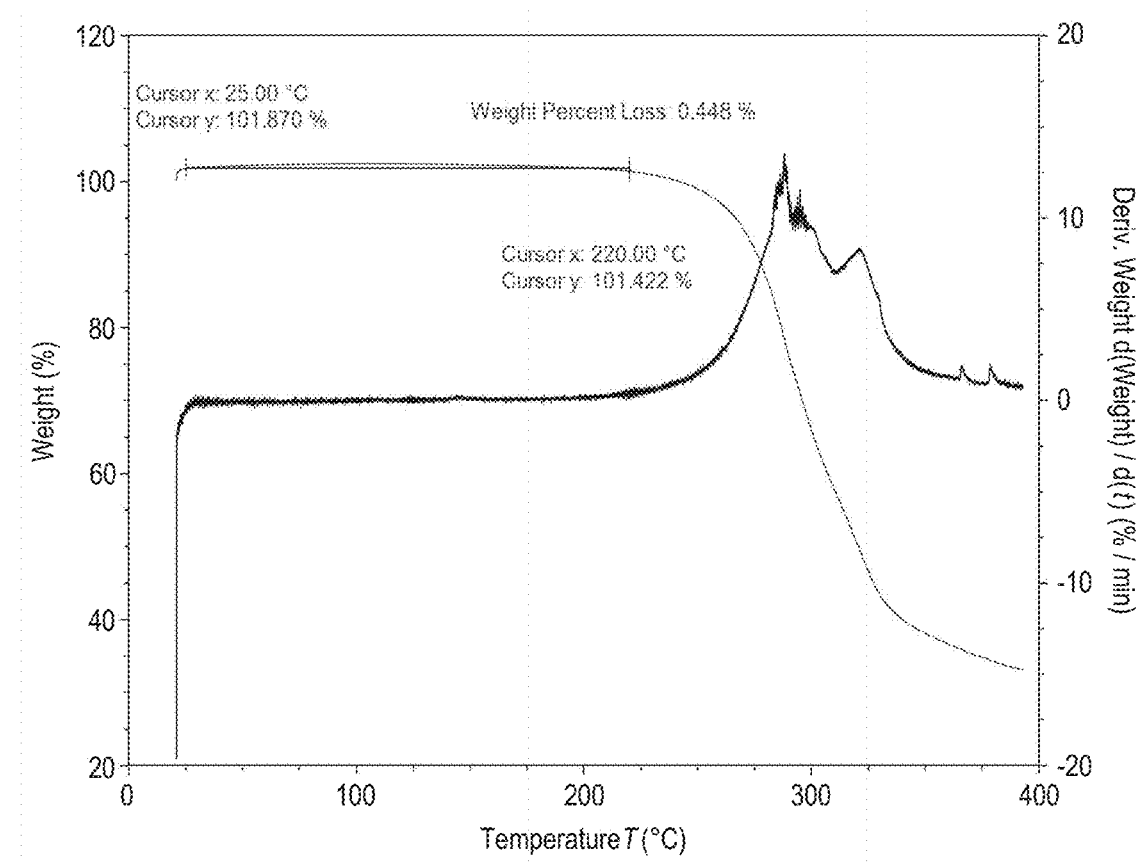
FIG. 58. TGA Thermogram of Hydrobromide salt, Batch: DXD2203-010-02.

The TGA thermogram of Hydrobromide salt in FIG. 58 showed that the material is thermally stable up to 220° C., then the thermal degradation occurs. 0.45% weight loss between 25-220° C. is due to release of volatiles.

Figure 59:
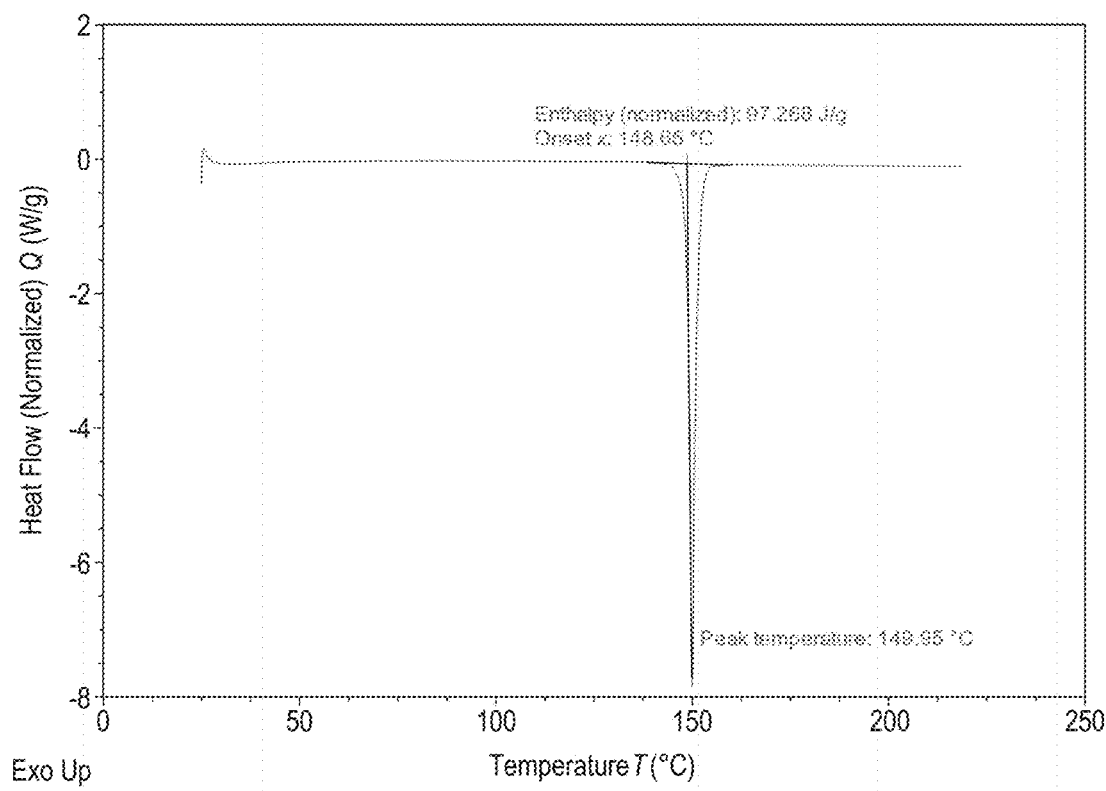
FIG. 59. DSC Thermogram (1st heating) of Hydrobromide salt, Batch: DXD2203-010-02.

The DSC analysis of the Hydrobromide salt was performed and thermograms are presented in FIG. 59. The 1st heating DSC thermogram shows a single endothermic event with the onset temperature of 148.7° C. and heat of fusion of 97.3 J/g, which corresponds to the melting of the Hydrobromide salt.

Figure 60:
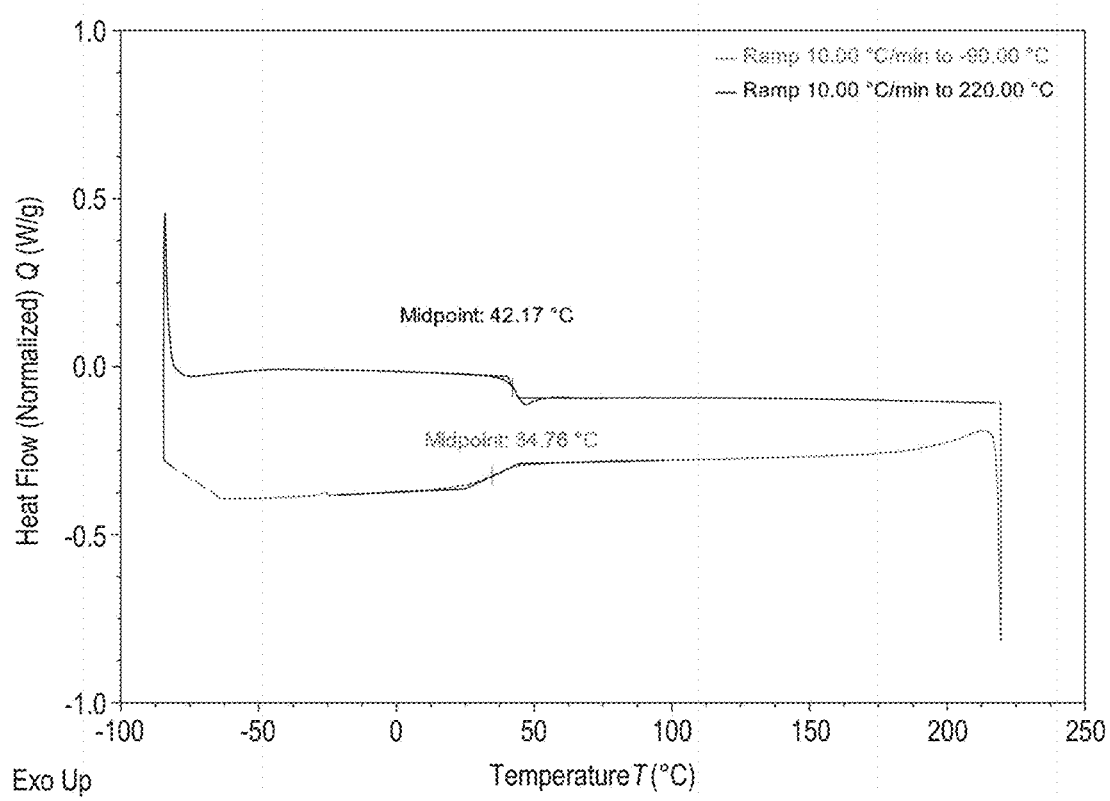
FIG. 60. DSC Thermograms of Hydrobromide salt, cooling (blue trace) and 2nd heating (green trace).

The cooling ramp of 10° C./min from 220° C. to −90° C. displayed a vitrification at around 34.8° C. and the 2$^{nd}$ heating cycle a glass transition at around 42.2° C. as shown in, or substantially as shown in, FIG. 60.

Figure 61:
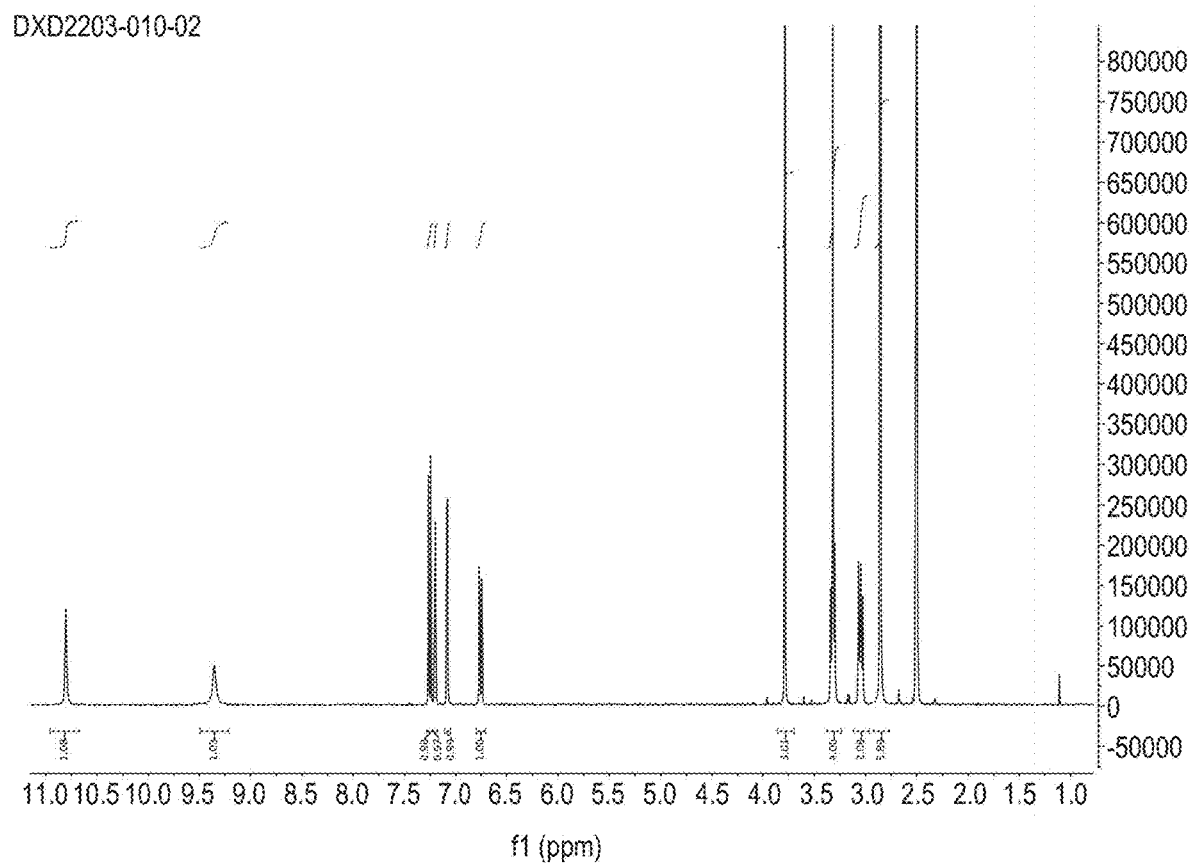
FIG. 61. 1H NMR (d6-DMSO) Spectrum of Hydrobromide salt, Batch: DXD2203-010-02.

$^1$H NMR spectrum of Hydrobromide salt in d$_6$-DMSO is shown in FIG. 61. It displayed traces of MTBE. The observed proton chemical shift changes in the NMR spectrum are indicative of the salt formation.

In one embodiment, there is provided 5-MeO-DMT hydrobromide. In one embodiment, there is provided a pharmaceutical composition comprising 5-MeO-DMT hydrobromide. In one embodiment, there is provided crystalline 5-MeO-DMT hydrobromide, or a pharmaceutical composition comprising crystalline 5-MeO-DMT hydrobromide, as characterised by one or more of:

An XRPD pattern as shown in, or substantially as shown in, FIG. 57;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, or twenty six peaks in an XRPD diffractogram as detailed in Table 16, Table 16a or Table 16b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 16, Table 16a or Table 16b;

A TGA thermogram as shown in, or substantially as shown in, FIG. 58;

A weight loss of about 0.45% between 25-220° C., as measured by TGA thermogram;

A weight loss of about 0.35-0.55% between 25-220° C., as measured by TGA thermogram;

A weight loss of about 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54 or 0.55% between 25-220° C., as measured by TGA thermogram;

A weight loss of about 0.1-1.0% between 25-220° C., as measured by TGA thermogram;

A weight loss of about 0.1, 0.2, 0.3, 0.4, 0.5, 0.6, 0.7, 0.8, 0.9 or 1.0% between 25-220° C., as measured by TGA thermogram;

A DSC thermogram as shown in, or substantially as shown in, FIG. 59 or FIG. 60;

A melting endothermic event with an onset of around 148.7° C. and an enthalpy of 97.3 J/g, as measured in a DSC thermogram;

A melting endothermic event with an onset of around 143-153° C. and an enthalpy of around 92-102 J/g, as measured in a DSC thermogram;

A melting endothermic event with an onset of around 143, 144, 145, 146, 147, 148, 149, 150, 151, 152 or 153 and an enthalpy of around 92, 93, 94, 95, 96, 97, 98, 99, 100, 101, or 102 J/g, as measured in a DSC thermogram;

A vitrification around 34.8° C., as measured in a DSC thermogram with a cooling ramp of 10° C./min from 220° C. to −90° C.;

A vitrification around 30-40° C. as measured in a DSC thermogram with a cooling ramp of 10° C./min from 220° C. to −90° C.;

A vitrification around 30, 31, 32, 33, 34, 35, 36, 37, 38, 39, or 40° C. as measured in a DSC thermogram with a cooling ramp of 10° C./min from 220° C. to −90° C.;

A glass transition around 42.2° C., as measured in a DSC thermogram with a cooling ramp of 10° C./min from 220° C. to −90° C.;

A glass transition around 37-47° C., as measured in a DSC thermogram with a cooling ramp of 10° C./min from 220° C. to −90° C.;

A glass transition around 37, 38, 39, 40, 41, 42, 43, 44, 45, 46 or 47° C., as measured in a DSC thermogram with a cooling ramp of 10° C./min from 220° C. to −90° C.; and/or A $^1$H NMR spectrum as shown in, or substantially as shown in, FIG. 61.

Glycolate Salt

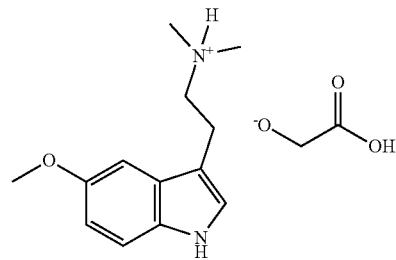

Figure 62:
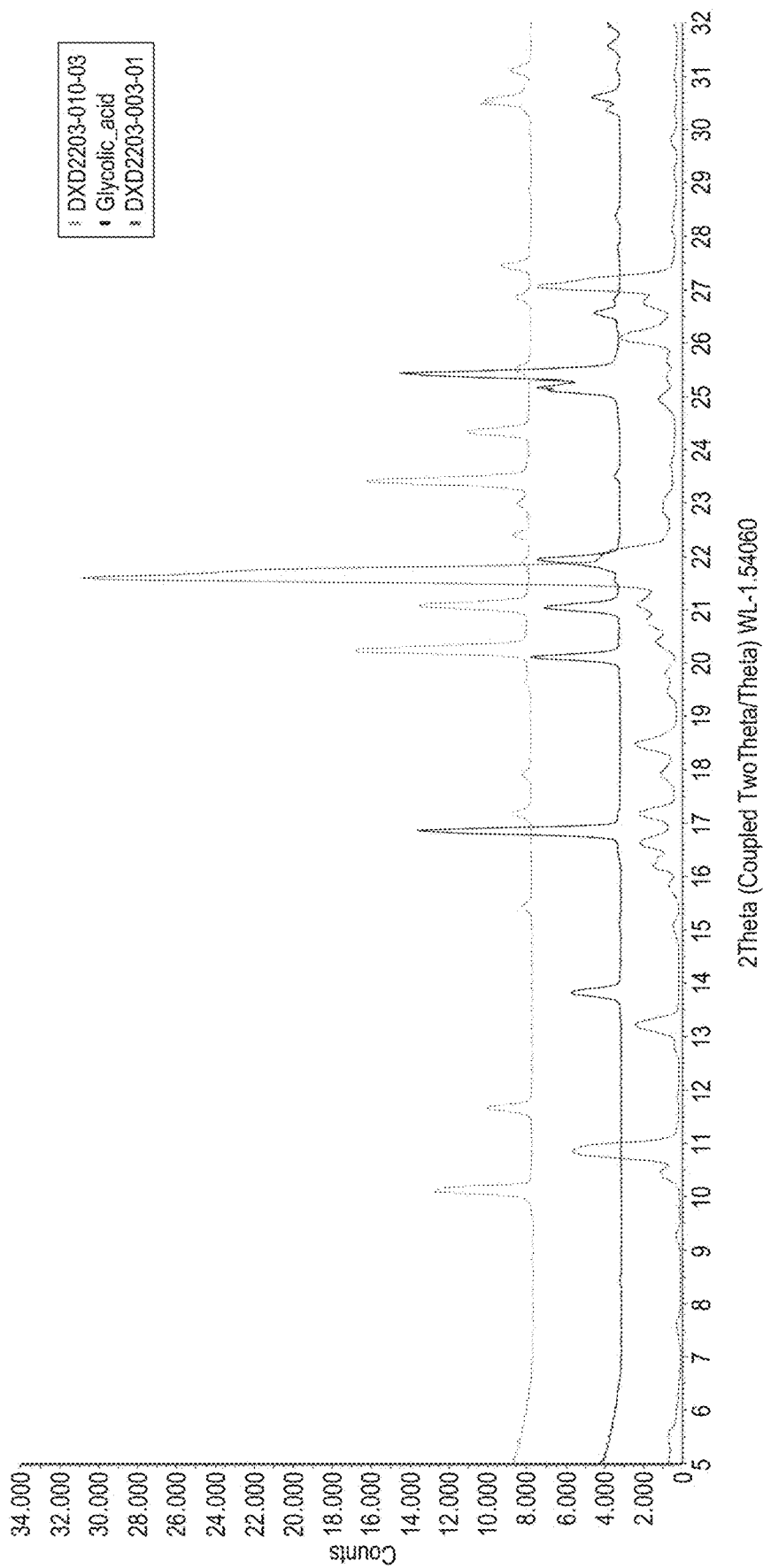
FIG. 62. XRPD Diffractograms of glycolate salt isolated from IPAC-40° C. (red trace, top), Glycolic acid (black trace, middle) and Free Base (blue trace, bottom).

The XRPD diffractogram of the glycolate salt exhibited a crystalline form which has a different XRPD pattern when compared to the free base and glycolic acid as shown in, or substantially as shown in, FIG. 62. This form was nominated as pattern 1 with XRPD peak data presented in Table 17, Table 17a or Table 17b.

TABLE 17

XRPD Peak data for
glycolate pattern 1.

| Peak No. | Angle 2 θ | d Value | Rel. Intensity |
|---|---|---|---|
| 1 | 8.837° | 9.999 | 0.004 |
| 2 | 10.114° | 8.739 | 0.551 |

TABLE 17-continued

XRPD Peak data for glycolate pattern 1.

| Peak No. | Angle 2 θ | d Value | Rel. Intensity |
|---|---|---|---|
| 3 | 11.674° | 7.574 | 0.255 |
| 4 | 15.436° | 5.736 | 0.063 |
| 5 | 16.557° | 5.350 | 0.011 |
| 6 | 17.187° | 5.155 | 0.107 |
| 7 | 17.923° | 4.945 | 0.047 |
| 8 | 19.656° | 4.513 | 0.025 |
| 9 | 20.235° | 4.385 | 1.000 |
| 10 | 21.085° | 4.210 | 0.624 |
| 11 | 21.908° | 4.054 | 0.034 |
| 12 | 22.401° | 3.966 | 0.088 |
| 13 | 22.979° | 3.867 | 0.073 |
| 14 | 23.408° | 3.797 | 0.923 |
| 15 | 24.340° | 3.654 | 0.364 |
| 16 | 24.944° | 3.567 | 0.011 |
| 17 | 25.495° | 3.491 | 0.081 |
| 18 | 26.873° | 3.315 | 0.079 |
| 19 | 27.449° | 3.247 | 0.169 |
| 20 | 27.781° | 3.209 | 0.012 |
| 21 | 28.878° | 3.089 | 0.015 |
| 22 | 29.704° | 3.005 | 0.005 |
| 23 | 30.565° | 2.922 | 0.267 |
| 24 | 31.124° | 2.871 | 0.113 |
| 25 | 31.793° | 2.812 | 0.008 |

TABLE 17a

XRPD Peak data for glycolate pattern 1. (2 d.p.)

| Peak No. | Angle 2 θ | d Value | Rel. Intensity |
|---|---|---|---|
| 1 | 8.84° | 10.00 | 0.00 |
| 2 | 10.11° | 8.74 | 0.55 |
| 3 | 11.67° | 7.57 | 0.26 |
| 4 | 15.44° | 5.74 | 0.06 |
| 5 | 16.56° | 5.35 | 0.01 |
| 6 | 17.19° | 5.16 | 0.11 |
| 7 | 17.92° | 4.95 | 0.05 |
| 8 | 19.66° | 4.51 | 0.03 |
| 9 | 20.24° | 4.39 | 1.00 |
| 10 | 21.09° | 4.21 | 0.62 |
| 11 | 21.91° | 4.05 | 0.03 |
| 12 | 22.40° | 3.97 | 0.09 |
| 13 | 22.98° | 3.87 | 0.07 |
| 14 | 23.41° | 3.80 | 0.92 |
| 15 | 24.34° | 3.65 | 0.36 |
| 16 | 24.94° | 3.57 | 0.01 |
| 17 | 25.50° | 3.49 | 0.08 |
| 18 | 26.87° | 3.32 | 0.08 |
| 19 | 27.45° | 3.25 | 0.17 |
| 20 | 27.78° | 3.21 | 0.01 |
| 21 | 28.88° | 3.09 | 0.02 |
| 22 | 29.70° | 3.01 | 0.01 |
| 23 | 30.57° | 2.92 | 0.27 |
| 24 | 31.12° | 2.87 | 0.11 |
| 25 | 31.79° | 2.81 | 0.01 |

TABLE 17b

XRPD Peak data for glycolate pattern 1. (1 d.p.)

| Peak No. | Angle 2 θ | d Value | Rel. Intensity |
|---|---|---|---|
| 1 | 8.8° | 10.0 | 0.0 |
| 2 | 10.1° | 8.7 | 0.6 |
| 3 | 11.7° | 7.6 | 0.3 |
| 4 | 15.4° | 5.7 | 0.1 |
| 5 | 16.6° | 5.4 | 0.0 |
| 6 | 17.2° | 5.2 | 0.1 |
| 7 | 17.9° | 4.9 | 0.0 |
| 8 | 19.7° | 4.5 | 0.0 |
| 9 | 20.2° | 4.4 | 1.0 |
| 10 | 21.1° | 4.2 | 0.6 |
| 11 | 21.9° | 4.1 | 0.0 |
| 12 | 22.4° | 4.0 | 0.1 |
| 13 | 23.0° | 3.9 | 0.1 |
| 14 | 23.4° | 3.8 | 0.9 |
| 15 | 24.3° | 3.7 | 0.4 |
| 16 | 24.9° | 3.6 | 0.0 |
| 17 | 25.5° | 3.5 | 0.1 |
| 18 | 26.9° | 3.3 | 0.1 |
| 19 | 27.4° | 3.2 | 0.2 |
| 20 | 27.8° | 3.2 | 0.0 |
| 21 | 28.9° | 3.1 | 0.0 |
| 22 | 29.7° | 3.0 | 0.0 |
| 23 | 30.6° | 2.9 | 0.3 |
| 24 | 31.1° | 2.9 | 0.1 |
| 25 | 31.8° | 2.8 | 0.0 |

The TGA thermogram of glycolate salt showed a weight loss of 1.4% between 25-155° C. (~0.07 moles IPAC). The material is thermally stable up to around 155° C. as demonstrated in FIG. 63. The DSC analysis of the glycolate salt was performed. The $1^{st}$ heating DSC thermogram displayed a melting endotherm with $T_{onst}$ around 95.2° C. and heat of fusion of 100.5 J/g, followed by the thermal degradation at higher temperature as shown in, or substantially as shown in, FIG. 64.

Figure 65:
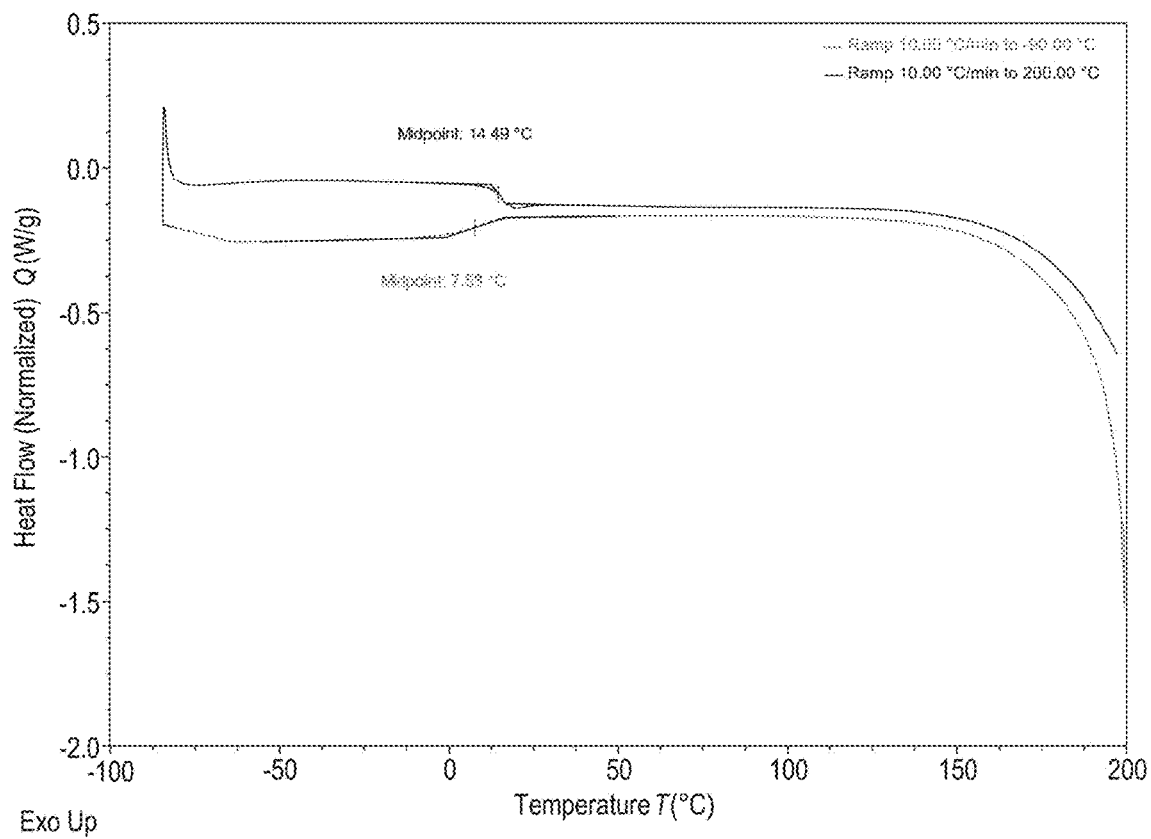
FIG. 65. DSC Thermograms of glycolate salt, cooling (blue trace) and 2nd heating (green trace).

The cooling ramp from 200° C. to −90° C. displayed a vitrification around 7.5° C. and the $2^{nd}$ heating cycle showed a glass transition around 14.5° C. as presented in FIG. 65.

Figure 66:
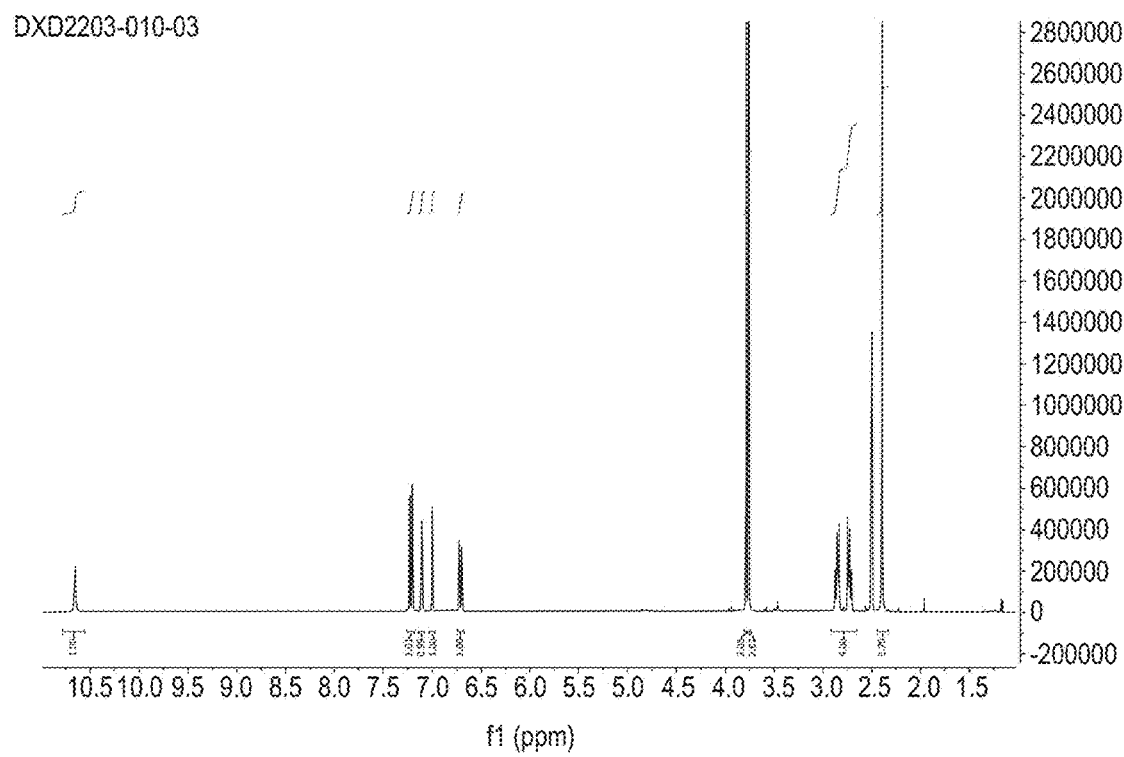
FIG. 66. 1H NMR (d6-DMSO) Spectrum of glycolate salt, Batch: DXD2203-010-03.

$^1$H NMR spectrum in $d_6$-DMSO of glycolate salt shown in FIG. 66, confirmed the presence of 1.0 eq glycolic acid. Traces of isopropyl acetate were also observed in the spectrum.

Figure 67:
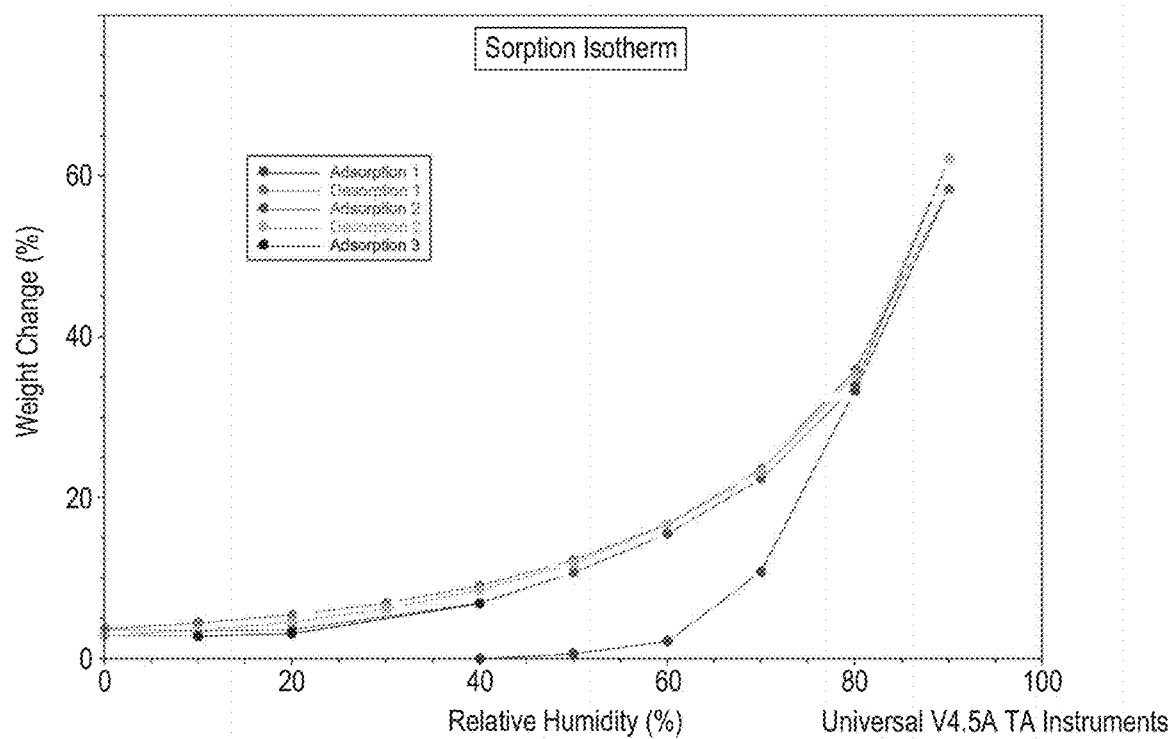
FIG. 67. DVS Isotherm plot of glycolate salt, Batch: DXD2203-010-03.

The FIG. 67 shows the DVS isotherm plot for glycolate salt. The first sorption isotherm showed hysteresis between 40-80% RH. Firstly, a slight water uptake up to 60% RH (2.3% w/w) was observed.

When the salt was exposed to 70% RH and 80% RH it exhibited moisture absorption 11% and 33% w/w respectively and the glycolate salt begins to deliquesce. The total moisture uptake between 0% RH and 90% RH at 25° C. was observed to be approximately 62% w/w for $1^{st}$ cycle and 59% w/w for $2^{nd}$ cycle.

As the glycolate salt underwent deliquescence during the DVS experiment, XRPD analyses were not carry out on post DVS sample.

Figure 63:
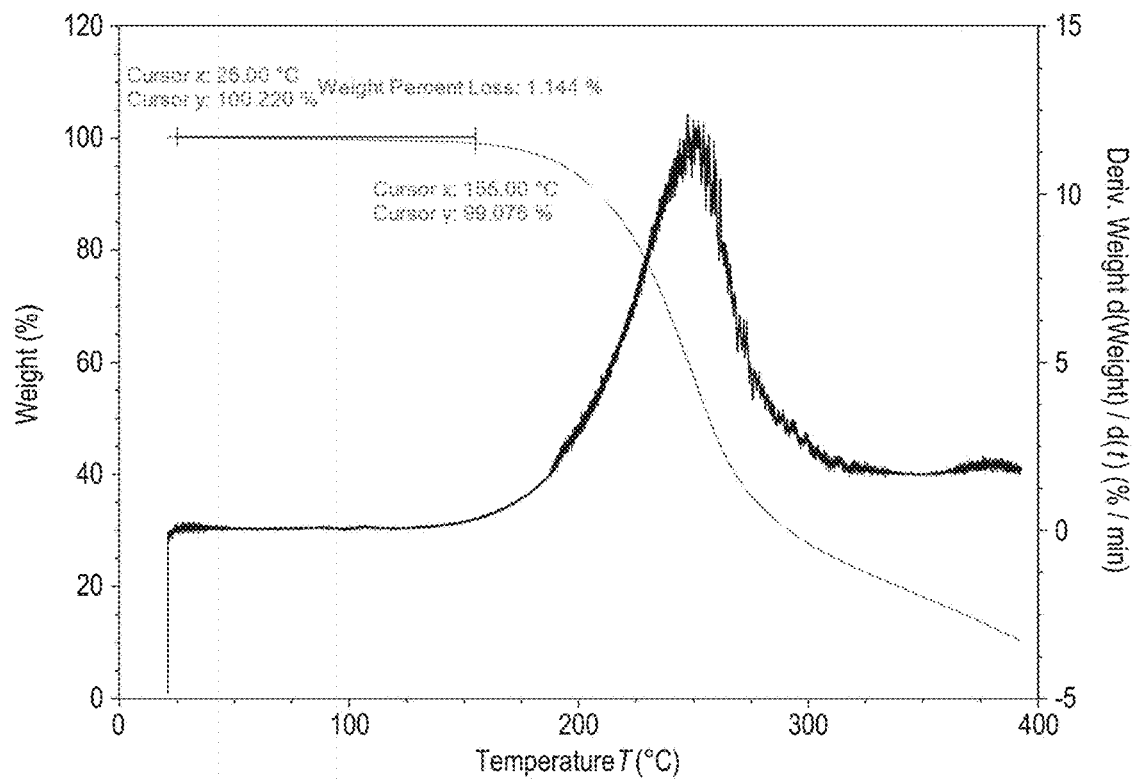
FIG. 63. TGA Thermogram of glycolate salt, Batch: DXD2203-010-03.
Figure 64:
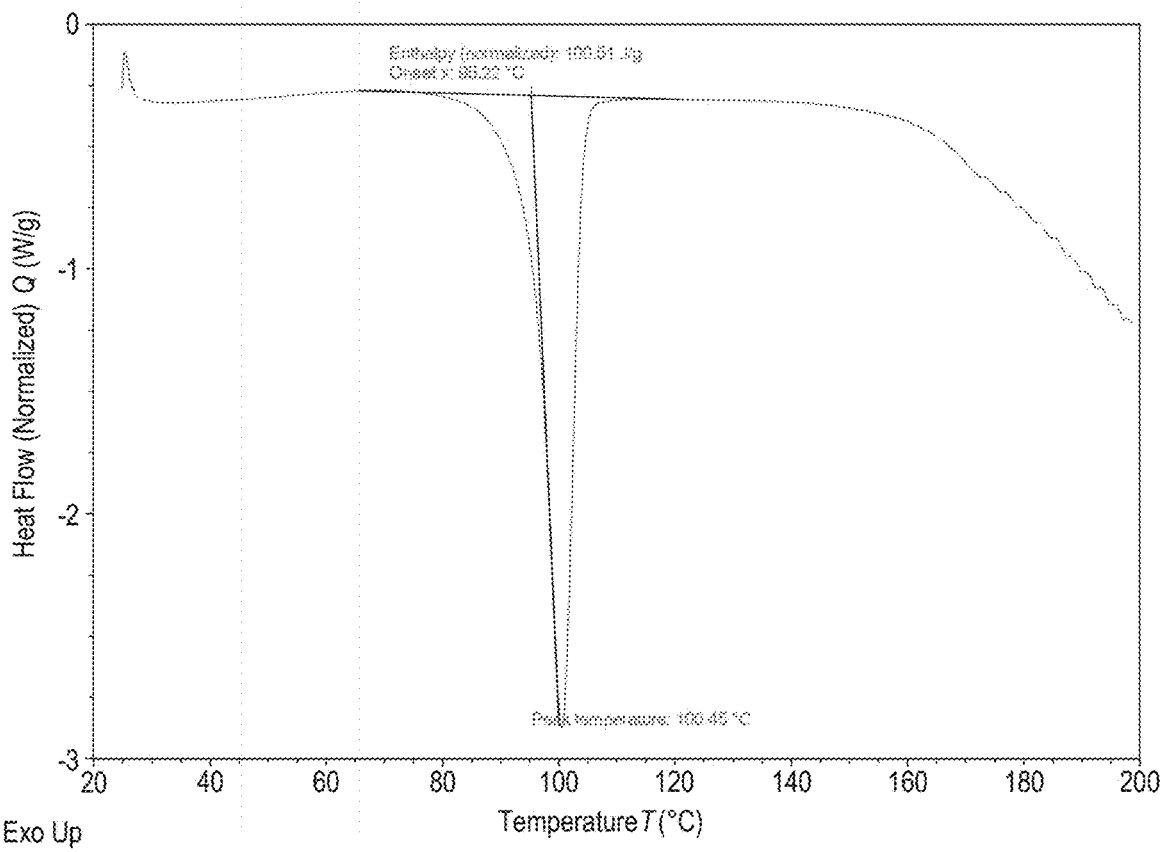
FIG. 64. DSC Thermogram (1st heating) of glycolate salt, Batch: DXD2203-010-03.

In one embodiment, there is provided 5-MeO-DMT glycolate. In one embodiment, there is provided a pharmaceutical composition comprising 5-MeO-DMT glycolate. In one embodiment, there is provided crystalline 5-MeO-DMT glycolate, or a pharmaceutical composition comprising crystalline 5-MeO-DMT glycolate, as characterised by one or more of:

An XRPD pattern as shown in, or substantially as shown in, FIG. 62;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, or twenty five peaks in an XRPD diffractogram as detailed in Table 17, Table 17a or Table 17b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 17, Table 17a or Table 17b;

A TGA thermogram as shown in, or substantially as shown in, FIG. 63;

A weight loss of about 1.4% between 25-155° C., as measured by TGA thermogram;

A weight loss of about 0.9-1.9% between 25-155° C., as measured by TGA thermogram;

A weight loss of about 0.9, 1.0, 1.1, 1.2, 1.3, 1.4, 1.5, 1.6, 1.7, 1.8 or 1.9% between 25-155° C., as measured by TGA thermogram;

A DSC thermogram as shown in, or substantially as shown in, FIG. 64 or FIG. 65;

A melting endothermic event with an onset of around 95.2° C. and an enthalpy of 100.5 J/g, as measured in a DSC thermogram;

A melting endothermic event with an onset of around 90-100° C. and an enthalpy of around 95-105 J/g, as measured in a DSC thermogram;

A melting endothermic event with an onset of around 90, 91, 92, 93, 94, 95, 96, 97, 98, 99 or 100° C. and an enthalpy of around 95, 96, 97, 98, 99, 100, 101, 102, 103, 104 or 105 J/g, as measured in a DSC thermogram;

A vitrification around 7.5° C., as measured in a DSC thermogram with a cooling ramp of 10° C./min from 200° C. to −90° C.;

A vitrification around 2-12° C., as measured in a DSC thermogram with a cooling ramp of 10° C./min from 200° C. to −90° C.;

A vitrification around 2, 3, 4, 5, 6, 7, 8, 9, 10, 11 or 12° C., as measured in a DSC thermogram with a cooling ramp of 10° C./min from 200° C. to −90° C.;

A glass transition around 14.5° C., as measured in a DSC thermogram with a cooling ramp of 10° C./min from 200° C. to −90° C.;

A glass transition around 10-20° C., as measured in a DSC thermogram with a cooling ramp of 10° C./min from 200° C. to −90° C.;

A glass transition around 10, 11, 12, 13, 14, 15, 16, 17, 18, 19 or 20° C., as measured in a DSC thermogram with a cooling ramp of 10° C./min from 200° C. to −90° C.;

A $^1$H NMR spectrum as shown in, or substantially as shown in, FIG. 66;

A DVS isotherm plot as shown in, or substantially as shown in, FIG. 67; and/or

Figure 68:
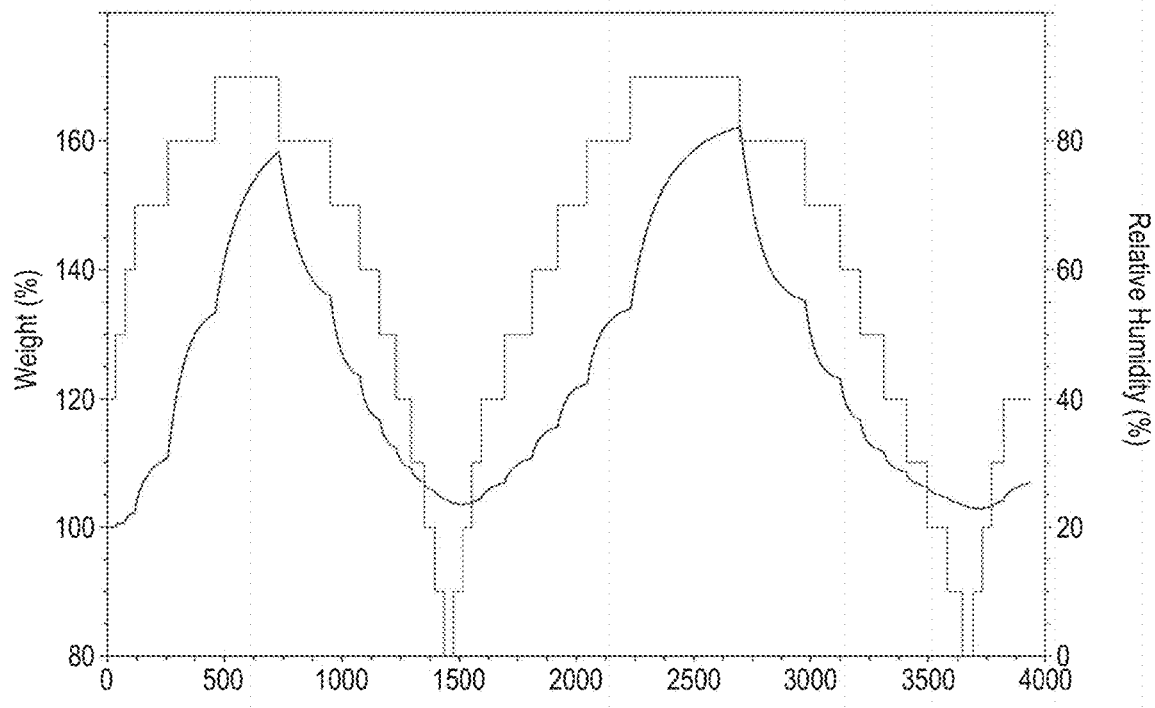
FIG. 68. DVS Kinetic plot of glycolate salt, Batch: DXD2203-010-03.

A DVS kinetic plot as shown in, or substantially as shown in, FIG. 68.

Ketoglutarate Salt

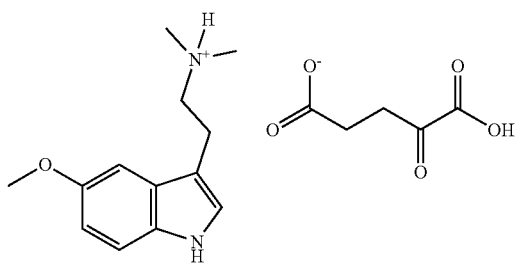

Figure 69:
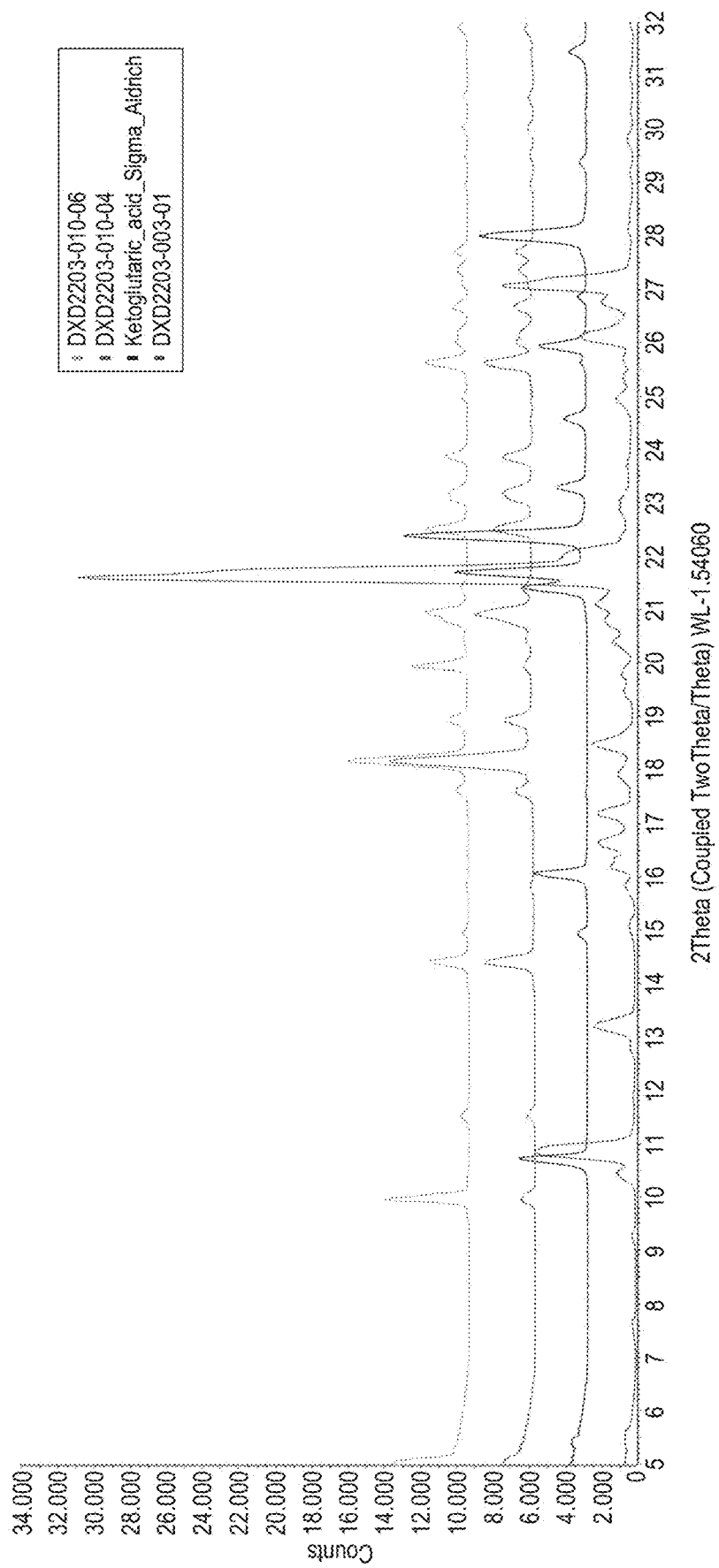
FIG. 69. XRPD Diffractograms (from top to bottom) of Ketoglutarate salt isolated from methanol/MTBE (red trace), ethanol/MTBE (green trace), Ketoglutaric acid (black trace) and Free Base (blue trace).

Both samples isolated from different solvent/anti-solvent systems displayed the same XRPD crystalline pattern which is distinctively different when compared to free base and ketoglutaric acid confirming the salt formation as shown in, or substantially as shown in, FIG. 69. This was nominated as pattern 1 with XRPD peak data displayed in Table 18, Table 18a or Table 18b.

TABLE 18

XRPD Peak data for Ketoglutarate pattern 1.

| Peak No. | Angle 2 θ | d Value | Rel. Intensity |
|---|---|---|---|
| 1 | 9.964° | 8.870 | 0.098 |
| 2 | 11.503° | 7.687 | 0.056 |
| 3 | 14.386° | 6.152 | 0.348 |
| 4 | 15.796° | 5.606 | 0.020 |
| 5 | 17.613° | 5.031 | 0.116 |
| 6 | 18.157° | 4.882 | 1.000 |
| 7 | 18.922° | 4.686 | 0.185 |
| 8 | 19.940° | 4.449 | 0.053 |
| 9 | 20.460° | 4.337 | 0.039 |
| 10 | 20.914° | 4.244 | 0.399 |
| 11 | 21.420° | 4.145 | 0.057 |
| 12 | 22.517° | 3.946 | 0.263 |
| 13 | 23.165° | 3.836 | 0.208 |
| 14 | 23.861° | 3.726 | 0.202 |
| 15 | 24.534° | 3.625 | 0.010 |
| 16 | 25.616° | 3.475 | 0.337 |
| 17 | 26.071° | 3.415 | 0.083 |
| 18 | 26.670° | 3.340 | 0.130 |
| 19 | 27.361° | 3.257 | 0.091 |
| 20 | 27.700° | 3.218 | 0.115 |
| 21 | 28.957° | 3.081 | 0.016 |
| 22 | 29.518° | 3.024 | 0.026 |
| 23 | 30.025° | 2.974 | 0.042 |
| 24 | 30.580° | 2.921 | 0.035 |

TABLE 18a

XRPD Peak data for Ketoglutarate pattern 1. (2 d p.)

| Peak No. | Angle 2 θ | d Value | Rel. Intensity |
|---|---|---|---|
| 1 | 9.96° | 8.87 | 0.10 |
| 2 | 11.50° | 7.69 | 0.06 |
| 3 | 14.39° | 6.15 | 0.35 |
| 4 | 15.80° | 5.61 | 0.02 |
| 5 | 17.61° | 5.03 | 0.12 |
| 6 | 18.16° | 4.83 | 1.00 |
| 7 | 18.92° | 4.69 | 0.19 |
| 8 | 19.94° | 4.45 | 0.05 |
| 9 | 20.46° | 4.34 | 0.04 |
| 10 | 20.91° | 4.24 | 0.40 |
| 11 | 21.42° | 4.15 | 0.06 |
| 12 | 22.52° | 3.95 | 0.26 |
| 13 | 23.17° | 3.84 | 0.21 |
| 14 | 23.86° | 3.73 | 0.20 |
| 15 | 24.53° | 3.63 | 0.01 |
| 16 | 25.62° | 3.48 | 0.34 |
| 17 | 26.07° | 3.42 | 0.08 |
| 18 | 26.67° | 3.34 | 0.13 |
| 19 | 27.36° | 3.26 | 0.09 |
| 20 | 27.70° | 3.22 | 0.12 |
| 21 | 28.96° | 3.08 | 0.02 |
| 22 | 29.52° | 3.02 | 0.03 |
| 23 | 30.03° | 2.97 | 0.04 |
| 24 | 30.58° | 2.92 | 0.04 |

TABLE 18b

XRPD Peak data for Ketoglutarate pattern 1. (1 d.p.)

| Peak No. | Angle 2 θ | d Value | Rel. Intensity |
|---|---|---|---|
| 1 | 10.0° | 8.9 | 0.1 |
| 2 | 11.5° | 7.7 | 0.1 |
| 3 | 14.4° | 6.2 | 0.3 |
| 4 | 15.8° | 5.6 | 0.0 |
| 5 | 17.6° | 5.0 | 0.1 |
| 6 | 18.2° | 4.9 | 1.0 |
| 7 | 13.9° | 4.7 | 0.2 |
| 8 | 19.9° | 4.4 | 0.1 |
| 9 | 20.5° | 4.3 | 0.0 |
| 10 | 20.9° | 4.2 | 0.4 |
| 11 | 21.4° | 4.1 | 0.1 |
| 12 | 22.5° | 3.9 | 0.3 |
| 13 | 23.2° | 3.8 | 0.2 |
| 14 | 23.9° | 3.7 | 0.2 |
| 15 | 24.5° | 3.6 | 0.0 |
| 16 | 25.6° | 3.5 | 0.3 |
| 17 | 26.1° | 3.4 | 0.1 |
| 18 | 26.7° | 3.3 | 0.1 |
| 19 | 27.4° | 3.3 | 0.1 |
| 20 | 27.7° | 3.2 | 0.1 |
| 21 | 29.0° | 3.1 | 0.0 |
| 22 | 29.5° | 3.0 | 0.0 |
| 23 | 30.0° | 3.0 | 0.0 |
| 24 | 30.6° | 2.9 | 0.0 |

The TGA thermogram of Ketoglutarate salt displayed a weight loss of 1.2% between 25-150° C., which corresponds to ~0.1 moles EtOH and 0.05 moles MTBE. The Ketoglutaric salt is thermally stable up to 150° C. as shown in, or substantially as shown in, FIG. 70.

Figure 71:
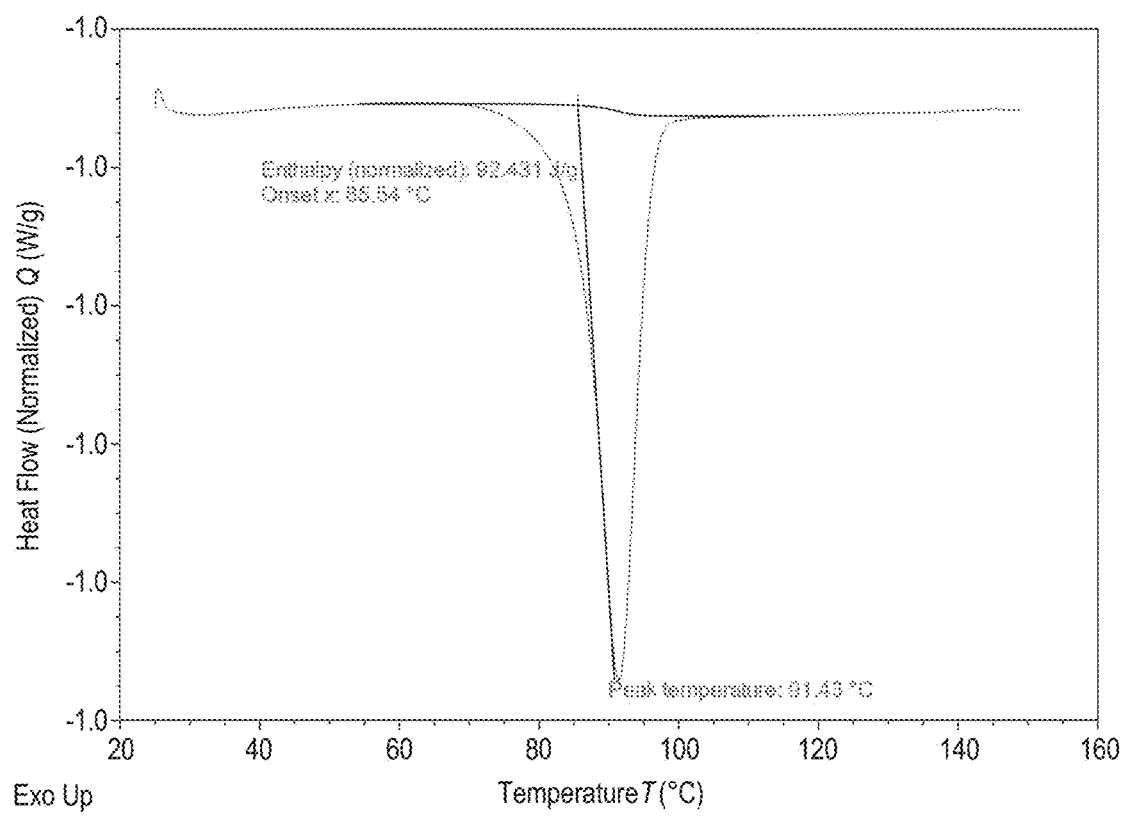
FIG. 71. DSC Thermogram (1st heating) of Ketoglutarate salt, Batch: DXD2203-010-04.

The DSC analysis of the ketoglutaric salt was performed and the results displayed in FIG. 71. The $1^{st}$ heating DSC thermogram of Ketoglutarate salt exhibited a single endothermic event with the onset temperature of 85.5° C. and heat of fusion of 92.4 J/g, which corresponds to the melting of the material.

Figure 72:
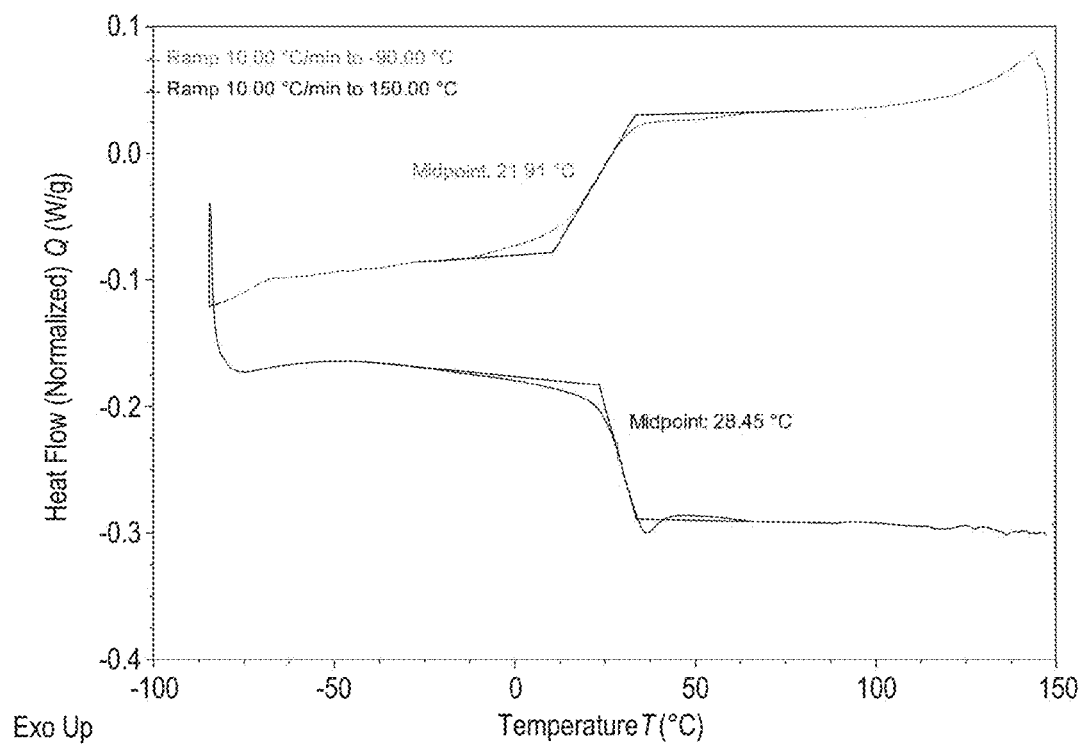
FIG. 72. DSC Thermograms of Ketoglutarate salt, cooling (blue trace) and 2nd heating (green trace).

During cooling from 150° C. to −90° C./10 min a vitrification around 21.9° C. was observed and the $2^{nd}$ heating cycle displayed a glass transition of 28.5° C. as shown in, or substantially as shown in, FIG. 72.

Figure 73:
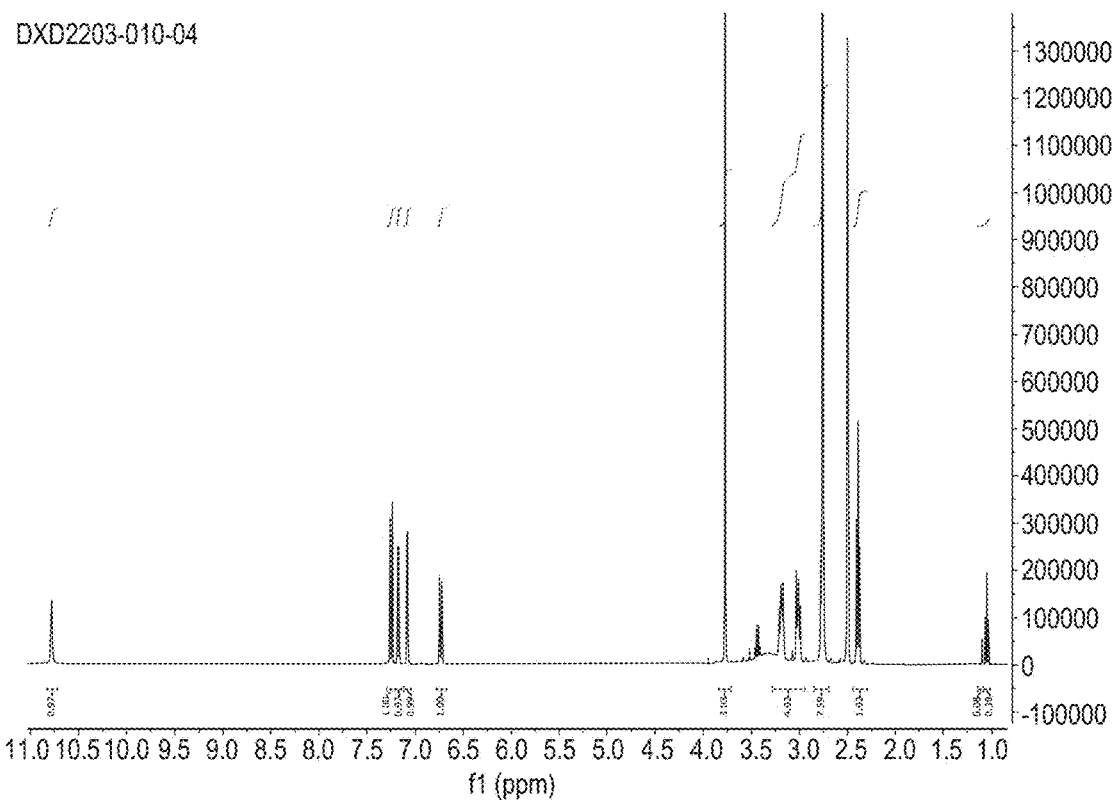
FIG. 73. 1H NMR (d6-DMSO) Spectrum of Ketoglutarate salt, Batch: DXD2203-010-04.

$^1$H NMR spectrum of Ketoglutarate salt in $d_6$-DMSO presented in FIG. 73, showed all associated peaks with approximately 1.0 eq of ketoglutaric acid being present. The spectrum also displayed 0.13 eq EtOH and 0.1 eq MTBE in the sample.

Figure 74:
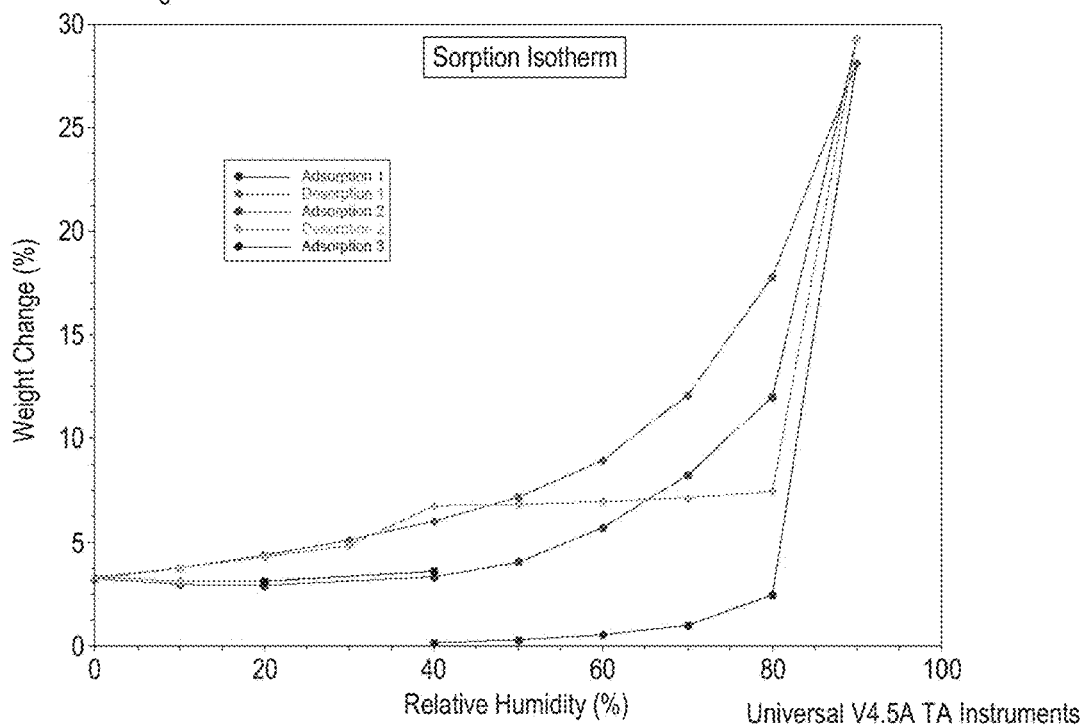
FIG. 74. DVS Isotherm plot of Ketoglutarate salt, Batch: DXD2203-010-04.

The isotherm plot of Ketoglutarate salt is presented in FIG. 74. The first sorption isotherm displayed a gradual water uptake between 40% RH (0.13% w/w) to 80% RH (2.55% w/w). A rapid increase to 28.14% w/w was observed at 90% RH. This indicates that Ketoglutarate salt deliquesce at high RH. The sorption kinetic plot of Ketoglutarate salt is presented in FIG. 75.

Due to deliquescence of the Ketoglutarate salt during DVS analyses, the post DVS sample was not analysed by XRPD.

Figure 70:
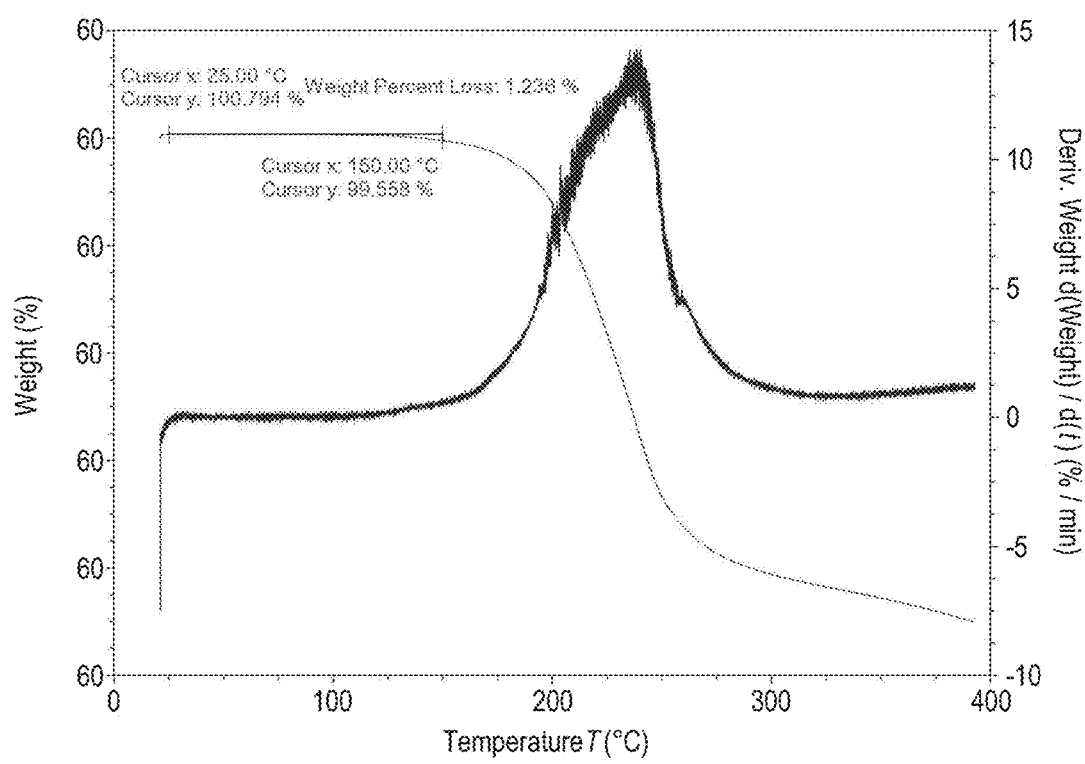
FIG. 70. TGA Thermogram of Ketoglutarate salt, Batch: DXD2203-010-04.

In one embodiment, there is provided 5-MeO-DMT ketoglutarate. In one embodiment, there is provided a pharmaceutical composition comprising 5-MeO-DMT ketoglutarate. In one embodiment, there is provided crystalline 5-MeO-DMT ketoglutarate, or a pharmaceutical composition comprising crystalline 5-MeO-DMT ketoglutarate, as characterised by one or more of:

An XRPD pattern as shown in, or substantially as shown in, FIG. 69;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, or twenty four peaks in an XRPD diffractogram as detailed in Table 18, Table 18a or Table 18b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 18, Table 18a or Table 18b;

A TGA thermogram as shown in, or substantially as shown in, FIG. 70;

A weight loss of about 1.2% between 25-150° C., as measured by TGA thermogram;

A weight loss of about 0.7-1.7% between 25-150° C., as measured by TGA thermogram;

A weight loss of about 0.7, 0.8, 0.9, 1.0, 1.1, 1.2, 1.3, 1.4, 1.5, 1.6 or 1.7% between 25-150° C., as measured by TGA thermogram;

A DSC thermogram as shown in, or substantially as shown in, FIG. 71 or FIG. 72;

A melting endothermic event with an onset of around 85.5° C. and an enthalpy of 92.4 J/g, as measured in a DSC thermogram;

A melting endothermic event with an onset of around 80-90° C. and an enthalpy of around 87-97 J/g, as measured in a DSC thermogram;

A melting endothermic event with an onset of around 80, 81, 82, 83, 84, 85, 86, 87, 88, 89 or 90 C and an enthalpy of around 87, 88, 89, 90, 91, 92, 93, 94, 95, 96 or 97 J/g, as measured in a DSC thermogram;

A vitrification around 21.9° C., as measured in a DSC thermogram with a cooling ramp of 10° C./min from 150° C. to −90° C.;

A vitrification around 16-26° C., as measured in a DSC thermogram with a cooling ramp of 10° C./min from 150° C. to −90° C.;

A vitrification around 16, 17, 18, 19, 20, 21, 22, 23, 24, 25 or 26° C., as measured in a DSC thermogram with a cooling ramp of 10° C./min from 150° C. to −90° C.;

A glass transition around 28.5° C., as measured in a DSC thermogram with a cooling ramp of 10° C./min from 150° C. to −90° C.;

A glass transition around 23-33° C., as measured in a DSC thermogram with a cooling ramp of 10° C./min from 150° C. to −90° C.;

A glass transition around 23, 24, 25, 26, 27, 28, 29, 30, 31, 32 or 33° C., as measured in a DSC thermogram with a cooling ramp of 10° C./min from 150° C. to −90° C.;

A $^1$H NMR spectrum as shown in, or substantially as shown in, FIG. 73;

A gradual water uptake between 40% RH (0.13% w/w) to 80% RH (2.55% w/w), optionally with a rapid increase to 28.14% w/w at 90% RH;

A gradual water uptake between 40% RH (0.05-0.2% w/w) to 80% RH (1.50-3.5% w/w), optionally with a rapid increase to 20-40% w/w at 90% RH;

A DVS isotherm plot as shown in, or substantially as shown in, FIG. 74; and/or

Figure 75:
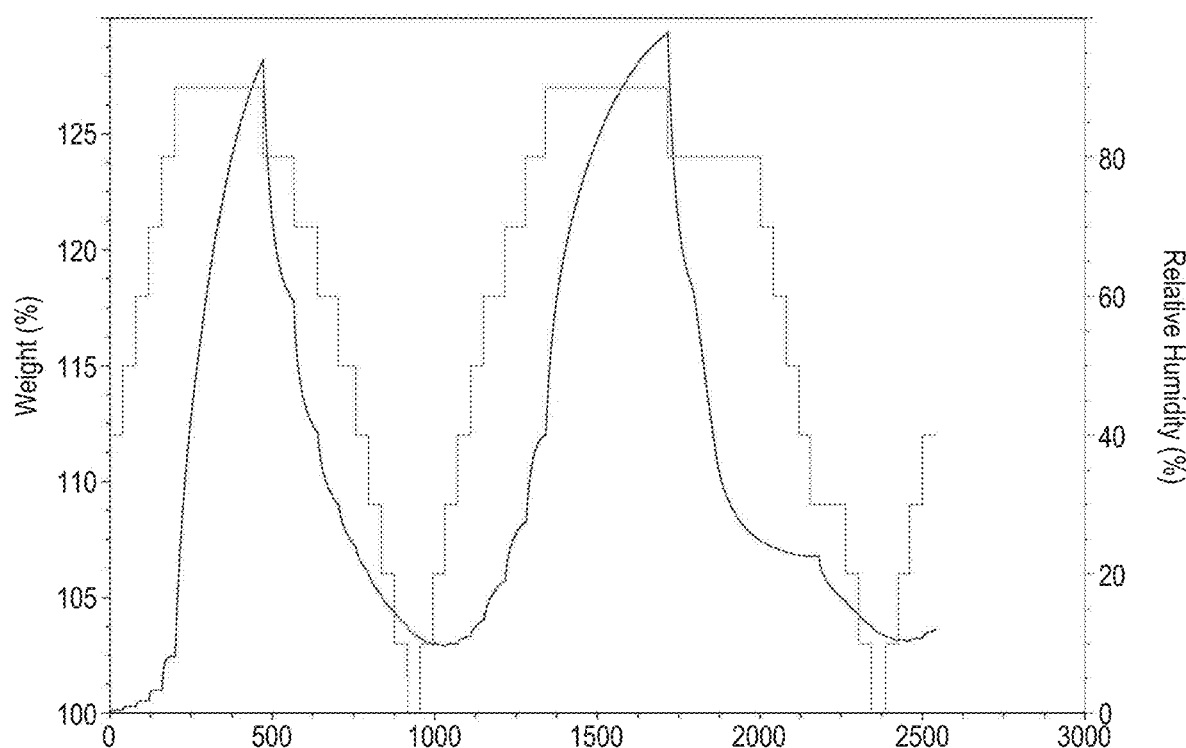
FIG. 75. Sorption kinetic plot of Ketoglutarate salt, Batch: DXD2203-010-04.

A DVS kinetic plot as shown in, or substantially as shown in, FIG. 75.

Malate Salt

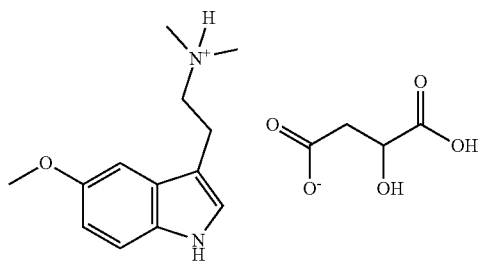

Figure 76:
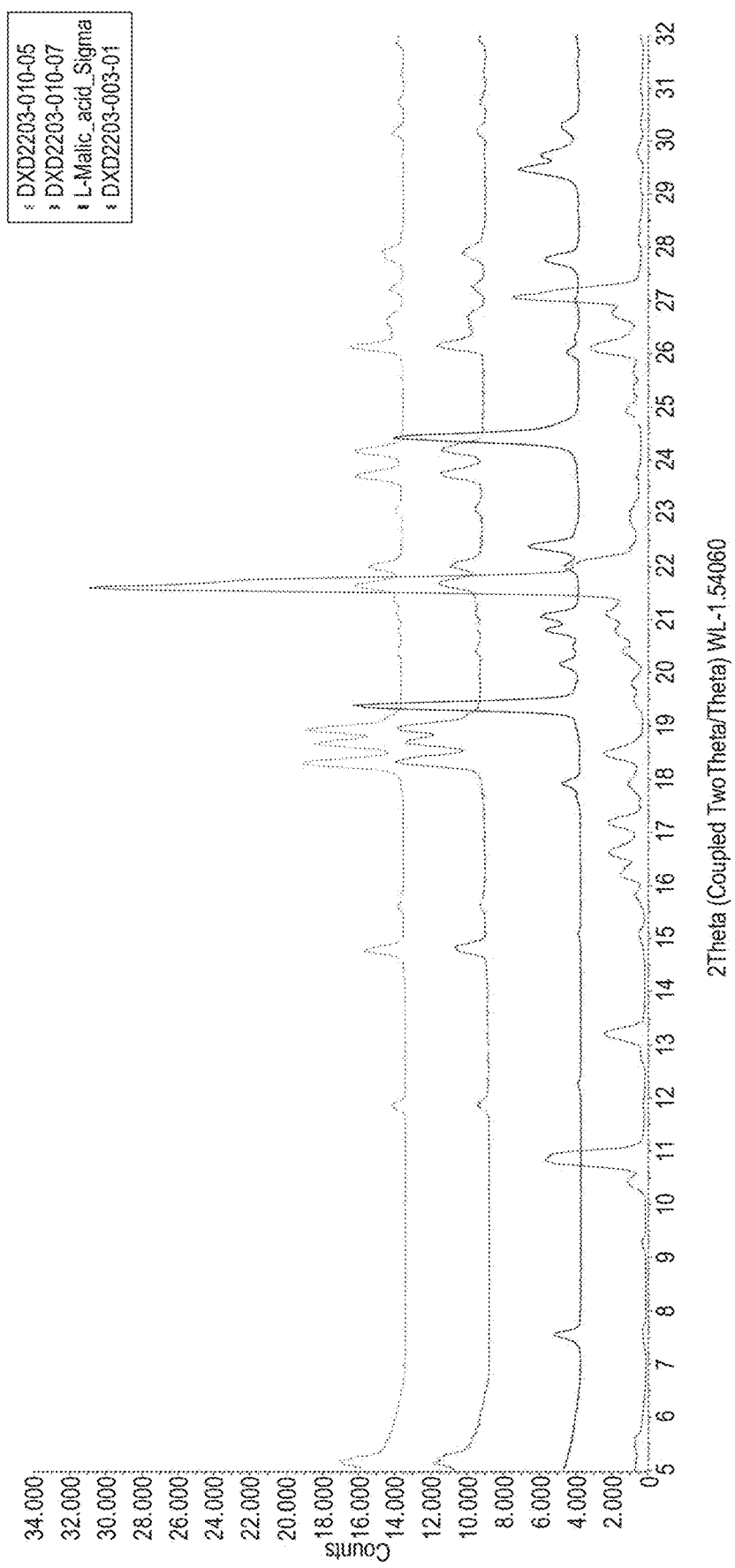
FIG. 76. XRPD Diffractograms (from top to bottom) of Malate salt isolated from ethanol/MTBE (red trace), IPAC/MTBE (green trace), L-Malic acid (black trace) and Free Base (blue trace).

XRPD diffractograms showed that same crystalline forms were produced from ethanol/MTBE and IPAC/MTBE solvent/anti-solvent systems, which does not correspond to free base and/or L-malic acid as demonstrated in FIG. 76. This was nominated as pattern 1 with XRPD peak data presented in Table 19, 19a or 19b.

TABLE 19

XRPD Peak data for Malate pattern 1.

| Peak No. | Angle 2 θ | d Value | Rel. Intensity |
|---|---|---|---|
| 1 | 11.823° | 7.479 | 0.136 |
| 2 | 14.733° | 6.008 | 0.392 |
| 3 | 15.588° | 5.680 | 0.058 |
| 4 | 18.254° | 4.856 | 1.000 |
| 5 | 18.666° | 4.750 | 0.746 |
| 6 | 18.889° | 4.694 | 0.963 |
| 7 | 20.330° | 4.365 | 0.035 |
| 8 | 20.782° | 4.271 | 0.025 |
| 9 | 21.080° | 4.211 | 0.052 |
| 10 | 21.608° | 4.109 | 0.475 |
| 11 | 21.963° | 4.044 | 0.335 |
| 12 | 23.014° | 3.861 | 0.068 |
| 13 | 23.662° | 3.757 | 0.456 |
| 14 | 24.119° | 3.687 | 0.474 |
| 15 | 26.084° | 3.413 | 0.505 |
| 16 | 26.608° | 3.347 | 0.168 |
| 17 | 27.179° | 3.278 | 0.131 |
| 18 | 27.839° | 3.202 | 0.210 |
| 19 | 29.242° | 3.052 | 0.011 |
| 20 | 29.649° | 3.011 | 0.022 |
| 21 | 30.113° | 2.965 | 0.113 |
| 22 | 30.700° | 2.910 | 0.046 |
| 23 | 31.219° | 2.863 | 0.024 |
| 24 | 31.821° | 2.810 | 0.056 |

TABLE 19a

XRPD Peak data for Malate pattern 1. (2 d .p.)

| Peak No. | Angle 2 θ | d Value | Rel. Intensity |
|---|---|---|---|
| 1 | 11.82° | 7.48 | 0.14 |
| 2 | 14.73° | 6.01 | 0.39 |
| 3 | 15.59° | 5.68 | 0.06 |
| 4 | 18.25° | 4.86 | 1.00 |
| 5 | 18.67° | 4.75 | 0.75 |
| 6 | 18.89° | 4.69 | 0.97 |
| 7 | 20.33° | 4.37 | 0.04 |
| 8 | 20.78° | 4.27 | 0.03 |
| 9 | 21.08° | 4.21 | 0.05 |
| 10 | 21.61° | 4.11 | 0.48 |
| 11 | 21.96° | 4.04 | 0.34 |
| 12 | 23.01° | 3.86 | 0.07 |
| 13 | 23.66° | 3.76 | 0.46 |
| 14 | 24.12° | 3.69 | 0.47 |
| 15 | 26.08° | 3.41 | 0.51 |
| 16 | 26.61° | 3.35 | 0.17 |
| 17 | 27.18° | 3.28 | 0.13 |
| 18 | 27.84° | 3.20 | 0.21 |
| 19 | 29.24° | 3.05 | 0.01 |
| 20 | 29.65° | 3.01 | 0.02 |
| 21 | 30.11° | 2.97 | 0.11 |
| 22 | 30.70° | 2.91 | 0.05 |
| 23 | 31.22° | 2.86 | 0.02 |
| 24 | 31.82° | 2.81 | 0.06 |

TABLE 19b

XRPD Peak data for Malate pattern 1. (1 d.p.)

| Peak No. | Angle 2 θ | d Value | Rel. Intensity |
|---|---|---|---|
| 1 | 11.8° | 7.5 | 0.1 |
| 2 | 14.7° | 6.0 | 0.4 |
| 3 | 15.6° | 5.7 | 0.1 |
| 4 | 13.3° | 4.9 | 1.0 |
| 5 | 13.7° | 4.8 | 0.7 |
| 6 | 18.9° | 4.7 | 1.0 |
| 7 | 20.3° | 4.4 | 0.0 |
| 8 | 20.8° | 4.3 | 0.0 |
| 9 | 21.1° | 4.2 | 0.1 |
| 10 | 21.6° | 4.1 | 0.5 |
| 11 | 22.0° | 4.0 | 0.3 |
| 12 | 23.0° | 3.9 | 0.1 |
| 13 | 23.7° | 3.8 | 0.5 |
| 14 | 24.1° | 3.7 | 0.5 |
| 15 | 26.1° | 3.4 | 0.5 |
| 16 | 26.6° | 3.3 | 0.2 |
| 17 | 27.2° | 3.3 | 0.1 |
| 18 | 27.8° | 3.2 | 0.2 |
| 19 | 29.2° | 3.1 | 0.0 |
| 20 | 29.6° | 3.0 | 0.0 |
| 21 | 30.1° | 3.0 | 0.1 |
| 22 | 30.7° | 2.9 | 0.0 |
| 23 | 31.2° | 2.9 | 0.0 |
| 24 | 31.8° | 2.8 | 0.1 |

The TGA thermogram of Malate salt displayed a weight loss of 2.6% between ambient temperature and 170° C., due to loss of moisture from surface of particles. The material is thermally stable up to around 170° C. as shown in, or substantially as shown in, FIG. 77.

The DSC analysis of the Malate salt was performed. The $1^{st}$ heating DSC thermogram of Malate salt exhibited a broad endothermic event with onset temperature of 80.9° C. and heat of fusion of 87.0 J/g, which corresponds to the melting of the salt as shown in, or substantially as shown in, FIG. 78.

Figure 79:
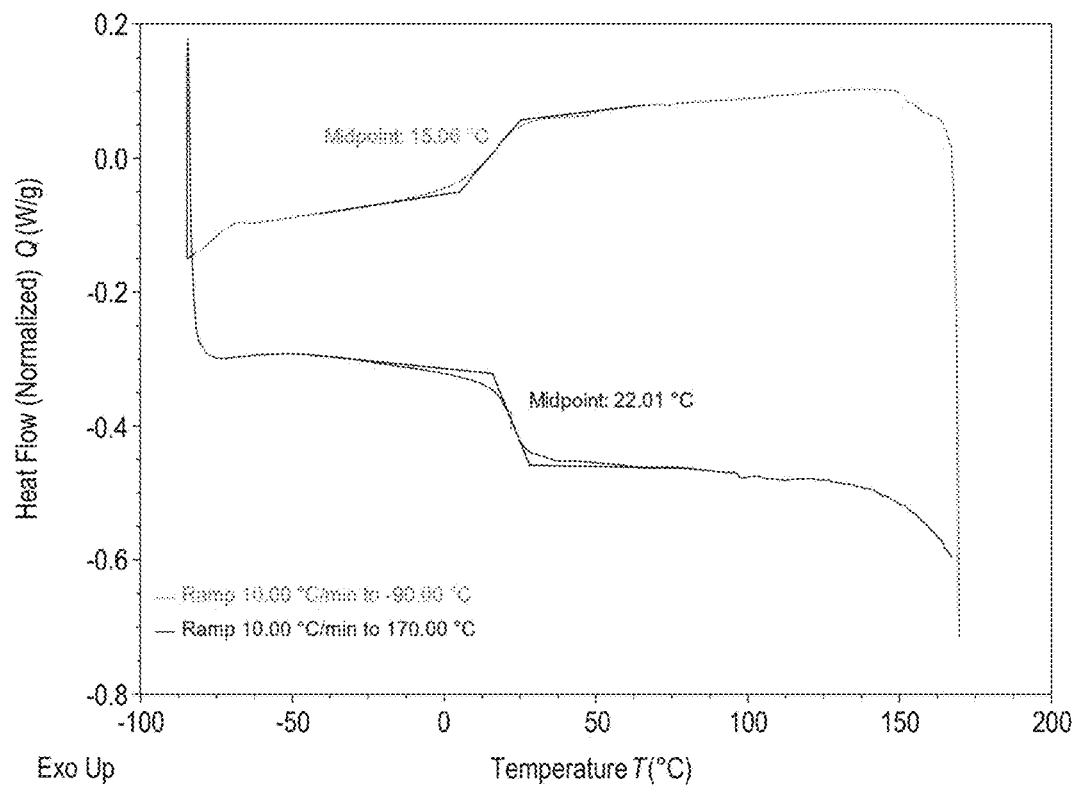
FIG. 79. DSC Thermograms of Malate salt, cooling (blue trace) and 2nd heating (green trace).

The cooling ramp 10° C./min from 170 to −90° C. displayed vitrification around 15.1° C. and the $2^{nd}$ heating cycle showed a glass transition around 22.0° C. as demonstrated in FIG. 79.

Figure 80:
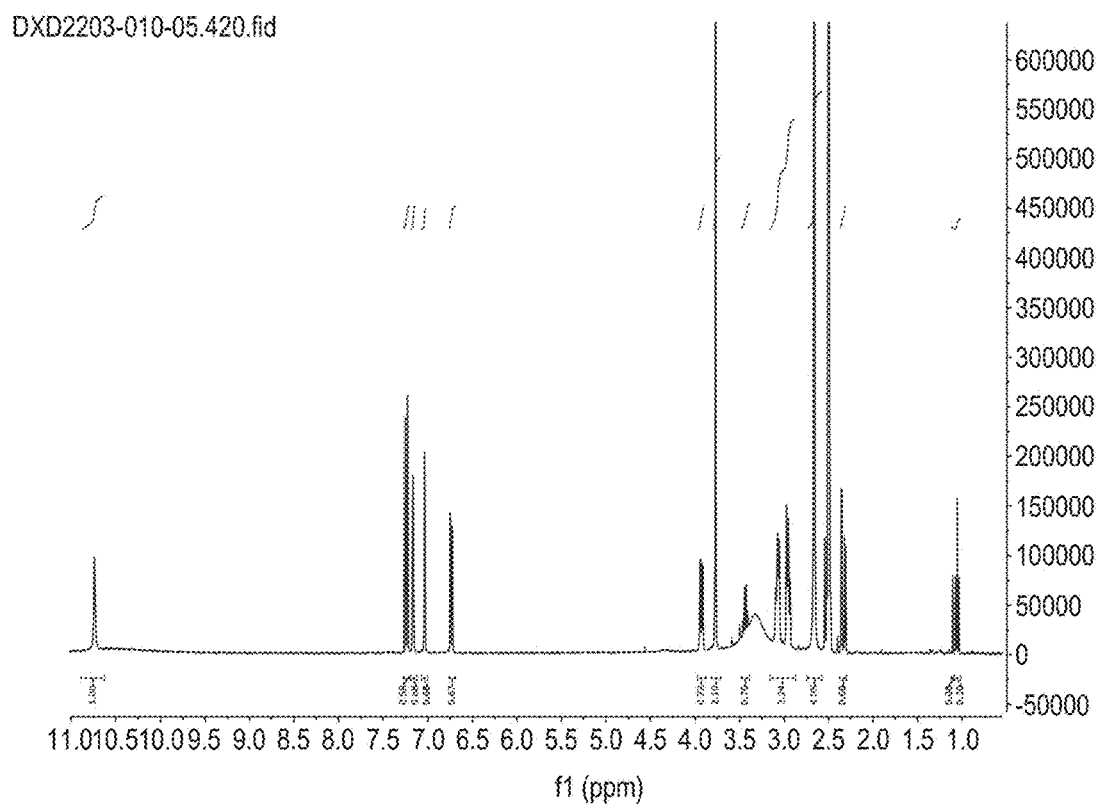
FIG. 80. $^1$H NMR ($d_6$-DMSO) Spectrum of Malate salt, Batch: DXD2203-015-05.

$^{1}$H NMR spectrum of Malate salt in $d_6$-DMSO is shown in FIG. 80. It displayed traces of ethanol (~0.1 eq) and MTBE (~0.08 eq). Signals corresponding to L-Malic acid were integrated as approximately 0.7 eq.

Figure 77:
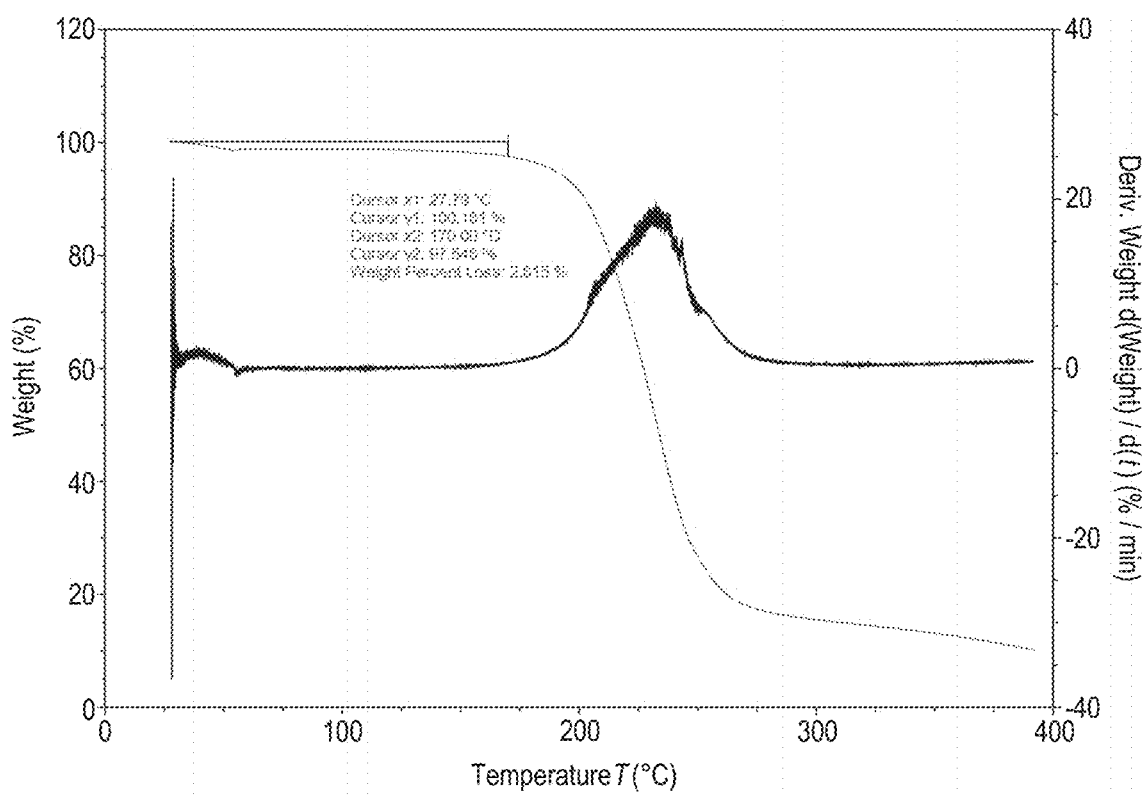
FIG. 77. TGA Thermogram of Malate salt, Batch: DXD2203-010-05.
Figure 78:
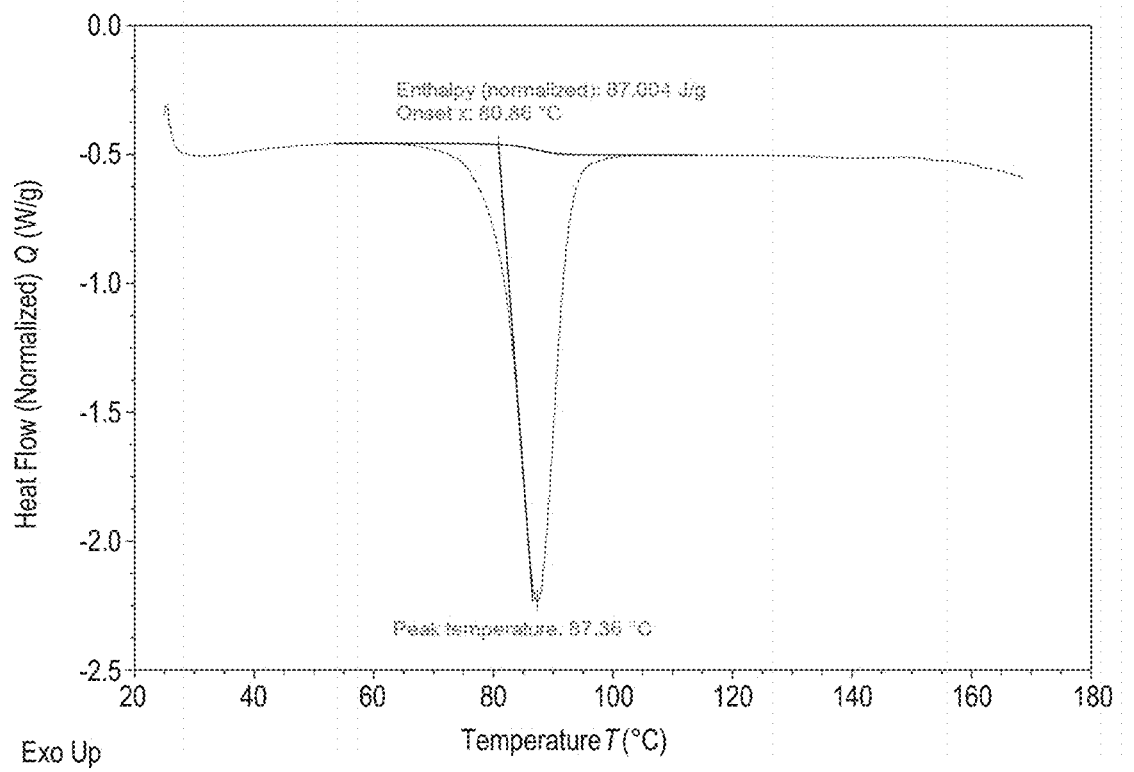
FIG. 78. DSC Thermogram (1st heating) of Malate salt, Batch: DXD2203-010-05.

In one embodiment, there is provided 5-MeO-DMT malate. In one embodiment, there is provided a pharmaceutical composition comprising 5-MeO-DMT malate. In one embodiment, there is provided crystalline 5-MeO-DMT malate, or a pharmaceutical composition comprising crystalline 5-MeO-DMT malate, as characterised by one or more of:

An XRPD pattern as shown in, or substantially as shown in, FIG. 76;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, or twenty four peaks in an XRPD diffractogram as detailed in Table 19, Table 19a or Table 19b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 19, Table 19a or Table 19b;

A TGA thermogram as shown in, or substantially as shown in, FIG. 77;

A weight loss of about 2.6% between ambient temperature and 170° C., as measured by TGA thermogram;

A weight loss of about 2.0-3.0% between ambient temperature and 170° C., as measured by TGA thermogram;

A weight loss of about 2.0, 2.1, 2.2, 2.3, 2.4, 2.5, 2.6, 2.7, 2.8, 2.9 or 3.0% between ambient temperature and 170° C., as measured by TGA thermogram;

A DSC thermogram as shown in, or substantially as shown in, FIG. 78 or FIG. 79;

A melting endothermic event with an onset of around 80.9° C. and an enthalpy of 87.0 J/g, as measured in a DSC thermogram;

A melting endothermic event with an onset of around 75-85° C. and an enthalpy of around 82-92 J/g, as measured in a DSC thermogram;

A melting endothermic event with an onset of around 75, 76, 77, 78, 79, 80, 81, 82, 83, 84 or 85° C. and an enthalpy of around 82, 83, 84, 85, 86, 87, 88, 89, 90, 91 or 92 J/g, as measured in a DSC thermogram;

A vitrification around 15.1° C., as measured in a DSC thermogram with a cooling ramp of 10° C./min from 170° C. to −90° C.;

A vitrification around 10-20° C., as measured in a DSC thermogram with a cooling ramp of 10° C./min from 170° C. to −90° C.;

A vitrification around 10, 11, 12, 13, 14, 15, 16, 17, 18, 19 or 20° C., as measured in a DSC thermogram with a cooling ramp of 10° C./min from 170° C. to −90° C.;

A glass transition around 22° C., as measured in a DSC thermogram with a cooling ramp of 10° C./min from 170° C. to −90° C.;

A glass transition around 17-27° C., as measured in a DSC thermogram with a cooling ramp of 10° C./min from 170° C. to −90° C.;

A glass transition around 17, 18, 19, 20, 21, 22, 23, 24, 25, 26 or 27° C., as measured in a DSC thermogram with a cooling ramp of 10° C./min from 170° C. to −90° C.; and/or A $^1$H NMR spectrum as shown in, or substantially as shown in, FIG. 80.

Saccharinate Salt

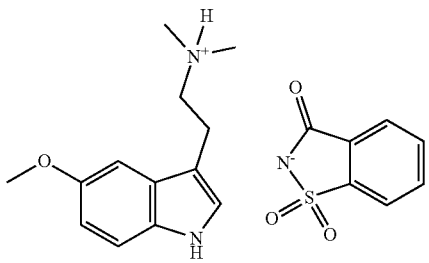

Figure 81:
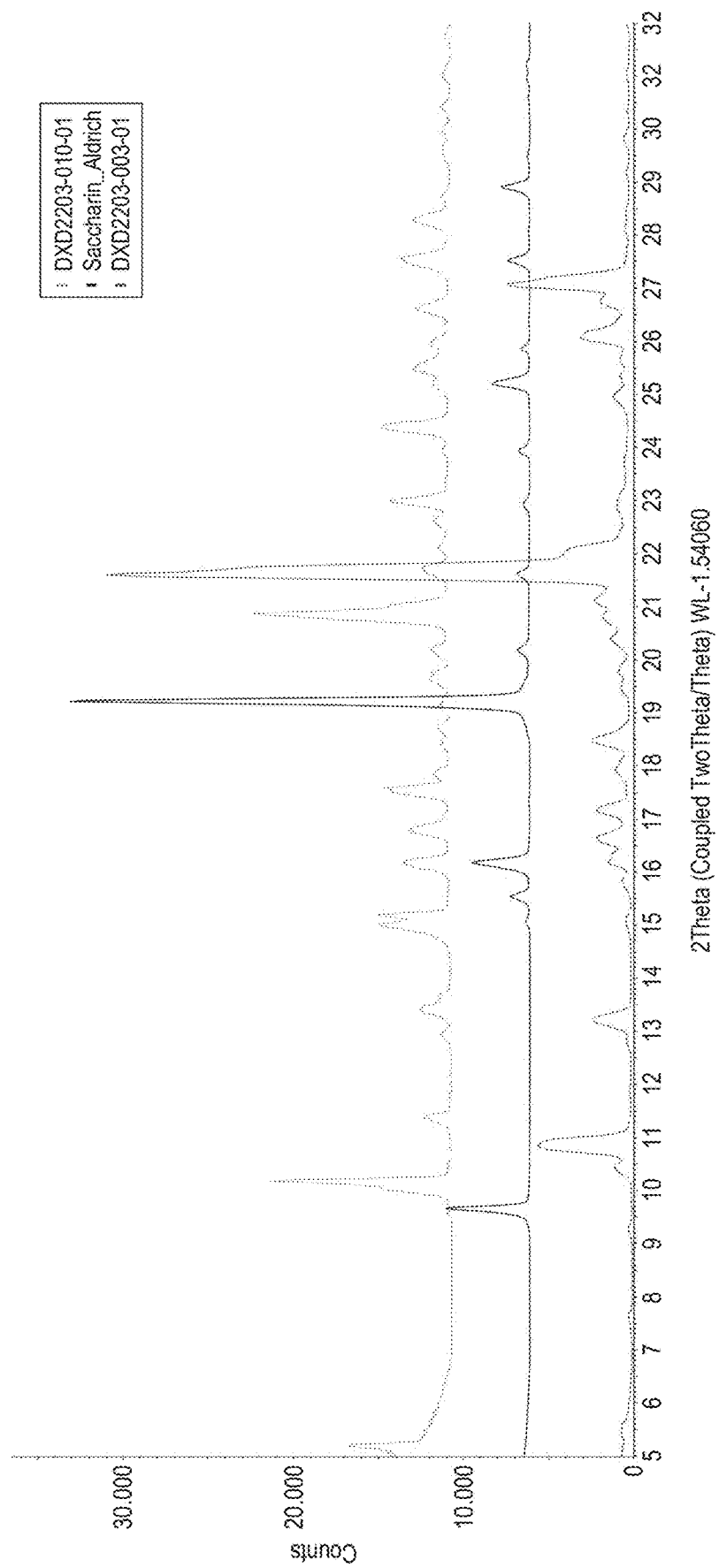
FIG. 81. XRPD Diffractograms of Saccharinate salt (red trace, top), Saccharine (black trace, middle) and Free Base (blue trace, bottom).

As shown in, or substantially as shown in, FIG. 81 the crystalline form of Saccharinate salt exhibited a different XRPD pattern when compared to free base and saccharin, which suggests the salt formation. This was nominated as pattern 1 with XRPD peak data tabulated in Table 20, 20a or 20b.

TABLE 20

XRPD Peak data for Saccharinate pattern 1.

| Peak No. | Angle 2 θ | d Value | Rel. Intensity |
| --- | --- | --- | --- |
| 1 | 5.196° | 16.993 | 0.314 |
| 2 | 9.572° | 9.232 | 0.019 |
| 3 | 10.180° | 8.682 | 0.928 |
| 4 | 11.395° | 7.759 | 0.138 |
| 5 | 12.951° | 6.830 | 0.051 |
| 6 | 13.423° | 6.591 | 0.159 |
| 7 | 14.998° | 5.902 | 0.362 |
| 8 | 15.182° | 5.331 | 0.366 |
| 9 | 16.169° | 5.477 | 0.228 |
| 10 | 16.806° | 5.271 | 0.206 |
| 11 | 17.542° | 5.052 | 0.295 |
| 12 | 17.845° | 4.966 | 0.075 |
| 13 | 18.421° | 4.813 | 0.027 |
| 14 | 18.736° | 4.732 | 0.056 |
| 15 | 19.167° | 4.627 | 0.037 |
| 16 | 19.672° | 4.509 | 0.092 |
| 17 | 20.213° | 4.390 | 0.034 |
| 18 | 20.868° | 4.253 | 1.000 |
| 19 | 21.701° | 4.092 | 0.113 |
| 20 | 22.138° | 4.012 | 0.036 |
| 21 | 22.613° | 3.929 | 0.069 |
| 22 | 22.987° | 3.866 | 0.293 |
| 23 | 23.949° | 3.713 | 0.025 |
| 24 | 24.396° | 3.646 | 0.337 |
| 25 | 25.231° | 3.527 | 0.076 |
| 26 | 25.463° | 3.495 | 0.175 |
| 27 | 25.948° | 3.431 | 0.084 |
| 28 | 26.616° | 3.346 | 0.165 |
| 29 | 27.555° | 3.234 | 0.247 |
| 30 | 23.286° | 3.153 | 0.137 |
| 31 | 28.735° | 3.104 | 0.039 |
| 32 | 29.676° | 3.008 | 0.032 |
| 33 | 29.961° | 2.980 | 0.037 |
| 34 | 30.413° | 2.937 | 0.048 |
| 35 | 31.037° | 2.879 | 0.040 |
| 36 | 31.781° | 2.813 | 0.025 |

TABLE 20a

XRPD Peak data for Saccharinate pattern 1. (2 d.p.)

| Peak No. | Angle 2 θ | d Value | Rel. Intensity |
| --- | --- | --- | --- |
| 1 | 5.20° | 16.99 | 0.31 |
| 2 | 9.57° | 9.23 | 0.02 |
| 3 | 10.18° | 8.68 | 0.93 |

TABLE 20a-continued

XRPD Peak data for Saccharinate pattern 1. (2 d.p.)

| Peak No. | Angle 2 θ | d Value | Rel. Intensity |
|---|---|---|---|
| 4 | 11.40° | 7.76 | 0.14 |
| 5 | 12.95° | 6.83 | 0.05 |
| 6 | 13.42° | 6.59 | 0.16 |
| 7 | 15.00° | 5.90 | 0.36 |
| 8 | 15.13° | 5.83 | 0.37 |
| 9 | 16.17° | 5.48 | 0.23 |
| 10 | 16.81° | 5.27 | 0.21 |
| 11 | 17.54° | 5.05 | 0.30 |
| 12 | 17.85° | 4.97 | 0.08 |
| 13 | 18.42° | 4.81 | 0.03 |
| 14 | 18.74° | 4.73 | 0.06 |
| 15 | 19.17° | 4.63 | 0.04 |
| 16 | 19.67° | 4.51 | 0.09 |
| 17 | 20.21° | 4.39 | 0.08 |
| 18 | 20.87° | 4.25 | 1.00 |
| 19 | 21.70° | 4.09 | 0.11 |
| 20 | 22.14° | 4.01 | 0.04 |
| 21 | 22.61° | 3.93 | 0.07 |
| 22 | 22.99° | 3.87 | 0.29 |
| 23 | 23.95° | 3.71 | 0.03 |
| 24 | 24.40° | 3.65 | 0.34 |
| 25 | 25.23° | 3.53 | 0.08 |
| 26 | 25.46° | 3.50 | 0.18 |
| 27 | 25.95° | 3.43 | 0.08 |
| 28 | 26.62° | 3.35 | 0.17 |
| 29 | 27.56° | 3.23 | 0.25 |
| 30 | 28.29° | 3.15 | 0.19 |
| 31 | 28.74° | 3.10 | 0.04 |
| 32 | 29.68° | 3.01 | 0.03 |
| 33 | 29.96° | 2.98 | 0.04 |
| 34 | 30.41° | 2.94 | 0.05 |
| 35 | 31.04° | 2.88 | 0.04 |
| 36 | 31.78° | 2.81 | 0.03 |

TABLE 20b

XRPD Peak data for Saccharinate pattern 1. (1 d.p.)

| Peak No. | Angle 2 θ | d Value | Rel. Intensity |
|---|---|---|---|
| 1 | 5.2° | 17.0 | 0.3 |
| 2 | 9.6° | 9.2 | 0.0 |
| 3 | 10.2° | 8.7 | 0.9 |
| 4 | 11.4° | 7.8 | 0.1 |
| 5 | 13.0° | 6.8 | 0.1 |
| 6 | 13.4° | 6.6 | 0.2 |
| 7 | 15.0° | 5.9 | 0.4 |
| 8 | 15.2° | 5.8 | 0.4 |
| 9 | 16.2° | 5.5 | 0.2 |
| 10 | 16.8° | 5.3 | 0.2 |
| 11 | 17.5° | 5.1 | 0.3 |
| 12 | 17.8° | 5.0 | 0.1 |
| 13 | 18.4° | 4.8 | 0.0 |
| 14 | 18.7° | 4.7 | 0.1 |
| 15 | 19.2° | 4.6 | 0.0 |
| 16 | 19.7° | 4.5 | 0.1 |
| 17 | 20.2° | 4.4 | 0.1 |
| 18 | 20.9° | 4.3 | 1.0 |
| 19 | 21.7° | 4.1 | 0.1 |
| 20 | 22.1° | 4.0 | 0.0 |
| 21 | 22.6° | 3.9 | 0.1 |
| 22 | 23.0° | 3.9 | 0.3 |
| 23 | 23.9° | 3.7 | 0.0 |
| 24 | 24.4° | 3.6 | 0.3 |
| 25 | 25.2° | 3.5 | 0.1 |
| 26 | 25.5° | 3.5 | 0.2 |
| 27 | 25.9° | 3.4 | 0.1 |
| 28 | 26.6° | 3.3 | 0.2 |
| 29 | 27.6° | 3.2 | 0.2 |
| 30 | 28.3° | 3.2 | 0.2 |
| 31 | 28.7° | 3.1 | 0.0 |
| 32 | 29.7° | 3.0 | 0.0 |
| 33 | 30.0° | 3.0 | 0.0 |
| 34 | 30.4° | 2.9 | 0.0 |
| 35 | 31.0° | 2.9 | 0.0 |
| 36 | 31.8° | 2.8 | 0.0 |

Figure 82:
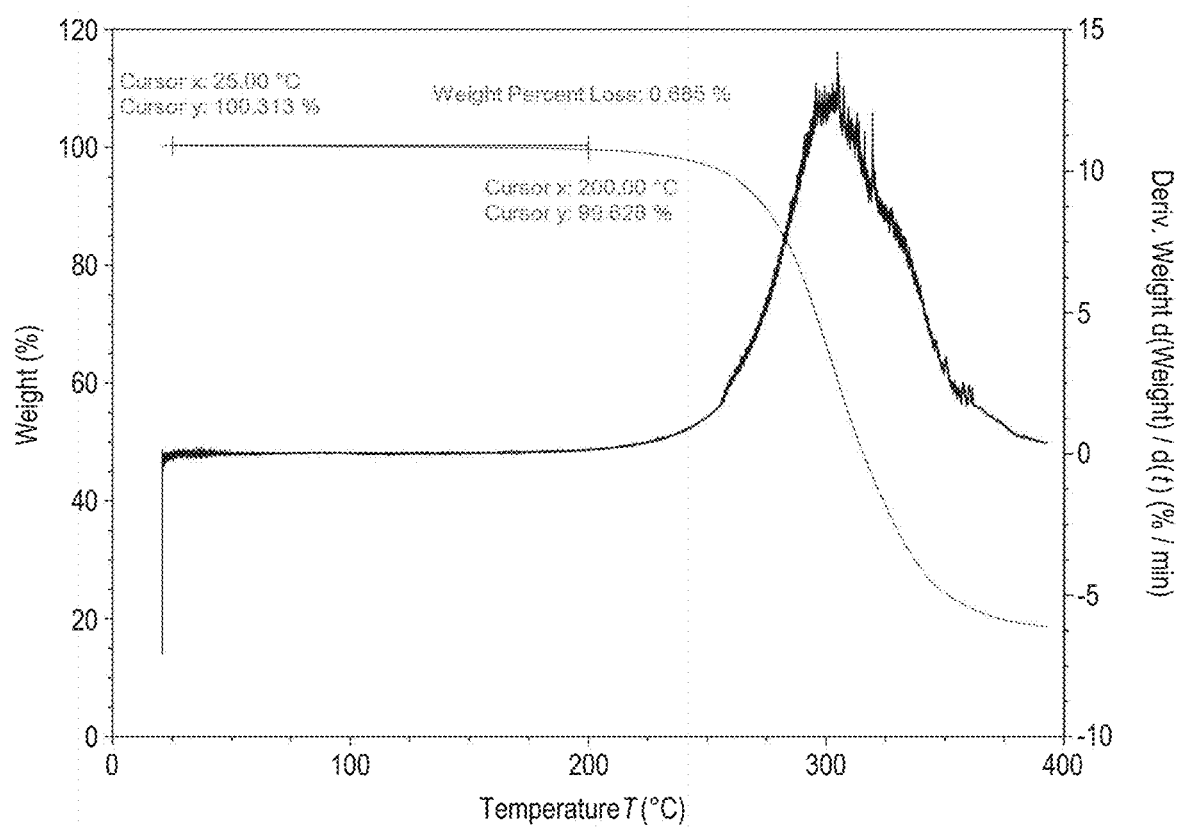
FIG. 82. TGA Thermogram of Saccharinate salt, Batch: DXD2203-010-01.

The TGA thermogram of Saccharinate salt presented in FIG. 82, showed that the material is thermally stable up to 200° C., then a single step thermal degradation follows. 0.7% of weight loss was observed between 25-200° C., due to desolation of process solvents.

Figure 83:
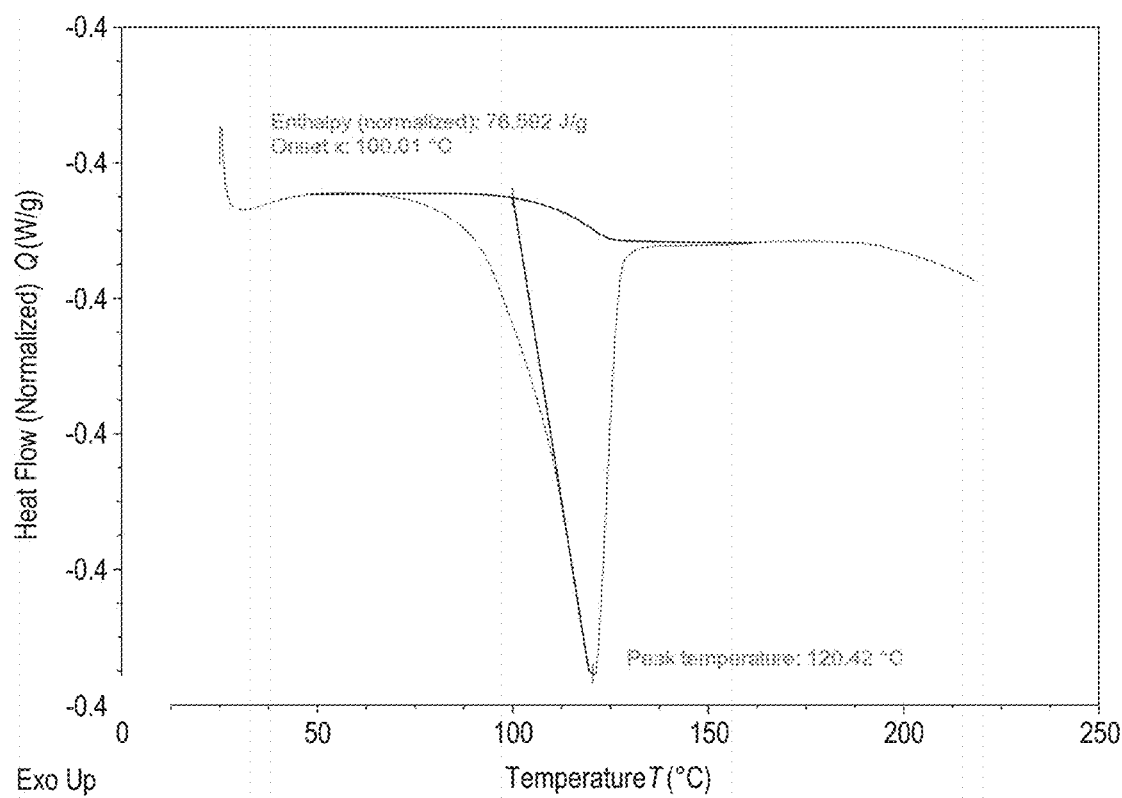
FIG. 83. DSC Thermogram (1st heating) of Saccharinate salt, Batch: DXD2203-010-01.

The DSC thermogram of Saccharinate salt presented in FIG. 83 showed a broad endothermic melting peak with onset temperature at 100.0° C. and heat of fusion of 76.6 J/g.

Figure 84:
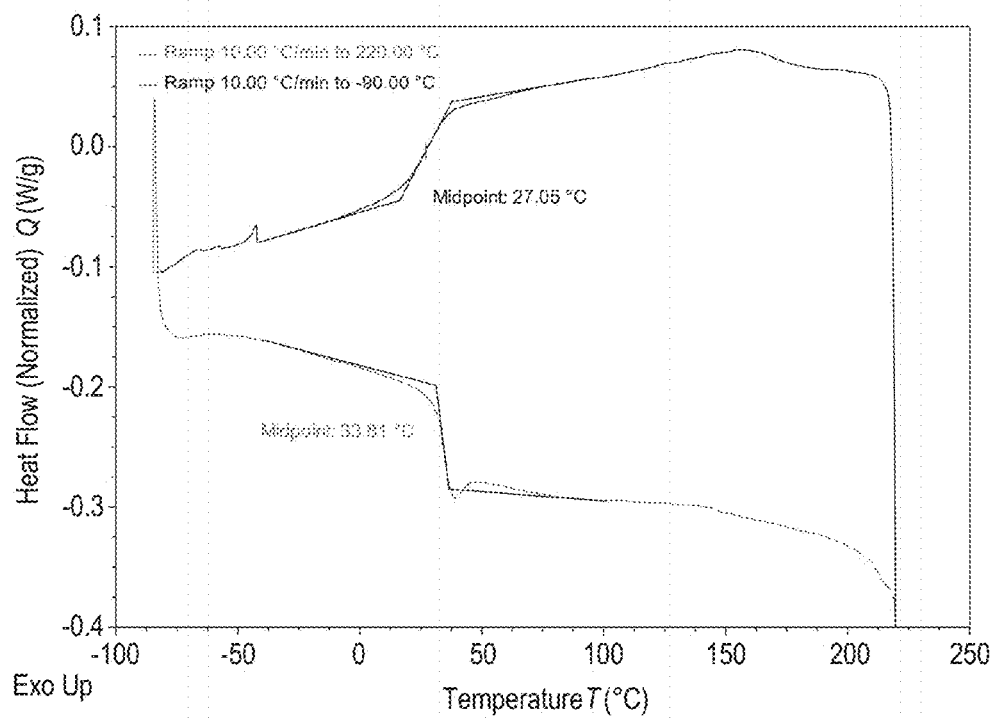
FIG. 84. DSC Thermograms of Saccharinate salt, cooling (green trace) and 2nd heating (blue trace).

The cooling ramp at 10° C./min from 220° C. to −90° C. showed a vitrification around 27.1° C. and the $2^{nd}$ heat cycle displayed a glass transition around 33.8° C. as demonstrated in FIG. 84.

Figure 85:
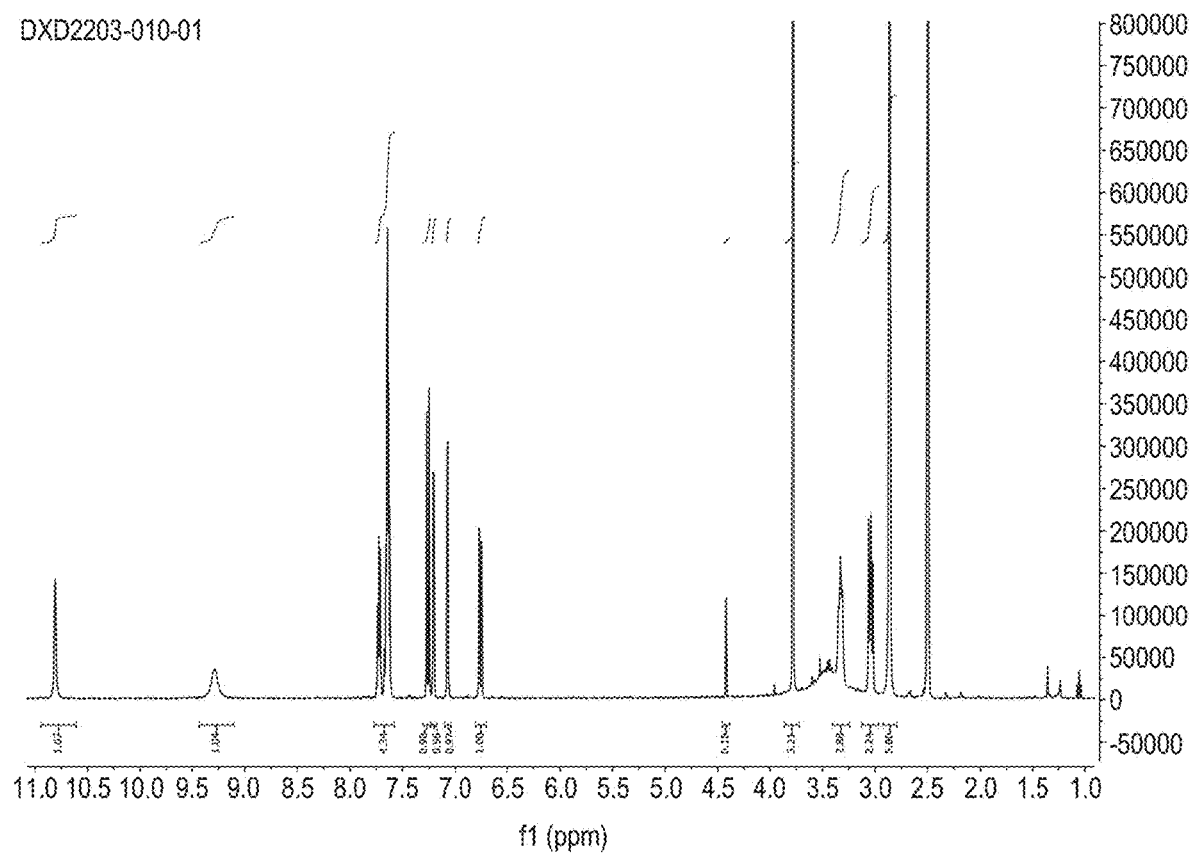
FIG. 85. 1H NMR (d6-DMSO) Spectrum of Saccharinate salt, Batch: DXD2203-010-01.

$^1$H NMR spectrum in $d_6$-DMSO for Saccharinate salt is displayed in FIG. 85. The signals in the spectrum confirmed a presence of 1.0 eq saccharin. Traces of residual process solvents were also observed in the spectrum.

In one embodiment, there is provided 5-MeO-DMT saccharinate. In one embodiment, there is provided a pharmaceutical composition comprising 5-MeO-DMT saccharinate. In one embodiment, there is provided crystalline 5-MeO-DMT saccharinate, or a pharmaceutical composition comprising crystalline 5-MeO-DMT saccharinate, as characterised by one or more of:

An XRPD pattern as shown in, or substantially as shown in, FIG. 81;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, thirty three or more, thirty four or more, thirty five or more, or thirty six peaks in an XRPD diffractogram as detailed in Table 20, Table 20a or Table 20b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 20, Table 20a or Table 20b;

A TGA thermogram as shown in, or substantially as shown in, FIG. 82;

A weight loss of about 0.7% between 25-200° C., as measured by TGA thermogram;

A weight loss of about 0.2-1.2% between 25-200° C., as measured by TGA thermogram;

A weight loss of about 0.2, 0.3, 0.4, 0.5, 0.6, 0.7, 0.8, 0.9, 1.0, 1.1 or 1.2% between 25-200° C., as measured by TGA thermogram;

A DSC thermogram as shown in, or substantially as shown in, FIG. 83 or FIG. 84;

A melting endothermic event with an onset of around 100.0° C. and an enthalpy of 76.6 J/g, as measured in a DSC thermogram;
A melting endothermic event with an onset of around 95-105° C. and an enthalpy of around 70-80 J/g, as measured in a DSC thermogram;
A melting endothermic event with an onset of around 95, 96, 97, 98, 99, 100, 101, 102, 103, 104 or 105° C. and an enthalpy of around 70, 71, 72, 73, 74, 75, 76, 77, 78, 79 or 80 J/g, as measured in a DSC thermogram;
A vitrification around 27.1° C., as measured in a DSC thermogram with a cooling ramp of 10° C./min from 220° C. to −90° C.;
A vitrification around 22-32° C., as measured in a DSC thermogram with a cooling ramp of 10° C./min from 220° C. to −90° C.;
A vitrification around 22, 23, 24, 25, 26, 27, 28, 29, 30, 31 or 32° C., as measured in a DSC thermogram with a cooling ramp of 10° C./min from 220° C. to −90° C.;
A glass transition around 33.8° C., as measured in a DSC thermogram with a cooling ramp of 10° C./min from 220° C. to −90° C.; and/or
A glass transition around 28-38° C., as measured in a DSC thermogram with a cooling ramp of 10° C./min from 220° C. to −90° C.;
A glass transition around 28, 29, 30, 31, 32, 33, 34, 35, 36, 37 or 38° C., as measured in a DSC thermogram with a cooling ramp of 10° C./min from 220° C. to −90° C.;
A $^1$H NMR spectrum as shown in, or substantially as shown in, FIG. 85.

Physical Stability of Salts

Physical stability stress tests were conducted on generated crystalline salts at controlled temperature and relative humidity. The powder samples were stored at 40° C./75% RH for three days. After this time samples were analysed by XRPD to see whether the physical state of salts changed during the storage.

Phosphate Salt

Figure 86:
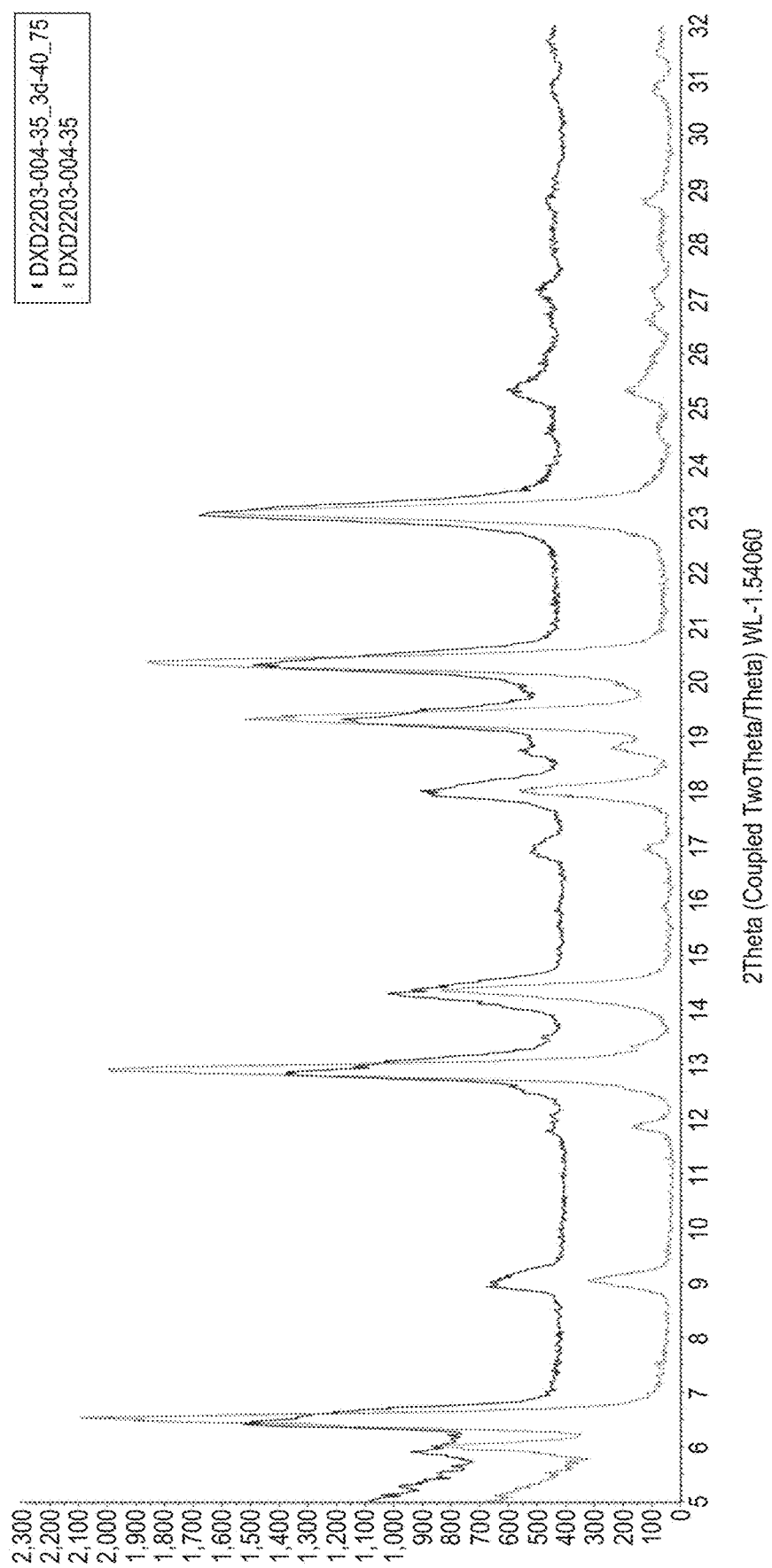
FIG. 86. XRPD Diffractograms of Phosphate salt, initial (red trace, bottom) and after 3 days at 40° C./75% RH (black trace, top).

As shown in, or substantially as shown in, FIG. 86, the crystalline Phosphate salt did not undergo any transformation. The XRPD diffractogram of Phosphate salt after three days of storage at 40° C./75% RH agrees with the input material.

Fumarate Salt

Figure 87:
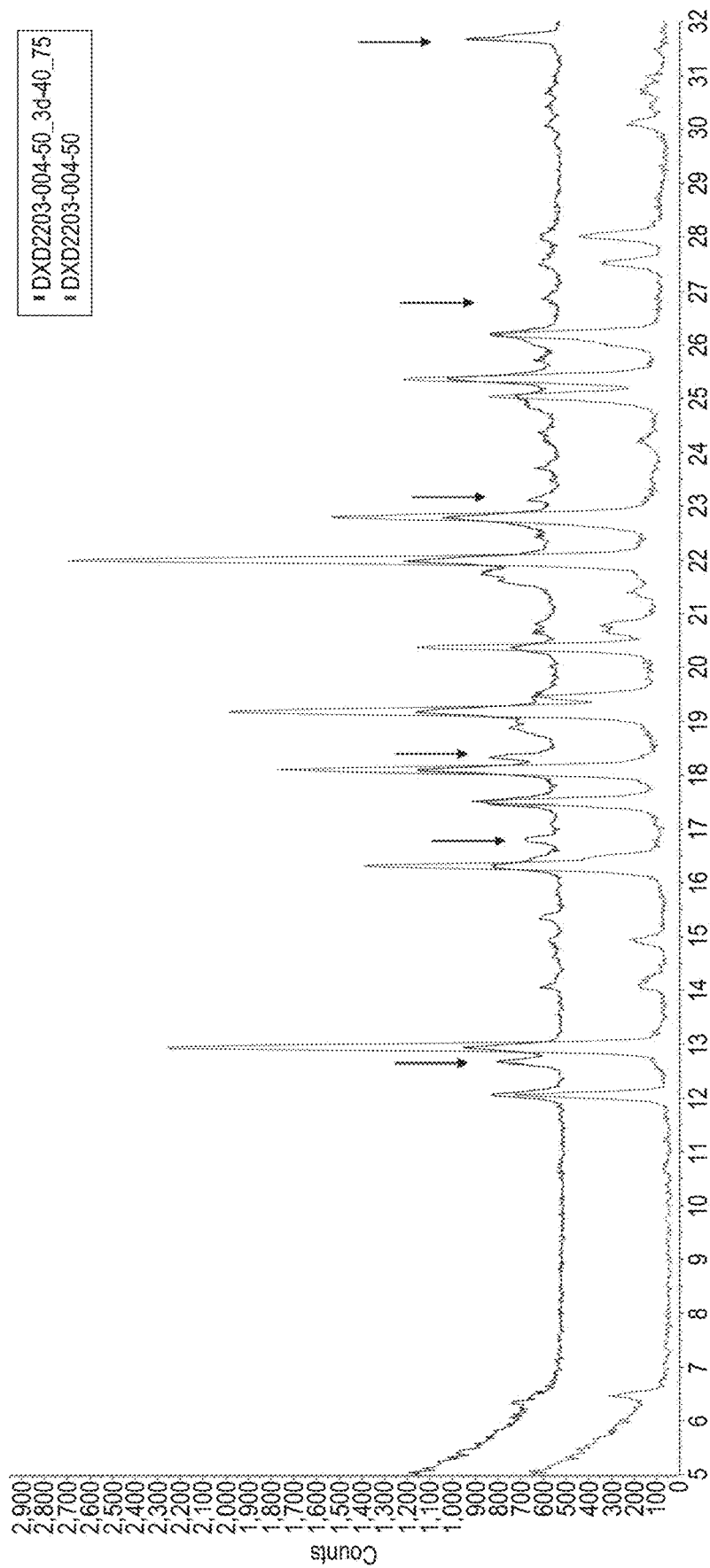
FIG. 87. XRPD Diffractograms of Fumarate salt, initial (red trace, bottom) and after 3 days at 40° C./75% RH (black trace, top).

XRPD of Fumarate salt after three days of storage at 40° C./75% RH showed the same XRPD crystalline pattern when compared to XRPD diffractogram of the input material. However, some additional peaks were also observed as indicated by arrows in FIG. 87.

Figure 88:
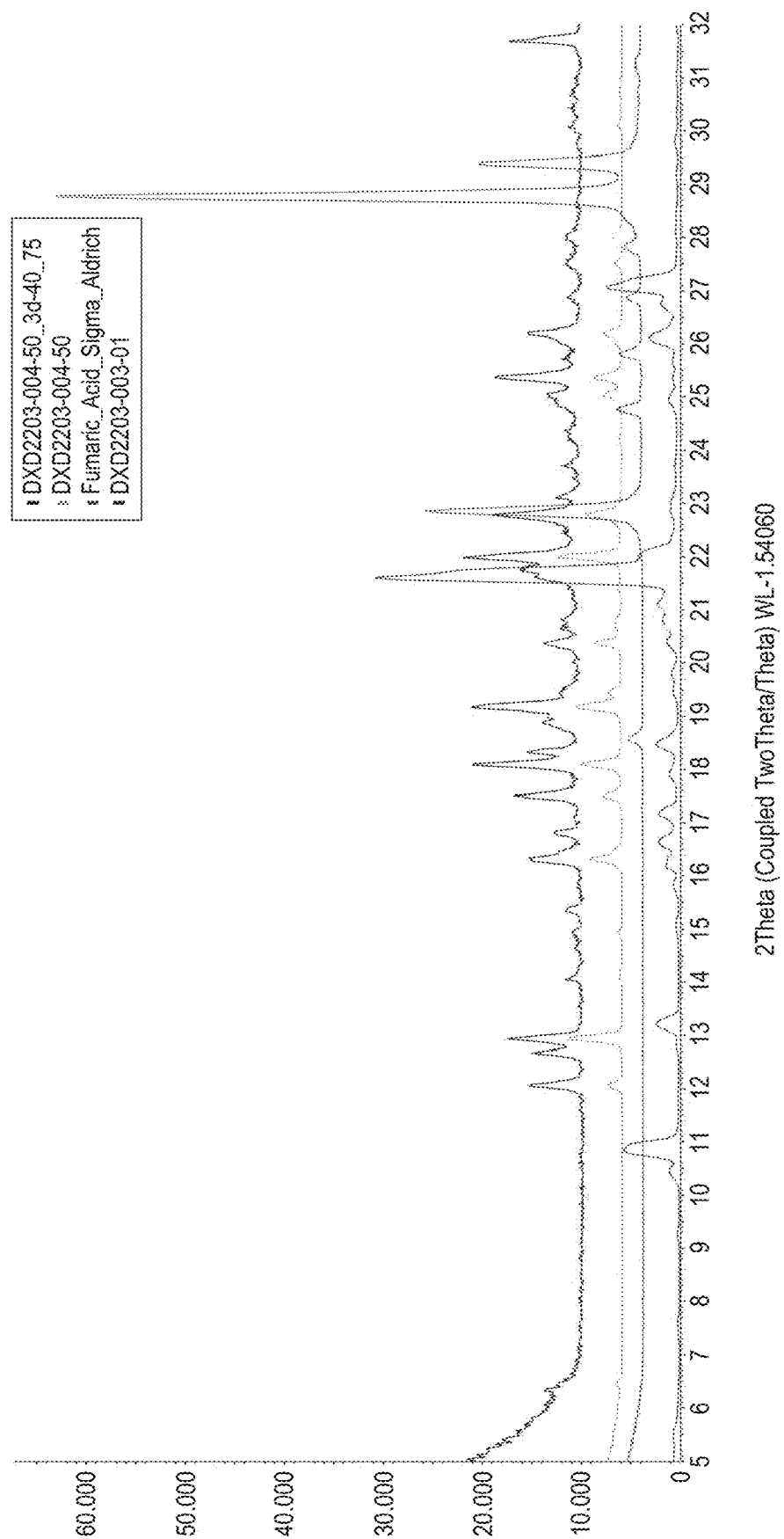
FIG. 88. XRPD Diffractograms of Fumarate salt, initial (red trace), after 3 days at 40° C./75% RH (black trace), Fumaric acid (green trace) and free base (blue trace).

To understand what phase transformation might happened during the storage, observed additional peaks were compared with XRPD pattern of free base and fumaric acid. XRPD diffractogram showed that positions of additional peaks are not characteristic of the free base and/or fumaric acid as displayed in FIG. 88. More experiments would need to be carried out to see if a new polymorph or hydrate form of Fumarate salt was generated during the storage for three days at 40° C./75% RH.

Tartrate Salt

Figure 89:
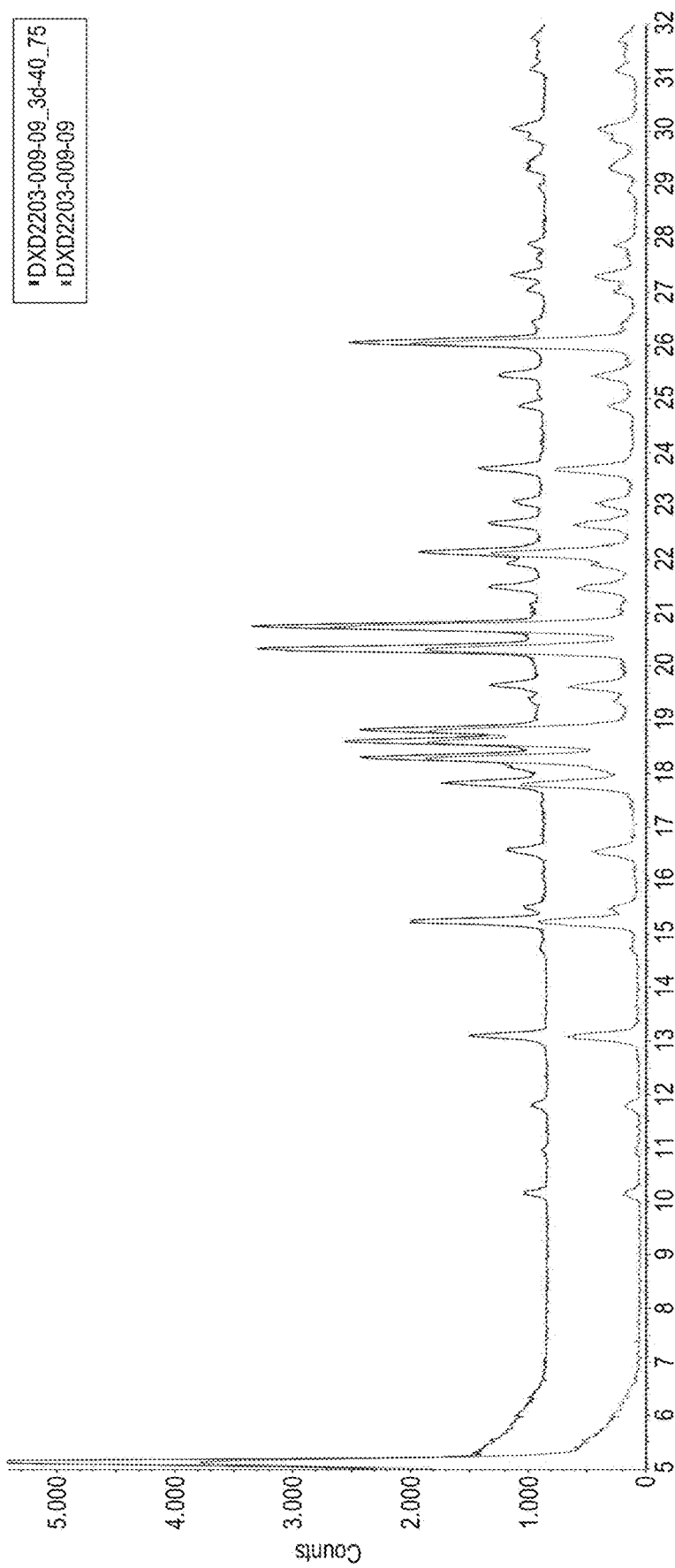
FIG. 89. XRPD Diffractograms of Tartrate salt, initial (red trace) and after 3 days at 40° C./75% RH (black trace).

No change in the crystalline form was observed for Tartrate salt after three days of storage at 40° C./75% RH as shown in, or substantially as shown in, FIG. 89.

Malate Salt

The crystalline Malate salt underwent conversion to a "gum" material after 3 days of storage at 40° C./75% RH, therefore XRPD analysis were not performed.

Tosylate Salt

Figure 90:
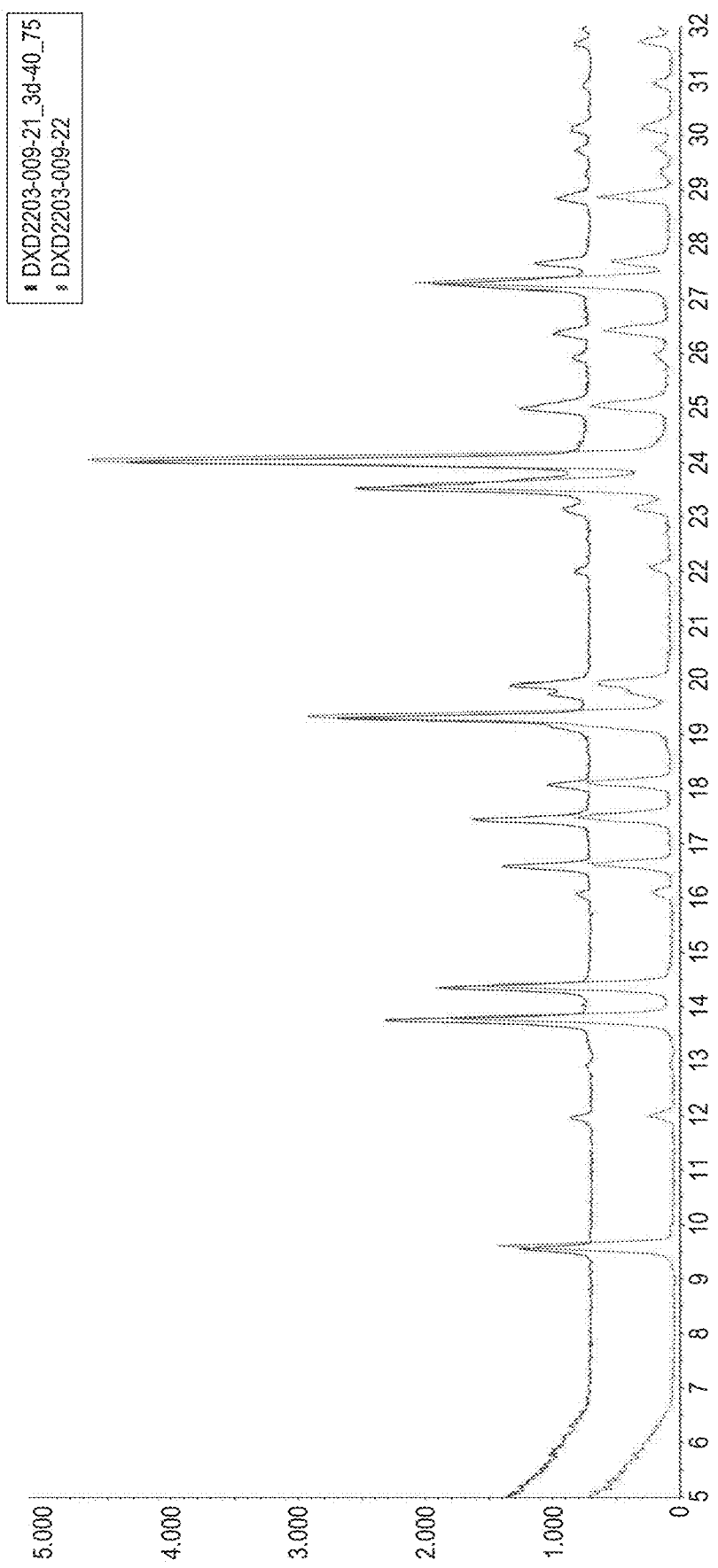
FIG. 90. XRPD Diffractograms of Tosylate salt, initial (red trace) and after 3 days at 40° C./75% RH (black trace).

Crystalline Tosylate salt after three days storage at 40° C./75% RH exhibited the identical XRPD pattern as the input material as demonstrated in FIG. 90.

Saccharinate Salt

Figure 91:
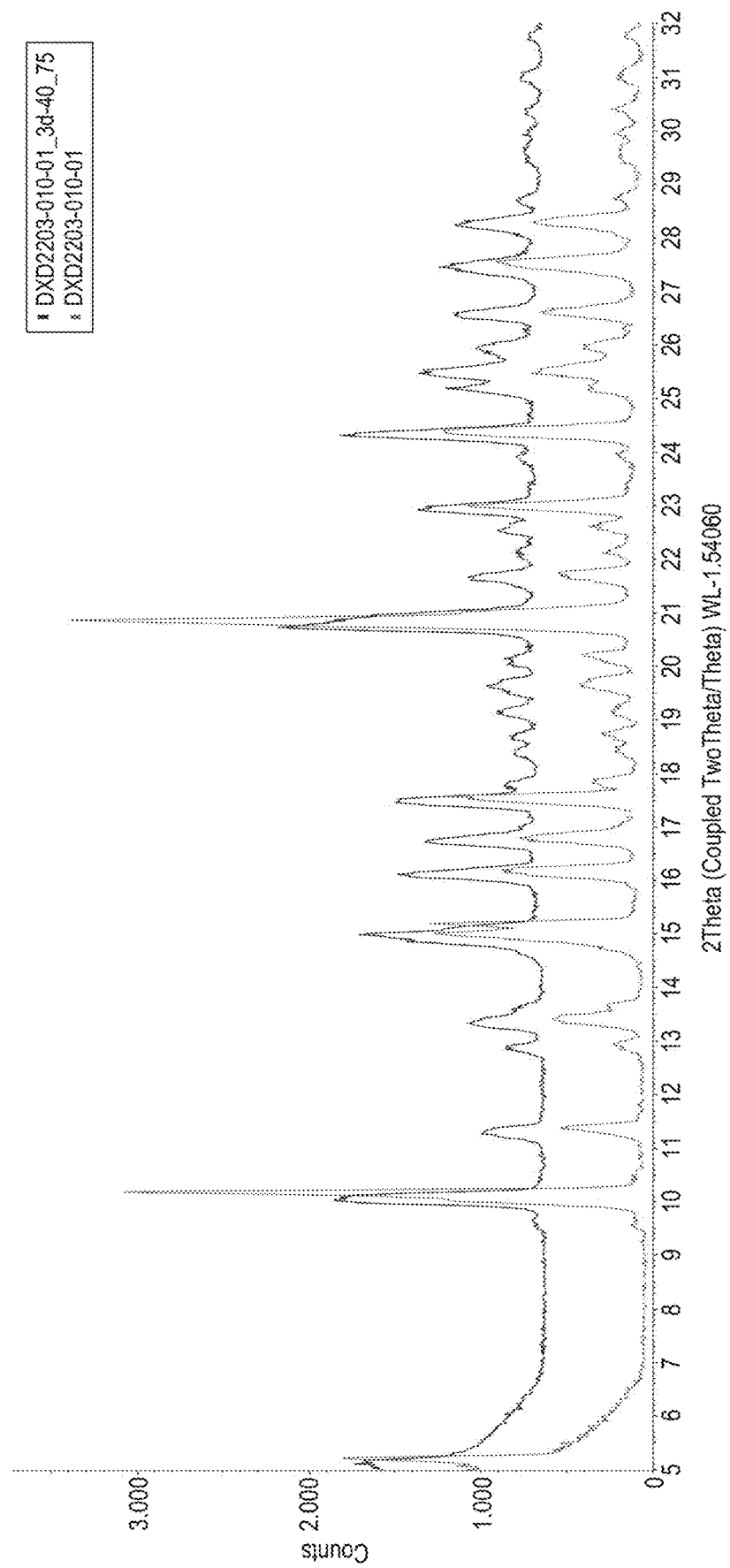
FIG. 91. XRPD Diffractograms of Saccharinate salt, initial (red trace) and after 3 days at 40° C./75% RH (black trace).

Saccharinate salt after the storage at 40° C./75% RH for three days displayed the same XRPD pattern as the input material (FIG. 91).

Hydrobromide Salt

Figure 92:
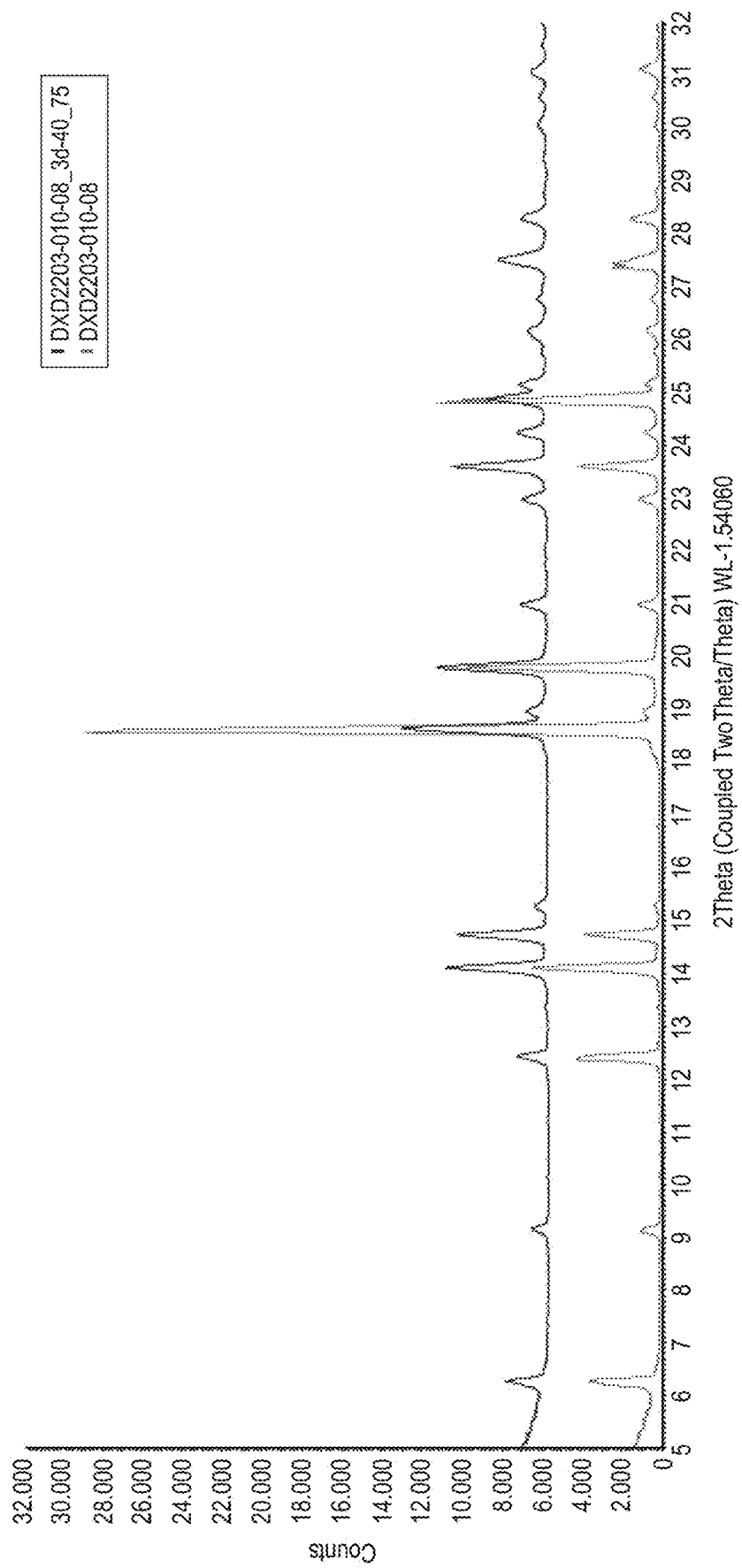
FIG. 92. XRPD Diffractograms of Hydrobromide salt, initial (red trace) and after 3 days at 40° C./75% RH (black trace).

XRPD diffractogram of Hydrobromide salt after three days of storage at 40° C./75% RH remained the same. No change in crystalline form was observed as shown in, or substantially as shown in, FIG. 92.

Example 2: Salt Scale-Up

Fumarate Salt

5-MeO-DMT Free Base (12.43 g) was dissolved in acetone (60 ml). 1.05 eqv. of Fumaric acid (0.5M in 5% water:EtOH (v/v)) was added. No precipitation was observed upon addition. The volume was reduced by rotary evaporation to form a "Honey" like liquid. This was then thermally cycled between ambient and 40° C. overnight—the temperature was held for 4 hrs at each condition. No precipitation was observed. To this THF (100 ml) was added. The sample was stirred for 30 mins at RT. The formation of an off-white (light brown) solid was observed. This solid was collected by filtration and dried under vacuum at 80° C. for ~20 hrs. A total of 12.64 g was produced (64.65% yield).

Figure 93:
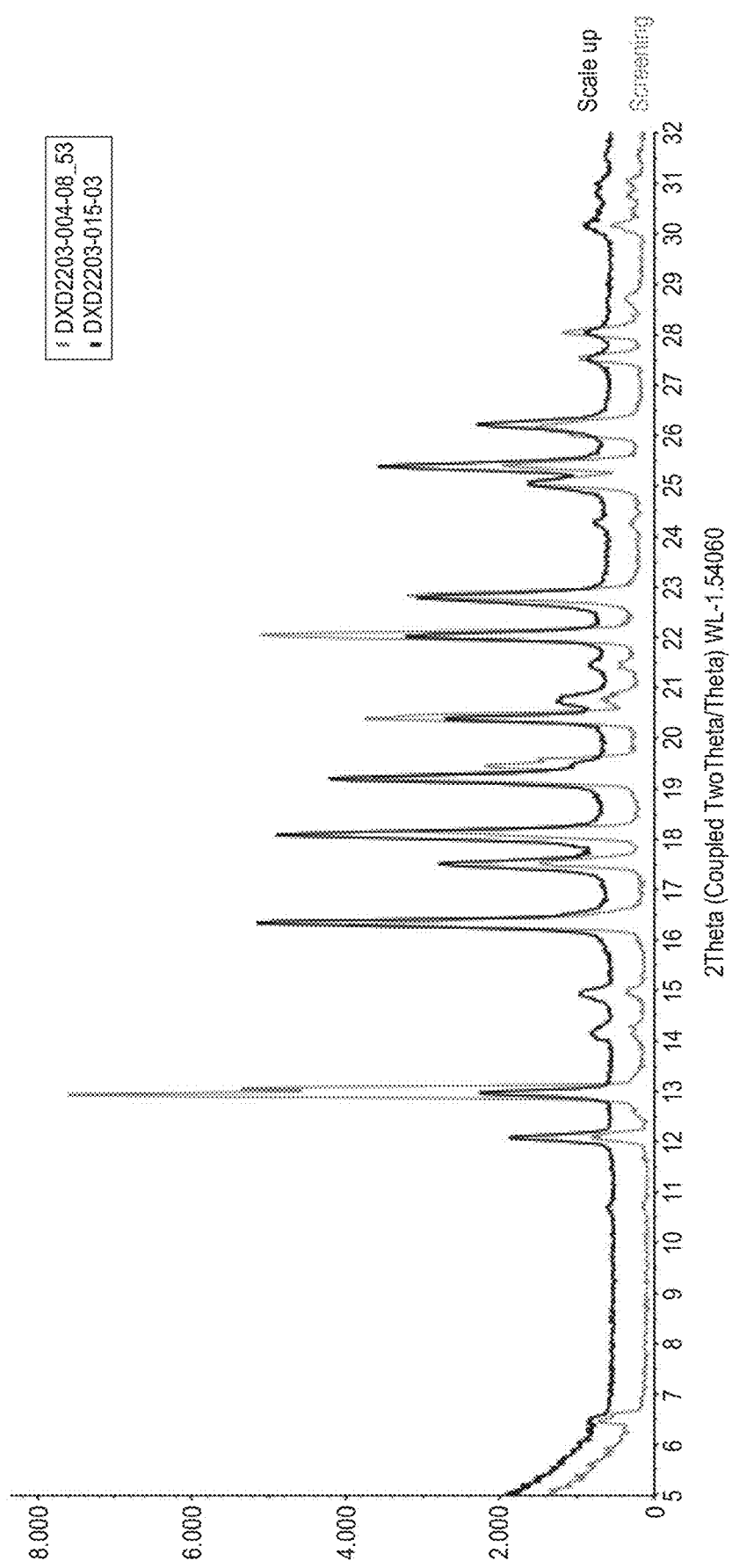
FIG. 93. XRPD Diffractograms of Fumarate salt produced during scale-up versus that initially analysed during the salt screen.

An XRPD diffractogram of the produced material versus that analysed in the screening can be seen in FIG. 93. The diffractograms are considered to represent the same crystalline form.

Oxalate Salt

5-MeO-DMT Free Base (2×5 g) was dissolved in acetone (50 ml). 1.05 eqv. of Oxalic acid (1.0 M in water) was added. No precipitation observed upon addition. The volume was reduced by rotary evaporation to form an off-white solid. The solid was collected by filtration and dried under vacuum at 80° C. overnight. A total of 10.39 g was produced (73.48% yield).

Figure 94:
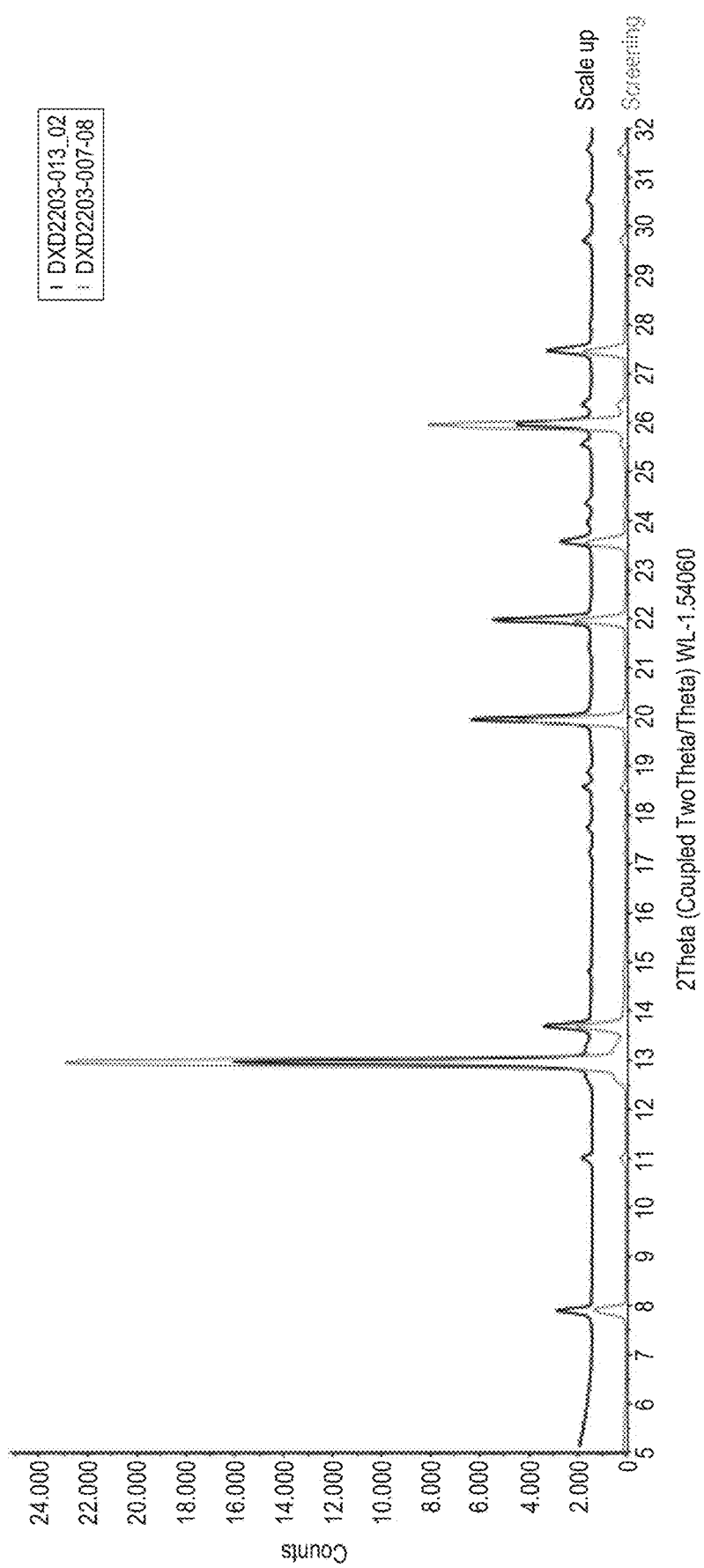
FIG. 94. XRPD Diffractograms of Oxalate salt produced during scale-up versus that initially analysed during the salt screen.

An XRPD diffractogram of the produced material versus that analysed in the screening can be seen in FIG. 94. The diffractograms are considered to represent the same crystalline form.

Figure 101:
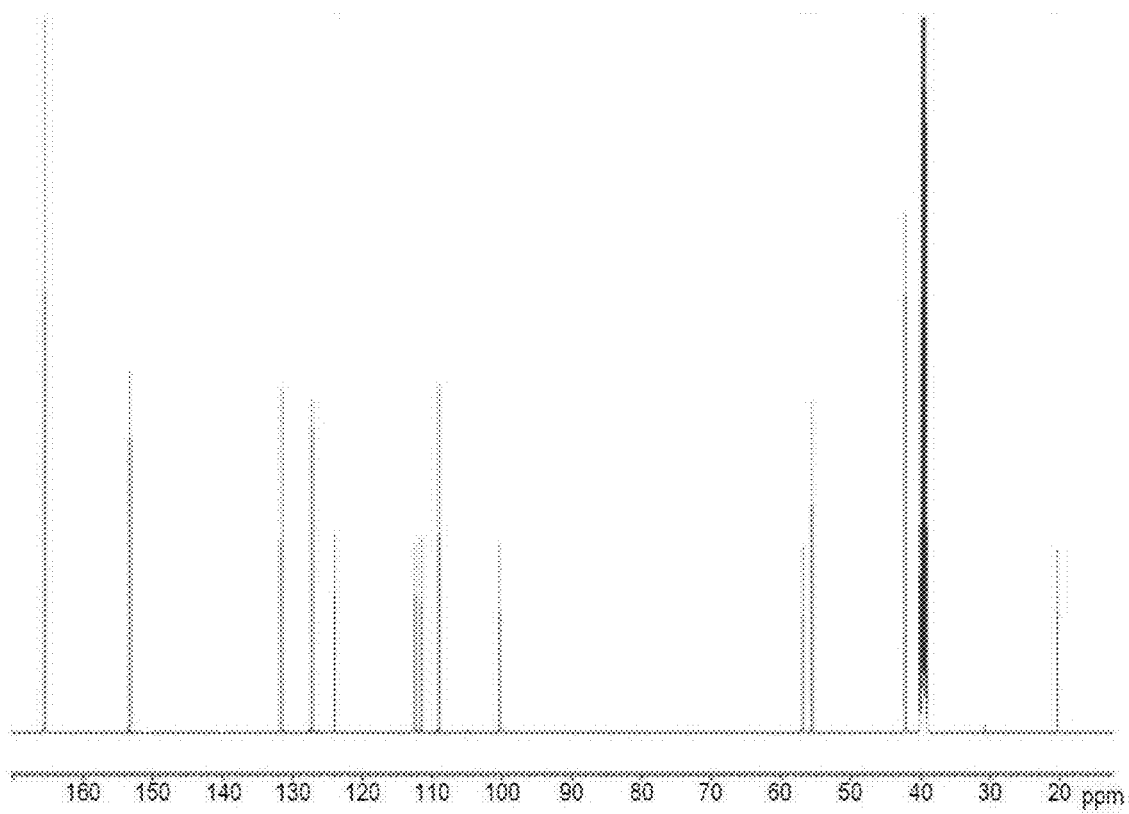
FIG. 101. $^{13}$C NMR spectrum of Oxalate salt produced during scale-up.

$^{13}$C NMR of Oxalate salt produced during scale-up can be seen in FIG. 101 (pp=ZGIG, D1=60 seconds, >35 hr acquisition time, mono salt).

Hydrobromide Salt

5-MeO-DMT Free Base (17.18 g) was dissolved in MeOH (80 ml). 1.05 eqv. of HBr acid (1.0 M in MeOH) was added. No precipitation observed upon addition. Volume reduced by rotary evaporation. No precipitation. Methyl tert-butyl ether (50 ml) was added. Formation of off-white (light brown) solid during addition. Solid collected by filtration and dried under vacuum at 80° C. for ~18 hrs. A total of 16.06 g was produced (68.20% yield).

Figure 95:
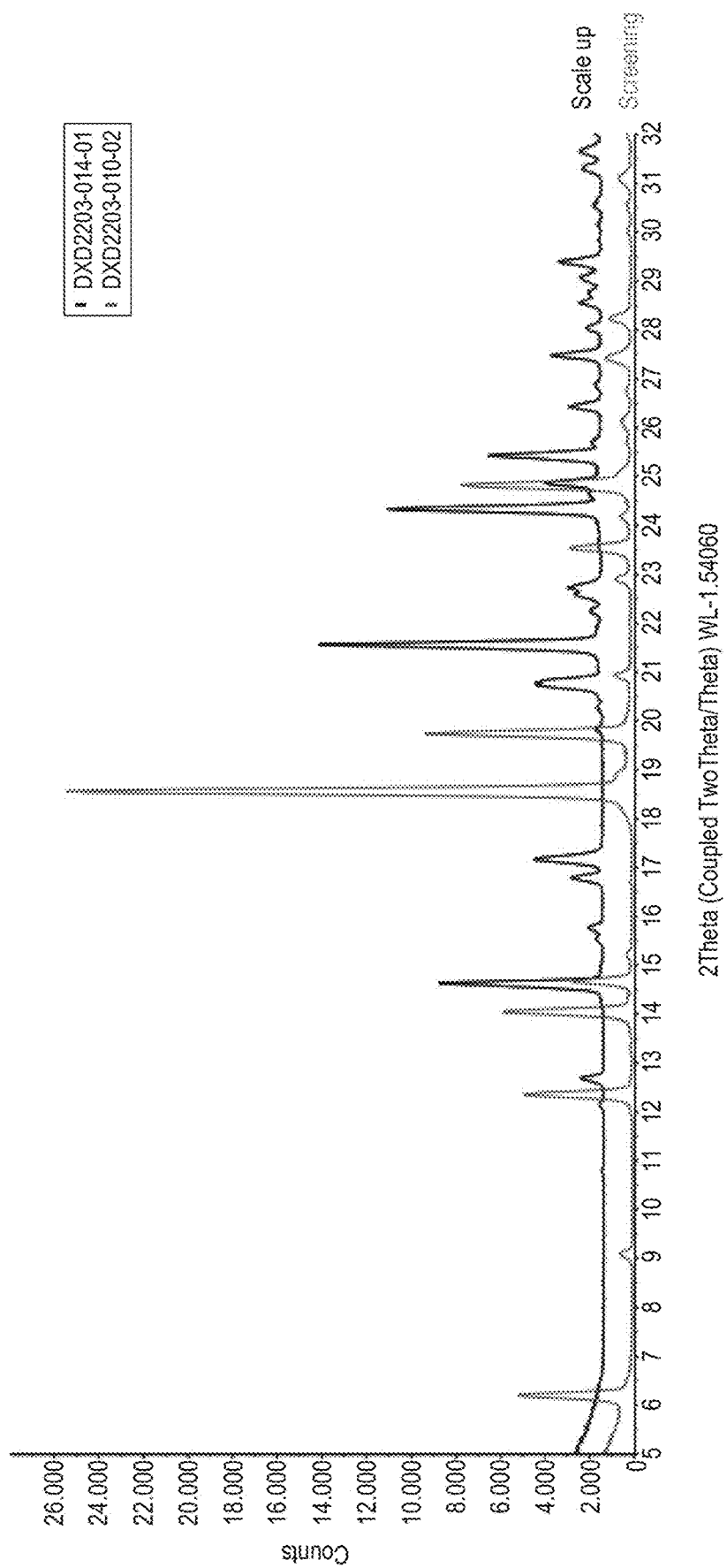
FIG. 95. XRPD Diffractograms of Hydrobromide salt produced during scale-up versus that initially analysed during the salt screen.

An XRPD diffractogram of the produced material versus that analysed in the screening can be seen in FIG. 95. The diffractograms are considered to represent two different crystalline forms, pattern or form 1 from the original screening and pattern or form 2 from the scale-up.

This was nominated as pattern 2 with XRPD peak data tabulated in Table 21, 21a and 21b. The XRPD can be seen in FIG. 171.

TABLE 21

XRPD Peak data for Hydrobromide pattern 2.

| 2θ | d Value | Rel. Intensity |
|---|---|---|
| 12.693° | 6.968 | 0.053 |
| 14.633° | 6.049 | 0.384 |
| 16.792° | 5.275 | 0.075 |
| 17.175° | 5.159 | 0.160 |
| 20.750° | 4.277 | 0.209 |
| 21.561° | 4.118 | 1.000 |
| 22.574° | 3.936 | 0.087 |
| 22.740° | 3.907 | 0.111 |
| 24.334° | 3.655 | 0.722 |
| 24.871° | 3.577 | 0.195 |
| 25.441° | 3.498 | 0.366 |
| 26.421° | 3.371 | 0.106 |
| 27.484° | 3.243 | 0.174 |
| 28.558° | 3.123 | 0.074 |
| 29.072° | 3.069 | 0.066 |
| 29.388° | 3.037 | 0.126 |
| 31.314° | 2.854 | 0.057 |
| 31.652° | 2.825 | 0.071 |

TABLE 21a

XRPD Peak data for Hydrobromide pattern 2. (2 d.p.)

| Peak No. | Angle 2 θ | d Value | Rel. Intensity |
|---|---|---|---|
| 1 | 12.69° | 6.97 | 0.05 |
| 2 | 14.63° | 6.05 | 0.33 |
| 3 | 16.79° | 5.28 | 0.08 |
| 4 | 17.18° | 5.16 | 0.16 |
| 5 | 20.75° | 4.28 | 0.21 |
| 6 | 21.56° | 4.12 | 1.00 |
| 7 | 22.57° | 3.94 | 0.09 |
| 8 | 22.74° | 3.91 | 0.11 |
| 9 | 24.33° | 3.66 | 0.72 |
| 10 | 24.87° | 3.58 | 0.20 |
| 11 | 25.44° | 3.50 | 0.37 |
| 12 | 26.42° | 3.37 | 0.11 |
| 13 | 27.48° | 3.24 | 0.17 |
| 14 | 28.56° | 3.12 | 0.07 |
| 15 | 29.07° | 3.07 | 0.07 |
| 16 | 29.39° | 3.04 | 0.13 |
| 17 | 31.31° | 2.85 | 0.06 |
| 18 | 31.65° | 2.83 | 0.07 |

TABLE 21b

XRPD Peak data for Hydrobromide pattern 2. (2 d.p.)

| Peak No. | Angle 2 θ | d Value | Rel. Intensity |
|---|---|---|---|
| 1 | 12.7° | 7.0 | 0.1 |
| 2 | 14.6° | 6.1 | 0.4 |
| 3 | 16.8° | 5.3 | 0.1 |
| 4 | 17.2° | 5.2 | 0.2 |
| 5 | 20.8° | 4.3 | 0.2 |
| 6 | 21.6° | 4.1 | 1.0 |
| 7 | 22.6° | 3.9 | 0.1 |
| 8 | 22.7° | 3.9 | 0.1 |
| 9 | 24.3° | 3.7 | 0.7 |
| 10 | 24.9° | 3.6 | 0.2 |
| 11 | 25.4° | 3.5 | 0.4 |
| 12 | 26.4° | 3.4 | 0.1 |
| 13 | 27.5° | 3.2 | 0.2 |
| 14 | 28.6° | 3.1 | 0.1 |
| 15 | 29.1° | 3.1 | 0.1 |
| 16 | 29.4° | 3.0 | 0.1 |
| 17 | 31.3° | 2.9 | 0.1 |
| 18 | 31.7° | 2.8 | 0.1 |

Figure 96:
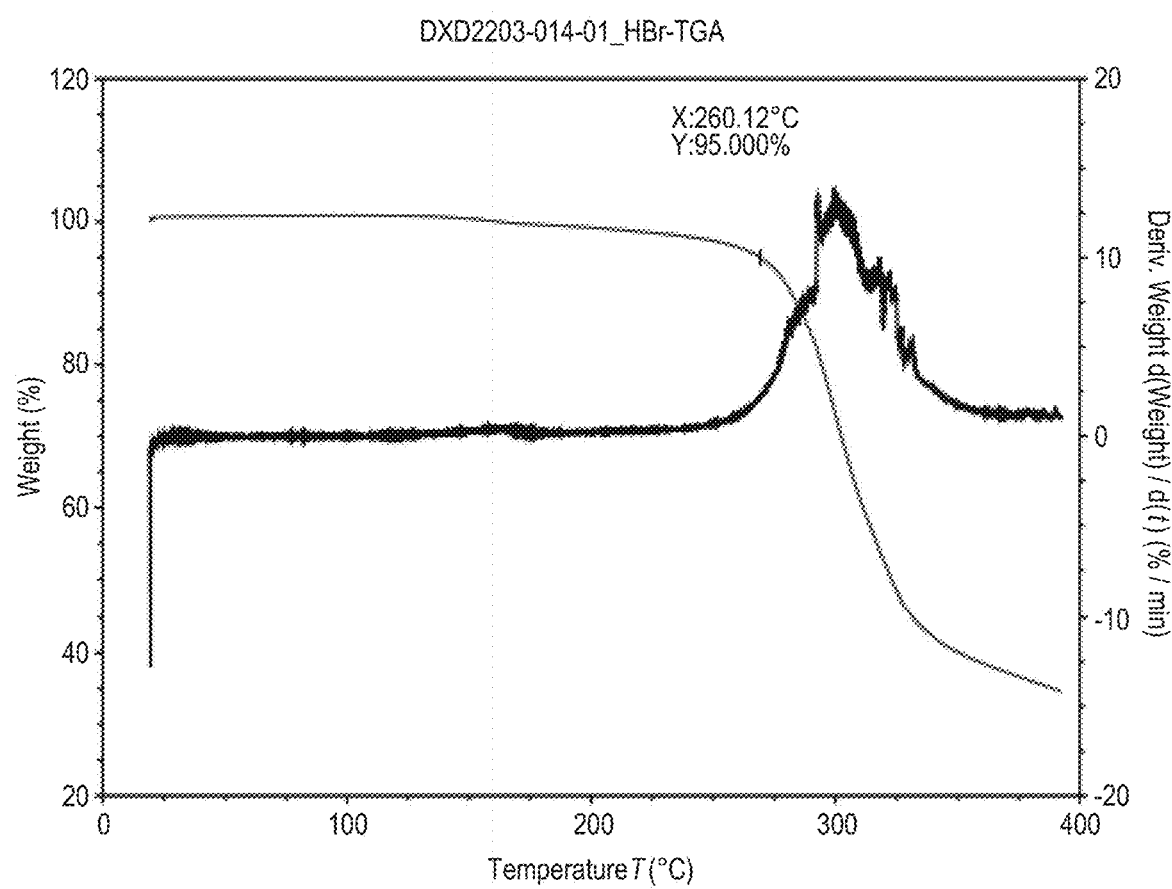
FIG. 96. TGA Thermogram of Hydrobromide salt produced during scale-up.

No weight loss for this crystalline form of the salt due to moisture content was observed during TGA (Ramp 10° C./min to 400° C.) with 95% of weight remaining at 269° C., as shown in, or substantially as shown in, FIG. 96.

Figure 97:
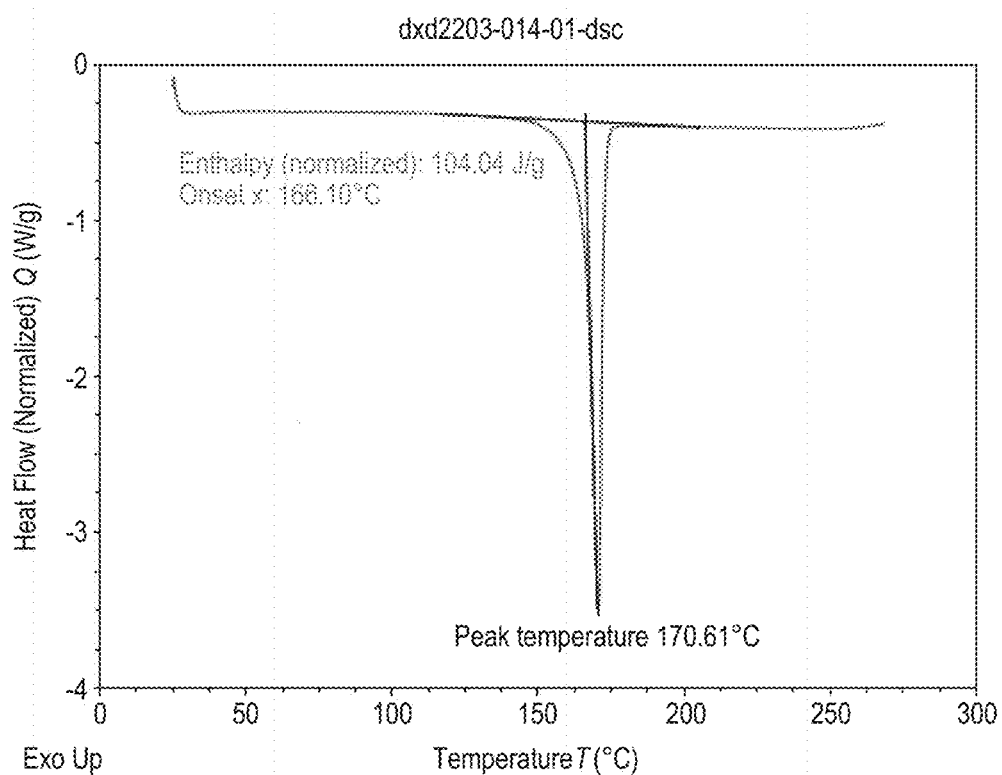
FIG. 97. DSC Thermogram (1st heating) of Hydrobromide salt produced during scale-up.

The DSC thermogram of Hydrobromide salt presented in FIG. 97 showed an onset temperature at 166.10° C. and heat of fusion of 104.04 J/g.

Figure 98:
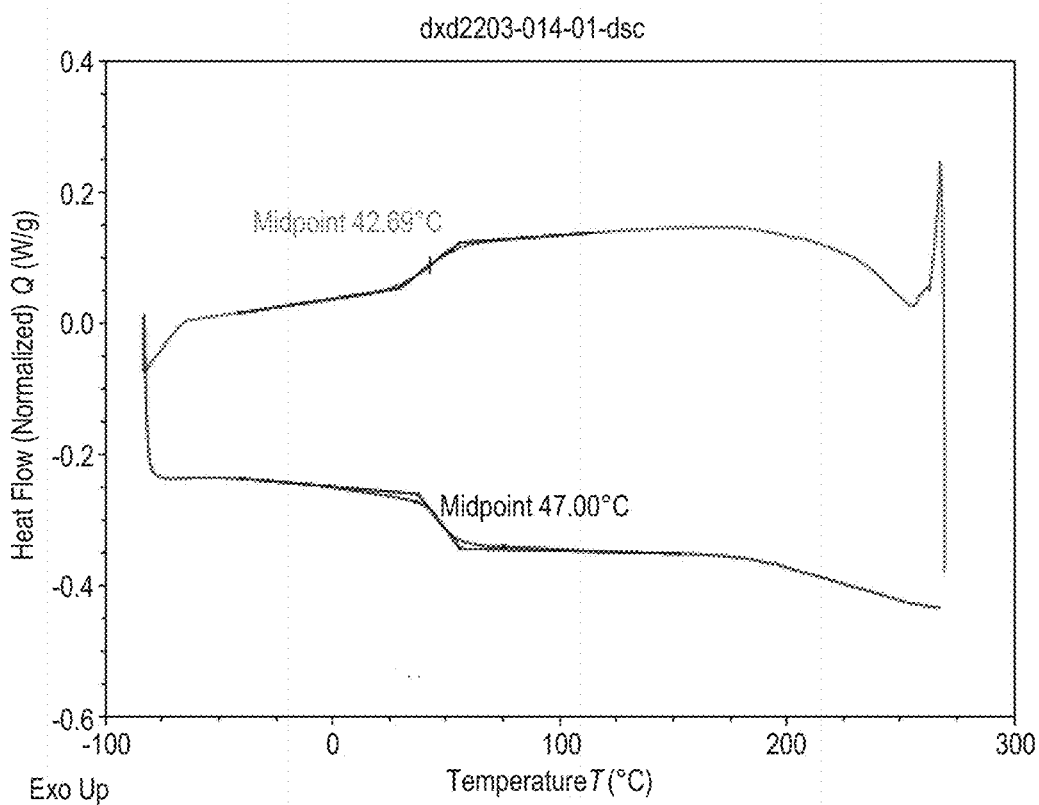
FIG. 98. DSC Thermogram (cooling) of Hydrobromide salt produced during scale-up.

The cooling ramp showed a vitrification around 42.7° C. and the $2^{nd}$ heat cycle displayed a glass transition around 47.0° C. as demonstrated in FIG. 98.

Figure 99:
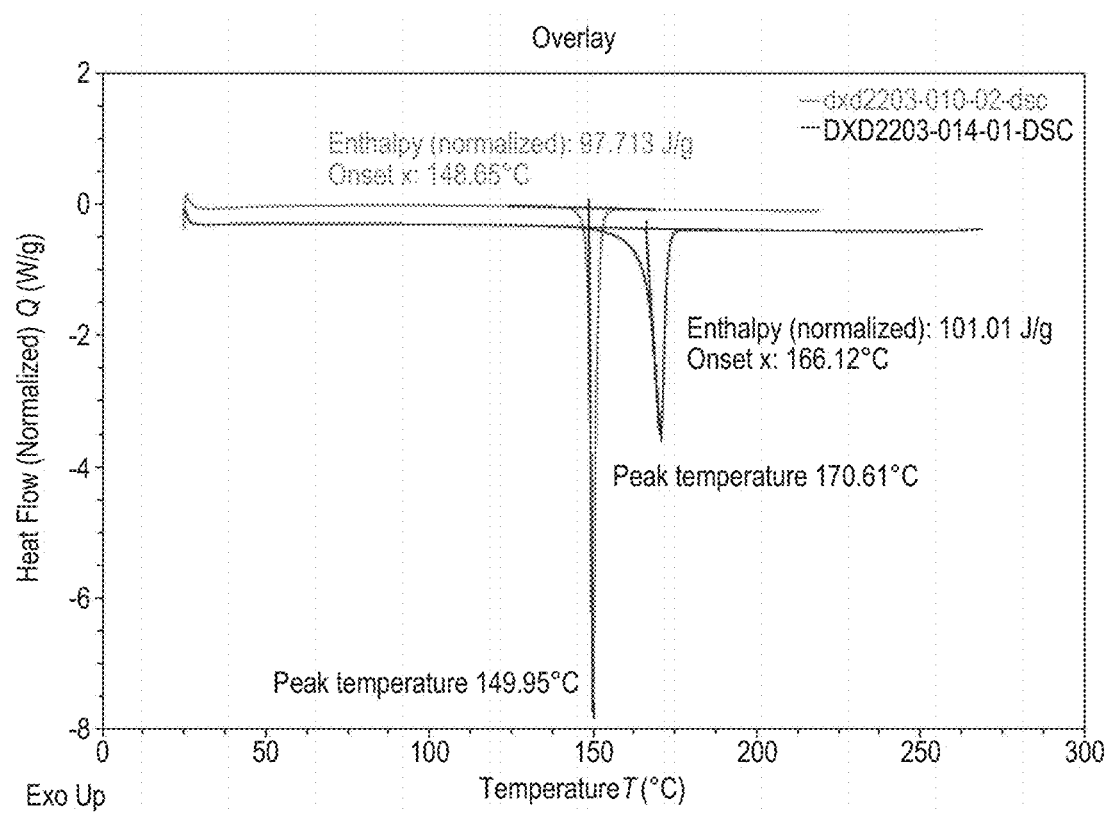
FIG. 99. DSC Thermograms of Hydrobromide salt produced during scale-up (top) versus that initially analysed during the salt screen (bottom).

The DSC Thermograms of Hydrobromide salt produced during scale-up (top) versus that initially analysed during the salt screen (bottom) can be seen in FIG. 99.

Figure 100:
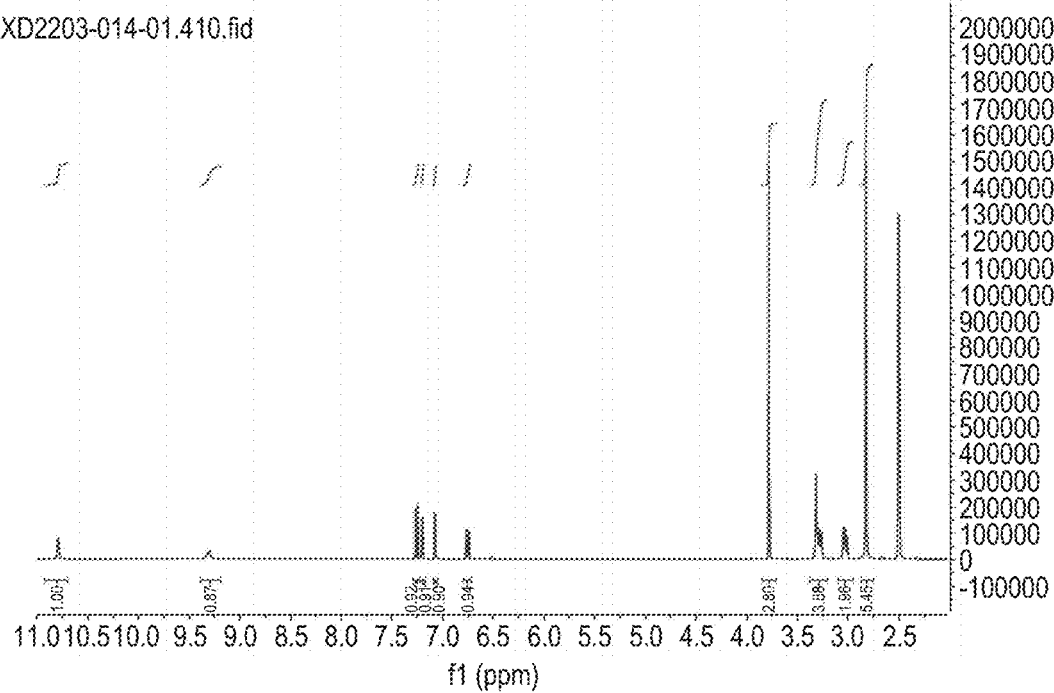
FIG. 100. $^1$H NMR spectrum of Hydrobromide salt produced during scale-up.

$^1$H NMR spectrum for the Hydrobromide salt produced during scale-up is displayed in FIG. 100.

Figure 106:
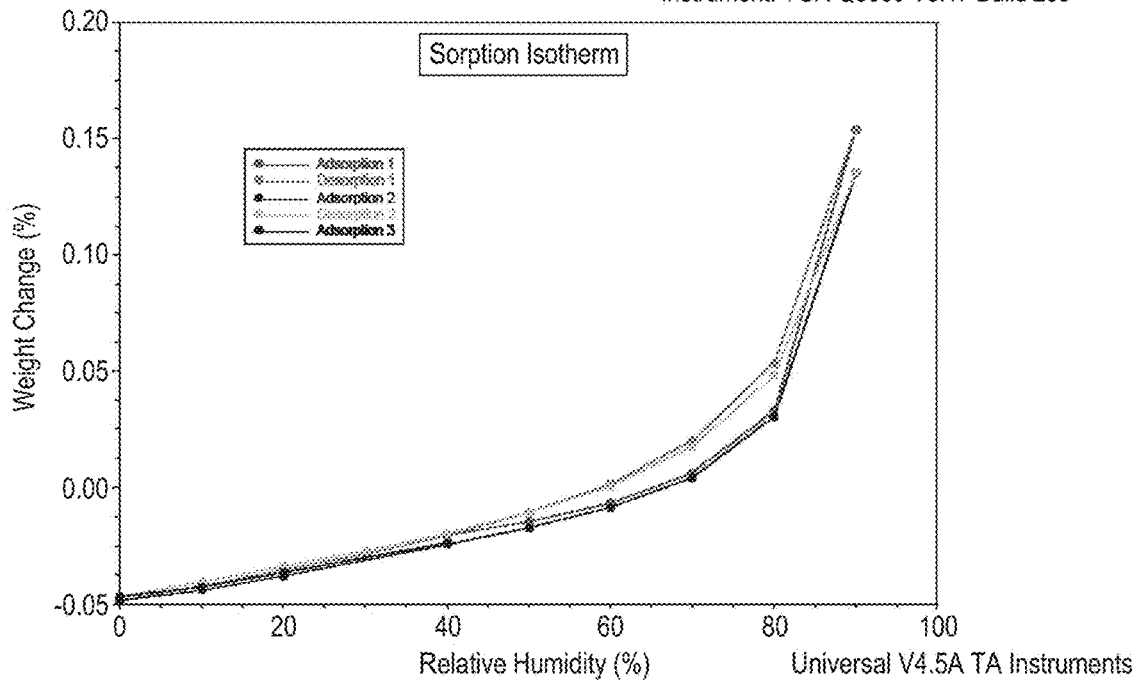
FIG. 106. DVS Isotherm plot of Hydrobromide salt produced during scale-up.
Figure 107:
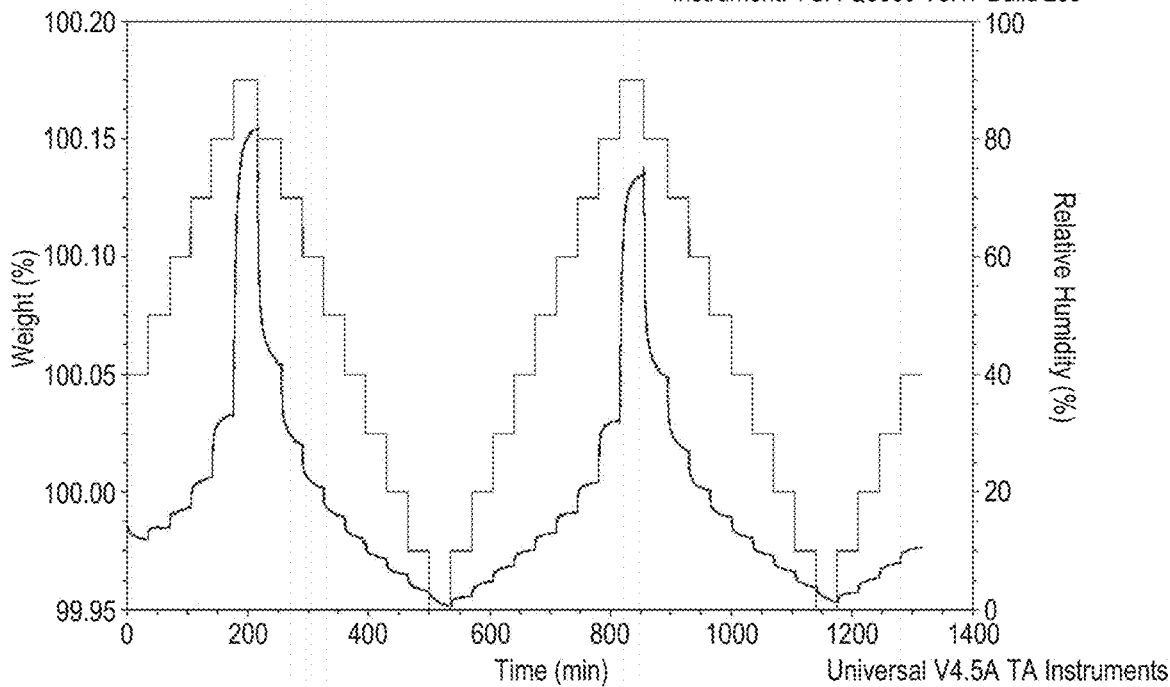
FIG. 107. Sorption kinetic plot of Hydrobromide salt produced during scale-up.
Figure 109:
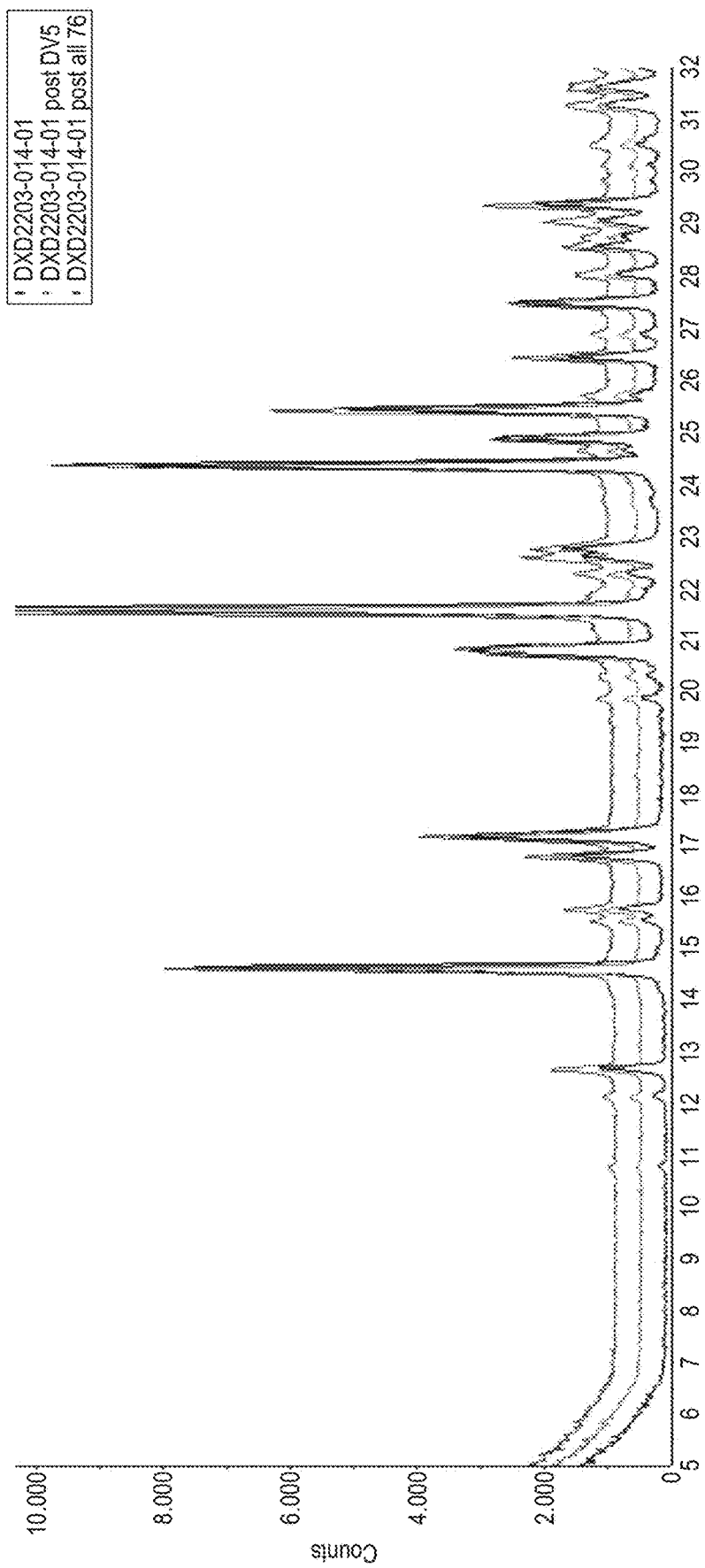
FIG. 109. XRPD Diffractograms of Hydrobromide salt produced during scale-up, (blue trace, top), post-DVS (red trace, middle) and post storage (bottom) at 40° C./75% RH for 1 week.

In one embodiment, there is provided 5-MeO-DMT Hydrobromide. In one embodiment, there is provided a pharmaceutical composition comprising 5-MeO-DMT Hydrobromide. In one embodiment, there is provided crystalline 5-MeO-DMT Hydrobromide, or a pharmaceutical composition comprising crystalline 5-MeO-DMT Hydrobromide, as characterised by one or more of:

An XRPD pattern as shown in, or substantially as shown in, FIG. 109 or FIG. 171;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more peaks in an XRPD diffractogram as detailed in Tables 21, 21a or 21b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Tables 21, 21a or 21b;

A DVS isotherm as shown in, or substantially as shown in, FIG. 106;

A DVS kinetic plot as shown in, or substantially as shown in, FIG. 107;

A TGA thermogram as shown in, or substantially as shown in, FIG. 96;

A DSC thermogram as shown in, or substantially as shown in, FIG. 97 or FIG. 98;

A melting endothermic event with an onset of around 166.10° C. and an enthalpy of 104.04 J/g, as measured in a DSC thermogram;

A melting endothermic event with an onset of around 160-170° C. and an enthalpy of 100-110 J/g, as measured in a DSC thermogram;

A melting endothermic event with an onset of around 160, 161, 162, 163, 164, 165, 166, 167, 168, 169 or 170° C. and an enthalpy of 100, 101, 102, 103, 104, 105, 106, 107, 108, 109 or 110 J/g, as measured in a DSC thermogram;

A vitrification around 42.7° C., as measured in a DSC thermogram with a cooling ramp of 10° C./min from 220° C. to −90° C.;

A vitrification around 35-45'C, as measured in a DSC thermogram with a cooling ramp of 10° C./min from 220° C. to −90° C.;

A vitrification around 35, 36, 37, 38, 39, 40, 41, 42, 43, 44 or 45° C., as measured in a DSC thermogram with a cooling ramp of 10° C./min from 220° C. to −90° C.;

A glass transition around 478° C., as measured in a DSC thermogram with a cooling ramp of 10° C./min from 220° C. to −90° C.;

A glass transition around 42-52° C., as measured in a DSC thermogram with a cooling ramp of 10° C./min from 220° C. to −90° C.;

A glass transition around 42, 43, 44, 45, 46, 47, 48, 49, 51, or 52° C., as measured in a DSC thermogram with a cooling ramp of 10° C./min from 220° C. to −90° C.; and/or A $^1$H NMR spectrum as shown in, or substantially as shown in, FIG. 100.

HPLC

The HPLC method was as detailed in the Table below:

| Column | XSelect CSH C18, 2.5 μm, 4.6 × 30 mm | |
|---|---|---|
| Mobile Phase | A | 10 mM Ammonium Acetate |
| | B | Acetonitrile |
| Autosampler Temperature | Ambient (28° C.) | |
| Column Temperature | 40° C. | |
| Injection volume | 5 μL | |
| Wavelength | 224 nm | |
| Flow Rate | 2.0 mL/min | |

| Gradient Time | % MPA | % MPB |
|---|---|---|
| 0.00 | 95 | 5 |
| 1.00 | 95 | 5 |
| 4.00 | 5 | 95 |
| 4.01 | 0 | 100 |
| 4.50 | 0 | 100 |
| 4.51 | 95 | 5 |
| 6.00 | 95 | 5 |
| Run Time | | 6 minutes |
| Sample Concentration | | 1 mg/mL |
| Typical RT | | 2.08 minutes |

Oxalate Salt HPLC Purity, DVS, Stability at 40° C./75% RH (XRPD and HPLC), PSD/Morphology Assessment Purity of Oxalate salt produced during scale-up:

| Sample ID | Description | Purity (Area %) |
|---|---|---|
| DXD2203-11-01 | Free base | 97.9 |
| DXD2203-13-03 | Oxalate Salt | 98.3 |

Figure 102:
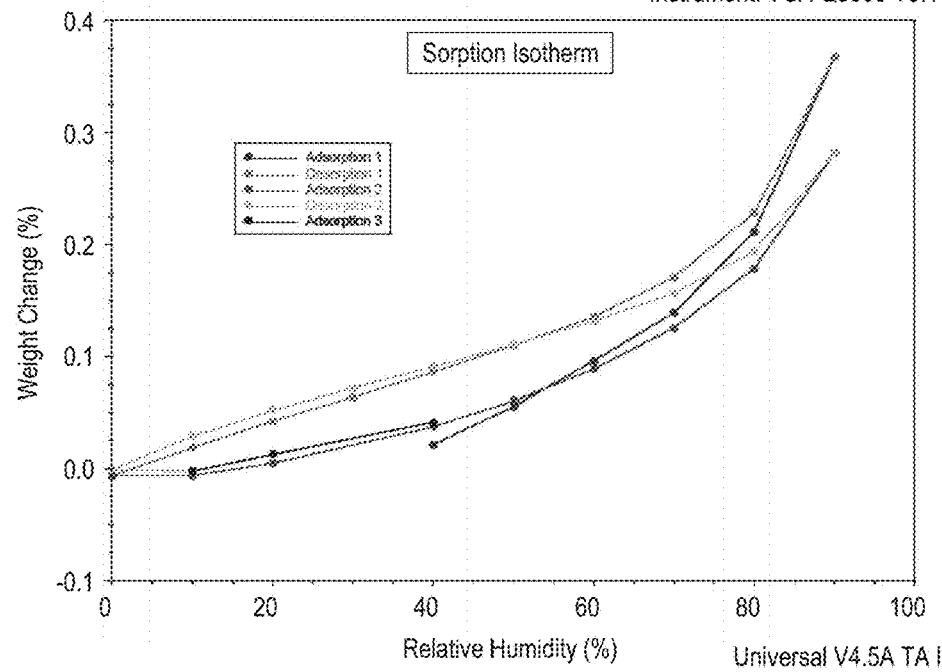
FIG. 102. DVS Isotherm plot of Oxalate salt produced during scale-up.
Figure 103:
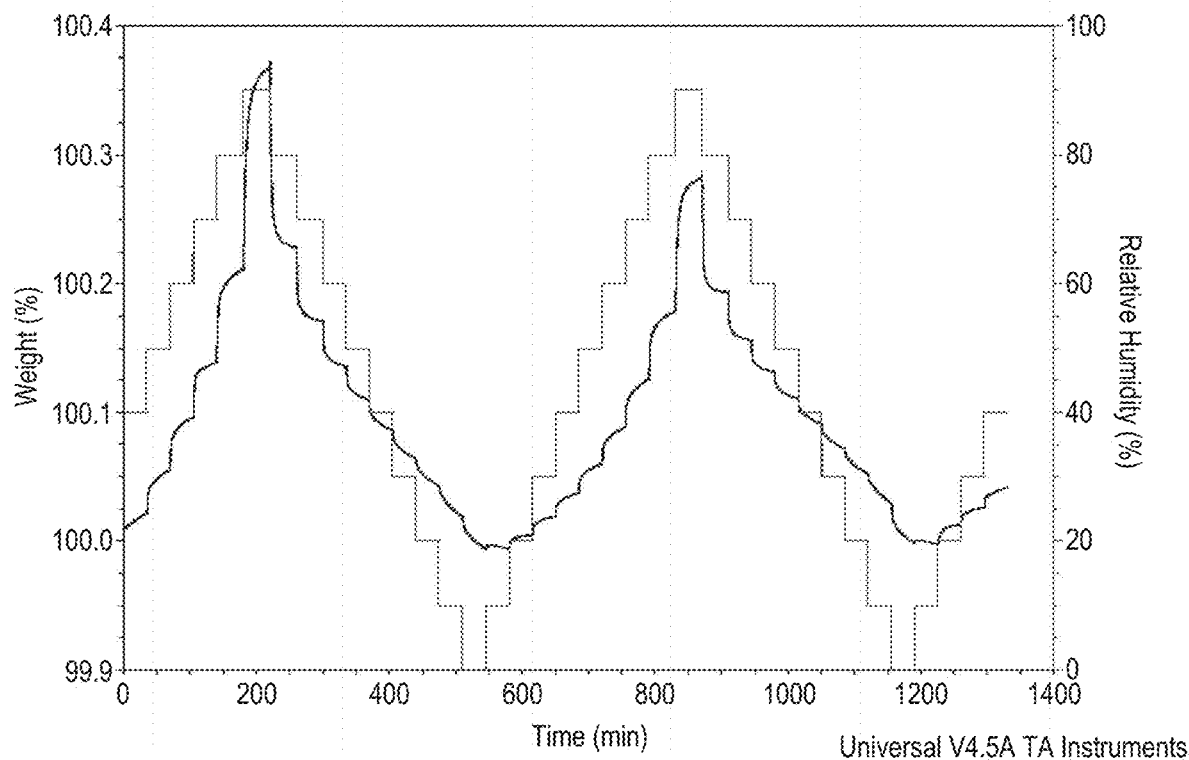
FIG. 103. Sorption kinetic plot of Oxalate salt produced during scale-up.
Figure 104:
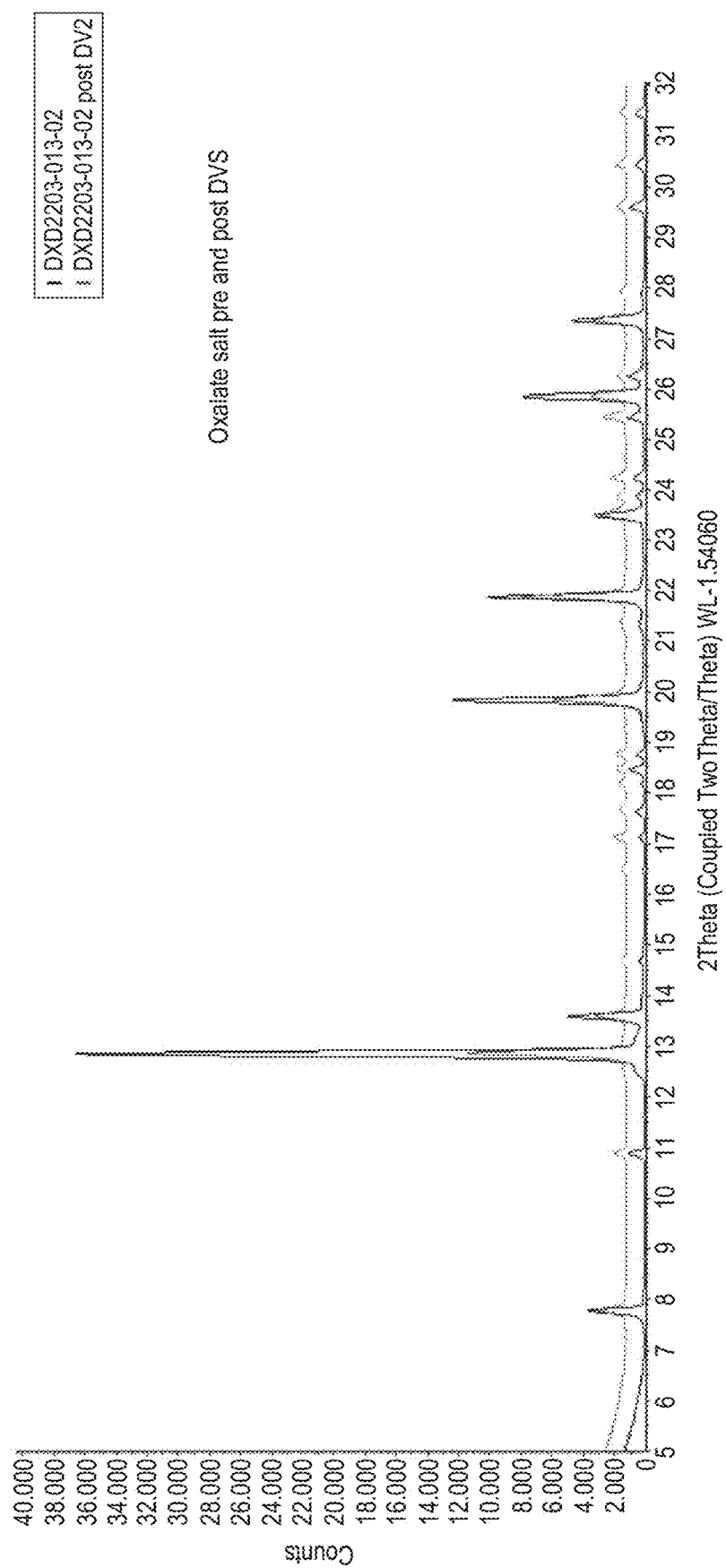
FIG. 104. XRPD Diffractograms of Oxalate salt produced during scale-up, (black trace, top) and post-DVS (red trace, bottom).
Figure 105:
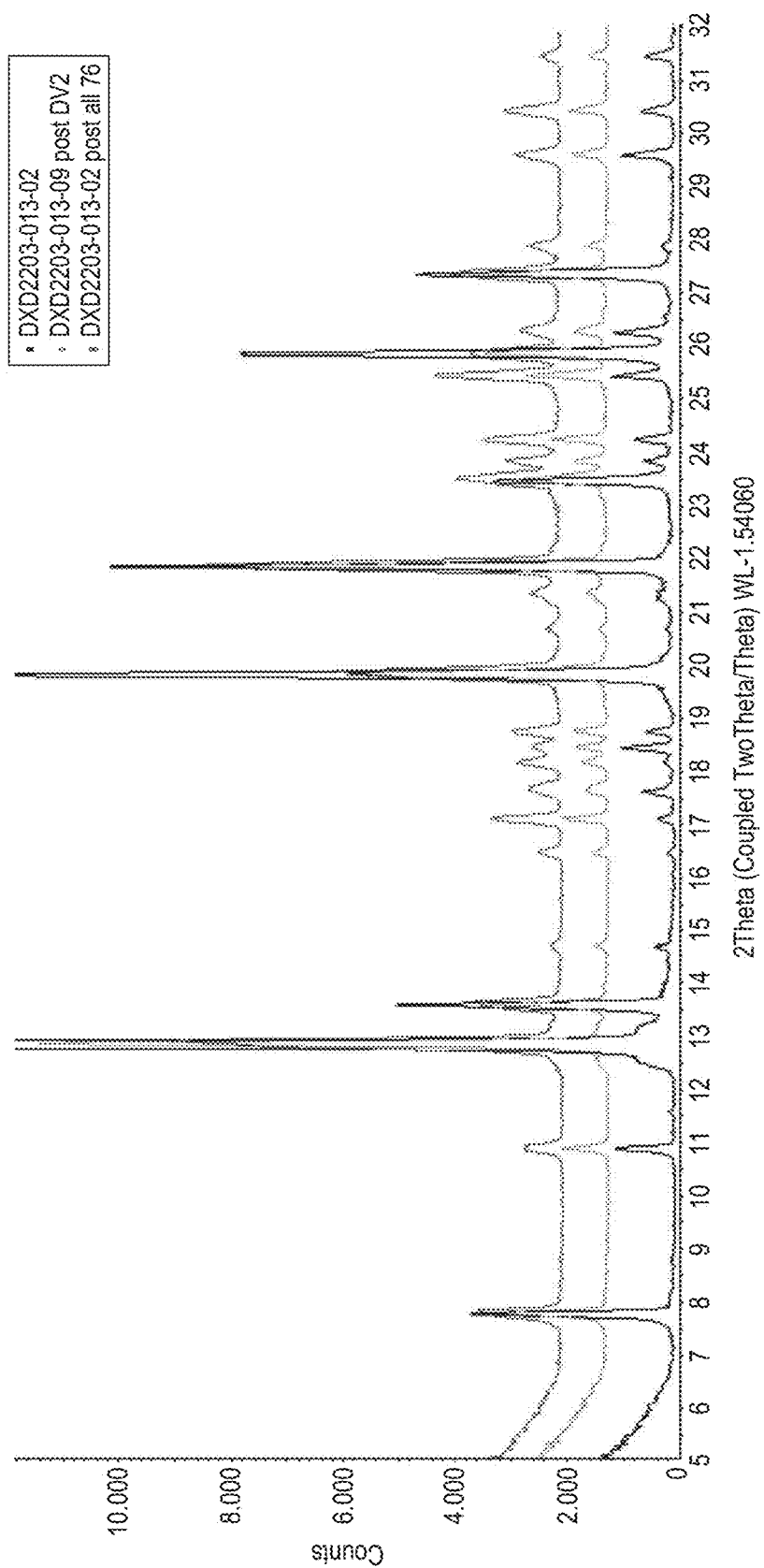
FIG. 105. XRPD Diffractograms of Oxalate salt produced during scale-up, (black trace, top), post-DVS (red trace, middle) and post storage (bottom) at 40° C./75% RH for 1 week.

DVS analysis of the Oxalate salt produced during scale-up was performed and the isotherm plot is shown in FIG. 102. The DVS kinetic plot of the salt is displayed in FIG. 103. XRPD analysis was performed on post DVS Oxalate salt and showed no change in crystalline form occurred during the DVS experiment as demonstrated in FIG. 104. XRPD analysis was performed post storage at 40° C./75% RH for 1 week and no change in crystalline form occurred as demonstrated in FIG. 105. No change in the purity, as analysed by HPLC, was seen after 1 week:

| | | Purity (Area %) | |
|---|---|---|---|
| Sample ID | Description | T = 0 | T = 7 days |
| DXD2203-13-03 | Oxalate Salt | 98.3 | 98.3 |

Hydrobromide Salt HPLC Purity, DVS, Stability at 40° C./75% RH (XRPD and HPLC), PSD/Morphology Assessment Purity of Hydrobromide salt produced during scale-up:

| Sample ID | Description | Purity (Area %) |
|---|---|---|
| DXD2203-11-01 | Free base | 97.9 |
| DXD2203-14-01 | Hydrogen Bromide Salt | 99.7 |

Figure 108:
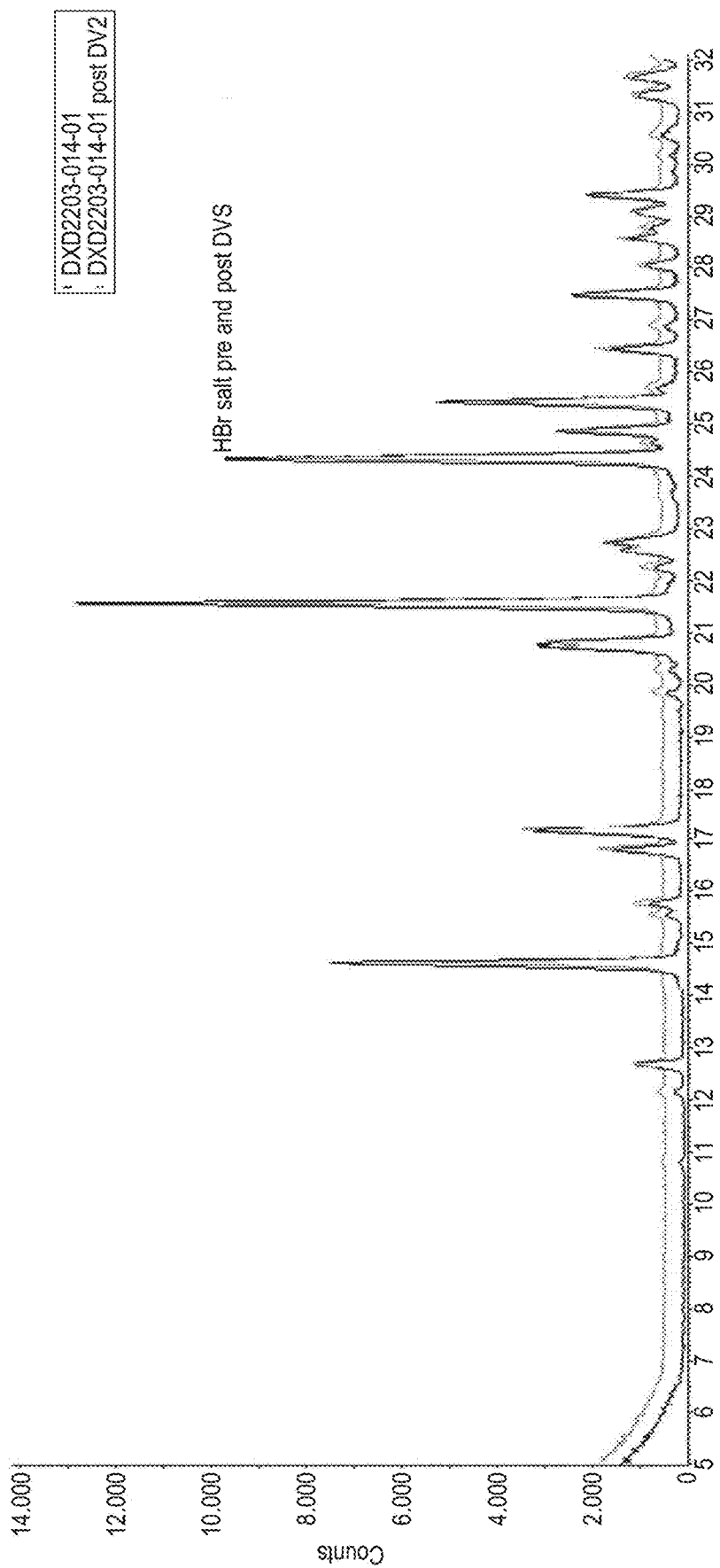
FIG. 108. XRPD Diffractograms of Hydrobromide salt produced during scale-up, (black trace, top) and post-DVS (red trace, bottom).

DVS analysis of the Hydrobromide salt produced during scale-up was performed and the isotherm plot is shown in FIG. 106. The DVS kinetic plot of the salt is displayed in FIG. 107. XRPD analysis was performed on post DVS Hydrobromide salt and showed no change in crystalline form occurred during the DVS experiment as demonstrated in FIG. 108. XRPD analysis was performed post storage at 40° C./75% RH for 1 week and no change in crystalline form occurred as demonstrated in FIG. 109. No change in the purity, as analysed by HPLC, was seen after 1 week:

| | | Purity (Area %) | |
|---|---|---|---|
| Sample ID | Description | T = 0 | T = 7 days |
| DXD2203-14-01 | Hydrogen Bromide Salt | 99.7 | 99.7 |

Fumarate Salt HPLC Purity, DVS, Stability at 40° C./75% RH (XRPD and HPLC), PSD/Morphology Assessment Purity of Fumarate salt produced during scale-up:

| Sample ID | Description | Purity (Area %) |
|---|---|---|
| DXD2203-11-01 | Free base | 97.9 |
| DXD2203-15-03 | Fumarate Salt | 99.0 |

Figure 110:
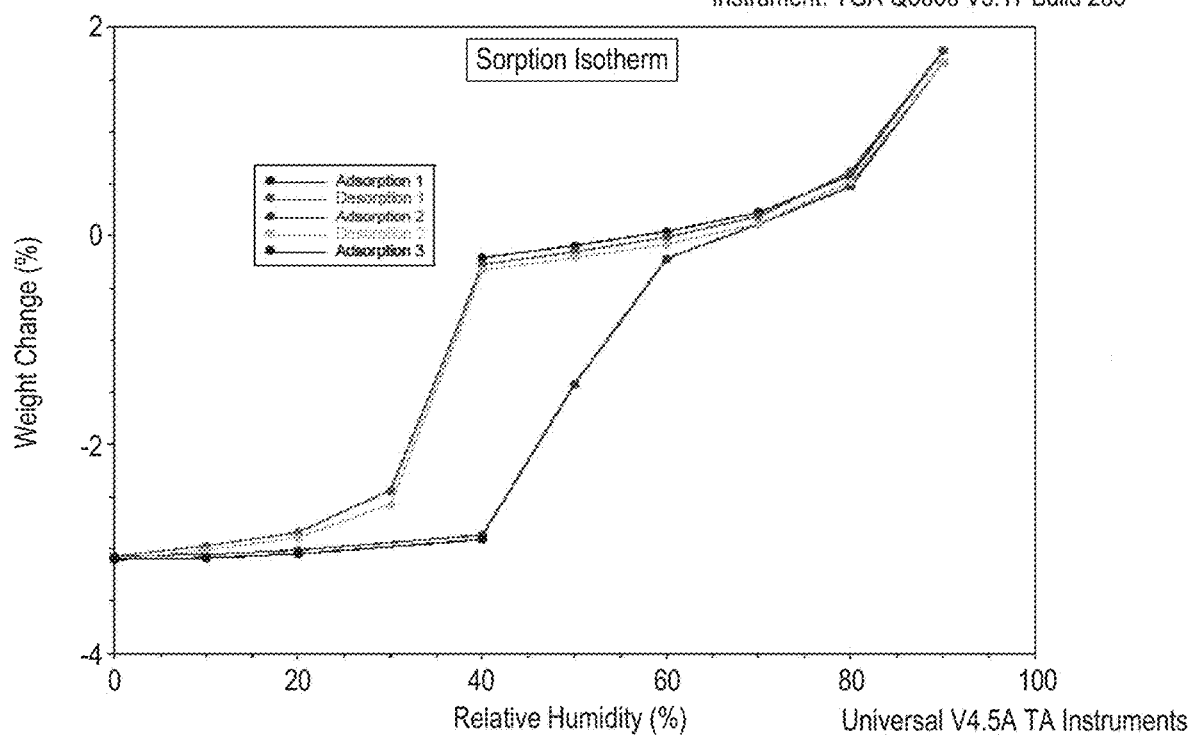
FIG. 110. DVS Isotherm plot of Fumarate salt produced during scale-up.

DVS analysis of the Fumarate salt produced during scale-up was performed and the isotherm plot is shown in FIG. 110. ~2.84% mass difference between 40% RH and 0% RH, ~0.45 eq water for hemi fumarate salt.

Figure 111:
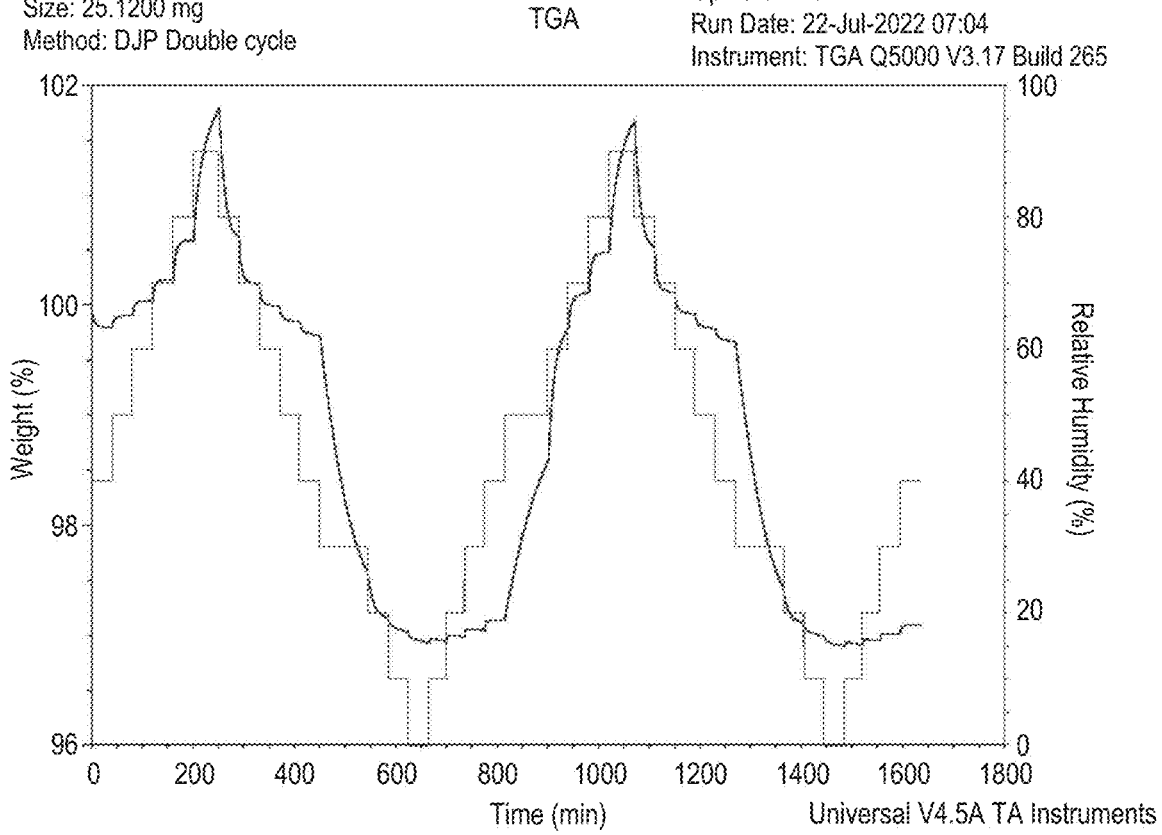
FIG. 111. Sorption kinetic plot of Fumarate salt produced during scale-up.

The DVS kinetic plot of the salt is displayed in FIG. 111. XRPD analysis was performed on post DVS Fumarate salt and showed a change in crystalline form occurred during the DVS experiment as demonstrated in FIG. 112. The new form has been nominated as form/pattern 2. TGA analysis was performed post DVS and the 2.52% loss correlates well with the DVS data and can be seen in FIG. 113. DSC analysis was also performed post-DVS and the results of this can be seen in FIG. 114.

XRPD analysis was performed post storage at 40° C./75% RH for 1 week and the material is a mixture of form/pattern 1 and form/pattern 2 as demonstrated in FIG. 109. No change in the purity, as analysed by HPLC, was seen after 1 week:

| | | Purity (Area %) | |
|---|---|---|---|
| Sample ID | Description | T = 0 | T = 7 days |
| DXD2203-15-03 | Fumarate Salt | 99.0 | 99.0 |

The XRPD Peak Data for Form/Pattern 2 can be Seen Tabulated in Table 28, 28a and 28b.

| | Table 28 | | | Table 28a | | | Table 28b | | |
|---|---|---|---|---|---|---|---|---|---|
| | Angle 2θ | d Value | Rel. Intensity | Angle 2θ | d Value | Rel. Intensity | Angle 2θ | d Value | Rel. Intensity |
| 1 | 6.355 | 13.896 | 0.172 | 6.36 | 13.90 | 0.17 | 6.4 | 13.9 | 0.2 |
| 2 | 10.830 | 8.162 | 0.045 | 10.83 | 8.16 | 0.05 | 10.8 | 8.2 | 0.0 |
| 3 | 12.111 | 7.302 | 0.281 | 12.11 | 7.30 | 0.28 | 12.1 | 7.3 | 0.3 |
| 4 | 12.683 | 6.974 | 0.656 | 12.68 | 6.97 | 0.66 | 12.7 | 7.0 | 0.7 |
| 5 | 13.607 | 6.502 | 0.067 | 13.61 | 6.50 | 0.07 | 13.6 | 6.5 | 0.1 |
| 6 | 14.097 | 6.277 | 0.071 | 14.10 | 6.28 | 0.07 | 14.1 | 6.3 | 0.1 |
| 7 | 14.651 | 6.041 | 0.149 | 14.65 | 6.04 | 0.15 | 14.7 | 6.0 | 0.1 |
| 8 | 15.372 | 5.759 | 0.828 | 15.37 | 5.76 | 0.83 | 15.4 | 5.8 | 0.8 |
| 9 | 16.332 | 5.423 | 0.137 | 16.33 | 5.42 | 0.14 | 16.3 | 5.4 | 0.1 |
| 10 | 16.823 | 5.266 | 0.731 | 16.82 | 5.27 | 0.73 | 16.8 | 5.3 | 0.7 |
| 11 | 17.098 | 5.182 | 0.211 | 17.10 | 5.18 | 0.21 | 17.1 | 5.2 | 0.2 |
| 12 | 17.522 | 5.057 | 0.482 | 17.52 | 5.06 | 0.48 | 17.5 | 5.1 | 0.5 |
| 13 | 18.119 | 4.892 | 0.217 | 18.12 | 4.89 | 0.22 | 18.1 | 4.9 | 0.2 |
| 14 | 18.348 | 4.831 | 1.000 | 18.35 | 4.83 | 1.00 | 18.3 | 4.8 | 1.0 |
| 15 | 18.882 | 4.696 | 0.448 | 18.88 | 4.70 | 0.45 | 18.9 | 4.7 | 0.4 |
| 16 | 19.210 | 4.617 | 0.320 | 19.21 | 4.62 | 0.32 | 19.2 | 4.6 | 0.3 |
| 17 | 19.545 | 4.538 | 0.104 | 19.55 | 4.54 | 0.10 | 19.5 | 4.5 | 0.1 |
| 18 | 20.328 | 4.365 | 0.176 | 20.33 | 4.37 | 0.18 | 20.3 | 4.4 | 0.2 |
| 19 | 20.799 | 4.267 | 0.053 | 20.80 | 4.27 | 0.05 | 20.8 | 4.3 | 0.1 |
| 20 | 20.961 | 4.235 | 0.092 | 20.96 | 4.23 | 0.09 | 21.0 | 4.2 | 0.1 |
| 21 | 21.593 | 4.112 | 0.554 | 21.59 | 4.11 | 0.55 | 21.6 | 4.1 | 0.6 |
| 22 | 21.770 | 4.079 | 0.383 | 21.77 | 4.08 | 0.38 | 21.8 | 4.1 | 0.4 |
| 23 | 22.063 | 4.026 | 0.243 | 22.06 | 4.03 | 0.24 | 22.1 | 4.0 | 0.2 |
| 24 | 22.432 | 3.960 | 0.099 | 22.43 | 3.96 | 0.10 | 22.4 | 4.0 | 0.1 |
| 25 | 22.781 | 3.900 | 0.226 | 22.78 | 3.90 | 0.23 | 22.8 | 3.9 | 0.2 |
| 26 | 23.148 | 3.839 | 0.225 | 23.15 | 3.84 | 0.23 | 23.1 | 3.8 | 0.2 |
| 27 | 23.732 | 3.746 | 0.125 | 23.73 | 3.75 | 0.13 | 23.7 | 3.7 | 0.1 |
| 28 | 24.242 | 3.669 | 0.063 | 24.24 | 3.67 | 0.06 | 24.2 | 3.7 | 0.1 |
| 29 | 24.385 | 3.647 | 0.147 | 24.39 | 3.65 | 0.15 | 24.4 | 3.6 | 0.1 |
| 30 | 24.877 | 3.576 | 0.296 | 24.88 | 3.58 | 0.30 | 24.9 | 3.6 | 0.3 |
| 31 | 25.396 | 3.504 | 0.320 | 25.40 | 3.50 | 0.32 | 25.4 | 3.5 | 0.3 |
| 32 | 25.719 | 3.461 | 0.164 | 25.72 | 3.46 | 0.16 | 25.7 | 3.5 | 0.2 |
| 33 | 26.035 | 3.420 | 0.113 | 26.04 | 3.42 | 0.11 | 26.0 | 3.4 | 0.1 |
| 34 | 26.197 | 3.399 | 0.193 | 26.20 | 3.40 | 0.19 | 26.2 | 3.4 | 0.2 |
| 35 | 26.921 | 3.309 | 0.150 | 26.92 | 3.31 | 0.15 | 26.9 | 3.3 | 0.1 |
| 36 | 27.621 | 3.227 | 0.052 | 27.62 | 3.23 | 0.05 | 27.6 | 3.2 | 0.1 |
| 37 | 28.715 | 3.106 | 0.035 | 28.71 | 3.11 | 0.03 | 28.7 | 3.1 | 0.0 |
| 38 | 29.125 | 3.064 | 0.034 | 29.13 | 3.06 | 0.03 | 29.1 | 3.1 | 0.0 |
| 39 | 30.132 | 2.964 | 0.032 | 30.13 | 2.96 | 0.03 | 30.1 | 3.0 | 0.0 |
| 40 | 30.429 | 2.935 | 0.044 | 30.43 | 2.94 | 0.04 | 30.4 | 2.9 | 0.0 |
| 41 | 30.764 | 2.904 | 0.040 | 30.76 | 2.90 | 0.04 | 30.8 | 2.9 | 0.0 |

Figure 112:
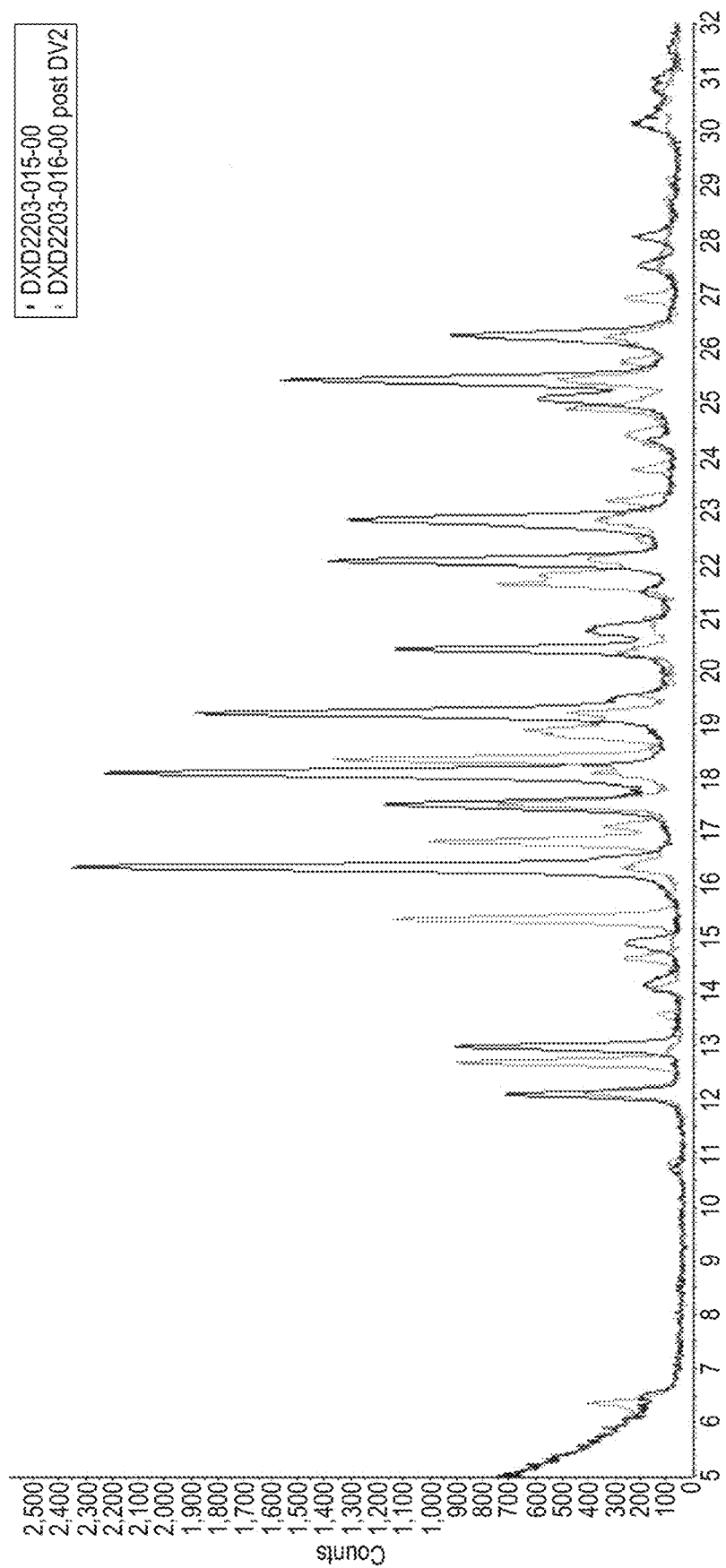
FIG. 112. XRPD Diffractograms of Fumarate salt produced during scale-up, (black trace, top) and post-DVS (red trace, bottom).
Figure 113:
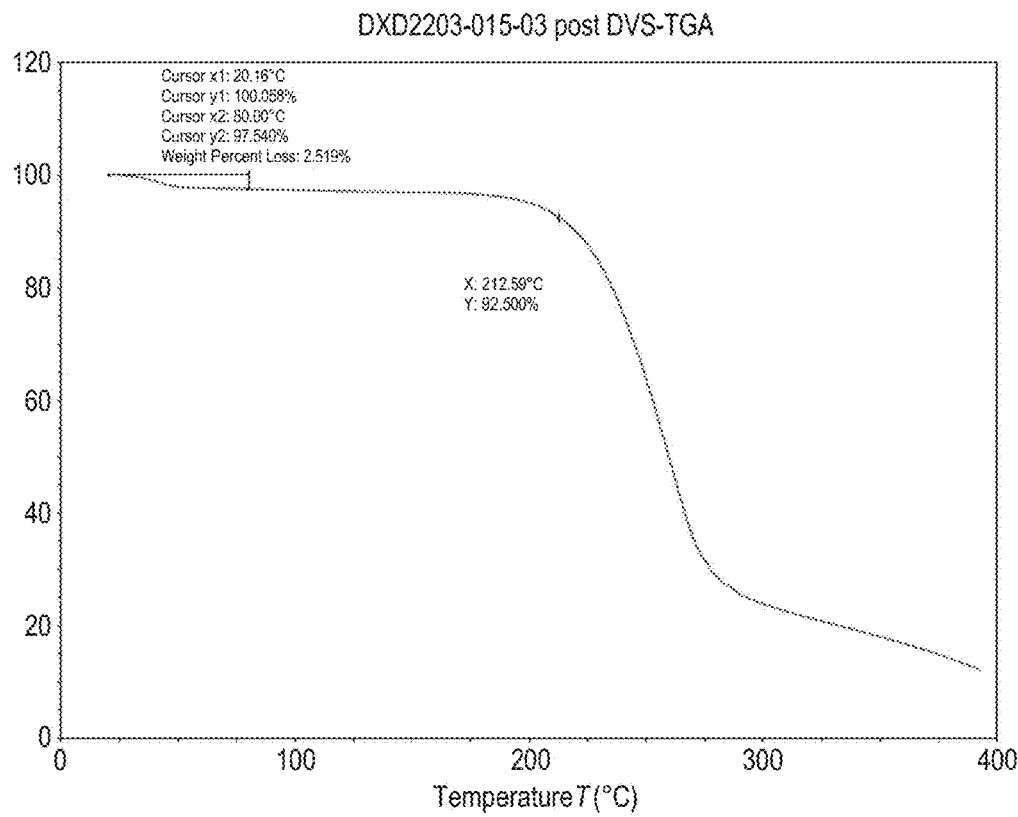
FIG. 113. TGA Thermogram of Fumarate salt produced during scale-up post-DVS.
Figure 114:
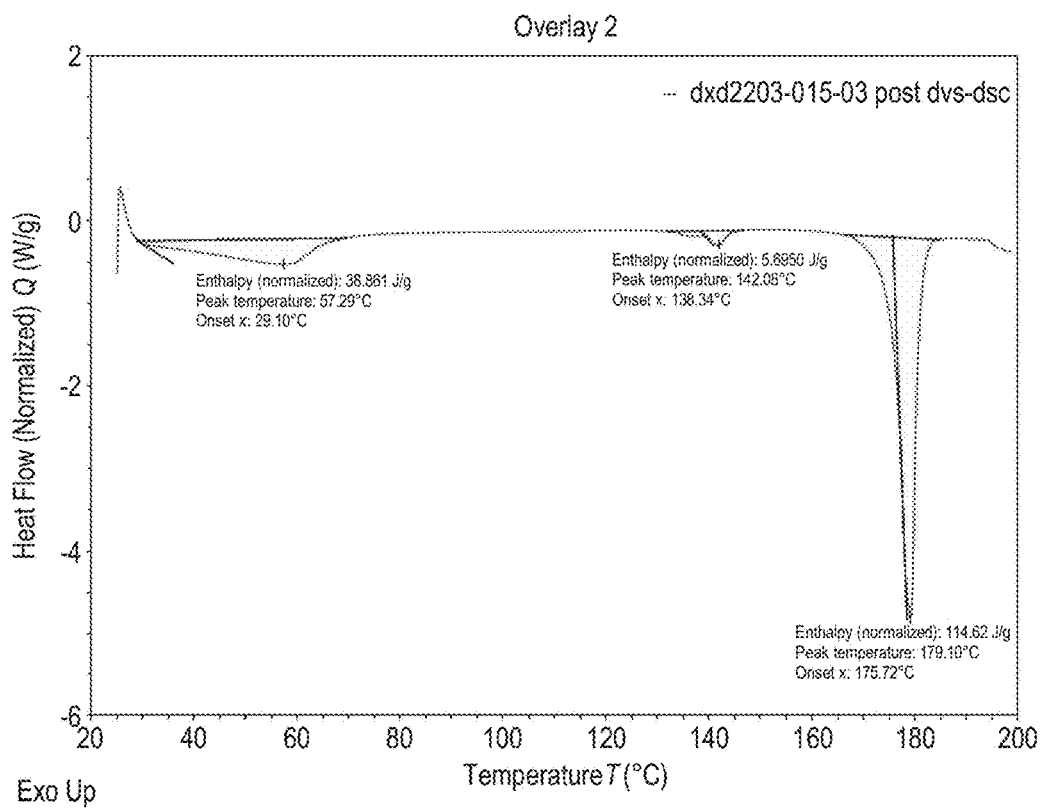
FIG. 114. DSC Thermogram of Fumarate salt produced during scale-up post-DVS.
Figure 115:
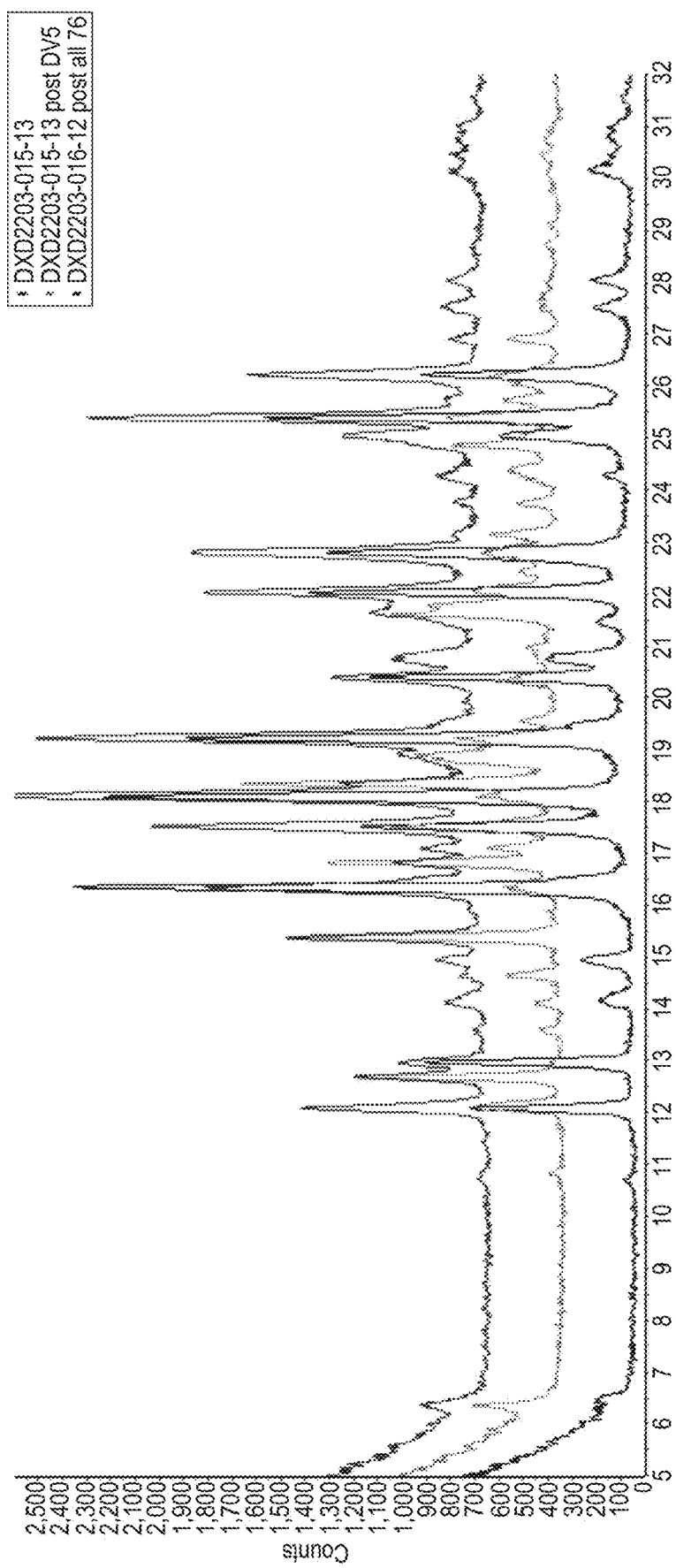
FIG. 115. XRPD Diffractograms of Fumarate salt produced during scale-up, (blue trace, top), post-DVS (red trace, middle) and post storage (bottom) at 40° C./75% RH for 1 week.

In one embodiment, there is provided crystalline 5-MeO-DMT fumarate form/pattern 2, or a pharmaceutical composition comprising crystalline 5-MeO-DMT fumarate form/pattern 2, as characterised by one or more of:

An XRPD pattern as shown in, or substantially as shown in, FIG. 112;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, thirty three or more, thirty four or more, thirty five or more, thirty six or more, thirty seven or more, thirty eight or more, thirty nine or more, forty or more or forty one peaks in an XRPD diffractogram as detailed in Tables 28, 28a or 28b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Tables 28, 28a or 28b;

A TGA thermogram as shown in, or substantially as shown in, FIG. 113; and/or A DSC thermogram as shown in, or substantially as shown in, FIG. 114.

Example 3: Further Salt Characterisation

Salt Cracking

5-MeO-DMT HCl (J11635, HCl Pattern 1, 4.94 g) was dissolved in 10 volumes (50 ml) of water giving a clear brown solution. To this was added 1 equivalent of NaOH dropwise as a 4M aqueous solution (4.85 mL) giving a tan suspension which after stirring for 10 minutes formed a brown oil. The oil was extracted with 3×10 vol (50 mL) of 2-MeTHF. The organic phases were combined and washed with brine before being concentrated using a rotary evaporator giving a thick brown oil. The oil was dissolved in 10 vol (50 mL) of 2-MeTHF and concentrated again to a brown oil with a small amount of solid material was present. The sample was dried further in a vacuum oven at RT overnight giving a tan solid. Sample ID: DR-2186-43-01. (Yield=3.856 g).

DR-2186-43-01 (3.865 g) was suspended in 5 volumes (19.3 mL) of water in a round bottom flask and stirred overnight at room temperature. The suspension was filtered through a Buchner funnel using a Whatman grade 1 filter paper and vacuum. The cake was dried under suction for 30 minutes before being transferred to a vacuum oven at RT for 2 hours. Yield=4.233 g (81.1%).

| Sample ID | DR-2186-43-02 |
|---|---|
| XRPD | Free Form Pattern 1 |
| $^1$H-NMR | Consistent with structure, trace residual solvent |
| IC | No ions detected |
| HPLC Purity (Pharmorphix Generic Method) | 96.5% |

Phosphate Formation

In a 20 mL scintillation vial 5-MeO-DMT (1.00 g, Free Form Pattern 1, DR-2186-46-02) was dissolved in 5 volumes (5 mL) of IPA:water 9:1 at 50° C. on a Polar Bear heat/cool block with magnetic bottom stirring (500 RPM), giving a brown solution. 1.1 mol eq. (5.05 mL) of phosphoric acid was added at a 1M solution in THF dropwise over 2 minutes. Initially this gave a white precipitate, on further addition a light brown gummy solid formed on the base of the vial which became more solid over 5 minutes of stirring. The encrusted solid was agitated using a spatula and after a further 5 minutes a light tan suspension was obtained. The crystallisation was then cooled to 5° C. at 0.1° C./min and held there overnight.

Figure 116:
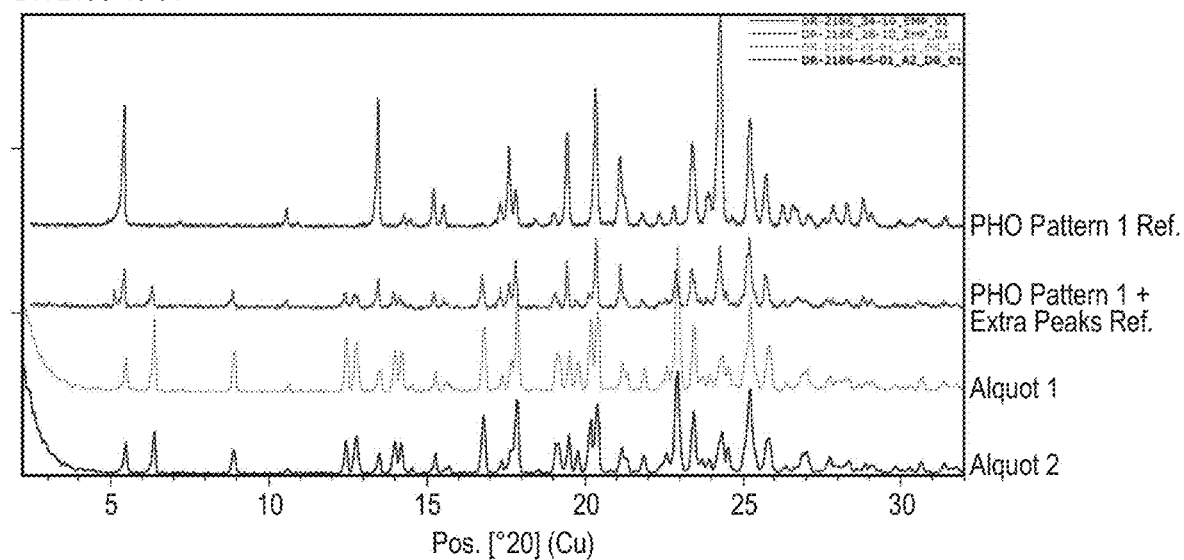
FIG. 116. XRPD Diffractograms of Phosphate salt.

An aliquot (ca. 0.3 mL) of suspension was filtered using a cartridge and frit along with positive pressure. The solid was dried briefly under a stream of N2 before collecting an XRPD (DR-2186-45-01_A1) shown in FIG. 116. This showed that PHO Pattern 1+extra peaks had been formed (matched DR-2186-26-10). The suspension was stirred at 5° C. for a further 24 hours and a second aliquot taken and XRPD collected (DR-2186-45-01_A2). This showed no change.

The bulk sample was isolated by vacuum filtration using a Buchner funnel and 55 mm Whatman grade 1 filter paper. The vial and cake were washed with 1 mL of cold IPA:water 9:1. The material was dried under suction for 30 minute.

Phosphate Formation—Re-Crystallisation

DR-2186-45-01 (1.00 g, PHO Pattern 1+extra peaks) was weighed into a 20 ml scintillation vial and a stirrer bar and 5 volumes (5 mL) of MeOH added. On a Polar Bear heating block the suspension was heated to 50° C., 500 RPM. Sequential aliquots of hot MeOH were added to the sample according to the Table below, noting observations, looking for sample dissolution.

| Volumes of | 50° C. | | | | | 60° C. | |
|---|---|---|---|---|---|---|---|
| MeOH | 5 | 8 | 12 | 16 | 18 | 18 | 20 |
| Observation | X | X | X | X | X | X | X |

At 20 vols (20 mL) dissolution had still not been achieved so the suspension was transferred to a 50 mL Easymax vessel fitted with overhead stirring.

| | 60° C., 150 RPM | | 60° C., 250 RPM | |
|---|---|---|---|---|
| Volumes of MeOH | 20 | 22 | 24 | 25 |
| Observation | X | X | ✓/X | ✓ |

✓ = solution, ✓/X = turbid solution, X = suspension

Figure 117:
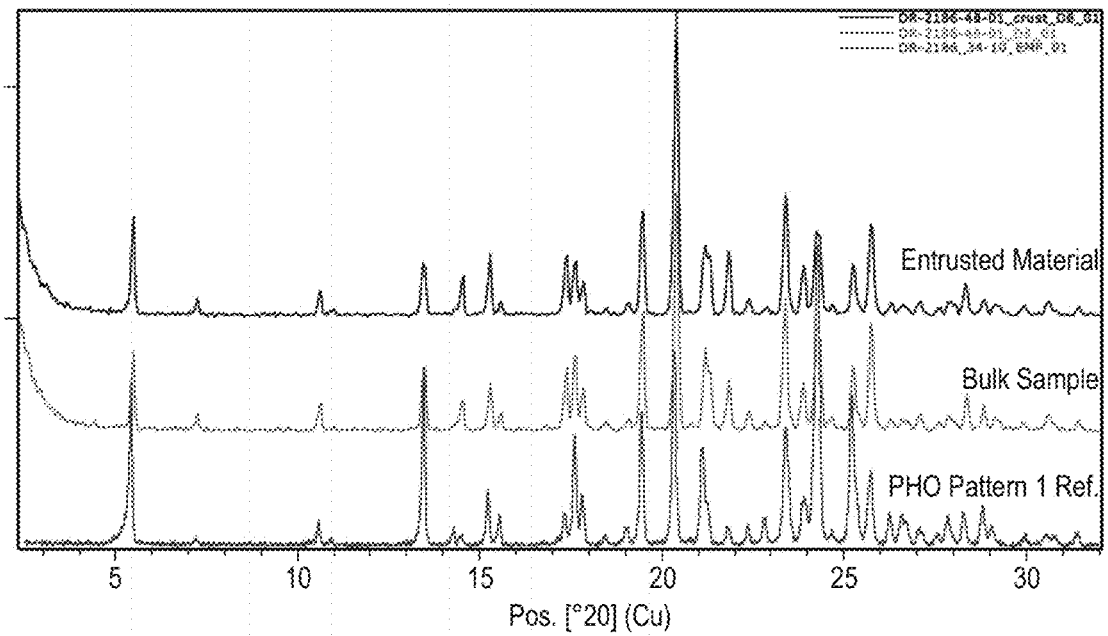
FIG. 117. XRPD Diffractograms of Phosphate salt.

Dissolution was achieved at 25 volumes of MeOH at 60° C. giving a clear yellow/brown solution. This was cooled at 0.5° C./min to 5° C. At 50° C. seeding was attempted with ca. 5 mg of PHO Pattern 1 (DR-2186-34-10), however, no visual change in solution turbidity was noted. Turbidity was observed to be starting to increase at 34° C. The crystallisation was held at 5° C. for 1 hour and was a thick off white suspension. The solid was isolated by vacuum filtration through a Whatman grade 1 filter paper and Buchner funnel. The cake was dried under suction for 30 mins. (Yield=296 mg, 29.7%). There was some fouling/encrustation on the vessel which a sample of was collected separately (ID: DR-2186-48-01_crust). An XRPD analysis of the bulk sample, the encrusted material and the Phosphate pattern 1 reference can be seen in FIG. 117.

A summary of the characteristics of the 5-MeO-DMT phosphate salt can be seen in the Table below:

| Sample ID | DR-2186-48-01 |
|---|---|
| XRPD | PHO Pattern 1 |
| $^1$H-NMR | Consistent with structure, 0.1 mol eq. of residual MeOH in sample |
| IC | 1.43 mol eq. of phosphate |
| SEM | Long, thin lath shaped particles with some larger particles that are more plat like, up to 200 μm long |
| PLM | Needle/long thin lath morphology with some larger plates ca. 200 μm in length. Crystals exhibit birefringence. |
| HSM (Hot Stage Microscopy) | Melting of sample occurs from 155-164° C. |
| TGA | 0.4 wt. % (0.04 mol. eq. MeOH) mass loss from 40-125° C. A further 0.95% (0.1 mol eq. MeOH) was lost during the melt, 130-170° C. Decomposition onset from 180° C. |
| DSC | Small endotherm onset 68.6° C. (3 J/g) associated with first mass loss. Large sharp endotherm onset at 161.7° C. (77 J/g), assigned as the melt based on the HSM data. This is immediately followed by an exotherm and charge in baseline which may indicate decomposition beginning. |
| GVS | Small total reversible mass change of 0.34 wt. % (0.06 mol eq. water) from 0-90% RH with a small hysteresis observed on the second desorption cycle. The material is classed as slightly hygroscopic (based on European Pharmacopeia definitions). The solid form of the material was largely unchanged by XRPD but very small peaks can be seen that may be consistent with the additional peaks previously observed. |
| HPLC Purity (Pharmorphix Generic Method 30 mins) | 98.0% |

| Sample ID | DR-2186-48-01 |
|---|---|
| Static Storage 7 days - 40° C./75% RH | XRPD - PHO Pattern 1<br>HPLC - 98.1% |
| Static Storage 7 days - 25° C./97% RH | XRPD - PHO Pattern 1<br>HPLC - 98.0% |

Assessment of Polymorphic Behaviour of 5-MeO-DMT Phosphate

DR-2186-45-01 (20 mg, PHO Pattern 1+Extra Peaks) was weighed into 10 HPLC vials. To this was added 10 volumes (200 μL) of solvent, a stirrer bar and the samples heated to 50° C. on a Polar Bear heat/cool block (400 RPM). After holding at 50° C. for 30 minutes and observation was made and the samples cooled to 5° C. where a further observation was made. All samples were than subjected to heat/cool cycles between 5 and 50° C. holding for 4 hours at each temperature for 24 hours.

| Sample | Solvent | Observation at 50° C. | Observation at 5° C. | Observation at Isolation | XPRD |
|---|---|---|---|---|---|
| DR-2186-52-01 | MeOH | X | X | White Suspension | PHO Pattern 1 |
| DR-2186-52-02 | Acetone | X | X | White Suspension | PHO Pattern 1 + Extra Peaks |
| DR-2186-52-03 | CAN | X | X | White Suspension | PHO Pattern 1 + Extra Peaks |
| DR-2186-52-04 | IPA:Water 9:1 | X | X | White Suspension | PHO Pattern 1 + Extra Peaks |
| DR-2186-52-05 | 2-MeTHF | X | X | White Suspension | PHO Pattern 1 + Extra Peaks |
| DR-2186-52-06 | EtOAc | X | X | White Suspension | PHO Pattern 1 + Extra Peaks |
| DR-2186-52-07 | Ethanol | X | X | White Suspension | PHO Pattern 1 + Extra Peaks |
| DR-2186-52-08 | Toluene | X | X | White Suspension | PHO Pattern 1 + Extra Peaks |
| DR-2186-52-09 | MEK | X | X | White Suspension | PHO Pattern 1 + Extra Peaks |
| DR-2186-52-10 | TBME | X | X | White Suspension | PHO Pattern 1 + Extra Peaks |

Figure 118:
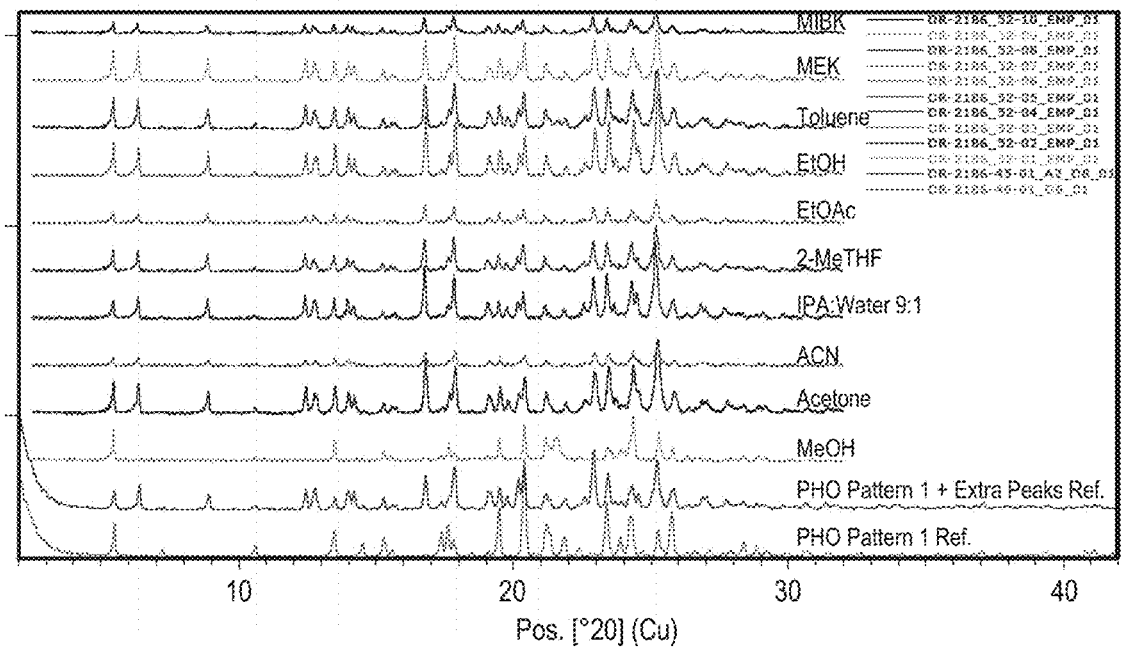
FIG. 118. XRPD Diffractograms of various samples of Phosphate salt.

The results of the XRPD analysis of the samples can be seen in FIG. 118.

Non of the samples completely dissolved during the experiment. PHO Pattern 1+Extra Peaks (which was the input material) was obtained from all solvents other than methanol which yielded pure PHO Pattern 1.

5-MeO-DMT Phosphate Pattern 1

5-MeO-DMT Phosphate Pattern 1 (XRPD analysis shown in FIG. 122, peaks in the Table below) was crystallised as a phase pure form by recrystallization of a mixture of Pattern 1 and another form from methanol. The resulting solid has a HPLC purity of 98.0% (input material 96.5%) and the IC showed that there was 1.43 mol. eq. of phosphate present in the sample (see FIG. 127).

| No. | Pos. [°2θ] | Rel. Int. [%] |
|---|---|---|
| 1 | 5.5 | 24 |
| 2 | 7.2 | 6.5 |
| 3 | 10.6 | 10.2 |
| 4 | 13.5 | 26.2 |
| 5 | 14.5 | 11.4 |
| 6 | 15.3 | 18.7 |
| 7 | 15.6 | 6 |
| 8 | 17.4 | 22 |
| 9 | 17.6 | 24.4 |
| 10 | 17.8 | 13.5 |
| 11 | 18.5 | 3.3 |
| 12 | 19.1 | 5.1 |
| 13 | 19.5 | 45.3 |
| 14 | 20.4 | 100 |
| 15 | 21.3 | 27 |
| 16 | 21.8 | 19.7 |
| 17 | 22.4 | 8 |
| 18 | 23.4 | 54.7 |
| 19 | 23.9 | 19.7 |
| 20 | 24.3 | 43.2 |
| 21 | 25.3 | 27.3 |
| 22 | 25.8 | 45.1 |
| 23 | 26.7 | 3.7 |
| 24 | 27.1 | 6.6 |
| 25 | 27.9 | 6 |
| 26 | 28.4 | 13.9 |
| 27 | 28.9 | 8.8 |
| 28 | 29.2 | 4 |
| 29 | 30.6 | 6.1 |
| 30 | 31.5 | 4 |

This higher stoichiometry maybe the driving force behind the formation of a mixture of forms in the initial salt formation step as only 1.1 equivalents of phosphoric acid were added. The solid crystallised as long thin colourless lath crystals with some of the larger ones reaching 200 µm in length and becoming more plate like.

The ¹H-NMR spectrum is (FIG. 121) consistent with the structure and the sample found to contain 0.1 mol. eq. of MeOH. The thermal data suggests a small amount of residual solvent, 0.4 wt. % lost between 40-125° C. and a further 0.95 wt. % (both losses equate to 0.14 mol. eq. of MeOH) of solvent lost from 130-170° C. The DSC contains a large sharp endotherm with an onset at 161.7° C. which is assigned as the melt, corroborated by the melt observed in the HSM. The TGA and DSC Thermograms can be seen in FIG. 123.

The sample is classed as slightly hygroscopic with a total reversible mass change of 0.3 wt. % between 0-90% RH. The DVS isotherm and DVS kinetic plot can be seen in FIGS. 124 and 125, respectively. The solid form was unchanged after a double-cycle experiment, the XRPD analysis confirming this can be seen in FIG. 126. Phosphate Pattern 1 was also found to be stable to stable to storage at both 40° C./75% RH and 25° C./97% RH, with no change observed by XRPD or HPLC, see FIGS. 128-130.

A polymorph assessment was carried out in 10 different solvents using PHO Pattern 1+extra peaks as the input material, maturating a slurry of the salt between 5° C. and 50° C. for 24 hours. The results of the XRPD analysis of the samples can be seen in FIG. 118. The isolated solid was the same as the input material in all cases other than MeOH.

In one embodiment, there is provided crystalline 5-MeO-DMT phosphate, or a pharmaceutical composition comprising crystalline 5-MeO-DMT phosphate, as characterised by one or more of:

An XRPD pattern as shown in, or substantially as shown in, FIG. 122;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more or thirty peaks in an XRPD diffractogram as detailed the Table above;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in the Table above;

A TGA thermogram as shown in, or substantially as shown in, FIG. 123;

A weight loss of about 0.4% between 40 and 125° C. and a weight loss of about 0.95% between 130 and 170° C., as measured by TGA thermogram;

A weight loss of about 0.2-0.6% between 40 and 125° C. and a weight loss of about 0.85-1.05% between 130 and 170° C., as measured by TGA thermogram;

A weight loss of about 0.2, 0.3, 0.4, 0.5 or 0.6% between 40 and 125° C. and a weight loss of about 0.85, 0.9, 0.95, 1.0 or 1.05% between 130 and 170° C., as measured by TGA thermogram;

A DSC thermogram as shown in, or substantially as shown in, FIG. 123;

A melting endothermic event with an onset of around 161.7° C., as measured in a DSC thermogram;

A melting endothermic event with an onset of around 155-165° C., as measured in a DSC thermogram; and/or A melting endothermic event with an onset of around 155, 156, 157, 158, 159, 160, 161, 162, 163, 164 or 165° C., as measured in a DSC thermogram.

L-Tartrate Formation

In a 20 mL scintillation vial 5-MeO-DMT (1.00 g, Free Form Pattern 1, DR-2186-46-02) was dissolved in 5 volumes (5 mL) of IPA:water 9:1 at 50° C. on a Polar Bear heat/cool block with magnetic bottom stirring (500 RPM), giving a brown solution. 1.1 mol eq. (5.05 mL) of L-tartaric acid was added at a 1M solution in THF dropwise over 2 minutes. This formed a brown oil, which formed a thick light tan suspension after stirring at 50° C. for 5 minutes. The crystallisation was then cooled to 5° C. at 0.1° C./min and held there overnight.

An aliquot (ca. 0.3 mL) of suspension was filtered using a cartridge and frit along with positive pressure. The solid was dried briefly under a stream of N2 before collecting an XRPD. This showed that TAR Pattern 1 had been formed. (XRPD analysis shown in FIGS. 131 and 132, peaks in the Table below).

| No. | Pos. [°2θ] | Rel. Int. [%] |
|---|---|---|
| 1 | 5.0 | 100 |
| 2 | 10.1 | 2.6 |
| 3 | 11.7 | 2.8 |
| 4 | 13.0 | 10.7 |
| 5 | 15.1 | 12.1 |
| 6 | 15.5 | 6.1 |
| 7 | 16.5 | 5.2 |
| 8 | 17.7 | 21.9 |
| 9 | 18.2 | 40.1 |
| 10 | 18.7 | 38.3 |
| 11 | 19.6 | 9.2 |
| 12 | 20.2 | 19.5 |
| 13 | 20.7 | 34.7 |
| 14 | 21.4 | 8 |
| 15 | 22.1 | 23.4 |
| 16 | 22.6 | 8.7 |
| 17 | 23.0 | 5 |
| 18 | 23.6 | 13.2 |
| 19 | 24.8 | 3.7 |
| 20 | 25.3 | 4.8 |
| 21 | 26.0 | 37.1 |
| 22 | 26.3 | 1.9 |
| 23 | 27.0 | 3.5 |
| 24 | 27.2 | 6.6 |
| 25 | 27.8 | 3 |
| 26 | 29.3 | 3.8 |
| 27 | 29.9 | 6.2 |
| 28 | 31.1 | 4.6 |
| 29 | 31.7 | 3.7 |

The bulk sample was isolated by vacuum filtration using a Buchner funnel and 55 mm Whatman grade 1 filter paper. The vial and cake were washed with 1 mL of cold IPA:water 9:1. The material was dried under suction for 15 minutes then transferred to a vacuum oven at RT for 4.5 hours. Yield=1.413 g (83.7%).

A summary of the characteristics of the 5-MeO-DMT tartrate salt can be seen in the Table below:

| Sample ID | DR-2186-46-01 |
|---|---|
| XRPD | TAR Pattern 1 |
| ¹H-NMR | Consistent with structure, 0.97 mol eq. tartrate, 0.02 mol eq. of residual THF and IPA |
| SEM | Very small plate particles <1-20 µm in size |
| PLM | Very small crystals exhibiting birefringence |

81

-continued

| Sample ID | DR-2186-46-01 |
|---|---|
| HSM (Hot Stage Microscopy) | Melting of sample observed from 135° C. and complete by 143° C. |
| TGA | No mass loss observed in sample before decomposition. |
| DSC | Large sharp endotherm with onset at 145.0° C. (116 J/g), this has been assigned as a melt due to good agreement with observations made during the hot stage microscopy |
| GVS | Total mass change of 0.58 wt. % from 0-90% RH (0.12 mol eq. of water) and is reversible with no hysteresis. The material is classed as slightly hygroscopic (based on European Pharmacopeia definitions). The solid form of the material was unchanged by XRPD. |
| HPLC Purity (Pharmorphix Generic Method 30 mins) | 98.0% |
| Static Storage 7 days-40° C./75% RH | KRPD-TAR Pattern 1 HPLC-97.8% |

DR-2186-46-01 (20 mg, TAR Pattern 1) was weighed into 10 HPLC vials. To this was added 10 volumes (200 μL) of solvent, a stirrer bar and the samples heated to 50° C. on a Polar Bear heat/cool block (400 RPM). After holding at 50° C. for 30 minutes and observation was made and the samples cooled to 5° C. where a further observation was made. All samples were than subjected to heat/cool cycles between 5 and 50° C. holding for 4 hours at each temperature for 24 hours.

| Sample | Solvent | Observation at 50° C. | Observation at 5° C. | Observation at Isolation | XRPD |
|---|---|---|---|---|---|
| DR-2186-52-01 | MeOH | X | X | White Suspension | TAR Pattern 1 |
| DR-2186-52-03 | Acetone | X | X | White Suspension | TAR Pattern 1 |
| DR-2186-52-03 | ACN | X | X | White Suspension | TAR Pattern 1 |
| DR-2186-52-04 | IPA:Water 9:1 | X | X | White Suspension | TAR Pattern 1 |
| DR-2186-52-05 | 2-MeTHF | X | X | White Suspension | TAR Pattern 1 |
| DR-2186-52-06 | EtOAc | X | X | White Suspension | TAR Pattern 1 |
| DR-2186-52-07 | Ethanol | X | X | White Suspension | TAR Pattern 1 |
| DR-2186-52-08 | Toluene | X | X | White Suspension | TAR Pattern 1 |
| DR-2186-52-09 | MEK | X | X | White Suspension | TAR Pattern 1 |
| DR-2186-52-10 | TBME | X | X | White Suspension | TAR Pattern 1 |

Figure 119:
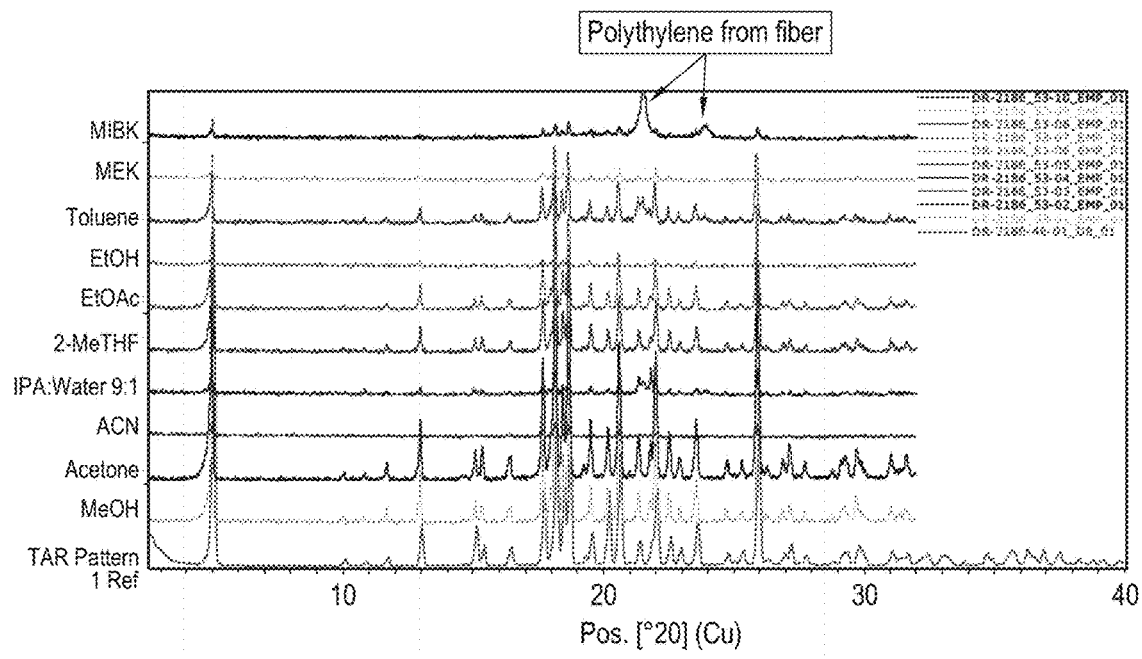
FIG. 119. XRPD Diffractograms of various samples of Tartrate salt.

The results of the XRPD analysis of the samples can be seen in FIG. 119. FIG. 120 shows the XRPD analysis results for low intensity samples (solvents: EtOH, ACN).

No dissolution was observed during the experiment and only TAR Pattern 1 was obtained after the 24 hours of maturation.

5-MeO-DMT Tartrate Pattern 1

5-MeO-DMT Tartrate Pattern 1 (FIG. 131) was crystallised from an THF:IPA:Water (ca. 10:9:1) solvent system. The resulting solid has a HPLC purity of 98.0% (input material 96.5%) and the $^1$H-NMR showed that there was 1.0 mol. eq. of tartrate present in the sample with very low amounts of residual IPA or THF (FIG. 133). The sample is comprised of very small plate like crystals 1-20 μm in size.

The TGA (FIG. 134) showed no mass loss until the onset of decomposition at 175° C. The DSC contains a large sharp endotherm with an onset at 145.0° C. which is assigned as the melt, corroborated by the melt observed in the HSM.

The sample is classed as slightly hygroscopic with a total reversible mass change of 0.6 wt. % between 0-90% RH (FIG. 135). The solid-form was unchanged after the double-cycle experiment (FIG. 136). Tartrate Pattern 1 was also found to be stable to storage at both 40° C./75% RH and 25° C./97% RH, with no change observed by XRPD or HPLC (FIGS. 137-141).

A polymorph assessment was carried out in 10 different solvents, maturating a slurry of the salt between 5° C. and 50° C. for 24 hours.

In one embodiment, there is provided crystalline 5-MeO-DMT tartrate, or a pharmaceutical composition comprising crystalline 5-MeO-DMT tartrate, as characterised by one or more of:

An XRPD pattern as shown in, or substantially as shown in, FIG. 131 or FIG. 132;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more or twenty nine peaks in an XRPD diffractogram as detailed the peak Table above;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in the peak Table above;

A TGA thermogram as shown in, or substantially as shown in, FIG. 134;

A DSC thermogram as shown in, or substantially as shown in, FIG. 134;

A melting endothermic event with an onset of around 145.0° C., as measured in a DSC thermogram;

A melting endothermic event with an onset of around 140-150° C., as measured in a DSC thermogram;

A melting endothermic event with an onset of around 140, 141, 142, 143, 144, 145, 146, 147, 148, 149, 150° C., as measured in a DSC thermogram;

A total reversible mass change of around 0.6% between 0-90% RH;

A total reversible mass change of around 0.4-0.8% between 0-90% RH;

A total reversible mass change of around 0.4, 0.5, 0.6, 0.7 or 0.8% between 0-90% RH; and/or A DVS Isotherm as shown in, or substantially as shown in, FIG. 135.

Example 4: Further Characterisation of 5-MeO-DMT Hydrochloride

Instruments

X-Ray Powder Diffraction (XRPD)

XRPD diffractograms were acquired using Bruker D2 Phaser diffractometer. A copper x-ray source at 300 W was used in conjunction with a Lynxeye detector. Samples were prepared using a zero-background sample holder. The samples were scanned from 5 to 32° (2☐) using a step size of 0.02° and a time per step of 0.13 second whilst spinning the sample. Diffractograms were plotted using the EVA program from Bruker.

Thermo—Gravimetric Analysis (TGA)

TGA thermograms were obtained with a TA Instrument Discovery 550 in Al pans. The heating rate used was 10° C./min linear ramp from 25 to 400° C. with a nitrogen purging at a rate of 60 ml/min. TGA thermograms were analysed using TRIOS software.

Differential Scanning Calorimetry (DSC)

DSC analyses were performed on a TA Instrument DSC250 with a Tzero cell purged at constant flow rate of 50 ml min$^{-1}$ with dry nitrogen and a refrigerated cooling system RCS90. The instrument was calibrated using Indium as a standard. A small quantity of the samples was weighed into TA Tzero Aluminium pan with pierced lid. Samples were heating at 10° C./min in heat-cool-reheat method. TRIOS software was used to analyse DSC scans.

Nuclear Magnetic Resonance Spectroscopy (NMR)

The NMR spectra were measured on Bruker NEO spectrometer operating at 400.13 MHz for protons. Samples were dissolved in d6-DMSO. Data were processed using MestReNovax64 software.

Initial Characterisation of Hydrochloride Salt

Baseline analysis of the hydrochloride salt was performed to compare to data generated in later studies. The hydrochloride was analysed by XRPD and the diffractogram is shown in FIG. 142. The material is crystalline and this was designated as pattern 1. The XRPD peak data is shown in Table 22, 22a or 22b:

TABLE 22

XRPD Peak data for hydrochloride pattern 1

| Peak No. | Angle 2 θ | d Value | Rel. Intensity |
|---|---|---|---|
| 1 | 9.191° | 9.614 | 0.59 |
| 2 | 12.275° | 7.205 | 0.24 |
| 3 | 13.601° | 6.505 | 0.16 |
| 4 | 14.030° | 6.307 | 0.34 |
| 5 | 14.925° | 5.931 | 1.00 |
| 6 | 15.513° | 5.708 | 0.01 |
| 7 | 18.403° | 4.817 | 0.59 |
| 8 | 18.396° | 4.693 | 0.06 |
| 9 | 19.613° | 4.523 | 0.58 |
| 10 | 21.305° | 4.167 | 0.13 |
| 11 | 22.899° | 3.881 | 0.02 |
| 12 | 23.133° | 3.842 | 0.06 |
| 13 | 23.436° | 3.793 | 0.03 |
| 14 | 23.826° | 3.732 | 0.53 |
| 15 | 24.565° | 3.621 | 0.08 |
| 16 | 25.048° | 3.552 | 0.23 |
| 17 | 25.716° | 3.461 | 0.04 |
| 18 | 25.974° | 3.428 | 0.14 |
| 19 | 26.226° | 3.395 | 0.03 |
| 20 | 26.783° | 3.326 | 0.13 |
| 21 | 27.271° | 3.268 | 0.04 |
| 22 | 27.547° | 3.235 | 0.06 |
| 23 | 28.110° | 3.172 | 0.16 |
| 24 | 23.955° | 3.081 | 0.05 |
| 25 | 30.045° | 2.972 | 0.01 |
| 26 | 30.670° | 2.913 | 0.06 |
| 27 | 31.009° | 2.882 | 0.03 |
| 28 | 31.431° | 2.844 | 0.02 |

TABLE 22a

XRPD Peak data for hydrochloride pattern 1. (2 d.p.)

| Peak No. | Angle 2 θ | d Value | Rel. Intensity |
|---|---|---|---|
| 1 | 9.19° | 9.61 | 0.59 |
| 2 | 12.28° | 7.21 | 0.24 |
| 3 | 13.60° | 6.51 | 0.16 |
| 4 | 14.03° | 6.31 | 0.34 |
| 5 | 14.93° | 5.93 | 1.00 |
| 6 | 15.51° | 5.71 | 0.01 |
| 7 | 18.40° | 4.82 | 0.59 |
| 8 | 18.90° | 4.69 | 0.06 |
| 9 | 19.61° | 4.52 | 0.58 |
| 10 | 21.31° | 4.17 | 0.13 |
| 11 | 22.90° | 3.88 | 0.02 |
| 12 | 23.13° | 3.84 | 0.06 |
| 13 | 23.44° | 3.79 | 0.03 |
| 14 | 23.83° | 3.73 | 0.53 |
| 15 | 24.57° | 3.62 | 0.08 |
| 16 | 25.05° | 3.55 | 0.23 |
| 17 | 25.72° | 3.46 | 0.04 |
| 18 | 25.97° | 3.43 | 0.14 |
| 19 | 26.23° | 3.40 | 0.03 |
| 20 | 26.78° | 3.33 | 0.13 |
| 21 | 27.27° | 3.27 | 0.04 |
| 22 | 27.55° | 3.24 | 0.06 |
| 23 | 28.11° | 3.17 | 0.16 |
| 24 | 28.96° | 3.08 | 0.05 |
| 25 | 30.05° | 2.97 | 0.01 |
| 26 | 30.67° | 2.91 | 0.06 |
| 27 | 31.01° | 2.88 | 0.03 |
| 28 | 31.43° | 2.84 | 0.02 |

TABLE 22b

XRPD Peak data for hydrochloride pattern 1. (1 d.p.)

| Peak No. | Angle 2 θ | d Value | Rel. Intensity |
|---|---|---|---|
| 1 | 9.2° | 9.6 | 0.6 |
| 2 | 12.3° | 7.2 | 0.2 |
| 3 | 13.6° | 6.5 | 0.2 |
| 4 | 14.0° | 6.3 | 0.3 |
| 5 | 14.9° | 5.9 | 1.0 |
| 6 | 15.5° | 5.7 | 0.0 |
| 7 | 18.4° | 4.8 | 0.6 |
| 8 | 18.9° | 4.7 | 0.1 |
| 9 | 19.6° | 4.5 | 0.6 |
| 10 | 21.3° | 4.2 | 0.1 |
| 11 | 22.9° | 3.9 | 0.0 |
| 12 | 23.1° | 3.8 | 0.1 |
| 13 | 23.4° | 3.8 | 0.0 |
| 14 | 23.8° | 3.7 | 0.5 |
| 15 | 24.6° | 3.6 | 0.1 |
| 16 | 25.1° | 3.6 | 0.2 |
| 17 | 25.7° | 3.5 | 0.0 |
| 18 | 26.0° | 3.4 | 0.1 |
| 19 | 26.2° | 3.4 | 0.0 |
| 20 | 26.8° | 3.3 | 0.1 |
| 21 | 27.3° | 3.3 | 0.0 |
| 22 | 27.6° | 3.2 | 0.1 |

TABLE 22b-continued

XRPD Peak data for hydrochloride pattern 1. (1 d.p.)

| Peak No. | Angle 2 θ | d Value | Rel. Intensity |
|---|---|---|---|
| 23 | 28.1° | 3.2 | 0.2 |
| 24 | 29.0° | 3.1 | 0.1 |
| 25 | 30.1° | 3.0 | 0.0 |
| 26 | 30.7° | 2.9 | 0.1 |
| 27 | 31.0° | 2.9 | 0.0 |
| 28 | 31.4° | 2.8 | 0.0 |

Thermal analysis was performed and the TGA thermogram is shown in FIG. 143. This shows the material is an anhydrous form with good thermal stability up to ~235° C. where gross decomposition is taking place. The DSC thermogram for the first heat cycle is shown in FIG. 144. This shows a single sharp endothermic event, melting, with an onset of 146.5° C. and an enthalpy of 121.7 J./g. The sample was then cooled in the DSC to ~−90†8 C and reheated. The thermograms are shown in FIG. 145 and show vitrification at 40.2° C. in the cool cycle and a Tg at 44.8° C. in the second heat cycle. There was no evidence of recrystallization during this experiment when performed at a heating or cooling rate of 10° C. min$^{-1}$.

To look for new crystal forms via recrystallisation from the melt, the DSC experiment was repeated but different cool and reheat rates were used in the second cycle. Three separate samples were all heated to 200° C. at 10° C. min$^{-1}$ and then cooled to −90° C. and reheated to 200° C. at three different rates of 5° C. min$^{-1}$, 2° C. min$^{-1}$ and 1° C. min$^{-1}$. The cool cycles only showed vitrification (data not shown) but the reheat cycles showed a recrystallisation event followed by a melt, but the melt is consistent with the recrystallised material being pattern 1 and as such, no new crystalline forms were observed in these experiments. The three thermograms are shown in FIG. 146.

The hydrochloride was analysed by $^1$H and $^1$H-$^{13}$C HSQC NMR. The $^1$H NMR spectrum is shown in FIG. 147 and is consistent with the supplied structure. There are no obvious evidence of residual process solvents and the material shows a high chemical purity. The $^1$H-$^{13}$C HSQC spectrum is shown in FIG. 148 and is consistent with the supplied structure and shows the expected DEPT editing.

In one embodiment, there is provided 5-MeO-DMT HCl. In one embodiment, there is provided a pharmaceutical composition comprising 5-MeO-DMT HCl. In one embodiment, there is provided crystalline 5-MeO-DMT HCl, or a pharmaceutical composition comprising crystalline 5-MeO-DMT HCl, as characterised by one or more of:

An XRPD pattern as shown in, or substantially as shown in, FIG. 142;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more or twenty eight peaks in an XRPD diffractogram as detailed in Table 22, Table 22a or Table 22b;

One or more, two or more, three or more, four or more, five or more peaks in an XRPD diffractogram with a relative intensity of over 0.1, 0.2, 0.3, 0.4, 0.5, 0.6, 0.7, 0.8 or 0.9 as detailed in Table 22, Table 22a or Table 22b;

A TGA thermogram as shown in, or substantially as shown in, FIG. 143;

A DSC thermogram as shown in, or substantially as shown in, FIG. 144;

A melting endothermic event with an onset of around 146.5° C. and an enthalpy of 121.7 J/g, as measured in a DSC thermogram;

A melting endothermic event with an onset of around 140 to 150° C. and an enthalpy of around 115 to 125 J/g, as measured in a DSC thermogram;

A melting endothermic event with an onset of around 140, 141, 142, 143, 144, 145, 146, 147, 148, 149, 150° C. and an enthalpy of around 155, 156, 157, 158, 159, 160, 161, 162, 163, 164, 165, 166, 167, 168, 169 or 170 J/g, as measured in a DSC thermogram;

A vitrification around 40.2° C., as measured in a DSC thermogram with a cooling ramp of 10° C./min from 230° C. to −90° C.;

A vitrification around 35-45° C., as measured in a DSC thermogram with a cooling ramp of 10° C./min from 230° C. to −90° C.;

A vitrification around 35, 36, 37, 38, 39, 40, 41, 42, 43, 44 or 45° C., as measured in a DSC thermogram with a cooling ramp of 10° C./min from 230° C. to −90° C.;

A glass transition around 44.8° C., as measured in a DSC thermogram with a cooling ramp of 10° C./min from 230° C. to −90° C.;

A glass transition around 40-50° C., as measured in a DSC thermogram with a cooling ramp of 10° C./min from 230° C. to −90° C.;

A glass transition around 41, 42, 43, 44, 45, 46, 47, 48, 49 or 50° C., as measured in a DSC thermogram with a cooling ramp of 10° C./min from 230° C. to −90° C.;

A $^1$H NMR spectrum as shown in, or substantially as shown in, FIG. 147; and/or A $^1$H-$^{13}$C HSQC NMR spectrum as shown in, or substantially as shown in, FIG. 148.

Polymorphism Screen

To render the material amorphous and thus remove seeds of the pattern 1 the material was rendered amorphous. To 2.605 g of the hydrochloride lot RPI-014-022 dioxane (55 ml) and water (5 ml) was added.

The mixture was agitated gently and warmed to aid dissolution. The clear solution was then divided equally between 60 HPLC vials (~40 mg salt in each vial) and the vials were then frozen at ~−18° C. for 6 hours and then dried by lyophilisation overnight. One sample was analysed by XRPD and the diffractogram shown in FIG. 149 demonstrates that although not 100% amorphous, the crystallinity is reduced, albeit still pattern 1 in nature.

Thermal Cycling

Twenty five of the lyophilised samples were treated with solvent and thermally cycled between ambient and 40° C. with four hours spent under each condition. After three days and solids were isolated by centrifuge filtration and analysed by XRPD. Any solutions were allowed to evaporate at RT but this did not yield any new solids. The solvents, observations, isolation and XRPD results are summarised in the Table below:

| Experiment | Solvent | Volume added (ml) | Initial Observations | 3-day Observations | Isolation | XRPD Result |
|---|---|---|---|---|---|---|
| DJP2202-007-01 | 1,4-Dioxane | 200 | no change | solid mass | After thermal cycle | Pattern 2 |
| DJP2202-007-02 | 1-Propanol | 200 | no change | few crystals | After thermal cycle | Pattern 1 |
| DJP2202-007-03 | 2-Butanol | 200 | no change | few crystals | After thermal cycle | Pattern 1 |
| DJP2202-007-04 | 2-Ethoxyethanol | 200 | dissolved | clear solution | Evaporated but no solid | n/a |
| DJP2202-007-05 | 2-Methyltetrahydrofuran | 200 | no change | few crystals | After thermal cycle | Pattern 1 |
| DJP2202-007-06 | 2-Propanol | 200 | no change | few crystals | After thermal cycle | Pattern 1 |
| DJP2202-007-07 | Acetone | 200 | no change | few crystals | After thermal cycle | Pattern 1 |
| DJP2202-007-08 | Acetonitrile | 200 | no change | lump of material | After thermal cycle | Pattern 1 |
| DJP2202-007-09 | Anisole | 200 | no change | lump of material | After thermal cycle | Pattern 1 |
| DJP2202-007-10 | Chlorobenzene | 200 | no change | white solid | After thermal cycle | Pattern 1 |
| DJP2202-007-11 | Ethanol | 150 | no change | white solid | After thermal cycle | Pattern 1 |
| DJP2202-007-12 | Ethyl acetate | 200 | no change | white solid | After thermal cycle | Pattern 1 |
| DJP2202-007-13 | Isopropyl acetate | 200 | no change | white solid | After thermal cycle | Pattern 1 |
| DJP2202-007-14 | Methanol | 200 | dissolved | clear solution | After thermal cycle | Pattern 3 |
| DJP2202-007-15 | Propyl acetate | 200 | no change | while solid | After thermal cycle | Pattern 1 |
| DJP2202-007-16 | Methylethyl ketone | 200 | no change | white crystals | After thermal cycle | Pattern 2 |
| DJP2202-007-17 | Formamide | 150 | dissolved | few crystals | Evaporated but no solid | n/a |
| DJP2202-007-18 | N,N-Dimethylacetamide | 200 | dissolved | clear solution | Evaporated but no solid | n/a |
| DJP2202-007-19 | N-Methylpyrrolidone | 200 | no change | clear solution | Evaporated but no solid | n/a |
| DJP2202-007-20 | iso-Propyl acetate | 200 | no change | few crystals | After thermal cycle | Pattern 1 |
| DJP2202-007-21 | 2-Me-1-PrOH | 200 | no change | few crystals | After thermal cycle | Pattern 1 |
| DJP2202-007-22 | Tetrahydrofuran | 200 | no change | few crystals | After thermal cycle | Pattern 1 |
| DJP2202-007-23 | MeOH/water 953/47 Calc Aw 0.214 | 200 | dissolved | clear solution | Evaporated to oil | n/a |
| DJP2202-007-24 | MeOH/water 693/307 Calc Aw 0.599 | 200 | dissolved | clear solution | Evaporated to oil | n/a |
| DJP2202-007-25 | MeOH/water 360/640 Calc Aw 0.821 | 200 | dissolved | clear solution | Evaporated but no solid | n/a |

The XRPD for the new pattern 2 is shown in FIG. 150 compared to the supplied pattern 1. The XRPD peak data is shown in Table 23, 23a or 23b:

TABLE 23

XRPD Peak data for hydrochloride pattern 2

| Peak No. | Angle 2 θ | d Value | Rel. Intensity |
|---|---|---|---|
| 1 | 8.454° | 10.450 | 0.01 |
| 2 | 11.786° | 7.502 | 0.17 |
| 3 | 12.650° | 6.992 | 0.01 |
| 4 | 13.042° | 6.783 | 0.25 |
| 5 | 13.789° | 6.417 | 0.02 |
| 6 | 14.600° | 6.062 | 0.01 |
| 7 | 14.968° | 5.914 | 0.49 |
| 8 | 16.120° | 5.494 | 0.02 |
| 9 | 17.283° | 5.127 | 0.14 |
| 10 | 17.529° | 5.055 | 0.29 |
| 11 | 17.791° | 4.982 | 1.00 |
| 12 | 18.363° | 4.828 | 0.05 |
| 13 | 18.530° | 4.784 | 0.90 |
| 14 | 19.571° | 4.532 | 0.37 |
| 15 | 19.858° | 4.467 | 0.05 |
| 16 | 20.354° | 4.360 | 0.18 |
| 17 | 20.883° | 4.250 | 0.06 |
| 18 | 21.344° | 4.160 | 0.08 |

TABLE 23-continued

XRPD Peak data for hydrochloride pattern 2

| Peak No. | Angle 2 θ | d Value | Rel. Intensity |
|---|---|---|---|
| 19 | 22.244° | 3.993 | 0.17 |
| 20 | 22.715° | 3.912 | 0.38 |
| 21 | 23.321° | 3.811 | 0.09 |
| 22 | 23.645° | 3.760 | 0.66 |
| 23 | 24.751° | 3.594 | 0.21 |
| 24 | 25.620° | 3.474 | 0.15 |
| 25 | 26.224° | 3.396 | 0.12 |
| 26 | 26.593° | 3.349 | 0.51 |
| 27 | 26.947° | 3.306 | 0.21 |
| 28 | 27.103° | 3.287 | 0.30 |
| 29 | 27.442° | 3.248 | 0.04 |
| 30 | 27.706° | 3.217 | 0.02 |
| 31 | 28.051° | 3.178 | 0.16 |
| 32 | 28.541° | 3.125 | 0.11 |
| 33 | 28.813° | 3.096 | 0.05 |
| 34 | 29.442° | 3.031 | 0.05 |
| 35 | 30.057° | 2.971 | 0.15 |
| 36 | 30.648° | 2.915 | 0.10 |
| 37 | 31.078° | 2.875 | 0.08 |
| 38 | 31.474° | 2.840 | 0.08 |

TABLE 23a

XRPD Peak data for hydrochloride pattern 2. (2. d.p.)

| Peak No. | Angle 2 θ | d Value | Rel. Intensity |
|---|---|---|---|
| 1 | 8.45° | 10.45 | 0.01 |
| 2 | 11.79° | 7.50 | 0.17 |
| 3 | 12.65° | 6.99 | 0.01 |
| 4 | 13.04° | 6.78 | 0.25 |
| 5 | 13.79° | 6.42 | 0.02 |
| 6 | 14.60° | 6.06 | 0.01 |
| 7 | 14.97° | 5.91 | 0.49 |
| 8 | 16.12° | 5.49 | 0.02 |
| 9 | 17.28° | 5.13 | 0.14 |
| 10 | 17.53° | 5.06 | 0.29 |
| 11 | 17.79° | 4.98 | 1.00 |
| 12 | 18.36° | 4.83 | 0.05 |
| 13 | 18.53° | 4.78 | 0.90 |
| 14 | 19.57° | 4.53 | 0.37 |
| 15 | 19.86° | 4.47 | 0.05 |
| 16 | 20.35° | 4.36 | 0.18 |
| 17 | 20.88° | 4.25 | 0.06 |
| 18 | 21.34° | 4.16 | 0.08 |
| 19 | 22.24° | 3.99 | 0.17 |
| 20 | 22.72° | 3.91 | 0.38 |
| 21 | 23.32° | 3.81 | 0.09 |
| 22 | 23.65° | 3.76 | 0.66 |
| 23 | 24.75° | 3.59 | 0.21 |
| 24 | 25.62° | 3.47 | 0.15 |
| 25 | 26.22° | 3.40 | 0.12 |
| 26 | 26.59° | 3.35 | 0.51 |
| 27 | 26.95° | 3.31 | 0.21 |
| 28 | 27.10° | 3.29 | 0.30 |
| 29 | 27.44° | 3.25 | 0.04 |
| 30 | 27.71° | 3.22 | 0.02 |
| 31 | 28.05° | 3.18 | 0.16 |
| 32 | 28.54° | 3.13 | 0.11 |
| 33 | 28.81° | 3.10 | 0.05 |
| 34 | 29.44° | 3.03 | 0.05 |
| 35 | 30.06° | 2.97 | 0.15 |
| 36 | 30.65° | 2.92 | 0.10 |
| 37 | 31.08° | 2.88 | 0.08 |
| 38 | 31.47° | 2.84 | 0.08 |

TABLE 23b

XRPD Peak data for hydrochloride pattern 2. (1 d.p.)

| Peak No. | Angle 2 θ | d Value | Rel. Intensity |
|---|---|---|---|
| 1 | 8.5° | 10.5 | 0.0 |
| 2 | 11.8° | 7.5 | 0.2 |
| 3 | 12.7° | 7.0 | 0.0 |
| 4 | 13.0° | 6.8 | 0.3 |
| 5 | 13.8° | 6.4 | 0.0 |
| 6 | 14.6° | 6.1 | 0.0 |
| 7 | 15.0° | 5.9 | 0.5 |
| 8 | 16.1° | 5.5 | 0.0 |
| 9 | 17.3° | 5.1 | 0.1 |
| 10 | 17.5° | 5.1 | 0.3 |
| 11 | 17.8° | 5.0 | 1.0 |
| 12 | 18.4° | 4.8 | 0.1 |
| 13 | 18.5° | 4.8 | 0.9 |
| 14 | 19.6° | 4.5 | 0.4 |
| 15 | 19.9° | 4.5 | 0.1 |
| 16 | 20.4° | 4.4 | 0.2 |
| 17 | 20.9° | 4.3 | 0.1 |
| 18 | 21.3° | 4.2 | 0.1 |
| 19 | 22.2° | 4.0 | 0.2 |
| 20 | 22.7° | 3.9 | 0.4 |
| 21 | 23.3° | 3.8 | 0.1 |
| 22 | 23.7° | 3.8 | 0.7 |
| 23 | 24.8° | 3.6 | 0.2 |
| 24 | 25.6° | 3.5 | 0.2 |
| 25 | 26.2° | 3.4 | 0.1 |
| 26 | 26.6° | 3.4 | 0.5 |
| 27 | 27.0° | 3.3 | 0.2 |
| 28 | 27.1° | 3.3 | 0.3 |
| 29 | 27.4° | 3.3 | 0.0 |
| 30 | 27.7° | 3.2 | 0.0 |
| 31 | 28.1° | 3.2 | 0.2 |
| 32 | 28.5° | 3.1 | 0.1 |
| 33 | 28.8° | 3.1 | 0.1 |
| 34 | 29.4° | 3.0 | 0.1 |
| 35 | 30.1° | 3.0 | 0.2 |
| 36 | 30.7° | 2.9 | 0.1 |
| 37 | 31.1° | 2.9 | 0.1 |
| 38 | 31.5° | 2.8 | 0.1 |

The pattern 2 material was analysed further by TGA and DSC. The TGA thermogram is shown in FIG. 151 and demonstrates that the material appears to be a non-solvated/hydrated form with gross decomposition starting at around 256° C. The DSC thermogram in FIG. 152 shows a small endothermic event with an onset of 136.8° C. followed by an exothermic event with an onset of 139.1° C. followed by a final large endothermic event with an onset of 146.1° C. It would appear that the pattern 2 material melts, recrystallizes to pattern 1 and then melts again. The pattern 2 material was analysed by 1H NMR and this showed that the material was still a salt, and only contained ~0.018 eq. of dioxane confirming it is not a solvated form. The $^1$H NMR spectrum is shown in FIG. 153.

In one embodiment, there is provided crystalline 5-MeO-DMT hydrochloride or a pharmaceutical composition comprising crystalline 5-MeO-DMT hydrochloride, as characterised by one or more of:

An XRPD pattern as shown in, or substantially as shown in, FIG. 150;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, thirty three or more, thirty four or more, thirty five or more, thirty six or more, thirty seven or more or thirty eight peaks in an XRPD diffractogram as detailed in Table 23, 23a or 23b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 23, 23a or 23b;

A TGA thermogram as shown in, or substantially as shown in, FIG. 151;

A DSC thermogram as shown in, or substantially as shown in, FIG. 152;

A small endothermic event with an onset of around 136.8° C. followed by an exothermic event with an onset of around 139.1° C. followed by a final large endothermic event with an onset of around 146.1° C.;

A small endothermic event with an onset of 134-138° C. followed by an exothermic event with an onset of 137-141° C. followed by a final large endothermic event with an onset of 144-148° C.;

A small endothermic event with an onset of 134, 135, 136, 137 or 138° C. followed by an exothermic event with an onset of 137, 138, 139, 140 or 141° C. followed by a final large endothermic event with an onset of 144, 145, 146, 147 or 148° C.; and/or An $^1$H NMR spectrum as shown, or substantially as shown, in FIG. 153.

The XRPD for the new pattern 3 is shown in FIG. 154 compared to the pattern 1 and pattern 2. The XRPD peak data is shown in the table below:

TABLE 24

XRPD Peak data for hydrochloride pattern 3

| Peak No. | Angle 2 θ | d Value | Rel. Intensity |
| --- | --- | --- | --- |
| 1 | 6.509° | 13.568 | 0.06 |
| 2 | 12.341° | 7.166 | 0.04 |
| 3 | 12.979° | 6.815 | 1.00 |
| 4 | 14.420° | 6.137 | 0.03 |
| 5 | 16.706° | 5.303 | 0.21 |
| 6 | 17.643° | 5.023 | 0.10 |
| 7 | 17.805° | 4.978 | 0.16 |
| 8 | 19.519° | 4.544 | 0.25 |
| 9 | 20.226° | 4.387 | 0.09 |
| 10 | 21.056° | 4.216 | 0.08 |
| 11 | 21.882° | 4.059 | 0.03 |
| 12 | 22.175° | 4.006 | 0.44 |
| 13 | 23.525° | 3.779 | 0.34 |
| 14 | 24.239° | 3.669 | 0.11 |
| 15 | 25.454° | 3.496 | 0.17 |
| 16 | 26.101° | 3.411 | 0.19 |
| 17 | 27.201° | 3.276 | 0.06 |
| 18 | 28.161° | 3.166 | 0.14 |
| 19 | 28.408° | 3.139 | 0.05 |
| 20 | 29.220° | 3.054 | 0.12 |
| 21 | 29.841° | 2.992 | 0.02 |
| 22 | 30.361° | 2.942 | 0.03 |
| 23 | 30.876° | 2.894 | 0.02 |

TABLE 24a

XRPD Peak data for hydrochloride pattern 3 (2 d.p.)

| Peak No. | Angle 2 θ | d Value | Rel. Intensity |
| --- | --- | --- | --- |
| 1 | 6.51° | 13.57 | 0.06 |
| 2 | 12.34° | 7.17 | 0.04 |
| 3 | 12.98° | 6.82 | 1.00 |
| 4 | 14.42° | 6.14 | 0.03 |
| 5 | 16.71° | 5.30 | 0.21 |
| 6 | 17.64° | 5.02 | 0.10 |
| 7 | 17 81° | 4.98 | 0.16 |
| 8 | 19.52° | 4.54 | 0.25 |
| 9 | 20.23° | 4.39 | 0.09 |
| 10 | 21.06° | 4.22 | 0.08 |
| 11 | 21.88° | 4.06 | 0.03 |
| 12 | 22.18° | 4.01 | 0.44 |
| 13 | 23.53° | 3.78 | 0.34 |
| 14 | 24.24° | 3.67 | 0.11 |
| 15 | 25.45° | 3.50 | 0.17 |
| 16 | 26.10° | 3.41 | 0.19 |
| 17 | 27.20° | 3.28 | 0.06 |
| 18 | 28.16° | 3.17 | 0.14 |
| 19 | 23.41° | 3.14 | 0.05 |
| 20 | 29.22° | 3.05 | 0.12 |
| 21 | 29.84° | 2.99 | 0.02 |
| 22 | 30.36° | 2.94 | 0.03 |
| 23 | 30.88° | 2.89 | 0.02 |

TABLE 24b

XRPD Peak data for hydrochloride pattern 3. (1 d.p.)

| Peak No. | Angle 2 θ | d Value | Rel. Intensity |
| --- | --- | --- | --- |
| 1 | 6.5° | 13.6 | 0.1 |
| 2 | 12.3° | 7.2 | 0.0 |
| 3 | 13.0° | 6.8 | 1.0 |
| 4 | 14.4° | 6.1 | 0.0 |
| 5 | 16.7° | 5.3 | 0.2 |
| 6 | 17.6° | 5.0 | 0.1 |
| 7 | 17.8° | 5.0 | 0.2 |
| 8 | 19.5° | 4.5 | 0.3 |
| 9 | 20.2° | 4.4 | 0.1 |
| 10 | 21.1° | 4.2 | 0.1 |
| 11 | 21.9° | 4.1 | 0.0 |
| 12 | 22.2° | 4.0 | 0.4 |
| 13 | 23.5° | 3.8 | 0.3 |
| 14 | 24.2° | 3.7 | 0.1 |
| 15 | 25.5° | 3.5 | 0.2 |
| 16 | 26.1° | 3.4 | 0.2 |
| 17 | 27.2° | 3.3 | 0.1 |
| 18 | 28.2° | 3.2 | 0.1 |
| 19 | 28.4° | 3.1 | 0.1 |
| 20 | 29.2° | 3.1 | 0.1 |
| 21 | 29.8° | 3.0 | 0.0 |
| 22 | 30.4° | 2.9 | 0.0 |
| 23 | 30.9° | 2.9 | 0.0 |

The pattern 3 material was analysed further by TGA and DSC. The TGA thermogram is shown in FIG. 155 and demonstrates that the material appears to be a solvated/hydrated form with gross decomposition starting at around 260° C. The DSC thermogram shown in FIG. 156 shows a large endothermic event with an onset of 49.0° C. which corresponds with the weight loss observed in the TGA.

There are no other significant thermal events observed apart from degradation.

The pattern 3 material was analysed by $^1$H NMR and this showed that the material was still a salt, and only contained a trace of dioxane and no methanol confirming it is not a solvated form. The $^1$H NMR spectrum is shown in FIG. 157. The weight loss in the TGA and lack of solvent in the $^1$H NMR suggest this material is a hydrated form.

In one embodiment, there is provided crystalline 5-MeO-DMT hydrochloride or a pharmaceutical composition comprising crystalline 5-MeO-DMT hydrochloride, as characterised by one or more of:

An XRPD pattern as shown in, or substantially as shown in, FIG. 154;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more or twenty three peaks in an XRPD diffractogram as detailed in Table 24, 24a or 24b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 24, 24a or 24b;

A TGA thermogram as shown in, or substantially as shown in, FIG. 155;

A DSC thermogram as shown in, or substantially as shown in, FIG. 156;

A large endothermic event with an onset of 49.0° C., as measured in a DSC thermogram;

A large endothermic event with an onset of 46-52° C., as measured in a DSC thermogram;

A large endothermic event with an onset of 46, 47, 48, 49, 50, 51 or 52° C., as measured in a DSC thermogram; and/or An $^1$H NMR spectrum as shown, or substantially as shown, in FIG. 157.

Evaporations of Hydrochloride Salt

Twelve samples of the lyophilised material were treated with a minimal volume (ca 0.5 ml) of warm solvent, syringe filtered through a 0.22 m filter and added to a clean HPLC vial and allowed to evaporate at RT. The solvents used and XRPD results following evaporation are detailed in the Table below:

Summary of Results from Evaporations of Hydrochloride Salt

| Experiment | Solvent | XRPD Results |
|---|---|---|
| DJP2202-011-01 | Ethylene glycol | Failed to evaporate fully |
| DJP2202-011-02 | 1-PrOH | Pattern 1 |
| DJP2202-011-03 | Water | Failed to evaporate fully |
| DJP2202-011-04 | MIBK | Insufficient material |
| DJP2202-011-05 | EtOH | Pattern 1 |
| DJP2202-011-06 | IPA | Pattern 1 |
| DJP2202-011-07 | THF | Insufficient material |
| DJP2202-011-08 | Dioxane | Insufficient material |
| DJP2202-011-09 | Chlorobenzene | Insufficient material |
| DJP2202-011-10 | IPAc | Insufficient material |
| DJP2202-011-11 | MEK | Pattern 1 |
| DJP2202-011-12 | MeCN | Oil |

The low solubility in many of the solvents meant that there was often insufficient solid for XRPD analysis. The XRPD diffractograms for the solids obtained can be seen in FIG. 158.

Example 5: Further Characterisation of 5-MeO-DMT Benzoate

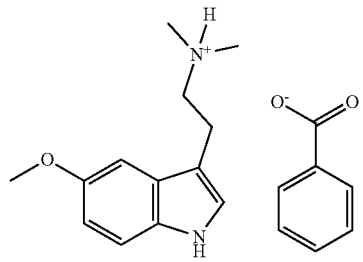

To render the amorphous and thus remove seeds of the supplied pattern 1 the supplied material was lyophilised in an attempt to render it amorphous. To 2.396 g of the supplied benzoate salt lot 800674000 dioxane (55 ml) and water (5 ml) was added. The mixture was agitated gently and warmed to aid dissolution. The clear solution was then divided equally between 60 HPLC vials (~40 mg salt in each vial) and the vials were then frozen at ~−18° C. overnight and then dried by lyophilisation overnight. One sample was analysed by XRPD and the diffractogram shown in FIG. 159 and shows this to be a new crystalline form, designated as pattern 2. The XRPD peak data is shown in the Tables 25, 25a or 25b below:

TABLE 25

XRPD Peak data for benzoate pattern 2

| Peak No. | Angle 2 θ | d Value | Rel. Intensity |
|---|---|---|---|
| 1 | 6.451° | 13.689 | 0.12 |
| 2 | 9.114° | 9.696 | 0.13 |
| 3 | 9.395° | 9.406 | 0.01 |
| 4 | 12.880° | 6.868 | 0.45 |
| 5 | 13.109° | 6.748 | 0.13 |
| 5 | 14.615° | 6.056 | 0.16 |
| 7 | 15.976° | 5.543 | 0.04 |
| 8 | 18.405° | 4.817 | 0.99 |
| 9 | 13.894° | 4.693 | 0.09 |
| 10 | 19.512° | 4.546 | 1.00 |
| 11 | 19.971° | 4.442 | 0.06 |
| 12 | 20.481° | 4.333 | 0.10 |
| 13 | 21.545° | 4.121 | 0.11 |
| 14 | 22.506° | 3.947 | 0.09 |
| 15 | 22.907° | 3.879 | 0.41 |
| 16 | 23.429° | 3.794 | 0.09 |
| 17 | 24.254° | 3.667 | 0.23 |
| 18 | 25.531° | 3.486 | 0.11 |
| 19 | 25.911° | 3.436 | 0.03 |
| 20 | 26.360° | 3.378 | 0.02 |
| 21 | 26.812° | 3.322 | 0.07 |
| 22 | 27.149° | 3.282 | 0.06 |
| 23 | 27.599° | 3.229 | 0.08 |
| 24 | 29.065° | 3.070 | 0.11 |
| 25 | 29.420° | 3.034 | 0.03 |
| 26 | 30.607° | 2.919 | 0.01 |
| 27 | 31.288° | 2.857 | 0.06 |

TABLE 25a

XRPD Peak data for benzoate pattern 2 (2 d.p.)

| Peak No. | Angle 2 θ | d Value | Rel. Intensity |
|---|---|---|---|
| 1 | 6.45° | 13.69 | 0.12 |
| 2 | 9.11° | 9.70 | 0.13 |
| 3 | 9.40° | 9.41 | 0.01 |
| 4 | 12.88° | 6.87 | 0.45 |
| 5 | 13.11° | 6.75 | 0.13 |
| 6 | 14.62° | 6.06 | 0.16 |
| 7 | 15.98° | 5.54 | 0.04 |
| 8 | 18.41° | 4.82 | 0.99 |
| 9 | 18.89° | 4.69 | 0.09 |
| 10 | 19.51° | 4.55 | 1.00 |
| 11 | 19.97° | 4.44 | 0.06 |
| 12 | 20.48° | 4.33 | 0.10 |
| 13 | 21.55° | 4.12 | 0.11 |
| 14 | 22.51° | 3.95 | 0.09 |
| 15 | 22.91° | 3.88 | 0.41 |
| 16 | 23.43° | 3.79 | 0.09 |
| 17 | 24.25° | 3.67 | 0.23 |
| 18 | 25.53° | 3.49 | 0.11 |
| 19 | 25.91° | 3.44 | 0.03 |
| 20 | 26.36° | 3.38 | 0.02 |
| 21 | 26.81° | 3.32 | 0.07 |
| 22 | 27.15° | 3.28 | 0.06 |
| 23 | 27.60° | 3.23 | 0.08 |
| 24 | 29.07° | 3.07 | 0.11 |
| 25 | 29.42° | 3.03 | 0.03 |
| 26 | 30.61° | 2.92 | 0.01 |
| 27 | 31.29° | 2.86 | 0.06 |

TABLE 25b

XRPD Peak data for benzoate pattern 2 (1 d.p.)

| Peak No. | Angle 2 θ | d Value | Rel. Intensity |
|---|---|---|---|
| 1 | 6.5° | 13.7 | 0.1 |
| 2 | 9.1° | 9.7 | 0.1 |
| 3 | 9.4° | 9.4 | 0.0 |
| 4 | 12.9° | 6.9 | 0.5 |
| 5 | 13.1° | 6.8 | 0.1 |
| 6 | 14.6° | 6.1 | 0.2 |
| 7 | 16.0° | 5.5 | 0.0 |
| 8 | 18.4° | 4.8 | 1.0 |
| 9 | 18.9° | 4.7 | 0.1 |
| 10 | 19.5° | 4.6 | 1.0 |
| 11 | 20.0° | 4.4 | 0.1 |
| 12 | 20.5° | 4.3 | 0.1 |
| 13 | 21.6° | 4.1 | 0.1 |
| 14 | 22.5° | 4.0 | 0.1 |
| 15 | 22.9° | 3.9 | 0.4 |
| 16 | 23.4° | 3.8 | 0.1 |
| 17 | 24.3° | 3.7 | 0.2 |
| 18 | 25.5° | 3.5 | 0.1 |
| 19 | 25.9° | 3.4 | 0.0 |
| 20 | 26.4° | 3.4 | 0.0 |
| 21 | 26.8° | 3.3 | 0.1 |
| 22 | 27.2° | 3.3 | 0.1 |
| 23 | 27.6° | 3.2 | 0.1 |
| 24 | 29.1° | 3.1 | 0.1 |
| 25 | 29.4° | 3.0 | 0.0 |
| 26 | 30.6° | 2.9 | 0.0 |
| 27 | 31.3° | 2.9 | 0.1 |

The samples were used in further experiments.

The pattern 2 material was analysed further by TGA and DSC and the TGA thermogram is shown in FIG. 160. This shows the material is non-hydrated non-solvated form and shows good thermal stability to ~170° C. The DSC thermogram is shown in FIG. 161 and shows two endothermic events very close to each other. The first has an onset of 119.6° C. and an enthalpy of 32.6 J/g and the second has an onset of 123.2° C. and an enthalpy of 34.5 J/g. It should be noted that the enthalpy values are probably under reported due to the integration algorithm, and that both of these endothermic events are at higher temperature compared to the pattern 1 material.

The material was analysed by $^1$H NMR and the spectrum (FIG. 162) confirmed that the material is non solvated and still the benzoate salt and not a free form. Only traces of dioxane, ~0.04 eq. were observed.

In one embodiment, there is provided crystalline 5-MeO-DMT benzoate or a pharmaceutical composition comprising crystalline 5-MeO-DMT benzoate, as characterised by one or more of:

An XRPD pattern as shown in, or substantially as shown in, FIG. 159;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more or twenty seven peaks in an XRPD diffractogram as detailed in Table 25, 25a or 25b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 25, 25a or 25b;

A TGA thermogram as shown in, or substantially as shown in, FIG. 160;

A DSC thermogram as shown in, or substantially as shown in, FIG. 161;

Two endothermic events very close to each other, the first having an onset of around 119.6° C. and an enthalpy of around 32.6 J/g and the second having an onset of around 123.2° C. and an enthalpy of around 34.5 J/g, as measured in a DSC thermogram;

Two endothermic events very close to each other, the first having an onset of around 117-122° C. and an enthalpy of around 30-33 J/g and the second having an onset of around 122-125° C. and an enthalpy of around 33-36 J/g, as measured in a DSC thermogram;

Two endothermic events very close to each other, the first having an onset of around 117, 118, 119, 120, 121 or 122° C. and an enthalpy of around 30, 31, 32 or 33 J/g and the second having an onset of around 122, 123, 124 or 125° C. and an enthalpy of around 33, 34, 35 or 36 J/g, as measured in a DSC thermogram; and/or An $^1$H NMR spectrum as shown, or substantially as shown, in FIG. 162.

Thermal Cycling of Benzoate Salt

Twenty five of the lyophilised samples were treated with solvent and thermally cycled between ambient and 40° C. with four hours spent under each condition. After three days and solids were isolated by centrifuge filtration and analysed by XRPD. Any solutions were allowed to evaporate at RT but this did not yield any new solids. The solvents, observations, isolation and XRPD results are summarised in the Table below:

Summary of thermal cycle of benzoate salt

| Experiment | Solvent | Volume added μl | Initial Observations | 3-day Observations | Isolation | XRPD Result |
|---|---|---|---|---|---|---|
| DJP2202-006-01 | 1,4-Dioxane | 200 | no change | solid mass | After thermal cycle | Pattern 3 |
| DJP2202-006-02 | 1-Propanol | 200 | no change | few crystals | After thermal cycle | Pattern 4 |
| DJP2202-006-03 | 2-Butanol | 200 | no change | few crystals | After thermal cycle | Pattern 4 |
| DJP2202-006-04 | 2-Ethoxyethanol | 200 | dissolved | clear solution | Evaporated to oil | n/a |
| DJP2202-006-05 | 2-Methyltetrahydrofuran | 200 | no change | few crystals | After thermal cycle | Pattern 4 |
| DJP2202-006-06 | 2-Propanol | 200 | no change | few crystals | After thermal cycle | Pattern 4 |
| DJP2202-006-07 | Acetone | 200 | no change | few crystals | After thermal cycle | Pattern 4 |
| DJP2202-006-08 | Acetonitrile | 200 | no change | lump of material | After thermal cycle | Pattern 4 |
| DJP2202-006-09 | Anisole | 200 | no change | lump of material | After thermal cycle | Pattern 4 |
| DJP2202-006-10 | Chlorobenzene | 200 | no change | white solid | After thermal cycle | Pattern 4 + extra peaks |
| DJP2202-006-11 | Ethanol | 150 | no change | white solid | After thermal cycle | Pattern 4 |
| DJP2202-006-12 | Ethyl acetate | 200 | no change | white solid | After thermal cycle | Pattern 4 |
| DJP2202-006-13 | Isopropyl acetate | 200 | no change | white solid | After thermal cycle | Pattern 4 |
| DJP2202-006-14 | Methanol | 200 | dissolved | clear solution | Evaporated to solid | Pattern 1 |
| DJP2202-006-15 | Propyl acetate | 200 | no change | white solid | After thermal cycle | Pattern 4 |
| DJP2202-006-16 | Methylethyl ketone | 200 | no change | white crystals | After thermal cycle | Pattern 4 |
| DJP2202-006-17 | Formamide | 150 | dissolved | few crystals | After thermal cycle | Pattern 4 |
| DJP2202-006-18 | N,N-Dimethylacetamide | 200 | dissolved | clear solution | Evaporated-no solid | n/a |
| DJP2202-006-19 | N-Methylpyrrolidone | 200 | no change | clear solution | Evaporated-no solid | n/a |
| DJP2202-006-20 | iso-Propyl acetate | 200 | no change | few crystals | After thermal cycle | Pattern 4 |
| DJP2202-006-21 | 2-Me-1-PrOH | 200 | no change | few crystals | After thermal cycle | Pattern 4 |
| DJP2202-006-22 | Tetrahydrofuran | 200 | no change | few crystals | After thermal cycle | Pattern 4 |
| DJP2202-006-23 | MeOH/water 953/47 Calc Aw 0.214 | 200 | dissolved | clear solution | Evaporated to oil | n/a |
| DJP2202-006-24 | MeOH/water 693/307 Calc Aw 0.599 | 200 | dissolved | clear solution | Evaporated to solid | Pattern 1 |
| DJP2202-006-25 | MeOH/water 360/640 Calc Aw 0.821 | 200 | dissolved | clear solution | Evaporated to solid | Pattern 1 |

The XRPD for the new pattern 3 is shown in FIG. 164 compared to the supplied pattern 1 and pattern 2. The XRPD peak data is shown in the Tables 26, 26a or 26b below:

TABLE 26

XRPD Peak pick of Benzoate pattern 3

| Peak No. | Angle 2 θ | d Value | Rel. Intensity |
|---|---|---|---|
| 1 | 5.193° | 17.002 | 0.29 |
| 2 | 6.122° | 14.426 | 0.33 |
| 3 | 9.563° | 9.241 | 0.01 |
| 4 | 10.220° | 8.649 | 0.03 |
| 5 | 11.373° | 7.774 | 0.03 |
| 6 | 14.018° | 6.313 | 0.01 |
| 7 | 14.806° | 5.979 | 0.02 |
| 8 | 15.320° | 5.779 | 0.16 |

TABLE 26-continued

XRPD Peak pick of Benzoate pattern 3

| Peak No. | Angle 2 θ | d Value | Rel. Intensity |
|---|---|---|---|
| 9 | 18.254° | 4.856 | 0.93 |
| 10 | 19.260° | 4.605 | 0.12 |
| 11 | 20.450° | 4.339 | 1.00 |
| 12 | 22.663° | 3.920 | 0.02 |
| 13 | 23.666° | 3.756 | 0.04 |
| 14 | 24.400° | 3.645 | 0.18 |
| 15 | 25.593° | 3.478 | 0.08 |
| 16 | 26.232° | 3.395 | 0.01 |
| 17 | 27.407° | 3.252 | 0.01 |
| 18 | 29.826° | 2.993 | 0.01 |
| 19 | 30.812° | 2.900 | 0.01 |

TABLE 26a

XRPD Peak pick of Benzoate pattern 3. (2 d.p.)

| Peak No. | Angle 2 θ | d Value | Rel. Intensity |
| --- | --- | --- | --- |
| 1 | 5.19° | 17.00 | 0.29 |
| 2 | 6.12° | 14.43 | 0.33 |
| 3 | 9.56° | 9.24 | 0.01 |
| 4 | 10.22° | 8.65 | 0.03 |
| 5 | 11.37° | 7.77 | 0.03 |
| 6 | 14.02° | 6.31 | 0.01 |
| 7 | 14.81° | 5.98 | 0.02 |
| 8 | 15.32° | 5.78 | 0.16 |
| 9 | 18.25° | 4.86 | 0.93 |
| 10 | 19.26° | 4.61 | 0.12 |
| 11 | 20.45° | 4.34 | 1.00 |
| 12 | 22.66° | 3.92 | 0.02 |
| 13 | 23.67° | 3.76 | 0.04 |
| 14 | 24.40° | 3.65 | 0.18 |
| 15 | 25.59° | 3.48 | 0.08 |
| 16 | 26.23° | 3.40 | 0.01 |
| 17 | 27.41° | 3.25 | 0.01 |
| 18 | 29.83° | 2.99 | 0.01 |
| 19 | 30.81° | 2.90 | 0.01 |

TABLE 26b

XRPD Peak pick of Benzoate pattern 3. (1 d.p.)

| Peak No. | Angle 2 θ | d Value | Rel. Intensity |
| --- | --- | --- | --- |
| 1 | 5.2° | 17.0 | 0.3 |
| 2 | 6.1° | 14.4 | 0.3 |
| 3 | 9.6° | 9.2 | 0.0 |
| 4 | 10.2° | 8.7 | 0.0 |
| 5 | 11.4° | 7.8 | 0.0 |
| 6 | 14.0° | 6.3 | 0.0 |
| 7 | 14.8° | 6.0 | 0.0 |
| 8 | 15.3° | 5.8 | 0.2 |
| 9 | 18.3° | 4.9 | 0.9 |
| 10 | 19.3° | 4.6 | 0.1 |
| 11 | 20.5° | 4.3 | 1.0 |
| 12 | 22.7° | 3.9 | 0.0 |
| 13 | 23.7° | 3.3 | 0.0 |
| 14 | 24.4° | 3.7 | 0.2 |
| 15 | 25.6° | 3.5 | 0.1 |
| 16 | 26.2° | 3.4 | 0.0 |
| 17 | 27.4° | 3.3 | 0.0 |
| 18 | 29.8° | 3.0 | 0.0 |
| 19 | 30.8° | 2.9 | 0.0 |

The new pattern 3 material was analysed further by TGA and DSC. The TGA thermogram is shown in FIG. 164 and shows an initial loss of 9.77% which would equate to 0.42 eq of dioxane. The material then undergoes complete mass loss starting at approximately 190° C. The DSC thermogram is shown in FIG. 165. This shows a single endothermic event with an onset of 123.2° C., which is similar to the second thermal event observed in the pattern 2 material.

The material was analysed further by $^1$H NMR and the spectrum is shown in FIG. 166. This shows the material is still the benzoate salt, but also shows ~1.22 eq of dioxane indicating this is probably a solvated form of the material.

In one embodiment, there is provided crystalline 5-MeO-DMT benzoate or a pharmaceutical composition comprising crystalline 5-MeO-DMT benzoate, as characterised by one or more of:
  An XRPD pattern as shown in, or substantially as shown in, FIG. 163;
  One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more or nineteen peaks in an XRPD diffractogram as detailed in Table 26, 26a or 26b;
  One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 26, 26a or 26b;
  A TGA thermogram as shown in, or substantially as shown in, FIG. 164;
  A DSC thermogram as shown in, or substantially as shown in, FIG. 165;
  A single endothermic event with an onset of around 123.2° C., as measured in a DSC thermogram;
  A single endothermic event with an onset of around 120-125° C., as measured in a DSC thermogram;
  A single endothermic event with an onset of around 120, 121, 122, 123, 124 or 125° C., as measured in a DSC thermogram; and/or
  An $^1$H NMR spectrum as shown, or substantially as shown, in FIG. 166.

The XRPD for the new pattern 4 is shown in FIG. 167 compared to the supplied pattern 1, pattern 2 and pattern 3. The XRPD peak data is shown in the Tables below:

TABLE 27

XRPD Peak pick of benzoate pattern 4

| Peak No. | Angle 2 θ | d Value | Rel. Intensity |
| --- | --- | --- | --- |
| 1 | 8.761° | 10.085 | 0.06 |
| 2 | 9.053° | 9.760 | 1.00 |
| 3 | 10.763° | 8.213 | 0.04 |
| 4 | 11.411° | 7.748 | 0.10 |
| 5 | 12.275° | 7.205 | 0.08 |
| 6 | 14.401° | 6.146 | 0.02 |
| 7 | 16.154° | 5.482 | 0.15 |
| 8 | 16.409° | 5.398 | 0.14 |
| 9 | 17.439° | 5.081 | 0.39 |
| 10 | 17.745° | 4.994 | 0.11 |
| 11 | 18.029° | 4.916 | 0.03 |
| 12 | 18.387° | 4.821 | 0.22 |
| 13 | 20.033° | 4.429 | 0.04 |
| 14 | 20.514° | 4.326 | 0.01 |
| 15 | 20.823° | 4.262 | 0.29 |
| 16 | 21.519° | 4.126 | 0.02 |
| 17 | 21.783° | 4.077 | 0.02 |
| 18 | 22.116° | 4.016 | 0.01 |
| 19 | 22.738° | 3.908 | 0.20 |
| 20 | 23.039° | 3.857 | 0.03 |
| 21 | 24.222° | 3.672 | 0.01 |
| 22 | 24.640° | 3.610 | 0.18 |
| 23 | 25.215° | 3.529 | 0.21 |
| 24 | 26.134° | 3.407 | 0.01 |
| 25 | 26.371° | 3.377 | 0.04 |
| 26 | 27.153° | 3.281 | 0.10 |
| 27 | 28.203° | 3.162 | 0.03 |
| 28 | 28.730° | 3.105 | 0.02 |
| 29 | 30.215° | 2.955 | 0.06 |
| 30 | 30.822° | 2.899 | 0.02 |
| 31 | 31.411° | 2.846 | 0.01 |
| 32 | 31.695° | 2.821 | 0.01 |

TABLE 27a

XRPD Peak pick of benzoate pattern 4. (2 d.p.)

| Peak No. | Angle 2 θ | d Value | Rel. Intensity |
| --- | --- | --- | --- |
| 1 | 8.76° | 10.09 | 0.06 |
| 2 | 9.05° | 9.76 | 1.00 |
| 3 | 10.76° | 8.21 | 0.04 |
| 4 | 11.41° | 7.75 | 0.10 |
| 5 | 12.28° | 7.21 | 0.08 |

TABLE 27a-continued

XRPD Peak pick of benzoate pattern 4. (2 d.p.)

| Peak No. | Angle 2 θ | d Value | Rel. Intensity |
|---|---|---|---|
| 6 | 14.40° | 6.15 | 0.02 |
| 7 | 16.15° | 5.48 | 0.15 |
| 8 | 16.41° | 5.40 | 0.14 |
| 9 | 17.44° | 5.08 | 0.39 |
| 10 | 17.75° | 4.99 | 0.11 |
| 11 | 18.03° | 4.92 | 0.03 |
| 12 | 18.39° | 4.82 | 0.22 |
| 13 | 20.03° | 4.43 | 0.04 |
| 14 | 20.51° | 4.33 | 0.01 |
| 15 | 20.82° | 4.26 | 0.29 |
| 16 | 21.52° | 4.13 | 0.02 |
| 17 | 21.78° | 4.08 | 0.02 |
| 18 | 22.12° | 4.02 | 0.01 |
| 19 | 22.74° | 3.91 | 0.20 |
| 20 | 23.04° | 3.86 | 0.03 |
| 21 | 24.22° | 3.67 | 0.01 |
| 22 | 24.64° | 3.61 | 0.18 |
| 23 | 25.22° | 3.53 | 0.21 |
| 24 | 26.13° | 3.41 | 0.01 |
| 25 | 26.37° | 3.38 | 0.04 |
| 26 | 27.15° | 3.28 | 0.10 |
| 27 | 28.20° | 3.16 | 0.03 |
| 28 | 28.73° | 3.11 | 0.02 |
| 29 | 30.22° | 2.96 | 0.06 |
| 30 | 30.82° | 2.90 | 0.02 |
| 31 | 31.41° | 2.85 | 0.01 |
| 32 | 31.70° | 2.82 | 0.01 |

TABLE 27b

XRPD Peak pick of benzoate pattern 4. (1 d.p.)

| Peak No. | Angle 2 θ | d Value | Rel. Intensity |
|---|---|---|---|
| 1 | 8.8° | 10.1 | 0.1 |
| 2 | 9.1° | 9.8 | 1.0 |
| 3 | 10.8° | 8.2 | 0.0 |
| 4 | 11.4° | 7.8 | 0.1 |
| 5 | 12.3° | 7.2 | 0.1 |
| 6 | 14.4° | 6.2 | 0.0 |
| 7 | 16.2° | 5.5 | 0.2 |
| 8 | 16.4° | 5.4 | 0.1 |
| 9 | 17.4° | 5.1 | 0.4 |
| 10 | 17.8° | 5.0 | 0.1 |
| 11 | 18.0° | 4.9 | 0.0 |
| 12 | 18.4° | 4.8 | 0.2 |
| 13 | 20.0° | 4.4 | 0.0 |
| 14 | 20.5° | 4.3 | 0.0 |
| 15 | 20.8° | 4.3 | 0.3 |
| 16 | 21.5° | 4.1 | 0.0 |
| 17 | 21.8° | 4.1 | 0.0 |
| 18 | 22.1° | 4.0 | 0.0 |
| 19 | 22.7° | 3.9 | 0.2 |
| 20 | 23.0° | 3.9 | 0.0 |
| 21 | 24.2° | 3.7 | 0.0 |
| 22 | 24.6° | 3.6 | 0.2 |
| 23 | 25.2° | 3.5 | 0.2 |
| 24 | 26.1° | 3.4 | 0.0 |
| 25 | 26.4° | 3.4 | 0.0 |
| 26 | 27.2° | 3.3 | 0.1 |
| 27 | 28.2° | 3.2 | 0.0 |
| 28 | 28.7° | 3.1 | 0.0 |
| 29 | 30.2° | 3.0 | 0.1 |
| 30 | 30.8° | 2.9 | 0.0 |
| 31 | 31.4° | 2.9 | 0.0 |
| 32 | 31.7° | 2.8 | 0.0 |

The new pattern 4 material was analysed further by TGA and DSC. The TGA thermogram is shown in FIG. 168 and shows the material to be an anhydrous non solvated form with good thermal stability to ~190°. The material then undergoes complete mass loss starting at approximately 190° C. The DSC thermogram is shown in FIG. 169. This shows a single endothermic event with an onset of 123.4° C., which is similar to the second thermal event observed in the pattern 2 material.

The material was analysed further by $^1$H NMR and the spectrum is shown in FIG. 170. This shows the material is still the benzoate salt and only shows trace amounts of the process solvent (2-BuOH).

In one embodiment, there is provided crystalline 5-MeO-DMT benzoate or a pharmaceutical composition comprising crystalline 5-MeO-DMT benzoate, as characterised by one or more of:

An XRPD pattern as shown in, or substantially as shown in, FIG. 167;

One or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more or thirty two peaks in an XRPD diffractogram as detailed in Table 27, 27a or 27b;

One or more, two or more, three or more, four or more or five or more peaks in an XRPD diffractogram with a relative intensity of over 0.1, 0.2, 0.3, 0.4, 0.5, 0.6, 0.7, 0.8 or 0.9 as detailed in Table 27, 27a or 267;

A TGA thermogram as shown in, or substantially as shown in, FIG. 168;

A DSC thermogram as shown in, or substantially as shown in, FIG. 169;

A single endothermic event with an onset of around 123.4° C., as measured in a DSC thermogram;

A single endothermic event with an onset of around 120-125° C., as measured in a DSC thermogram;

A single endothermic event with an onset of around 120, 121, 122, 123, 124 or 125° C., as measured in a DSC thermogram; and/or An $^1$H NMR spectrum as shown, or substantially as shown, in FIG. 170.

Evaporations of Benzoate Salt

Twelve samples of the lyophilised material were treated with a minimal volume (ca 0.5 ml) of warm solvent, syringe filtered through a 0.22 micrometre filter and added to a clean HPLC vial and allowed to evaporate at RT. The solvents used and XRPD results following evaporation are detailed in the Table below:

Summary of Results from Evaporations of Benzoate Salt

| Experiment | Solvent | XRPD Result |
|---|---|---|
| DJP2202-010-01 | Ethylene glycol | Failed to evaporate fully |
| DJP2202-010-02 | 1-PrOH | Oil |
| DJP2202-010-03 | Water | Failed to evaporate fully |
| DJP2202-010-04 | MIBK | Oil |
| DJP2202-010-05 | EtOH | Oil |
| DJP2202-010-06 | IPA | Pattern 4 |
| DJP2202-010-07 | THF | Pattern 4 |
| DJP2202-010-08 | dioxane | Pattern 4 |

| Experiment | Solvent | XRPD Result |
|---|---|---|
| DJP2202-010-09 | chlorobenzene | Pattern 4 |
| DJP2202-010-10 | IPAc | Pattern 2 |
| DJP2202-010-11 | MEK | Pattern 4 |
| DJP2202-010-12 | MeCN | Pattern 4 |

Antisolvent Additions of Benzoate Salt

For antisolvent additions thirteen samples of the lyophilised material were dissolved in a small amount of hot solvent (~0.5 ml). Extra supplied material, ca 30 mg was added to each and the clear solution was syringe filtered through a 0.22 µm filter into a 20 ml scintillation vial. A large excess of antisolvent was then added, the vials sealed. After storage at RT overnight, and samples where no solid had been produced were first cooled to 4° C. for ~24 hrs, and again if no solid was produced, they were cooled to −18° C. Any solids were isolated by centrifuge filtration and analysed by XRPD. The solvents, antisolvents, isolation conditions and XRPD results are summarised in the Table below:

Summary of Results from Antisolvent Additions of Benzoate Salt

| Experiment | Solvent | Anti Solvent | Observations | XRPD Results |
|---|---|---|---|---|
| DJP2202-012-01 | MeOH/water Aw 0.2 | MeOH | Cooled −18 C. | No solid |
| DJP2202-012-02 | MeOH | TBME | Cooled −18 C. | No solid |
| DJP2202-012-03 | EtOH | TBME | Cooled −18 C. | No solid |
| DJP2202-012-04 | EtOH | Heptane | Some solid at RT | Pattern 1 |
| DJP2202-012-05 | THF | TBME | Cooled −18 C. | No solid |
| DJP2202-012-06 | dioxane | TBME | Cooled −18 C. | No solid |
| DJP2202-012-07 | DMF | PhMe | Cooled −18 C. | No solid |
| DJP2202-012-08 | IPAc | TBME | Cooled −18 C. | No solid |
| DJP2202-012-09 | MEK | TBME | Cooled −18 C. | No solid |
| DJP2202-012-10 | MEK | Heptane | Some solid at RT | Pattern 2 |
| DJP2202-012-11 | MeCN | TBME | Cooled −18 C. | No solid |
| DJP2202-012-12 | MeCN | PhMe | Some solid at RT | Pattern 4 |

Cooling of Benzoate Salt

For the cooling experiments twelve samples of the lyophilised material were dissolved in a small amount of hot solvent (~0.5 m) and syringe filtered through a 0.22 µm filter into a clean HPLC vial. Samples were allowed to cool to RT, and if no solid was produced to 4° C. and then to −18° C. Solids were isolated by centrifuge filtration and analysed by XRPD. The solvents, isolation conditions and XRPD results are summarised in the Table below:

Summary of Results from Cooling Experiments of Benzoate Salt

| Experiment | Solvent | Observations | XRPD Results |
|---|---|---|---|
| DJP2202-013-01 | MeOH/water Aw 0.2 | Cooled −18 C. | Pattern 4 |
| DJP2202-013-02 | MeOH/water Aw 0.6 | Cooled −18 C. | no solids |
| DJP2202-013-03 | Water | Cooled −18 C. | Pattern 4 |
| DJP2202-013-04 | MeOH | Cooled −18 C. | no solids |
| DJP2202-013-05 | EtOH | Solid at RT | Pattern 4 |
| DJP2202-013-06 | IPA | Solid at RT | Pattern 4 |
| DJP2202-013-07 | THF | Solid at RT | Pattern 4 |
| DJP2202-013-08 | dioxane | Solid at RT | Pattern 3 |
| DJP2202-013-09 | chlorobenzene | Solid at RT | Looks like mix #4 #2 |
| DJP2202-013-10 | IPAc | Solid at RT | Pattern 4 |
| DJP2202-013-11 | MEK | Solid at RT | Pattern 2 |
| DJP2202-013-12 | MeCN | Solid at RT | Pattern 4 |

Example 6: Solubility Experiments

Solubility assessments of 5-MeO-DMT oxalate, hydrobromide fumarate and benzoate were performed in four different media:

| Media | 100 mM buffer |
|---|---|
| SNF | Sodium chloride/Calcium chloride/Potassium chloride |
| pH 1.2 buffer | Potassium chloride/Hydrochloric acid |
| pH 4.5 buffer | Sodium acetate/Acetic acid |
| pH 6.8 buffer | Sodium phosphate dibasic/Potassium dihydrogen phosphate |

Oxalate Salt (DXD2203-013-02) 250 mg per vial results

| Media | pH after addition of 1.5 ml media at 37° C. | Observation |
|---|---|---|
| SNF | 2.13 | Suspension |
| pH 1.2 | 1.87 | Suspension |
| pH 4.5 | 3.05 | Suspension |
| pH 6.8 | 3.45 | Suspension |

Hydrobromide Salt (DXD2203-014-01) 250 mg per vial results

| Media | pH after addition of 1.0 ml media at 37° C. | Observation |
|---|---|---|
| SNF | 8.13 | Clear solution |
| pH 1.2 | 8.09 | Clear solution |
| pH 4.5 | 7.65 | Clear solution |
| pH 6.8 | 7.82 | Clear solution |

The hydrobromide salt has a solubility of, at least, 250 mg/ml.

Fumarate Salt (DXD2203-015-03) 250 mg per vial results

| Media | pH after addition of 1.0 ml media at 37° C. | Observation |
|---|---|---|
| SNF | 5.14 | Clear solution |
| pH 1.2 | 5.24 | Clear solution |
| pH 4.5 | 5.31 | Clear solution |
| pH 6.8 | 5.79 | Clear solution |

The fumarate salt has a solubility of, at least, 250 mg/ml.

Benzoate Salt (21/32/68/FP1) 50 mg per vial results

| Media | pH after addition of 0.5 ml media at 37° C. | Observation |
|---|---|---|
| SNF | 6.77 | Clear solution |
| pH 1.2 | 5.28 | Clear solution |

-continued

| Media | pH after addition of 0.5 ml media at 37° C. | Observation |
|---|---|---|
| pH 4.5 | 5.22 | Clear solution |
| pH 6.8 | 6.82 | Clear solution |

The benzoate salt has a solubility of, at least, 100 mg/ml.
The calibration curve of the free base was prepared between 0.031-0.500 mg/ml and can be seen in FIG. 172.

Oxalate Salt Solubility by HPLC

Mother liquors were adjusted to the desired pH before HPLC quantification.

| Media | Solubility (mg/ml) of free base |
|---|---|
| SNF | 20.22 |
| pH 12. | 19.02 |
| pH 4.5 | 35.53 |
| pH 6.8 | 26.85 |

Isolated solids were analyzed by XRPD and no change in form was observed.

CLAUSES

1. A non-hygroscopic salt of 5-MeO-DMT wherein the non-hygroscopic salt is 5-MeO-DMT hydrobromide.
2. A crystalline form of the non-hygroscopic salt of clause 1.
3. A crystalline form of the non-hygroscopic salt of clause 1, characterised by peaks in an XRPD diffractogram at 14.6, 16.8, 20.8, 24.3, 24.9 and 27.5° 2θ±0.1° 2θ as measured by x-ray powder diffraction using an x-ray wavelength of 1.5406 Å.
4. A crystalline form of the non-hygroscopic salt of clause 1, characterised by peaks in an XRPD diffractogram at 14.6, 21.6 and 24.3° 2θ±0.1° 2θ as measured by x-ray powder diffraction using an x-ray wavelength of 1.5406 Å.
5. A crystalline form of the non-hygroscopic salt of clause 1, characterised by peaks in an XRPD diffractogram at 18.6, 19.7 and 24.8° 2θ±0.1° 2θ as measured by x-ray powder diffraction using an x-ray wavelength of 1.5406 Å.
6. The crystalline form of the non-hygroscopic salt of clause 4, characterised by peaks in an XRPD diffractogram at 14.6, 20.8, 21.6, 24.3 and 25.4*2 θ±0.1° 2θ as measured by x-ray powder diffraction using an x-ray wavelength of 1.5406 Å.
7. A pharmaceutical composition comprising the non-hygroscopic salt of 5-MeO-DMT of clause 1.
8. A pharmaceutical composition comprising the crystalline form of the non-hygroscopic salt of 5-MeO-DMT of any one of clauses 3 to 6.
9. The pharmaceutical composition of clause 7 for use as a medicament.
10. The pharmaceutical composition of clause 8 for use as a medicament.
11. 5-MeO-DMT phosphate.
12. A crystalline form of the 5-MeO-DMT phosphate of clause 11.
13. A crystalline form of the 5-MeO-DMT phosphate of clause 11, characterised by peaks in an XRPD diffractogram at 12.9, 20.4 and 23.1° 2θ±0.1° 2θ as measured by x-ray powder diffraction using an x-ray wavelength of 1.5406 Å.
14. The crystalline form of the 5-MeO-DMT phosphate of clause 13, characterised by peaks in an XRPD diffractogram at 12.9, 14.4, 19.3, 20.4 and 23.1° 2θ±0.1° 2θ as measured by x-ray powder diffraction using an x-ray wavelength of 1.5406 Å.
15. A pharmaceutical composition comprising the 5-MeO-DMT phosphate of clause 11.
16. A pharmaceutical composition comprising the crystalline form of 5-MeO-DMT phosphate of clause 13 or clause 14.
17. The pharmaceutical composition of clause 15 for use as a medicament.
18. The pharmaceutical composition of clause 16 for use as a medicament.
19. 5-MeO-DMT fumarate.
20. A crystalline form of the 5-MeO-DMT fumarate of clause 19.
21. A crystalline form of the 5-MeO-DMT fumarate of clause 19, characterised by peaks in an XRPD diffractogram at 13.0, 16.3 and 22.1° 2θ±0.1° 2θ as measured by x-ray powder diffraction using an x-ray wavelength of 1.5406 Å.
22. A crystalline form of the 5-MeO-DMT fumarate of clause 21, characterised by peaks in an XRPD diffractogram at 13.0, 16.3, 19.2, 20.4 and 22.1° 2 θ±0.1° 2θ as measured by x-ray powder diffraction using an x-ray wavelength of 1.5406 Å.
23. A pharmaceutical composition comprising the 5-MeO-DMT fumarate of clause 19.
24. A pharmaceutical composition comprising the crystalline form of 5-MeO-DMT fumarate of clause 21 or clause 22.
25. The pharmaceutical composition of clause 23 for use as a medicament.
26. The pharmaceutical composition of clause 24 for use as a medicament.
27. 5-MeO-DMT oxalate.
28. A crystalline form of the 5-MeO-DMT oxalate of clause 27.
29. A crystalline form of the 5-MeO-DMT oxalate of clause 28, characterised by peaks in an XRPD diffractogram at 13.0, 19.9 and 26.0° 2 θ±0.1° 2θ as measured by x-ray powder diffraction using an x-ray wavelength of 1.5406 Å.
30. A crystalline form of the 5-MeO-DMT oxalate of clause 29, characterised by peaks in an XRPD diffractogram at 13.0, 14.0, 19.9, 22.0 and 26.0° 2θ±0.1° 2θ as measured by x-ray powder diffraction using an x-ray wavelength of 1.5406 Å.
31. A pharmaceutical composition comprising the 5-MeO-DMT oxalate of clause 27.
32. A pharmaceutical composition comprising the crystalline form of 5-MeO-DMT oxalate of clause 29 or clause 30.
33. The pharmaceutical composition of clause 31 for use as a medicament.
34. The pharmaceutical composition of clause 32 for use as a medicament.
35. 5-MeO-DMT tartrate.
36. A crystalline form of the 5-MeO-DMT tartrate of clause 35.
37. A crystalline form of the 5-MeO-DMT tartrate of clause 35, characterised by peaks in an XRPD diffractogram at 18.3, 18.6, and 20.7° 2 θ±0.1° 2θ as measured by x-ray powder diffraction using an x-ray wavelength of 1.5406 Å.

38. A crystalline form of the 5-MeO-DMT tartrate of clause 35, characterised by peaks in an XRPD diffractogram at 18.3, 18.6, 18.8, 20.3 and 20.7° 2θ±0.1° 2θ as measured by x-ray powder diffraction using an x-ray wavelength of 1.5406 Å.

39. A pharmaceutical composition comprising the 5-MeO-DMT tartrate of clause 35.

40. A pharmaceutical composition comprising the crystalline form of 5-MeO-DMT tartrate of clause 37 or clause 38.

41. The pharmaceutical composition of clause 39 for use as a medicament.

42. The pharmaceutical composition of clause 40 for use as a medicament.

43. 5-MeO-DMT benzenesulfonate.

44. A crystalline form of the 5-MeO-DMT benzenesulfonate of clause 43.

45. A crystalline form of the 5-MeO-DMT benzenesulfonate of clause 44, characterised by peaks in an XRPD diffractogram at 9.5, 21.2, and 23.6° 2θ±0.1° 2θ as measured by x-ray powder diffraction using an x-ray wavelength of 1.5406 Å.

46. A crystalline form of the 5-MeO-DMT benzenesulfonate of clause 45, characterised by peaks in an XRPD diffractogram at 9.5, 18.0, 21.2, 23.6 and 24.4° 2θ±0.1° 2θ as measured by x-ray powder diffraction using an x-ray wavelength of 1.5406 Å.

47. A pharmaceutical composition comprising the 5-MeO-DMT benzenesulfonate of clause 43.

48. A pharmaceutical composition comprising the crystalline form of 5-MeO-DMT benzenesulfonate of clause 45 or clause 46.

49. The pharmaceutical composition of clause 47 for use as a medicament.

50. The pharmaceutical composition of clause 48 for use as a medicament.

51. 5-MeO-DMT tosylate.

52. A crystalline form of the 5-MeO-DMT tosylate of clause 51.

53. A crystalline form of the 5-MeO-DMT tosylate of clause 51, characterised by peaks in an XRPD diffractogram at 19.3, 23.6 and 24.1° 2θ±0.1° 2θ as measured by x-ray powder diffraction using an x-ray wavelength of 1.5406 Å.

54. A crystalline form of the 5-MeO-DMT tosylate of clause 51, characterised by peaks in an XRPD diffractogram at 13.8, 19.3, 23.6, 24.1 and 27.3° 2 θ±0.1° 2θ as measured by x-ray powder diffraction using an x-ray wavelength of 1.5406 Å.

55. A pharmaceutical composition comprising the 5-MeO-DMT tosylate of clause 51.

56. A pharmaceutical composition comprising the crystalline form of 5-MeO-DMT tosylate of clause 53 or clause 54.

57. The pharmaceutical composition of clause 55 for use as a medicament.

58. The pharmaceutical composition of clause 56 for use as a medicament.

59. 5-MeO-DMT glycolate.

60. A crystalline form of the 5-MeO-DMT glycolate of clause 59.

61. A crystalline form of the 5-MeO-DMT glycolate of clause 59, characterised by peaks in an XRPD diffractogram at 20.2, 21.1 and 23.4'2θ±0.1° 2θ as measured by x-ray powder diffraction using an x-ray wavelength of 1.5406 Å.

62. A crystalline form of the 5-MeO-DMT glycolate of clause 61, characterised by peaks in an XRPD diffractogram at 10.1, 20.2, 21.1, 23.4 and 24.3° 2θ±0.1° 2θ as measured by x-ray powder diffraction using an x-ray wavelength of 1.5406 Å.

63. A pharmaceutical composition comprising the 5-MeO-DMT glycolate of clause 59.

64. A pharmaceutical composition comprising the crystalline form of 5-MeO-DMT glycolate of clause 61 or clause 62.

65. The pharmaceutical composition of clause 63 for use as a medicament.

66. The pharmaceutical composition of clause 64 for use as a medicament.

67. 5-MeO-DMT ketoglutarate.

68. A crystalline form of the 5-MeO-DMT ketoglutarate of clause 67.

69. A crystalline form of the 5-MeO-DMT ketoglutarate of clause 67, characterised by peaks in an XRPD diffractogram at 14.4, 18.2 and 20.9° 2θ±0.1° 2θ as measured by x-ray powder diffraction using an x-ray wavelength of 1.5406 Å.

70. A crystalline form of the 5-MeO-DMT ketoglutarate of clause 69, characterised by peaks in an XRPD diffractogram at 14.4, 18.2, 20.9, 22.5 and 25.6° 2θ±0.1° 2θ as measured by x-ray powder diffraction using an x-ray wavelength of 1.5406 Å.

71. A pharmaceutical composition comprising the 5-MeO-DMT ketoglutarate of clause 67.

72. A pharmaceutical composition comprising the crystalline form of 5-MeO-DMT ketoglutarate of clause 69 or clause 70.

73. The pharmaceutical composition of clause 71 for use as a medicament.

74. The pharmaceutical composition of clause 72 for use as a medicament.

75. 5-MeO-DMT malate.

76. A crystalline form of the 5-MeO-DMT malate of clause 75.

77. A crystalline form of the 5-MeO-DMT malate of clause 75, characterised by peaks in an XRPD diffractogram at 18.3, 18.7 and 18.9° 2θ±0.1° 2θ as measured by x-ray powder diffraction using an x-ray wavelength of 1.5406 Å.

78. A crystalline form of the 5-MeO-DMT malate of clause 77, characterised by peaks in an XRPD diffractogram at 18.3, 18.7, 18.9, 21.6 and 26.1° 2θ±0.1° 2θ as measured by x-ray powder diffraction using an x-ray wavelength of 1.5406 Å.

79. A pharmaceutical composition comprising the 5-MeO-DMT malate of clause 75.

80. A pharmaceutical composition comprising the crystalline form of 5-MeO-DMT malate of clause 77 or clause 78.

81. The pharmaceutical composition of clause 79 for use as a medicament.

82. The pharmaceutical composition of clause 80 for use as a medicament.

83. 5-MeO-DMT saccharinate.

84. A crystalline form of the 5-MeO-DMT saccharinate of clause 83.

85. A crystalline form of the 5-MeO-DMT saccharinate of clause 83, characterised by peaks in an XRPD diffractogram at 8.7, 15.2 and 20.9° 2θ±0.1° 2θ as measured by x-ray powder diffraction using an x-ray wavelength of 1.5406 Å.

86. A crystalline form of the 5-MeO-DMT saccharinate of clause 85, characterised by peaks in an XRPD diffractogram at 5.2, 8.7, 15.0, 15.2 and 20.9'20±0.1° 2θ as measured by x-ray powder diffraction using an x-ray wavelength of 1.5406 Å.

87. A pharmaceutical composition comprising the 5-MeO-DMT saccharinate of clause 85.

88. A pharmaceutical composition comprising the crystalline form of 5-MeO-DMT saccharinate of clause 85 or clause 86.

89. The pharmaceutical composition of clause 87 for use as a medicament.

90. The pharmaceutical composition of clause 88 for use as a medicament.

The invention claimed is:

1. A non-hygroscopic salt of 5-methoxy-N,N-dimethyl-tryptamine (5-MeO-DMT), wherein the non-hygroscopic salt is 5-MeO-DMT hydrobromide and the non-hygroscopic salt is in crystalline form.

2. The non-hygroscopic salt of claim 1, characterised by peaks in an x-ray powder diffraction (XRPD) diffractogram at 2θ values of 14.6°±0.1°, 16.8°±0.1°, 20.8°±0.1°, 24.3°±0.1°, 24.9°±0.1°, and 27.5°±0.1° as measured using an x-ray wavelength of 1.5406 Å.

3. The non-hygroscopic salt of claim 1, characterised by peaks in an x-ray powder diffraction (XRPD) diffractogram at 2θ values of 14.6°±0.1°, 21.6°±0.1°, and 24.3°±0.1° as measured using an x-ray wavelength of 1.5406 Å.

4. The non-hygroscopic salt of claim 1, characterised by peaks in an x-ray powder diffraction (XRPD) diffractogram at 2θ values of 18.6°±0.1°, 19.7°±0.1°, and 24.8°±0.1° as measured using an x-ray wavelength of 1.5406 Å.

5. The non-hygroscopic salt of claim 3, characterised by peaks in an x-ray powder diffraction (XRPD) diffractogram at 2θ values of 14.6°±0.1°, 20.8°±0.1°, 21.6°±0.1°, 24.3°±0.1°, and 25.4°±0.1° as measured using an x-ray wavelength of 1.5406 Å.

6. A pharmaceutical composition comprising the non-hygroscopic salt of claim 1.

7. A pharmaceutical composition comprising the non-hygroscopic salt of claim 2.

8. A pharmaceutical composition comprising the non-hygroscopic salt of claim 3.

9. A pharmaceutical composition comprising the non-hygroscopic salt of claim 4.

10. A pharmaceutical composition comprising the non-hygroscopic salt of claim 5.

* * * * *

UNITED STATES PATENT AND TRADEMARK OFFICE
CERTIFICATE OF CORRECTION

PATENT NO. : 11,773,063 B1
APPLICATION NO. : 17/941410
DATED : October 3, 2023
INVENTOR(S) : Jason Gray et al.

It is certified that error appears in the above-identified patent and that said Letters Patent is hereby corrected as shown below:

In the Claims

In Claim 4, Column 110, Line 7, delete "20" and insert -- 2θ --.

Signed and Sealed this
Twenty-first Day of November, 2023

Katherine Kelly Vidal
*Director of the United States Patent and Trademark Office*